United States Patent
Kyratsous et al.

(10) Patent No.: US 12,404,505 B2
(45) Date of Patent: Sep. 2, 2025

(54) DELIVERY OF A GENE-EDITING SYSTEM WITH A SINGLE RETROVIRAL PARTICLE AND METHODS OF GENERATION AND USE

(71) Applicant: Regeneron Pharmaceuticals, Inc., Tarrytown, NY (US)

(72) Inventors: Christos Kyratsous, Irvington, NY (US); Andrew J. Murphy, Croton-on-Hudson, NY (US); Cheng Wang, White Plains, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1583 days.

(21) Appl. No.: 16/644,411

(22) PCT Filed: Sep. 5, 2018

(86) PCT No.: PCT/US2018/049547
§ 371 (c)(1),
(2) Date: Mar. 4, 2020

(87) PCT Pub. No.: WO2019/050948
PCT Pub. Date: Mar. 14, 2019

(65) Prior Publication Data
US 2020/0216860 A1 Jul. 9, 2020

Related U.S. Application Data

(60) Provisional application No. 62/554,500, filed on Sep. 5, 2017.

(51) Int. Cl.
| | |
|---|---|
| *C12N 15/113* | (2010.01) |
| *A61K 48/00* | (2006.01) |
| *C12N 7/02* | (2006.01) |
| *C12N 9/22* | (2006.01) |
| *C12N 11/00* | (2006.01) |

(52) U.S. Cl.
CPC .............. *C12N 15/113* (2013.01); *C12N 9/22* (2013.01); *A61K 48/0091* (2013.01); *C12N 7/02* (2013.01); *C12N 11/00* (2013.01); *C12N 2310/20* (2017.05); *C12N 2740/15043* (2013.01); *C12Y 502/01008* (2013.01)

(58) Field of Classification Search
CPC .... C12N 15/113; C12N 9/22; C12N 2310/20; C12N 7/02; C12N 2740/15043; A61K 48/0091; C12Y 502/01008
See application file for complete search history.

(56) References Cited

U.S. PATENT DOCUMENTS

| | | | |
|---|---|---|---|
| 8,697,359 B1 | 4/2014 | Zhang | |
| 8,945,839 B2 | 2/2015 | Zhang | |
| 9,228,208 B2 | 1/2016 | Frendewey et al. | |
| 9,546,384 B2 | 1/2017 | Frendewey et al. | |
| 9,580,712 B2 | 2/2017 | Schoenherr et al. | |
| 9,580,715 B2 | 2/2017 | Schoenherr et al. | |
| 10,113,167 B2 * | 10/2018 | Doudna | ............... A61P 43/00 |
| 2010/0251648 A1 | 10/2010 | Wilson et al. | |
| 2014/0068797 A1 | 3/2014 | Doudna et al. | |
| 2015/0152398 A1 | 6/2015 | Doudna et al. | |
| 2015/0376628 A1 | 12/2015 | Schoenherr et al. | |
| 2016/0251648 A1 | 9/2016 | Wang et al. | |
| 2016/0298135 A1 * | 10/2016 | Chen | ...................... C12N 7/00 |
| 2017/0037432 A1 | 2/2017 | Donohoue et al. | |
| 2017/0073674 A1 | 3/2017 | Maeder et al. | |
| 2017/0145438 A1 | 5/2017 | Kantor | |

FOREIGN PATENT DOCUMENTS

| | | |
|---|---|---|
| WO | 2013/176772 A1 | 11/2013 |
| WO | 2014089290 A1 | 6/2014 |
| WO | 2014191128 A1 | 12/2014 |
| WO | 2016205749 A1 | 6/2016 |
| WO | 2016196655 A1 | 12/2016 |
| WO | 2017059241 A1 | 4/2017 |

OTHER PUBLICATIONS

Wang W, Ye C, Liu J, Zhang D, Kimata JT, Zhou P. CCR5 gene disruption via lentiviral vectors expressing Cas9 and single guided RNA renders cells resistant to HIV-1 infection. PLoS One. Dec. 26, 2014;9(12):e115987. (Year: 2014).*
Choi JG, Dang Y, Abraham S, Ma H, Zhang J, Guo H, Cai Y, Mikkelsen JG, Wu H, Shankar P, Manjunath N. Lentivirus prepacked with Cas9 protein for safer gene editing. Gene Ther. Jul. 2016;23(7):627-33. (Year: 2016).*
Keene SE, Telesnitsky A. cis-Acting determinants of 7SL RNA packaging by HIV-1. J Virol. Aug. 2012;86(15):7934-42. (Year: 2012).*
Naoya Uchida, Anna Shvygin, Luke Skala, Lydia Raines, Josiah Ballantine, John Tisdale. Development of a Cas9 Protein Delivery System with Lentiviral Vectors for RNA-Guided Genome Editing. Molecular Therapy vol. 24, Supplement 1, May 2016. (Year: 2016).*

(Continued)

*Primary Examiner* — Janet L Andres
*Assistant Examiner* — Ruixue Wang
(74) *Attorney, Agent, or Firm* — Troutman Pepper Locke LLP

(57) ABSTRACT

The invention provides a recombinant RNA molecule comprising (i) a sequence of a gene-editing molecule mRNA, or a sequence of a functional fragment or derivative thereof, and (ii) at least one sequence of a coding or non-coding enrichment RNA, or a sequence of a functional fragment or derivative thereof, wherein the enrichment RNA, or functional fragment or derivative thereof, is capable of enhancing inclusion of the gene-editing molecule mRNA, or functional fragment or derivative thereof, into a retroviral particle. The invention provides a method of producing the retroviral particles of the invention, the method comprising culturing a packaging cell in conditions sufficient for the production of a plurality of retroviral particles.

28 Claims, 17 Drawing Sheets
Specification includes a Sequence Listing.

(56) References Cited

OTHER PUBLICATIONS

Naoya Uchida, Anna Shvygin, Luke Skala, Lydia Raines. Development of a Cas9 Protein Delivery System with Lentiviral Vectors for RNA-Guided Genome Editing. RNA Virus Vectors| vol. 24, Supplement 1, S2, May 2016. (Year: 2016).*

Onafuwa-Nuga AA, Telesnitsky A, King SR. 7SL RNA, but not the 54-kd signal recognition particle protein, is an abundant component of both infectious HIV-1 and minimal virus-like particles. RNA. Apr. 2006;12(4):542-6. ( (Year: 2006).*

Keene SE, Telesnitsky A. cis-Acting determinants of 7SL RNA packaging by HIV-1. J Virol. Aug. 2012;86(15):7934-42. doi: 10.1128/JVI.00856-12. Epub May 16, 2012. (Year: 2012).*

Eckwahl MJ, Telesnitsky A, Wolin SL. Host RNA Packaging by Retroviruses: A Newly Synthesized Story. mBio. Feb. 9, 2016;7(1):e02025-15 (Year: 2016).*

Stu Borman . Improved route to single-base genome editing. Biological Chemistry, vol. 94, Issue 17, Apr. 21, 2016. (https://cen.acs.org/articles/94/i17/Improved-route-single-base-genome.html), (Year: 2016).*

Luban J, Bossolt KL, Franke EK, Kalpana GV, Goff SP. Human immunodeficiency virus type 1 Gag protein binds to cyclophilins A and B. Cell. Jun. 18, 1993;73(6):1067-78. (Year: 1993).*

Communication (International Search Report) issued by the International Searching Authority in International Application No. PCT/US2018/049547 dated Jan. 15, 2019, 5 pages total.

Communication (Written Opinion) issued by the International Searching Authority in International Application No. PCT/US2018/049547 dated Jan. 15, 2019, 4 pages total.

Wang, T. et al., "7SL RNA Mediates Virion Packaging of the Antiviral Cytidine Deaminase APOBEC3G" Journal of Virology (2007) vol. 81, No. 23, pp. 13112-13124.

Weninger, A. et al., "Combinatorial Optimization of CRISPR/Cas9 Expression Enables Precision Genome Engineering in the Methylotrophic Yeast Pichia Pastoris" Journal of Biotechnology (2016) vol. 235, pp. 139-149.

Zhang, Z. et al., "A Multiplex CRISPR/Cas9 Platform for Fast and Efficient Editing of Multiple Genes in *Arabidopsis*" Plant Cell Reports (2015) vol. 35, No. 7, pp. 1519-1533.

Extended European Search Report from corresponding European application No. 18853626.2 dated Oct. 29, 2021.

Dana Carroll, "A Crispr Approach to Gene Targeting", Molecular Therapy, vol. 20, No. 9, Sep. 1, 2012, pp. 1658-1660.

Lei S. Qi et al., "Repurposing Crispr as an RNA-Guided Platform for Sequence-Specific Control of Gene Expression", Cell, vol. 152, No. 5, Feb. 1, 2013, pp. 1173-1183.

Choi, JG et al., "Lenitvirus Pre-Packed with Cas9 Protein for Safer Gene Editing" Gene Therapy (2016) vol. 23, pp. 627-633.

Eckwahl, M.J. et al., "Host RNA Packaging by Retroviruses: A Newly Synthesized Story" mBio (2016) vol. 7, Issue 1, 8 pages total.

Kabadi, A.M. et al., "Multiplex CRISPR/Cas9-based Genome Engineering from a Single Lentiviral Vector" Nucleic Acids Research (2014) vol. 42, No. 19, e147, 11 pages total.

Mout, R. et al., "Direct Cytosolic Delivery of CRISPR/Cas9-Ribonuceloprotein for Efficient Gene Editing" ACS Nano (2017) vol. 11, pp. 2452-2458.

Mout, R. et al., "In Vivo Delivery of CRISPR/Cas9 for Therapeutic Gene Editing: Progress and Challenges" Bioconjugate Chemistry (2017) vol. 28, pp. 880-884.

Onafuwa-Nuga, A.A. et al., "7SL RNA, but not the 54-kd Signal Recognition Particle Protein, is an Abundant Component of Both Infectious HIV-1 and Minimal Virus-like Particles" RNA (2006) vol. 12, pp. 542-546.

SBI System Biosciences, "Lenti-Cas9 SmartNuclease Systems: Ready-to-edit Cas9 packaged lentiviral particles & plasmids" (2014) 2 pages total.

Shalem, O. et al., "Genome-Scale CRISPR-Cas9 Knockout Screening in Human Cells" Science (2014) vol. 343, No. 6166, p. 84-87.

Tian, C. et al., "Virion Packaging Determinants and Reverse Transcription of SRP RNA in HIV-1 Particles" Nucleic Acids Research (2007) vol. 35, No. 21, pp. 7288-7302.

Transomic Technologies, "transEDIT CRISPR-Cas Reagents: Optimized gRNA Designs, Versatile Vectors and Flexible Formats for Efficient Gene Editing," (2011), 4 pages total,.

Ali, L.M. et al., "Cross- and Co-Packaging of Retroviral RNAs and Their Consequences" Viruses (2016) vol. 8, No. 276, 26 pages total.

Bukrinsky, M. et al., "Viral Protein R of HIV-1" Reviews in Medical Virology (1999) vol. 9, pp. 39-49.

Keene, S.E. et al., "7SL RNA is Retained in HIV-1 Minimal Virus-Like Particles as an S-Domain Fragment" Journal of Virology (2010) vol. 84, No. 18, pp. 9070-9077.

Keene, S.E. et al., "cis-Acting Determinants of 7SL RNA Packaging by HIV-1" Journal of Virology (2012) vol. 86, No. 15, pp. 7934-7942.

Communication (International Preliminary Report on Patentability) issued by the International Searching Authority in International Application No. PCT/US2018/049547 dated Mar. 10, 2020, 5 pages total.

Wang, et al.; In Vivo Delivery Systems for Therapeutic Genome Editing; International Journal of Molecular Sciences; 2016; 17, 626; doi:10.3390/ijms17050626.

LentiCRISPR lentiviral CRISPR/Cas9 and single guide RNA, Lentiviral CRISPR Toolbox, Zhang Lab, MIT, rev20140208, 2014.

* cited by examiner

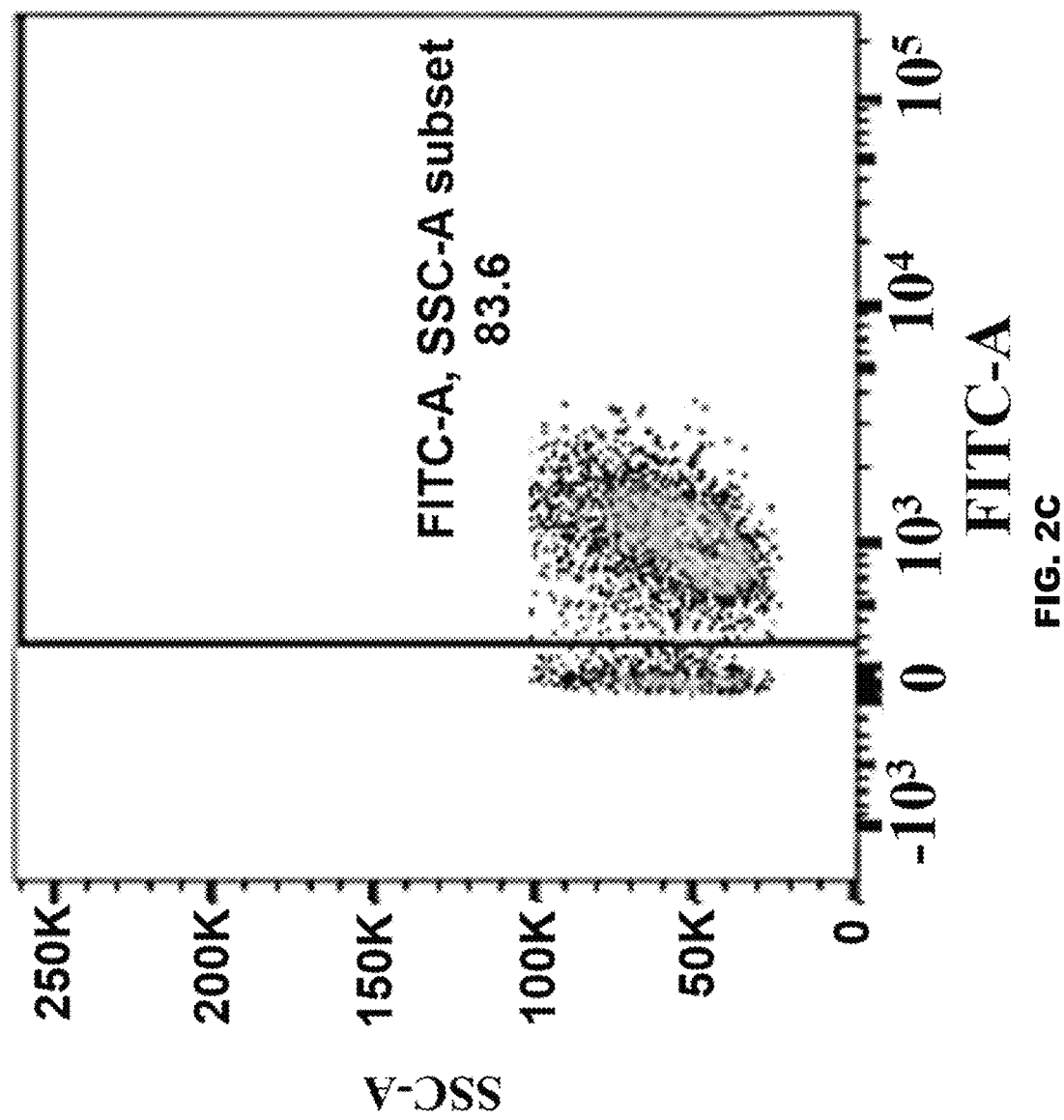

GCCCAGGAGUUC
GCCTGTGC

GTCCAGGAGUUC
GCCTGGGC

SEQUENCE LISTING

<160> NUMBER OF SEQ ID NOS: 156

<210> SEQ ID NO 1
<211> LENGTH: 299
<212> TYPE: DNA
<213> ORGANISM: Homo sapiens

<400> SEQUENCE: 1

| | | | | | |
|---|---|---|---|---|---|
| gccgggcgcg | gtggcgcgtg | cctgtagtcc | cagctactcg | ggaggctgag | gctggaggat | 60 |
| cgcttgagtc | caggagttct | gggctgtagt | gcgctatgcc | gatcgggtgt | ccgcactaag | 120 |
| ttcggcatca | atatggtgac | ctcccgggag | cgggggacca | ccaggttgcc | taaggagggg | 180 |
| tgaaccggcc | caggtcggaa | acggagcagg | tcaaaactcc | cgtgctgatc | agtagtggga | 240 |
| tcgcgcctgt | aatagccac | tgcactccag | cctgggcaac | atagcgagac | cccgtctct | 299 |

<210> SEQ ID NO 2
<211> LENGTH: 4176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | | | | | |
|---|---|---|---|---|---|
| atggacaagc | ccaagaaaaa | gcggaaagtg | aagtacagca | tcggcctgga | catcggcacc | 60 |
| aactctgtgg | gctgggccgt | gatcaccgac | gagtacaagg | tgcccagcaa | gaaattcaag | 120 |
| gtgctgggca | acaccgacag | gcacagcatc | aagaagaacc | tgatcggcgc | cctgctgttc | 180 |
| gacagcggcg | aaacagccga | ggccaccaga | ctgaagagaa | ccgccagaag | aagatacacc | 240 |
| aggcggaaga | acaggatctg | ctatctgcaa | gagatcttca | gcaacgagat | ggccaaggtg | 300 |
| gacgacagct | tcttccacag | actggaagag | tccttcctgg | tggaagagga | caagaagcac | 360 |
| gagagacacc | ccatcttcgg | caacatcgtg | gacgaggtgg | cctaccacga | gaagtacccc | 420 |
| accatctacc | acctgagaaa | gaaactggtg | gacagcaccg | acaaggccga | cctgagactg | 480 |
| atctacctgg | ccctggccca | catgatcaag | ttcagaggcc | acttcctgat | cgagggcgac | 540 |
| ctgaaccccg | acaacagcga | cgtggacaag | ctgttcatcc | agctggtgca | gacctacaac | 600 |
| cagctgttcg | aggaaaaccc | catcaacgcc | agcggcgtgg | acgccaaggc | tatcctgtct | 660 |
| gccagactga | gcaagagcag | aaggctggaa | aatctgatcg | cccagctgcc | cggcgagaag | 720 |
| aagaacggcc | tgttcggcaa | cctgattgcc | ctgagcctgg | gcctgacccc | caacttcaag | 780 |
| agcaacttcg | acctggccga | ggatgccaaa | ctgcagctga | gcaaggacac | ctacgacgac | 840 |
| gacctggaca | acctgctggc | ccagatcggc | gaccagtacg | ccgacctgtt | cctggccgcc | 900 |
| aagaacctgt | ctgacgccat | cctgctgagc | gacatcctga | gagtgaacac | cgagatcacc | 960 |
| aaggcccccc | tgagcgcctc | tatgatcaag | agatacgacg | agcaccacca | ggacctgacc | 1020 |
| ctgctgaaag | ctctcgtgcg | gcagcagctg | cctgagaagt | acaaagaaat | cttcttcgac | 1080 |
| cagagcaaga | acggctacgc | cggctacatc | gatggcggcg | ctagccagga | agagttctac | 1140 |
| aagttcatca | agcccatcct | ggaaaagatg | gacggcaccg | aggaactgct | cgtgaagctg | 1200 |
| aacagagagg | acctgctgag | aaagcagaga | accttcgaca | acggcagcat | cccccaccag | 1260 |
| atccacctgg | gagagctgca | cgctatcctg | agaaggcagg | aagatttta | cccattcctg | 1320 |
| aaggacaacc | gggaaaagat | cgagaagatc | ctgaccttca | ggatccccta | ctacgtgggc | 1380 |
| cccctggcca | gaggcaacag | cagattcgcc | tggatgacca | gaaagagcga | ggaaaccatc | 1440 |

```
accccctgga acttcgagga agtggtggac aagggcgcca gcgcccagag cttcatcgag   1500
agaatgacaa acttcgataa gaacctgccc aacgagaagg tgctgcccaa gcacagcctg   1560
ctgtacgagt acttcaccgt gtacaacgag ctgaccaaag tgaaatacgt gaccgaggga   1620
atgagaaagc ccgccttcct gagcggcgag cagaaaaagg ccatcgtgga cctgctgttc   1680
aagaccaaca gaaaagtgac cgtgaagcag ctgaaagagg actacttcaa gaaaatcgag   1740
tgcttcgact ccgtggaaat ctccggcgtg gaagatagat tcaacgcctc cctgggcaca   1800
taccacgatc tgctgaaaat tatcaaggac aaggacttcc tggataacga agagaacgag   1860
gacattctgg aagatatcgt gctgaccctg acactgtttg aggaccgcga gatgatcgag   1920
gaaaggctga aacctacgc tcacctgttc gacgacaaag tgatgaagca gctgaagaga   1980
aggcggtaca ccggctgggg caggctgagc agaaagctga tcaacggcat cagagacaag   2040
cagagcggca agacaatcct ggatttcctg aagtccgacg gcttcgccaa ccggaacttc   2100
atgcagctga ccacgacga cagcctgaca ttcaaagagg acatccagaa agcccaggtg   2160
tccggccagg gcgactctct gcacgagcat atcgctaacc tggccggcag ccccgctatc   2220
aagaagggca tcctgcagac agtgaaggtg gtggacgagc tcgtgaaagt gatgggcaga   2280
cacaagcccg agaacatcgt gatcgagatg gctagagaga accagaccac ccagaaggga   2340
cagaagaact cccgcgagag gatgaagaga atcgaagagg gcatcaaaga gctgggcagc   2400
cagatcctga aagaacaccc cgtggaaaac acccagctgc agaacgagaa gctgtacctg   2460
tactacctgc agaatggccg ggatatgtac gtggaccagg aactggacat caacagactg   2520
tccgactacg atgtggacca tatcgtgcct cagagctttc tgaaggacga ctccatcgat   2580
aacaaagtgc tgactcggag cgacaagaac agaggcaaga gcgacaacgt gcccctccgaa   2640 gaggtcgtga gaagatgaa gaactactgg cgacagctgc tgaacgccaa gctgattacc   2700
cagaggaagt tcgataacct gaccaaggcc gagagaggcg gcctgagcga gctggataag   2760
gccggcttca tcaagaggca gctggtggaa accagacaga tcacaaagca cgtggcacag   2820
atcctggact cccggatgaa cactaagtac gacgaaaacg ataagctgat ccgggaagtg   2880
aaagtgatca ccctgaagtc caagctggtg tccgatttcc ggaaggattt ccagttttac   2940
aaagtgcgcg agatcaacaa ctaccaccac gcccacgacg cctacctgaa cgccgtcgtg   3000
ggaaccgccc tgatcaaaaa gtaccctaag ctggaaagcg agttcgtgta cggcgactac   3060
aaggtgtacg acgtgcggaa gatgatcgcc aagagcgagc aggaaatcgg caaggctacc   3120
gccaagtact tcttctacag caacatcatg aactttttca agaccgaaat cacccctggcc   3180 aacggcgaga tcagaaagcg ccctctgatc gagacaaacg gcgaaaccgg ggagatcgtg   3240
tgggataagg gcagagactt cgccacagtg cgaaaggtgc tgagcatgcc ccaagtgaat   3300
atcgtgaaaa agaccgaggt gcagacaggc ggcttcagca agagtctat cctgcccaag   3360 aggaacagcg acaagctgat cgccagaaag aaggactggg accccaagaa gtacggcggc   3420
ttcgacagcc ctaccgtggc ctactctgtg ctggtggtgg ctaaggtgga aaagggcaag   3480
tccaagaaac tgaagagtgt gaaagagctg ctggggatca ccatcatgga agaagcagc   3540 tttgagaaga accctatcga ctttctggaa gccaagggct acaaagaagt gaaaaaggac   3600
ctgatcatca agctgcctaa gtactccctg ttcgagctgg aaaacggcag aaagagaatg   3660
ctggcctctg ccggcgaact gcagaaggga acgagctgg ccctgcctag caaatatgtg   3720
aacttcctgt acctggcctc ccactatgag aagctgaagg gcagccctga ggacaacgaa   3780
cagaaacagc tgtttgtgga acagcataag cactacctgg acgagatcat cgagcagatc   3840
```

```
agcgagttct ccaagagagt gatcctggcc gacgccaatc tggacaaggt gctgtctgcc    3900
tacaacaagc acagggacaa gcctatcaga gagcaggccg agaatatcat ccacctgttc    3960
accctgacaa acctgggcgc tcctgccgcc ttcaagtact tgacaccac catcgaccgg     4020 aagaggtaca ccagcaccaa agaggtgctg acgccaccc tgatccacca gagcatcacc    4080
ggcctgtacg agacaagaat cgacctgtct cagctgggag cgacaagag acctgccgcc    4140 actaagaagg ccggacaggc caaaaagaag aagtga                              4176
```

<210> SEQ ID NO 3
<211> LENGTH: 4487
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
gccgggcgcg gtggcgcgtg cctgtagtcc cagctactcg ggaggctgag gctggaggat     60
cgcttgagtc caggagttct gggctgtagt gcgctatgcc gatcgggtgt ccgcactaag    120
ttcggcatca atatggtgac ctcccgggag cgggggacca ccaggttgcc taaggagggg    180
tgaaccggcc caggtcggaa acggagcagg tcaaaactcc cgtgctgatc agtagtggga    240
tcgcgcctgt gaatagccac tgcactccag cctgggcaac atagcgagac cccgtctcta    300
ctagtgccac catggacaag cccaagaaaa agcggaaagt gaagtacagc atcggcctgg    360
acatcggcac caactctgtg ggctgggccg tgatcaccga cgagtacaag gtgcccagca    420
agaaattcaa ggtgctgggc aacaccgaca ggcacagcat caagaagaac ctgatcggcg    480
ccctgctgtt cgacagcggc gaaacagccg aggccaccag actgaagaga accgccagaa    540
gaagatacac caggcggaag aacaggatct gctatctgca agagatcttc agcaacgaga    600
tggccaaggt ggacgacagc ttcttccaca gactggaaga gtccttcctg gtggaagagg    660
acaagaagca cgagagacac cccatcttcg gcaacatcgt ggacgaggtg gcctaccacg    720
agaagtaccc caccatctac cacctgagaa agaaactggt ggacagcacc gacaaggccg    780
acctgagact gatctacctg gcctggccc acatgatcaa gttcagaggc cacttcctga    840
tcgagggcga cctgaacccc gacaacgcg acgtggacaa gctgttcatc cagctggtgc    900
agacctacaa ccagctgttc gaggaaaacc ccatcaacgc cagcggcgtg gacgccaagg    960
ctatcctgtc tgccagactg agcaagagca aaggctgga aaatctgatc gcccagctgc   1020
ccggcgagaa gaagaacggc ctgttcggca acctgattgc cctgagcctg ggcctgaccc   1080
ccaacttcaa gagcaacttc gacctggccg aggatgccaa actgcagctg agcaaggaca   1140
cctacgacga cgacctggac aacctgctgg cccagatcgg cgaccagtac gccgacctgt   1200
tcctggccgc caagaacctg tctgacgcca tcctgctgag cgacatcctg agagtgaaca   1260
ccgagatcac caaggccccc ctgagcgcct ctatgatcaa gagatacgac gagcaccacc   1320
aggacctgac cctgctgaaa gctctcgtgc ggcagcagct gcctgagaag tacaaagaaa   1380
tcttcttcga ccagagcaag aacggctacg ccggctacat cgatgccggc gctagccagg   1440
aagagttcta caagttcatc aagcccatcc tggaaaagat ggacggcacc gaggaactgc   1500
tcgtgaagct gaacagagag gacctgctga aaagcagag aaccttcgac aacggcagca   1560 tccccccacca gatccacctg ggagagctgc acgctatcct gagaaggcag gaagattttt   1620
acccattcct gaaggacaac cgggaaaaga tcgagaagat cctgaccttc aggatcccct   1680
```

```
actacgtggg cccnctggcc agaggcaaca gcagattcgc ctggatgacc agaaagagcg    1740
aggaaaccat cacccnctgg aacttcgagg aagtggtgga caagggcgcc agcgcccaga   1800
gcttcatcga gagaatgaca aacttcgata agaacctgcc caacgagaag gtgctgccca   1860
agcacagcct gctgtacgag tacttcaccg tgtacaacga gctgaccaaa gtgaaatacg   1920
tgaccgaggg aatgagaaag cccgccttcc tgagcggcga gcagaaaaag gccatcgtgg   1980
acctgctgtt caagaccaac agaaaagtga ccgtgaagca gctgaaagag gactacttca   2040
agaaaatcga gtgcttcgac tccgtggaaa tctccggcgt ggaagataga ttcaacgcct   2100
ccctgggcac ataccacgat ctgctgaaaa ttatcaagga caaggacttc ctggataacg   2160
aagagaacga ggacattctg gaagatatcg tgctgaccct gacactgttt gaggaccgcg   2220
agatgatcga ggaaaggctg aaaacctacg ctcacctgtt cgacgacaaa gtgatgaagc   2280
agctgaagag aaggcggtac accggctggg gcaggctgag cagaaagctg atcaacggca   2340
tcagagacaa gcagagcggc aagacaatcc tggatttcct gaagtccgac ggcttcgcca   2400
accggaactt catgcagctg atccacgacg acagcctgac attcaaagag gacatccaga   2460
aagcccaggt gtccggccag ggcgactctc tgcacgagca tatcgctaac ctggccggca   2520
gccccgctat caagaagggc atcctgcaga cagtgaaggt ggtggacgag ctcgtgaaag   2580
tgatgggcag acacaagccc gagaacatcg tgatcgagat ggctagagag aaccagacca   2640
cccagaaggg acagaagaac tcccgcgaga ggatgaagag aatcgaagag ggcatcaaag   2700
agctgggcag ccagatcctg aaagaacacc ccgtggaaaa cacccagctg cagaacgaga   2760
agctgtacct gtactacctg cagaatggcc gggatatgta cgtggaccag gaactggaca   2820
tcaacagact gtccgactac gatgtggacc atatcgtgcc tcagagcttt ctgaaggacg   2880
actccatcga taacaaagtg ctgactcgga gcgacaagaa cagaggcaag agcgacaacg   2940
tgccctccga agaggtcgtg aagaagatga aaaactactg gcgacagctg ctgaacgcca   3000
agctgattac ccagaggaag ttcgataacc tgaccaaggc cgagagaggc ggcctgagcg   3060
agctggataa ggccggcttc atcaagaggc agctggtgga aaccagacag atcacaaagc   3120
acgtggcaca gatcctggac tcccggatga acactaagta cgacgaaaac gataagctga   3180
tccgggaagt gaaagtgatc accctgaagt ccaagctggt gtccgatttc cggaaggatt   3240
tccagtttta caaagtgcgc gagatcaaca actaccacca cgcccacgac gcctacctga   3300
acgccgtcgt gggaaccgcc ctgatcaaaa agtaccctaa gctggaaagc gagttcgtgt   3360
acggcgacta caaggtgtac gacgtgcgga agatgatcgc caagagcgag caggaaatcg   3420
gcaaggctac cgccaagtac ttcttctaca gcaacatcat gaacttttc aagaccgaaa    3480 tcaccctggc caacggcgag atcagaaagc gccctctgat cgagacaaac ggcgaaaccg   3540
gggagatcgt gtgggataag ggcagagact cgccacagt gcgaaaggtg ctgagcatgc    3600
cccaagtgaa tatcgtgaaa aagaccgagg tgcagacagg cggcttcagc aaagagtcta   3660
tcctgcccaa gaggaacagc gacaagctga tcgccagaaa gaaggactgg gaccccaaga   3720
agtacgcggg cttcgacagc cctaccgtgg cctactctgt gctggtggtg gctaaggtgg   3780
aaaagggcaa gtccaagaaa ctgaagagtg tgaaagagct gctggggatc accatcatgg   3840
aaagaagcag ctttgagaag aaccctatcg actttctgga agccaagggc tacaaagaag   3900
tgaaaaagga cctgatcatc aagctgccta agtactccct gttcgagctg gaaaacggca   3960
gaaagagaat gctggcctct gccggcgaac tgcagaaggg aaacgagctg gccctgccta   4020
```

| | |
|---|---:|
| gcaaatatgt gaacttcctg tacctggcct cccactatga gaagctgaag ggcagccctg | 4080 |
| aggacaacga acagaaacag ctgtttgtgg aacagcataa gcactacctg gacgagatca | 4140 |
| tcgagcagat cagcgagttc tccaagagag tgatcctggc cgacgccaat ctggacaagg | 4200 |
| tgctgtctgc ctacaacaag cacagggaca agcctatcag agagcaggcc gagaatatca | 4260 |
| tccacctgtt caccctgaca aacctgggcg ctcctgccgc cttcaagtac tttgacacca | 4320 |
| ccatcgaccg gaagaggtac accagcacca agaggtgct ggacgccacc ctgatccacc | 4380 |
| agagcatcac cggcctgtac gagacaagaa tcgacctgtc tcagctggga ggcgacaaga | 4440 |
| gacctgccgc cactaagaag gccggacagg ccaaaaagaa gaagtga | 4487 |

<210> SEQ ID NO 4
<211> LENGTH: 4481
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | |
|---|---:|
| atggacaagc ccaagaaaaa gcggaaagtg aagtacagca tcggcctgga catcggcacc | 60 |
| aactctgtgg gctgggccgt gatcaccgac gagtacaagg tgcccagcaa gaaattcaag | 120 |
| gtgctgggca acaccgacag gcacagcatc aagaagaacc tgatcggcgc cctgctgttc | 180 |
| gacagcggcg aaacagccga ggccaccaga ctgaagagaa ccgccagaag aagatacacc | 240 |
| aggcggaaga acaggatctg ctatctgcaa gagatcttca gcaacgagat ggccaaggtg | 300 |
| gacgacagct tcttccacag actggaagag tccttcctgg tggaagagga caagaagcac | 360 |
| gagagacacc ccatcttcgg caacatcgtg gacgaggtgg cctaccacga gaagtacccc | 420 |
| accatctacc acctgagaaa gaaactggtg gacagcacca caaggccga cctgagactg | 480 |
| atctacctgg ccctggccca catgatcaag ttcagaggcc acttcctgat cgagggcgac | 540 |
| ctgaaccccg acaacagcga cgtggacaag ctgttcatcc agctggtgca gacctacaac | 600 |
| cagctgttcg aggaaaaccc catcaacgcc agcggcgtgg acgccaaggc tatcctgtct | 660 |
| gccagactga gcaagagcag aaggctggaa aatctgatcg cccagctgcc cggcgagaag | 720 |
| aagaacggcc tgttcggcaa cctgattgcc ctgagcctgg gcctgacccc caacttcaag | 780 |
| agcaacttcg acctggccga ggatgccaaa ctgcagctga gcaaggacac ctacgacgac | 840 |
| gacctggaca acctgctggc ccagatcggc gaccagtacg ccgacctgtt cctggccgcc | 900 |
| aagaacctgt ctgacgccat cctgctgagc gacatcctga gagtgaacac cgagatcacc | 960 |
| aaggcccccc tgagcgcctc tatgatcaag agatacgacg agcaccacca ggacctgacc | 1020 |
| ctgctgaaag ctctcgtgcg gcagcagctg cctgagaagt acaaagaaat cttcttcgac | 1080 |
| cagagcaaga acggctacgc cggctacatc gatggcggcg ctagccagga agagttctac | 1140 |
| aagttcatca agcccatcct ggaaaagatg gacggcaccg aggaactgct cgtgaagctg | 1200 |
| aacagagagg acctgctgag aaagcagaga accttcgaca acggcagcat cccccaccag | 1260 |
| atccacctgg gagagctgca cgctatcctg agaaggcagg aagattttta cccattcctg | 1320 |
| aaggacaacc gggaaaagat cgagaagatc ctgaccttca ggatccccta ctacgtgggc | 1380 |
| cccctggcca gaggcaacag cagattcgcc tggatgacca aaagagcga ggaaaccatc | 1440 |
| acccccctgga acttcgagga agtggtggac aagggcgcca cgcccagag cttcatcgag | 1500 |
| agaatgacaa acttcgataa gaacctgccc aacgagaagg tgctgcccaa gcacagcctg | 1560 |

```
ctgtacgagt acttcaccgt gtacaacgag ctgaccaaag tgaaatacgt gaccgaggga    1620
atgagaaagc ccgccttcct gagcggcgag cagaaaaagg ccatcgtgga cctgctgttc    1680
aagaccaaca gaaaagtgac cgtgaagcag ctgaaagagg actacttcaa gaaaatcgag    1740
tgcttcgact ccgtggaaat ctccggcgtg gaagatagat tcaacgcctc cctgggcaca    1800
taccacgatc tgctgaaaat tatcaaggac aaggacttcc tggataacga agagaacgag    1860
gacattctgg aagatatcgt gctgaccctg acactgtttg aggaccgcga gatgatcgag    1920
gaaaggctga aacctacgc tcacctgttc gacgacaaag tgatgaagca gctgaagaga    1980
aggcggtaca ccggctgggg caggctgagc agaaagctga tcaacggcat cagagacaag    2040
cagagcggca agacaatcct ggatttcctg aagtccgacg gcttcgccaa ccggaacttc    2100
atgcagctga tccacgacga cagcctgaca ttcaaagagg acatccagaa agcccaggtg    2160
tccggccagg gcgactctct gcacgagcat atcgctaacc tggccggcag ccccgctatc    2220
aagaagggca tcctgcagac agtgaaggtg gtggacgagc tcgtgaaagt gatgggcaga    2280
cacaagcccg agaacatcgt gatcgagatg gctagagaa accagaccac ccagaaggga    2340
cagaagaact cccgcgagag gatgaagaga atcgaagagg gcatcaaaga gctgggcagc    2400
cagatcctga agaacacccc cgtggaaaac acccagctgc agaacgagaa gctgtacctg    2460
tactacctgc agaatggccg ggatatgtac gtggaccagg aactggacat caacagactg    2520
tccgactacg atgtggacca tatcgtgcct cagagctttc tgaaggacga ctccatcgat    2580
aacaaagtgc tgactcggag cgacaagaac agaggcaaga gcgacaacgt gccctccgaa    2640
gaggtcgtga gaagatgaa gaactactgg cgacagctgc tgaacgccaa gctgattacc    2700
cagaggaagt tcgataacct gaccaaggcc gagagaggcg gcctgagcga gctggataag    2760
gccggcttca tcaagaggca gctggtggaa accagacaga tcacaaagca cgtggcacag    2820
atcctggact cccggatgaa cactaagtac gacgaaaacg ataagctgat ccgggaagtg    2880
aaagtgatca ccctgaagtc caagctggtg tccgatttcc ggaaggattt ccagttttac    2940
aaagtgcgcg agatcaacaa ctaccaccac gcccacgacg cctacctgaa cgccgtcgtg    3000
ggaaccgccc tgatcaaaaa gtaccctaag ctggaaagcg agttcgtgta cggcgactac    3060
aaggtgtacg acgtgcggaa gatgatcgcc aagagcgagc aggaaatcgg caaggctacc    3120
gccaagtact cttctacag caacatcatg aacttttca agaccgaaat caccctggcc    3180
aacggcgaga tcagaaagcg ccctctgatc gagacaaacg gcgaaaccgg ggagatcgtg    3240
tgggataagg gcagagactt cgccacagtg cgaaaggtgc tgagcatgcc ccaagtgaat    3300
atcgtgaaaa agaccgaggt gcagacaggc ggcttcagca aagagtctat cctgcccaag    3360
aggaacagcg acaagctgat cgccagaaag aaggactggg accccaagaa gtacggcggc    3420
ttcgacagcc ctaccgtggc ctactctgtg ctggtggtgg ctaaggtgga aaagggcaag    3480
tccaagaaac tgaagagtgt gaaagagctg ctgggatca ccatcatgga agaagcagc    3540 tttgagaaga accctatcga ctttctggaa gccaagggct acaagaagt gaaaaaggac    3600 ctgatcatca agctgcctaa gtactccctg ttcgagctgg aaaacggcag aaagagaatg    3660
ctggcctctg ccggcgaact gcagaaggga acgagctgg ccctgcctag caaatatgtg    3720
aacttcctgt acctggcctc ccactatgag aagctgaagg gcagccctga ggacaacgaa    3780
cagaaacagc tgtttgtgga acagcataag cactacctgg acgagatcat cgagcagatc    3840
agcgagttct ccaagagagt gatcctggcc gacgccaatc tggacaaggt gctgtctgcc    3900
tacaacaagc acagggacaa gcctatcaga gagcaggccg agaatatcat ccacctgttc    3960
```

```
accctgacaa acctgggcgc tcctgccgcc ttcaagtact ttgacaccac catcgaccgg    4020
aagaggtaca ccagcaccaa agaggtgctg acgccaccc tgatccacca gagcatcacc    4080
ggcctgtacg agacaagaat cgacctgtct cagctgggag gcgacaagag acctgccgcc    4140
actaagaagg ccggacaggc caaaaagaag aagtgatcta gagccgggcg cggtggcgcg    4200
tgcctgtagt cccagctact cgggaggctg aggctggagg atcgcttgag tccaggagtt    4260
ctgggctgta gtgcgctatg ccgatcgggt gtccgcacta agttcggcat caatatggtg    4320
acctcccggg agcgggggac caccaggttg cctaaggagg ggtgaaccgg cccaggtcgg    4380
aaacggagca ggtcaaaact cccgtgctga tcagtagtgg gatcgcgcct gtgaatagcc    4440
actgcactcc agcctgggca acatagcgag accccgtctc t                       4481
```

<210> SEQ ID NO 5
<211> LENGTH: 288
<212> TYPE: DNA
<213> ORGANISM: Human immunodeficiency virus

<400> SEQUENCE: 5

```
atggaacaag ccccagaaga ccaagggcca cagagggagc cacacaatga atggacacta     60
gagcttttag aggagcttaa gaatgaagct gttagacatt ttcctaggat ttggctccat    120
ggcttagggc aacatatcta tgaaacttat ggggatactt gggcaggagt ggaagccata    180
ataagaattc tgcaacaact gctgtttatc catttcagaa ttgggtgtcg acatagcaga    240
ataggcgtta ctcgacagag gagagcaaga aatggagcca gtagatcc                288
```

<210> SEQ ID NO 6
<211> LENGTH: 96
<212> TYPE: PRT
<213> ORGANISM: Human immunodeficiency virus

<400> SEQUENCE: 6

```
Met Glu Gln Ala Pro Glu Asp Gln Gly Pro Gln Arg Glu Pro His Asn
1               5                   10                  15

Glu Trp Thr Leu Glu Leu Leu Glu Glu Leu Lys Asn Glu Ala Val Arg
            20                  25                  30

His Phe Pro Arg Ile Trp Leu His Gly Leu Gly Gln His Ile Tyr Glu
        35                  40                  45

Thr Tyr Gly Asp Thr Trp Ala Gly Val Glu Ala Ile Ile Arg Ile Leu
    50                  55                  60

Gln Gln Leu Leu Phe Ile His Phe Arg Ile Gly Cys Arg His Ser Arg
65                  70                  75                  80

Ile Gly Val Thr Arg Gln Arg Arg Ala Arg Asn Gly Ala Ser Arg Ser
                85                  90                  95
```

<210> SEQ ID NO 7
<211> LENGTH: 339
<212> TYPE: DNA
<213> ORGANISM: Human immunodeficiency virus

<400> SEQUENCE: 7

```
atgacagacc ccagagaaag ggtaccgcca ggaaacagtg agaagagac cattggagag     60 gccttcgagt ggctagagag gaccatagaa gccttaaaca gggaggcagt gaaccatctg    120
ccccgagagc tcattttcca ggtgtggcaa aggtcctgga gatattgca tgatgaacaa    180 gggatgtcag caagctacac aaagtataga tatttgtgcc taatgcaaaa agctatattt    240
```

```
acacatttca agagagggtg cacttgctgg ggggaggaca tgggccggga aggattggaa    300
gaccaaggac ctccccctcc tcccccctcca ggtctagtc                          339
```

<210> SEQ ID NO 8
<211> LENGTH: 113
<212> TYPE: PRT
<213> ORGANISM: Human immunodeficiency virus

<400> SEQUENCE: 8

```
Met Thr Asp Pro Arg Glu Arg Val Pro Pro Gly Asn Ser Gly Glu Glu
1               5                   10                  15
Thr Ile Gly Glu Ala Phe Glu Trp Leu Glu Arg Thr Ile Glu Ala Leu
            20                  25                  30
Asn Arg Glu Ala Val Asn His Leu Pro Arg Glu Leu Ile Phe Gln Val
        35                  40                  45
Trp Gln Arg Ser Trp Arg Tyr Trp His Asp Glu Gln Gly Met Ser Ala
    50                  55                  60
Ser Tyr Thr Lys Tyr Arg Tyr Leu Cys Leu Met Gln Lys Ala Ile Phe
65                  70                  75                  80
Thr His Phe Lys Arg Gly Cys Thr Cys Trp Gly Glu Asp Met Gly Arg
                85                  90                  95
Glu Gly Leu Glu Asp Gln Gly Pro Pro Pro Pro Pro Pro Gly Leu
            100                 105                 110
Val
```

<210> SEQ ID NO 9
<211> LENGTH: 495
<212> TYPE: DNA
<213> ORGANISM: Human immunodeficiency virus

<400> SEQUENCE: 9

```
atggttaatc cgaccgtttt ttttgatatc gcagttgatg gcgaaccgtt gggcagggtt    60
tccttcgagc tcttcgccga taaagtgccg aaaaccgcag aaaactttcg cgcgctcagt   120
acgggtgaaa aggggtttgg ttacaaaggg agctgttttc atcgaatcat tcctggtttc   180
atgtgtcagg gcggagattt caccccgacat aacgggactg gcgggaagag tatatatgga   240
gagaagttcg aggatgagaa ctttatactg aaacacaccg gacccggaat tttgagtatg   300
gcaaatgcag ggcctaacac caatggctcc cagttcttta tttgtacggc caagacagag   360
tggctcgacg ggaagcacgt tgtgttcgga aaggtcaaag aaggtatgaa tatagtagag   420
gcgatggaac ggtttggctc acgcaatggc aagacatcca aaaaaatcac aatagctgac   480
tgtggccaat tggag                                                    495
```

<210> SEQ ID NO 10
<211> LENGTH: 165
<212> TYPE: PRT
<213> ORGANISM: Human immunodeficiency virus

<400> SEQUENCE: 10

```
Met Val Asn Pro Thr Val Phe Phe Asp Ile Ala Val Asp Gly Glu Pro
1               5                   10                  15
Leu Gly Arg Val Ser Phe Glu Leu Phe Ala Asp Lys Val Pro Lys Thr
            20                  25                  30
Ala Glu Asn Phe Arg Ala Leu Ser Thr Gly Glu Lys Gly Phe Gly Tyr
        35                  40                  45
Lys Gly Ser Cys Phe His Arg Ile Ile Pro Gly Phe Met Cys Gln Gly
```

```
            50                  55                  60
Gly Asp Phe Thr Arg His Asn Gly Thr Gly Lys Ser Ile Tyr Gly
 65                  70                  75                  80

Glu Lys Phe Glu Asp Glu Asn Phe Ile Leu Lys His Thr Gly Pro Gly
                 85                  90                  95

Ile Leu Ser Met Ala Asn Ala Gly Pro Asn Thr Asn Gly Ser Gln Phe
                100                 105                 110

Phe Ile Cys Thr Ala Lys Thr Glu Trp Leu Asp Gly Lys His Val Val
            115                 120                 125

Phe Gly Lys Val Lys Glu Gly Met Asn Ile Val Glu Ala Met Glu Arg
        130                 135                 140

Phe Gly Ser Arg Asn Gly Lys Thr Ser Lys Lys Ile Thr Ile Ala Asp
145                 150                 155                 160

Cys Gly Gln Leu Glu
                165

<210> SEQ ID NO 11
<211> LENGTH: 1391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asp Lys Pro Lys Lys Lys Arg Lys Val Lys Tyr Ser Ile Gly Leu
 1               5                  10                  15

Asp Ile Gly Thr Asn Ser Val Gly Trp Ala Val Ile Thr Asp Glu Tyr
                20                  25                  30

Lys Val Pro Ser Lys Lys Phe Lys Val Leu Gly Asn Thr Asp Arg His
             35                  40                  45

Ser Ile Lys Lys Asn Leu Ile Gly Ala Leu Leu Phe Asp Ser Gly Glu
         50                  55                  60

Thr Ala Glu Ala Thr Arg Leu Lys Arg Thr Ala Arg Arg Arg Tyr Thr
 65                  70                  75                  80

Arg Arg Lys Asn Arg Ile Cys Tyr Leu Gln Glu Ile Phe Ser Asn Glu
                 85                  90                  95

Met Ala Lys Val Asp Asp Ser Phe Phe His Arg Leu Glu Glu Ser Phe
            100                 105                 110

Leu Val Glu Glu Asp Lys Lys His Glu Arg His Pro Ile Phe Gly Asn
        115                 120                 125

Ile Val Asp Glu Val Ala Tyr His Glu Lys Tyr Pro Thr Ile Tyr His
    130                 135                 140

Leu Arg Lys Lys Leu Val Asp Ser Thr Asp Lys Ala Asp Leu Arg Leu
145                 150                 155                 160

Ile Tyr Leu Ala Leu Ala His Met Ile Lys Phe Arg Gly His Phe Leu
                165                 170                 175

Ile Glu Gly Asp Leu Asn Pro Asp Asn Ser Asp Val Asp Lys Leu Phe
            180                 185                 190

Ile Gln Leu Val Gln Thr Tyr Asn Gln Leu Phe Glu Glu Asn Pro Ile
        195                 200                 205

Asn Ala Ser Gly Val Asp Ala Lys Ala Ile Leu Ser Ala Arg Leu Ser
    210                 215                 220

Lys Ser Arg Arg Leu Glu Asn Leu Ile Ala Gln Leu Pro Gly Glu Lys
225                 230                 235                 240
```

-continued

Lys Asn Gly Leu Phe Gly Asn Leu Ile Ala Leu Ser Leu Gly Leu Thr
              245                 250                 255

Pro Asn Phe Lys Ser Asn Phe Asp Leu Ala Glu Asp Ala Lys Leu Gln
          260                 265                 270

Leu Ser Lys Asp Thr Tyr Asp Asp Leu Asp Asn Leu Leu Ala Gln
              275                 280                 285

Ile Gly Asp Gln Tyr Ala Asp Leu Phe Leu Ala Ala Lys Asn Leu Ser
      290                 295                 300

Asp Ala Ile Leu Leu Ser Asp Ile Leu Arg Val Asn Thr Glu Ile Thr
305                 310                 315                 320

Lys Ala Pro Leu Ser Ala Ser Met Ile Lys Arg Tyr Asp Glu His His
              325                 330                 335

Gln Asp Leu Thr Leu Leu Lys Ala Leu Val Arg Gln Gln Leu Pro Glu
              340                 345                 350

Lys Tyr Lys Glu Ile Phe Phe Asp Gln Ser Lys Asn Gly Tyr Ala Gly
              355                 360                 365

Tyr Ile Asp Gly Gly Ala Ser Gln Glu Glu Phe Tyr Lys Phe Ile Lys
      370                 375                 380

Pro Ile Leu Glu Lys Met Asp Gly Thr Glu Glu Leu Leu Val Lys Leu
385                 390                 395                 400

Asn Arg Glu Asp Leu Leu Arg Lys Gln Arg Thr Phe Asp Asn Gly Ser
              405                 410                 415

Ile Pro His Gln Ile His Leu Gly Glu Leu His Ala Ile Leu Arg Arg
              420                 425                 430

Gln Glu Asp Phe Tyr Pro Phe Leu Lys Asp Asn Arg Glu Lys Ile Glu
              435                 440                 445

Lys Ile Leu Thr Phe Arg Ile Pro Tyr Tyr Val Gly Pro Leu Ala Arg
          450                 455                 460

Gly Asn Ser Arg Phe Ala Trp Met Thr Arg Lys Ser Glu Glu Thr Ile
465                 470                 475                 480

Thr Pro Trp Asn Phe Glu Glu Val Val Asp Lys Gly Ala Ser Ala Gln
              485                 490                 495

Ser Phe Ile Glu Arg Met Thr Asn Phe Asp Lys Asn Leu Pro Asn Glu
              500                 505                 510

Lys Val Leu Pro Lys His Ser Leu Leu Tyr Glu Tyr Phe Thr Val Tyr
          515                 520                 525

Asn Glu Leu Thr Lys Val Lys Tyr Val Thr Glu Gly Met Arg Lys Pro
          530                 535                 540

Ala Phe Leu Ser Gly Glu Gln Lys Lys Ala Ile Val Asp Leu Leu Phe
545                 550                 555                 560

Lys Thr Asn Arg Lys Val Thr Val Lys Gln Leu Lys Glu Asp Tyr Phe
              565                 570                 575

Lys Lys Ile Glu Cys Phe Asp Ser Val Glu Ile Ser Gly Val Glu Asp
              580                 585                 590

Arg Phe Asn Ala Ser Leu Gly Thr Tyr His Asp Leu Leu Lys Ile Ile
              595                 600                 605

Lys Asp Lys Asp Phe Leu Asp Asn Glu Glu Asn Glu Asp Ile Leu Glu
      610                 615                 620

Asp Ile Val Leu Thr Leu Thr Leu Phe Glu Asp Arg Glu Met Ile Glu
625                 630                 635                 640

Glu Arg Leu Lys Thr Tyr Ala His Leu Phe Asp Asp Lys Val Met Lys
              645                 650                 655

Gln Leu Lys Arg Arg Arg Tyr Thr Gly Trp Gly Arg Leu Ser Arg Lys

```
                    660                 665                 670
Leu Ile Asn Gly Ile Arg Asp Lys Gln Ser Gly Lys Thr Ile Leu Asp
                675                 680                 685

Phe Leu Lys Ser Asp Gly Phe Ala Asn Arg Asn Phe Met Gln Leu Ile
                690                 695                 700

His Asp Asp Ser Leu Thr Phe Lys Glu Asp Ile Gln Lys Ala Gln Val
705                 710                 715                 720

Ser Gly Gln Gly Asp Ser Leu His Glu His Ile Ala Asn Leu Ala Gly
                    725                 730                 735

Ser Pro Ala Ile Lys Lys Gly Ile Leu Gln Thr Val Lys Val Val Asp
                740                 745                 750

Glu Leu Val Lys Val Met Gly Arg His Lys Pro Glu Asn Ile Val Ile
                755                 760                 765

Glu Met Ala Arg Glu Asn Gln Thr Thr Gln Lys Gly Gln Lys Asn Ser
                770                 775                 780

Arg Glu Arg Met Lys Arg Ile Glu Glu Gly Ile Lys Glu Leu Gly Ser
785                 790                 795                 800

Gln Ile Leu Lys Glu His Pro Val Glu Asn Thr Gln Leu Gln Asn Glu
                    805                 810                 815

Lys Leu Tyr Leu Tyr Tyr Leu Gln Asn Gly Arg Asp Met Tyr Val Asp
                820                 825                 830

Gln Glu Leu Asp Ile Asn Arg Leu Ser Asp Tyr Asp Val Asp His Ile
                835                 840                 845

Val Pro Gln Ser Phe Leu Lys Asp Asp Ser Ile Asp Asn Lys Val Leu
850                 855                 860

Thr Arg Ser Asp Lys Asn Arg Gly Lys Ser Asp Asn Val Pro Ser Glu
865                 870                 875                 880

Glu Val Val Lys Lys Met Lys Asn Tyr Trp Arg Gln Leu Leu Asn Ala
                    885                 890                 895

Lys Leu Ile Thr Gln Arg Lys Phe Asp Asn Leu Thr Lys Ala Glu Arg
                900                 905                 910

Gly Gly Leu Ser Glu Leu Asp Lys Ala Gly Phe Ile Lys Arg Gln Leu
                915                 920                 925

Val Glu Thr Arg Gln Ile Thr Lys His Val Ala Gln Ile Leu Asp Ser
                930                 935                 940

Arg Met Asn Thr Lys Tyr Asp Glu Asn Asp Lys Leu Ile Arg Glu Val
945                 950                 955                 960

Lys Val Ile Thr Leu Lys Ser Lys Leu Val Ser Asp Phe Arg Lys Asp
                    965                 970                 975

Phe Gln Phe Tyr Lys Val Arg Glu Ile Asn Asn Tyr His His Ala His
                980                 985                 990

Asp Ala Tyr Leu Asn Ala Val Val  Gly Thr Ala Leu Ile  Lys Lys Tyr
                    995                 1000                1005

Pro Lys  Leu Glu Ser Glu  Phe Val Tyr Gly Asp Tyr  Lys Val Tyr
                1010                1015                1020

Asp Val  Arg Lys Met Ile Ala  Lys Ser Glu Gln Glu  Ile Gly Lys
                1025                1030                1035

Ala Thr  Ala Lys Tyr Phe Phe  Tyr Ser Asn Ile Met  Asn Phe Phe
                1040                1045                1050

Lys Thr  Glu Ile Thr Leu Ala  Asn Gly Glu Ile Arg  Lys Arg Pro
                1055                1060                1065

Leu Ile  Glu Thr Asn Gly Glu  Thr Gly Glu Ile Val  Trp Asp Lys
                1070                1075                1080
```

Gly Arg Asp Phe Ala Thr Val Arg Lys Val Leu Ser Met Pro Gln
1085                1090                1095

Val Asn Ile Val Lys Lys Thr Glu Val Gln Thr Gly Gly Phe Ser
    1100                1105                1110

Lys Glu Ser Ile Leu Pro Lys Arg Asn Ser Asp Lys Leu Ile Ala
1115                1120                1125

Arg Lys Lys Asp Trp Asp Pro Lys Lys Tyr Gly Gly Phe Asp Ser
1130                1135                1140

Pro Thr Val Ala Tyr Ser Val Leu Val Val Ala Lys Val Glu Lys
1145                1150                1155

Gly Lys Ser Lys Lys Leu Lys Ser Val Lys Glu Leu Leu Gly Ile
1160                1165                1170

Thr Ile Met Glu Arg Ser Ser Phe Glu Lys Asn Pro Ile Asp Phe
1175                1180                1185

Leu Glu Ala Lys Gly Tyr Lys Glu Val Lys Lys Asp Leu Ile Ile
1190                1195                1200

Lys Leu Pro Lys Tyr Ser Leu Phe Glu Leu Glu Asn Gly Arg Lys
1205                1210                1215

Arg Met Leu Ala Ser Ala Gly Glu Leu Gln Lys Gly Asn Glu Leu
1220                1225                1230

Ala Leu Pro Ser Lys Tyr Val Asn Phe Leu Tyr Leu Ala Ser His
1235                1240                1245

Tyr Glu Lys Leu Lys Gly Ser Pro Glu Asp Asn Glu Gln Lys Gln
1250                1255                1260

Leu Phe Val Glu Gln His Lys His Tyr Leu Asp Glu Ile Ile Glu
1265                1270                1275

Gln Ile Ser Glu Phe Ser Lys Arg Val Ile Leu Ala Asp Ala Asn
1280                1285                1290

Leu Asp Lys Val Leu Ser Ala Tyr Asn Lys His Arg Asp Lys Pro
1295                1300                1305

Ile Arg Glu Gln Ala Glu Asn Ile Ile His Leu Phe Thr Leu Thr
1310                1315                1320

Asn Leu Gly Ala Pro Ala Ala Phe Lys Tyr Phe Asp Thr Thr Ile
1325                1330                1335

Asp Arg Lys Arg Tyr Thr Ser Thr Lys Glu Val Leu Asp Ala Thr
1340                1345                1350

Leu Ile His Gln Ser Ile Thr Gly Leu Tyr Glu Thr Arg Ile Asp
1355                1360                1365

Leu Ser Gln Leu Gly Gly Asp Lys Arg Pro Ala Ala Thr Lys Lys
1370                1375                1380

Ala Gly Gln Ala Lys Lys Lys Lys
1385                1390

<210> SEQ ID NO 12
<211> LENGTH: 4506
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atggaacaag ccccagaaga ccaagggcca cagagggagc cacacaatga atggacacta      60
gagcttttag aggagcttaa gaatgaagct gttagacatt ttcctaggat ttggctccat     120

```
ggcttagggc aacatatcta tgaaacttat ggggatactt ggcaggagt ggaagccata      180 ataagaattc tgcaacaact gctgtttatc catttcagaa ttgggtgtcg acatagcaga      240
ataggcgtta ctcgacagag gagagcaaga aatggagcca gtagatccgg tggaggtgga      300
agtggaggag gcggctcagg tggaggtggt tccgacaagc ccaagaaaaa gcggaaagtg      360
aagtacagca tcggcctgga catcggcacc aactctgtgg gctgggccgt gatcaccgac      420
gagtacaagt gcccagcaa gaaattcaag gtgctgggca acaccgacag gcacagcatc      480
aagaagaacc tgatcggcgc cctgctgttc gacagcggcg aaacagccga ggccaccaga      540
ctgaagagaa ccgccagaag aagatacacc aggcggaaga acaggatctg ctatctgcaa      600
gagatcttca gcaacgagat ggccaaggtg gacgacagct tcttccacag actggaagag      660
tccttcctgg tggaagagga caagaagcac gagagacacc ccatcttcgg caacatcgtg      720
gacgaggtgg cctaccacga aagtacccc accatctacc acctgagaaa gaaactggtg      780
gacagcaccg acaaggccga cctgagacta atctacctgg ccctggccca catgatcaag      840
ttcagaggcc acttcctgat cgagggcgac ctgaaccccg acaacagcga cgtggacaag      900
ctgttcatcc agctggtgca gacctacaac cagctgttcg aggaaaaccc catcaacgcc      960
agcggcgtgg acgccaaggc tatcctgtct gccagactga gcaagagcag aaggctggaa     1020
aatctgatcg cccagctgcc cggcgagaag aagaacggcc tgttcggcaa cctgattgcc     1080
ctgagcctgg gcctgacccc caacttcaag agcaacttcg acctggccga ggatgccaaa     1140
ctgcagctga gcaaggacac ctacgacgac gacctggaca acctgctggc ccagatcggc     1200
gaccagtacg ccgacctgtt cctggccgcc aagaacctgt ctgacgccat cctgctgagc     1260
gacatcctga gagtgaacac cgagatcacc aaggccccc tgagcgcctc tatgatcaag     1320
agatacgacg agcaccacca ggacctgacc ctgctgaaag ctctcgtgcg gcagcagctg     1380
cctgagaagt acaaagaaat cttcttcgac cagagcaaga acggctacgc cggctacatc     1440 gatgcggcg ctagccagga agagttctac aagttcatca gcccatcct ggaaaagatg     1500 gacggcaccg aggaactgct cgtgaagctg aacagagagg acctgctgag aaagcagaga     1560
accttcgaca cggcagcat ccccaccag atccacctgg gagagctgca cgctatcctg     1620
agaaggcagg aagatttta cccattcctg aaggacaacc gggaaaagat cgagaagatc     1680
ctgaccttca ggatccccta ctacgtgggc cccctggcca gagcaacag cagattcgcc     1740 tggatgacca gaaagagcga ggaaaccatc accccctgga acttcgagga agtggtggac     1800
aagggcgcca gcgcccagag cttcatcgag agaatgacaa acttcgataa gaacctgccc     1860
aacgagaagg tgctgcccaa gcacagcctg ctgtacgagt acttcaccgt gtacaacgag     1920
ctgaccaaag tgaaatacgt gaccgaggga atgagaaagc ccgccttcct gagcggcgag     1980
cagaaaaagg ccatcgtgga cctgctgttc aagaccaaca gaaaagtgac cgtgaagcag     2040
ctgaagagag actacttcaa gaaaatcgag tgcttcgact ccgtggaaat ctccggcgtg     2100
gaagatagat tcaacgcctc cctgggcaca taccacgatc tgctgaaaat tatcaaggac     2160
aaggacttcc tggataacga agagaacgag gacattctgg aagatatcgt gctgaccctg     2220
acactgtttg aggaccgcga gatgatcgag gaaaggctga aaacctacgc tcacctgttc     2280
gacgacaaag tgatgaagca gctgaagaga aggcggtaca ccggctgggg caggctgagc     2340
agaaagctga tcaacggcat cagagacaag cagagcggca gacaatcct ggatttcctg     2400 aagtccgacg gcttcgccaa ccggaacttc atgcagctga tccacgacga cagcctgaca     2460
ttcaaagagg acatccagaa agcccaggtg tccggccagg cgactctct gcacgagcat     2520
```

```
atcgctaacc tggccggcag ccccgctatc aagaagggca tcctgcagac agtgaaggtg      2580
gtggacgagc tcgtgaaagt gatgggcaga cacaagcccg agaacatcgt gatcgagatg      2640
gctagagaga accagaccac ccagaaggga cagaagaact cccgcgagag gatgaagaga      2700
atcgaagagg catcaaagat gctgggcagc cagatcctga agaacaccc cgtggaaaac       2760 acccagctgc agaacgagaa gctgtacctg tactacctgc agaatggccg ggatatgtac      2820
gtggaccagg aactggacat caacagactg tccgactacg atgtggacca tatcgtgcct      2880
cagagctttc tgaaggacga ctccatcgat aacaaagtgc tgactcggag cgacaagaac      2940
agaggcaaga gcgacaacgt gccctccgaa gaggtcgtga agaagatgaa gaactactgg      3000
cgacagctgc tgaacgccaa gctgattacc agaggaagt tcgataacct gaccaaggcc       3060
gagagaggcg gcctgagcga gctggataag gccggcttca tcaagaggca gctggtggaa      3120
accagacaga tcacaaagca cgtggcacag atcctggact cccggatgaa cactaagtac      3180
gacgaaaacg ataagctgat ccgggaagtg aaagtgatca ccctgaagtc caagctggtg      3240
tccgatttcc ggaaggattt ccagttttac aaagtgcgcg agatcaacaa ctaccaccac      3300
gcccacgacg cctacctgaa cgccgtcgtg gaaccgccc tgatcaaaaa gtaccctaag       3360
ctggaaagcg agttcgtgta cggcgactac aaggtgtacg acgtgcggaa gatgatcgcc      3420
aagagcgagc aggaaatcgg caaggctacc gccaagtact tcttctacag caacatcatg      3480 aacttttttca gaccgaaat cacccctggcc aacggcgaga tcagaaagcg ccctctgatc     3540
gagacaaacg gcgaaaccgg ggagatcgtg tgggataagg gcagagactt cgccacagtg      3600
cgaaaggtgc tgagcatgcc ccaagtgaat atcgtgaaaa agaccgaggt gcagacaggc      3660
ggcttcagca agagtctat cctgcccaag aggaacagcg acaagctgat cgccagaaag       3720
aaggactggg acccccaagaa gtacggcggc ttcgacagcc ctaccgtggc ctactctgtg     3780
ctggtggtgg ctaaggtgga aaagggcaag tccaagaaac tgaagagtgt gaaagagctg      3840
ctggggatca ccatcatgga aagaagcagc tttgaagaga cccctatcga ctttctggaa      3900
gccaagggct acaaagaagt gaaaaaggac ctgatcatca gctgcctaa gtactccctg       3960 ttcgagctgg aaaacggcag aaagagaatg ctggcctctg ccggcgaact gcagaaggga      4020
aacgagctgg ccctgcctag caaatatgtg aacttcctgt acctggccctc ccactatgag     4080 aagctgaagg gcagccctga ggacaacgaa cagaaacagc tgtttgtgga acagcataag      4140
cactacctgg acgagatcat cgagcagatc agcgagttct ccaagagagt gatcctggcc      4200
gacgccaatc tggacaaggt gctgtctgcc tacaacaagc acagggacaa gcctatcaga      4260
gagcaggccg agaatatcat ccacctgttc accctgacaa acctgggcgc tcctgccgcc      4320
ttcaagtact tgacaccac catcgaccgg aagaggtaca ccagcaccaa agaggtgctg       4380
gacgccaccc tgatccacca gagcatcacc ggcctgtacg agacaagaat cgacctgtct      4440
cagctgggag cgacaagag acctgccgcc actaagaagg ccggacaggc caaaaagaag      4500
aagtga                                                                4506
```

<210> SEQ ID NO 13
<211> LENGTH: 1501
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Met Glu Gln Ala Pro Glu Asp Gln Gly Pro Gln Arg Glu Pro His Asn
1               5                   10                  15

Glu Trp Thr Leu Glu Leu Leu Glu Glu Leu Lys Asn Glu Ala Val Arg
            20                  25                  30

His Phe Pro Arg Ile Trp Leu His Gly Leu Gly Gln His Ile Tyr Glu
            35                  40                  45

Thr Tyr Gly Asp Thr Trp Ala Gly Val Glu Ala Ile Ile Arg Ile Leu
50                  55                  60

Gln Gln Leu Leu Phe Ile His Phe Arg Ile Gly Cys Arg His Ser Arg
65                  70                  75                  80

Ile Gly Val Thr Arg Gln Arg Ala Arg Asn Gly Ala Ser Arg Ser
                85                  90                  95

Gly Gly Gly Gly Ser Gly Gly Gly Ser Gly Gly Gly Gly Ser Asp
                100                 105                 110

Lys Pro Lys Lys Arg Lys Val Lys Tyr Ser Ile Gly Leu Asp Ile
            115                 120                 125

Gly Thr Asn Ser Val Gly Trp Ala Val Ile Thr Asp Glu Tyr Lys Val
    130                 135                 140

Pro Ser Lys Lys Phe Lys Val Leu Gly Asn Thr Asp Arg His Ser Ile
145                 150                 155                 160

Lys Lys Asn Leu Ile Gly Ala Leu Leu Phe Asp Ser Gly Glu Thr Ala
            165                 170                 175

Glu Ala Thr Arg Leu Lys Arg Thr Ala Arg Arg Arg Tyr Thr Arg Arg
                180                 185                 190

Lys Asn Arg Ile Cys Tyr Leu Gln Glu Ile Phe Ser Asn Glu Met Ala
            195                 200                 205

Lys Val Asp Asp Ser Phe Phe His Arg Leu Glu Glu Ser Phe Leu Val
210                 215                 220

Glu Glu Asp Lys Lys His Glu Arg His Pro Ile Phe Gly Asn Ile Val
225                 230                 235                 240

Asp Glu Val Ala Tyr His Glu Lys Tyr Pro Thr Ile Tyr His Leu Arg
                245                 250                 255

Lys Lys Leu Val Asp Ser Thr Asp Lys Ala Asp Leu Arg Leu Ile Tyr
            260                 265                 270

Leu Ala Leu Ala His Met Ile Lys Phe Arg Gly His Phe Leu Ile Glu
            275                 280                 285

Gly Asp Leu Asn Pro Asp Asn Ser Asp Val Asp Lys Leu Phe Ile Gln
    290                 295                 300

Leu Val Gln Thr Tyr Asn Gln Leu Phe Glu Glu Asn Pro Ile Asn Ala
305                 310                 315                 320

Ser Gly Val Asp Ala Lys Ala Ile Leu Ser Ala Arg Leu Ser Lys Ser
                325                 330                 335

Arg Arg Leu Glu Asn Leu Ile Ala Gln Leu Pro Gly Glu Lys Lys Asn
            340                 345                 350

Gly Leu Phe Gly Asn Leu Ile Ala Leu Ser Leu Gly Leu Thr Pro Asn
            355                 360                 365

Phe Lys Ser Asn Phe Asp Leu Ala Glu Asp Ala Lys Leu Gln Leu Ser
    370                 375                 380

Lys Asp Thr Tyr Asp Asp Asp Leu Asp Asn Leu Leu Ala Gln Ile Gly
385                 390                 395                 400

Asp Gln Tyr Ala Asp Leu Phe Leu Ala Ala Lys Asn Leu Ser Asp Ala
                405                 410                 415
```

```
Ile Leu Leu Ser Asp Ile Leu Arg Val Asn Thr Glu Ile Thr Lys Ala
            420                 425                 430

Pro Leu Ser Ala Ser Met Ile Lys Arg Tyr Asp Glu His His Gln Asp
        435                 440                 445

Leu Thr Leu Leu Lys Ala Leu Val Arg Gln Gln Leu Pro Glu Lys Tyr
        450                 455                 460

Lys Glu Ile Phe Phe Asp Gln Ser Lys Asn Gly Tyr Ala Gly Tyr Ile
465                 470                 475                 480

Asp Gly Gly Ala Ser Gln Glu Glu Phe Tyr Lys Phe Ile Lys Pro Ile
                485                 490                 495

Leu Glu Lys Met Asp Gly Thr Glu Glu Leu Leu Val Lys Leu Asn Arg
            500                 505                 510

Glu Asp Leu Leu Arg Lys Gln Arg Thr Phe Asp Asn Gly Ser Ile Pro
        515                 520                 525

His Gln Ile His Leu Gly Glu Leu His Ala Ile Leu Arg Arg Gln Glu
        530                 535                 540

Asp Phe Tyr Pro Phe Leu Lys Asp Asn Arg Glu Lys Ile Glu Lys Ile
545                 550                 555                 560

Leu Thr Phe Arg Ile Pro Tyr Tyr Val Gly Pro Leu Ala Arg Gly Asn
                565                 570                 575

Ser Arg Phe Ala Trp Met Thr Arg Lys Ser Glu Glu Thr Ile Thr Pro
            580                 585                 590

Trp Asn Phe Glu Glu Val Val Asp Lys Gly Ala Ser Ala Gln Ser Phe
        595                 600                 605

Ile Glu Arg Met Thr Asn Phe Asp Lys Asn Leu Pro Asn Glu Lys Val
        610                 615                 620

Leu Pro Lys His Ser Leu Leu Tyr Glu Tyr Phe Thr Val Tyr Asn Glu
625                 630                 635                 640

Leu Thr Lys Val Lys Tyr Val Thr Glu Gly Met Arg Lys Pro Ala Phe
                645                 650                 655

Leu Ser Gly Glu Gln Lys Lys Ala Ile Val Asp Leu Leu Phe Lys Thr
            660                 665                 670

Asn Arg Lys Val Thr Val Lys Gln Leu Lys Glu Asp Tyr Phe Lys Lys
        675                 680                 685

Ile Glu Cys Phe Asp Ser Val Glu Ile Ser Gly Val Glu Asp Arg Phe
690                 695                 700

Asn Ala Ser Leu Gly Thr Tyr His Asp Leu Leu Lys Ile Ile Lys Asp
705                 710                 715                 720

Lys Asp Phe Leu Asp Asn Glu Glu Asn Glu Asp Ile Leu Glu Asp Ile
                725                 730                 735

Val Leu Thr Leu Thr Leu Phe Glu Asp Arg Glu Met Ile Glu Glu Arg
            740                 745                 750

Leu Lys Thr Tyr Ala His Leu Phe Asp Asp Lys Val Met Lys Gln Leu
        755                 760                 765

Lys Arg Arg Arg Tyr Thr Gly Trp Gly Arg Leu Ser Arg Lys Leu Ile
        770                 775                 780

Asn Gly Ile Arg Asp Lys Gln Ser Gly Lys Thr Ile Leu Asp Phe Leu
785                 790                 795                 800

Lys Ser Asp Gly Phe Ala Asn Arg Asn Phe Met Gln Leu Ile His Asp
                805                 810                 815

Asp Ser Leu Thr Phe Lys Glu Asp Ile Gln Lys Ala Gln Val Ser Gly
            820                 825                 830

Gln Gly Asp Ser Leu His Glu His Ile Ala Asn Leu Ala Gly Ser Pro
```

```
                835                 840                 845
Ala Ile Lys Lys Gly Ile Leu Gln Thr Val Lys Val Val Asp Glu Leu
        850                 855                 860

Val Lys Val Met Gly Arg His Lys Pro Glu Asn Ile Val Ile Glu Met
865                 870                 875                 880

Ala Arg Glu Asn Gln Thr Thr Gln Lys Gly Gln Lys Asn Ser Arg Glu
                885                 890                 895

Arg Met Lys Arg Ile Glu Glu Gly Ile Lys Glu Leu Gly Ser Gln Ile
                900                 905                 910

Leu Lys Glu His Pro Val Glu Asn Thr Gln Leu Gln Asn Glu Lys Leu
        915                 920                 925

Tyr Leu Tyr Tyr Leu Gln Asn Gly Arg Asp Met Tyr Val Asp Gln Glu
        930                 935                 940

Leu Asp Ile Asn Arg Leu Ser Asp Tyr Asp Val Asp His Ile Val Pro
945                 950                 955                 960

Gln Ser Phe Leu Lys Asp Asp Ser Ile Asp Asn Lys Val Leu Thr Arg
                965                 970                 975

Ser Asp Lys Asn Arg Gly Lys Ser Asp Asn Val Pro Ser Glu Glu Val
        980                 985                 990

Val Lys Lys Met Lys Asn Tyr Trp Arg Gln Leu Leu Asn Ala Lys Leu
        995                 1000                1005

Ile Thr Gln Arg Lys Phe Asp Asn Leu Thr Lys Ala Glu Arg Gly
    1010                1015                1020

Gly Leu Ser Glu Leu Asp Lys Ala Gly Phe Ile Lys Arg Gln Leu
    1025                1030                1035

Val Glu Thr Arg Gln Ile Thr Lys His Val Ala Gln Ile Leu Asp
    1040                1045                1050

Ser Arg Met Asn Thr Lys Tyr Asp Glu Asn Asp Lys Leu Ile Arg
    1055                1060                1065

Glu Val Lys Val Ile Thr Leu Lys Ser Lys Leu Val Ser Asp Phe
    1070                1075                1080

Arg Lys Asp Phe Gln Phe Tyr Lys Val Arg Glu Ile Asn Asn Tyr
    1085                1090                1095

His His Ala His Asp Ala Tyr Leu Asn Ala Val Gly Thr Ala
    1100                1105                1110

Leu Ile Lys Lys Tyr Pro Lys Leu Glu Ser Glu Phe Val Tyr Gly
    1115                1120                1125

Asp Tyr Lys Val Tyr Asp Val Arg Lys Met Ile Ala Lys Ser Glu
    1130                1135                1140

Gln Glu Ile Gly Lys Ala Thr Ala Lys Tyr Phe Phe Tyr Ser Asn
    1145                1150                1155

Ile Met Asn Phe Phe Lys Thr Glu Ile Thr Leu Ala Asn Gly Glu
    1160                1165                1170

Ile Arg Lys Arg Pro Leu Ile Glu Thr Asn Gly Glu Thr Gly Glu
    1175                1180                1185

Ile Val Trp Asp Lys Gly Arg Asp Phe Ala Thr Val Arg Lys Val
    1190                1195                1200

Leu Ser Met Pro Gln Val Asn Ile Val Lys Lys Thr Glu Val Gln
    1205                1210                1215

Thr Gly Gly Phe Ser Lys Glu Ser Ile Leu Pro Lys Arg Asn Ser
    1220                1225                1230

Asp Lys Leu Ile Ala Arg Lys Lys Asp Trp Asp Pro Lys Lys Tyr
    1235                1240                1245
```

Gly Gly Phe Asp Ser Pro Thr Val Ala Tyr Ser Val Leu Val Val
    1250                1255                1260

Ala Lys Val Glu Lys Gly Lys Ser Lys Lys Leu Lys Ser Val Lys
    1265                1270                1275

Glu Leu Leu Gly Ile Thr Ile Met Glu Arg Ser Ser Phe Glu Lys
    1280                1285                1290

Asn Pro Ile Asp Phe Leu Glu Ala Lys Gly Tyr Lys Glu Val Lys
    1295                1300                1305

Lys Asp Leu Ile Ile Lys Leu Pro Lys Tyr Ser Leu Phe Glu Leu
    1310                1315                1320

Glu Asn Gly Arg Lys Arg Met Leu Ala Ser Ala Gly Glu Leu Gln
    1325                1330                1335

Lys Gly Asn Glu Leu Ala Leu Pro Ser Lys Tyr Val Asn Phe Leu
    1340                1345                1350

Tyr Leu Ala Ser His Tyr Glu Lys Leu Lys Gly Ser Pro Glu Asp
    1355                1360                1365

Asn Glu Gln Lys Gln Leu Phe Val Glu Gln His Lys His Tyr Leu
    1370                1375                1380

Asp Glu Ile Ile Glu Gln Ile Ser Glu Phe Ser Lys Arg Val Ile
    1385                1390                1395

Leu Ala Asp Ala Asn Leu Asp Lys Val Leu Ser Ala Tyr Asn Lys
    1400                1405                1410

His Arg Asp Lys Pro Ile Arg Glu Gln Ala Glu Asn Ile Ile His
    1415                1420                1425

Leu Phe Thr Leu Thr Asn Leu Gly Ala Pro Ala Ala Phe Lys Tyr
    1430                1435                1440

Phe Asp Thr Thr Ile Asp Arg Lys Arg Tyr Thr Ser Thr Lys Glu
    1445                1450                1455

Val Leu Asp Ala Thr Leu Ile His Gln Ser Ile Thr Gly Leu Tyr
    1460                1465                1470

Glu Thr Arg Ile Asp Leu Ser Gln Leu Gly Gly Asp Lys Arg Pro
    1475                1480                1485

Ala Ala Thr Lys Lys Ala Gly Gln Ala Lys Lys Lys Lys
    1490                1495                1500

<210> SEQ ID NO 14
<211> LENGTH: 4506
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atggacaagc ccaagaaaaa gcggaaagtg aagtacagca tcggcctgga catcggcacc      60
aactctgtgg ctgggccgt gatcaccgac gagtacaagg tgcccagcaa gaaattcaag     120
gtgctgggca acaccgacag gcacagcatc aagaagaacc tgatcggcgc cctgctgttc     180
gacagcggcg aaacagccga ggccaccaga ctgaagagaa ccgccagaag aagatacacc     240
aggcggaaga caggatctg ctatctgcaa gagatcttca gcaacgagat ggccaaggtg     300
gacgacagct tcttccacag actggaagag tccttcctgg tggaagagga caagaagcac     360
gagagacacc ccatcttcgg caacatcgtg gacgaggtgg cctaccacga agtaccccc     420 accatctacc acctgagaaa gaaactggtg gacagcaccg acaaggccga cctgagactg     480

```
atctacctgg ccctggccca catgatcaag ttcagaggcc acttcctgat cgagggcgac    540
ctgaaccccg acaacagcga cgtggacaag ctgttcatcc agctggtgca gacctacaac    600
cagctgttcg aggaaaaccc catcaacgcc agcggcgtgg acgccaaggc tatcctgtct    660
gccagactga gcaagagcag aaggctggaa aatctgatcg cccagctgcc cggcgagaag    720
aagaacggcc tgttcggcaa cctgattgcc ctgagcctgg gcctgacccc caacttcaag    780
agcaacttcg acctggccga ggatgccaaa ctgcagctga gcaaggacac ctacgacgac    840
gacctggaca acctgctggc ccagatcggc gaccagtacg ccgacctgtt cctggccgcc    900
aagaacctgt ctgacgccat cctgctgagc gacatcctga gagtgaacac cgagatcacc    960
aaggcccccc tgagcgcctc tatgatcaag agatacgacg agcaccacca ggacctgacc   1020
ctgctgaaag ctctcgtgcg gcagcagctg cctgagaagt acaaagaaat cttcttcgac   1080
cagagcaaga acggctacgc cggctacatc gatgcggcg ctagccagga agagttctac   1140
aagttcatca gcccatcct ggaaaagatg acggcaccg aggaactgct cgtgaagctg   1200
aacagagagg acctgctgag aaagcagaga accttcgaca cggcagcat ccccaccag   1260 atccacctgg agagctgca cgctatcctg agaaggcagg aagatttta cccattcctg   1320 aaggacaacc gggaaaagat cgagaagatc ctgaccttca ggatcccta ctacgtgggc   1380 cccctggcca gaggcaacag cagattcgcc tggatgacca aaagagcga ggaaaccatc   1440 accccctgga acttcgagga agtggtggac aagggcgcca cgcccagag cttcatcgag   1500 agaatgacaa acttcgataa gaacctgccc aacgagaagg tgctgcccaa gcacagcctg   1560
ctgtacgagt acttcaccgt gtacaacgag ctgaccaaaa tgaaatacgt gaccgaggga   1620
atgagaaagc ccgccttcct gagcggcgag cagaaaaagg ccatcgtgga cctgctgttc   1680
aagaccaaca gaaaagtgac cgtgaagcag ctgaaagagg actacttcaa gaaaatcgag   1740
tgcttcgact ccgtggaaat ctccggcgtg gaagatagat caacgcctc cctgggcaca   1800 taccacgatc tgctgaaaat tatcaaggac aaggacttcc tggataacga agagaacgag   1860
gacattctgg aagatatcgt gctgaccctg acactgtttg aggaccgcga tgatcgag   1920 gaaaggctga aaacctacgc tcacctgttc gacgacaaag tgatgaagca gctgaagaga   1980
aggcggtaca ccggctgggg caggctgagc agaaagctga tcaacggcat cagagacaag   2040
cagagcggca gacaatcct ggatttcctg aagtccgacg gcttcgccaa ccggaacttc   2100
atgcagctga tccacgacga cagcctgaca ttcaaagagg acatccagaa agcccaggtg   2160
tccggccagg gcgactctct gcacgagcat atcgctaacc tggccggcag ccccgctatc   2220
aagaagggca tcctgcagac agtgaaggtg gtggacgagc tcgtgaaagt gatgggcaga   2280
cacaagcccg agaacatcgt gatcgagatg gctagagaga accagaccac ccagaaggga   2340
cagaagaact cccgcgagag gatgaagaga atcgaagagg catcaaagaa gctgggcagc   2400
cagatcctga agaacacccc cgtggaaaac acccagctgc agaacgagaa gctgtacctg   2460
tactacctgc agaatggccg ggatatgtac gtggaccagg aactggacat caacagactg   2520
tccgactacg atgtggacca tatcgtgcct cagagctttc tgaaggacga ctccatcgat   2580
aacaaagtgc tgactcggag cgacaagaac agaggcaaga gcgacaacgt gcctccgaa   2640 gaggtcgtga agaagatgaa gaactactgg cgacagctgc tgaacgccaa gctgattacc   2700
cagaggaagt tcgataacct gaccaaggcc gagagaggcg gcctgagcga gctggataag   2760
gccggcttca tcaagaggca gctggtggaa accagacaga tcacaaagca cgtggcacag   2820
atcctggact cccggatgaa cactaagtac gacgaaaacg ataagctgat ccgggaagtg   2880
```

-continued

```
aaagtgatca ccctgaagtc caagctggtg tccgatttcc ggaaggattt ccagttttac    2940
aaagtgcgcg agatcaacaa ctaccaccac gcccacgacg cctacctgaa cgccgtcgtg    3000
ggaaccgccc tgatcaaaaa gtaccctaag ctggaaagcg agttcgtgta cggcgactac    3060
aaggtgtacg acgtgcggaa gatgatcgcc aagagcgagc aggaaatcgg caaggctacc    3120
gccaagtact tcttctacag caacatcatg aacttttca agaccgaaat caccctggcc    3180
aacggcgaga tcagaaagcg ccctctgatc gagacaaacg gcgaaccgg ggagatcgtg    3240
tgggataagg gcagagactt cgccacagtg cgaaaggtgc tgagcatgcc ccaagtgaat    3300
atcgtgaaaa agaccgaggt gcagacaggc ggcttcagca agagtctat cctgcccaag    3360
aggaacagcg acaagctgat cgccagaaag aaggactggg accccaagaa gtacggcggc    3420
ttcgacagcc ctaccgtggc ctactctgtg ctggtggtgg ctaaggtgga aaagggcaag    3480
tccaagaaac tgaagagtgt gaaagagctg ctggggatca ccatcatgga agaagcagc    3540
tttgagaaga ccctatcga ctttctggaa gccaagggct acaaagaagt gaaaaaggac    3600
ctgatcatca agctgcctaa gtactccctg ttcgagctgg aaaacggcag aaagagaatg    3660
ctggcctctg ccggcgaact gcagaaggga acgagctgg ccctgcctag caaatatgtg    3720
aacttcctgt acctggcctc ccactatgag aagctgaagg gcagccctga ggacaacgaa    3780
cagaaacagc tgtttgtgga acagcataag cactacctgg acgagatcat cgagcagatc    3840
agcgagttct ccaagagagt gatcctggcc gacgccaatc tggacaaggt gctgtctgcc    3900
tacaacaagc acagggacaa gcctatcaga gagcaggccg agaatatcat ccacctgttc    3960
accctgacaa acctgggcgc tcctgccgcc ttcaagtact ttgacaccac catcgaccgg    4020
aagaggtaca ccagcaccaa agaggtgctg gacgccaccc tgatccacca gagcatcacc    4080
ggcctgtacg agacaagaat cgacctgtct cagctgggag gcgacaagag acctgccgcc    4140
actaagaagg ccggacaggc caaaaagaag aagggtggag gtggaagtgg aggaggcggc    4200
tcaggtggag gtggttccga caagccccca gaagaccaag ggccacagag ggagccacac    4260
aatgaatgga cactagagct tttagaggag cttaagaatg aagctgttag acattttcct    4320
aggatttggc tccatggctt agggcaacat atctatgaaa cttatgggga tacttgggca    4380
ggagtggaag ccataataag aattctgcaa caactgctgt ttatccattt cagaattggg    4440
tgtcgacata gcagaatagg cgttactcga cagaggagag caagaaatgg agccagtaga    4500
tcctag                                                              4506
```

<210> SEQ ID NO 15
<211> LENGTH: 1501
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Met Asp Lys Pro Lys Lys Lys Arg Lys Val Lys Tyr Ser Ile Gly Leu
1               5                   10                  15

Asp Ile Gly Thr Asn Ser Val Gly Trp Ala Val Ile Thr Asp Glu Tyr
            20                  25                  30

Lys Val Pro Ser Lys Lys Phe Lys Val Leu Gly Asn Thr Asp Arg His
        35                  40                  45

Ser Ile Lys Lys Asn Leu Ile Gly Ala Leu Leu Phe Asp Ser Gly Glu
    50                  55                  60
```

```
Thr Ala Glu Ala Thr Arg Leu Lys Arg Thr Ala Arg Arg Tyr Thr
 65                  70                  75                  80

Arg Arg Lys Asn Arg Ile Cys Tyr Leu Gln Glu Ile Phe Ser Asn Glu
                 85                  90                  95

Met Ala Lys Val Asp Asp Ser Phe Phe His Arg Leu Glu Glu Ser Phe
            100                 105                 110

Leu Val Glu Glu Asp Lys Lys His Glu Arg His Pro Ile Phe Gly Asn
        115                 120                 125

Ile Val Asp Glu Val Ala Tyr His Glu Lys Tyr Pro Thr Ile Tyr His
    130                 135                 140

Leu Arg Lys Lys Leu Val Asp Ser Thr Asp Lys Ala Asp Leu Arg Leu
145                 150                 155                 160

Ile Tyr Leu Ala Leu Ala His Met Ile Lys Phe Arg Gly His Phe Leu
                165                 170                 175

Ile Glu Gly Asp Leu Asn Pro Asp Asn Ser Asp Val Asp Lys Leu Phe
            180                 185                 190

Ile Gln Leu Val Gln Thr Tyr Asn Gln Leu Phe Glu Glu Asn Pro Ile
        195                 200                 205

Asn Ala Ser Gly Val Asp Ala Lys Ala Ile Leu Ser Ala Arg Leu Ser
    210                 215                 220

Lys Ser Arg Arg Leu Glu Asn Leu Ile Ala Gln Leu Pro Gly Glu Lys
225                 230                 235                 240

Lys Asn Gly Leu Phe Gly Asn Leu Ile Ala Leu Ser Leu Gly Leu Thr
                245                 250                 255

Pro Asn Phe Lys Ser Asn Phe Asp Leu Ala Glu Asp Ala Lys Leu Gln
            260                 265                 270

Leu Ser Lys Asp Thr Tyr Asp Asp Leu Asp Asn Leu Leu Ala Gln
        275                 280                 285

Ile Gly Asp Gln Tyr Ala Asp Leu Phe Leu Ala Ala Lys Asn Leu Ser
    290                 295                 300

Asp Ala Ile Leu Leu Ser Asp Ile Leu Arg Val Asn Thr Glu Ile Thr
305                 310                 315                 320

Lys Ala Pro Leu Ser Ala Ser Met Ile Lys Arg Tyr Asp Glu His His
                325                 330                 335

Gln Asp Leu Thr Leu Leu Lys Ala Leu Val Arg Gln Gln Leu Pro Glu
            340                 345                 350

Lys Tyr Lys Glu Ile Phe Phe Asp Gln Ser Lys Asn Gly Tyr Ala Gly
        355                 360                 365

Tyr Ile Asp Gly Gly Ala Ser Gln Glu Glu Phe Tyr Lys Phe Ile Lys
    370                 375                 380

Pro Ile Leu Glu Lys Met Asp Gly Thr Glu Glu Leu Leu Val Lys Leu
385                 390                 395                 400

Asn Arg Glu Asp Leu Leu Arg Lys Gln Arg Thr Phe Asp Asn Gly Ser
                405                 410                 415

Ile Pro His Gln Ile His Leu Gly Glu Leu His Ala Ile Leu Arg Arg
            420                 425                 430

Gln Glu Asp Phe Tyr Pro Phe Leu Lys Asp Asn Arg Glu Lys Ile Glu
        435                 440                 445

Lys Ile Leu Thr Phe Arg Ile Pro Tyr Tyr Val Gly Pro Leu Ala Arg
    450                 455                 460

Gly Asn Ser Arg Phe Ala Trp Met Thr Arg Lys Ser Glu Glu Thr Ile
465                 470                 475                 480
```

```
Thr Pro Trp Asn Phe Glu Glu Val Val Asp Lys Gly Ala Ser Ala Gln
                485                 490                 495
Ser Phe Ile Glu Arg Met Thr Asn Phe Asp Lys Asn Leu Pro Asn Glu
            500                 505                 510
Lys Val Leu Pro Lys His Ser Leu Leu Tyr Glu Tyr Phe Thr Val Tyr
        515                 520                 525
Asn Glu Leu Thr Lys Val Lys Tyr Val Thr Glu Gly Met Arg Lys Pro
    530                 535                 540
Ala Phe Leu Ser Gly Glu Gln Lys Lys Ala Ile Val Asp Leu Leu Phe
545                 550                 555                 560
Lys Thr Asn Arg Lys Val Thr Val Lys Gln Leu Lys Glu Asp Tyr Phe
                565                 570                 575
Lys Lys Ile Glu Cys Phe Asp Ser Val Glu Ile Ser Gly Val Glu Asp
            580                 585                 590
Arg Phe Asn Ala Ser Leu Gly Thr Tyr His Asp Leu Leu Lys Ile Ile
        595                 600                 605
Lys Asp Lys Asp Phe Leu Asp Asn Glu Glu Asn Glu Asp Ile Leu Glu
    610                 615                 620
Asp Ile Val Leu Thr Leu Thr Leu Phe Glu Asp Arg Glu Met Ile Glu
625                 630                 635                 640
Glu Arg Leu Lys Thr Tyr Ala His Leu Phe Asp Asp Lys Val Met Lys
                645                 650                 655
Gln Leu Lys Arg Arg Arg Tyr Thr Gly Trp Gly Arg Leu Ser Arg Lys
            660                 665                 670
Leu Ile Asn Gly Ile Arg Asp Lys Gln Ser Gly Lys Thr Ile Leu Asp
        675                 680                 685
Phe Leu Lys Ser Asp Gly Phe Ala Asn Arg Asn Phe Met Gln Leu Ile
    690                 695                 700
His Asp Asp Ser Leu Thr Phe Lys Glu Asp Ile Gln Lys Ala Gln Val
705                 710                 715                 720
Ser Gly Gln Gly Asp Ser Leu His Glu His Ile Ala Asn Leu Ala Gly
                725                 730                 735
Ser Pro Ala Ile Lys Lys Gly Ile Leu Gln Thr Val Lys Val Val Asp
            740                 745                 750
Glu Leu Val Lys Val Met Gly Arg His Lys Pro Glu Asn Ile Val Ile
        755                 760                 765
Glu Met Ala Arg Glu Asn Gln Thr Thr Gln Lys Gly Gln Lys Asn Ser
    770                 775                 780
Arg Glu Arg Met Lys Arg Ile Glu Glu Gly Ile Lys Glu Leu Gly Ser
785                 790                 795                 800
Gln Ile Leu Lys Glu His Pro Val Glu Asn Thr Gln Leu Gln Asn Glu
                805                 810                 815
Lys Leu Tyr Leu Tyr Tyr Leu Gln Asn Gly Arg Asp Met Tyr Val Asp
            820                 825                 830
Gln Glu Leu Asp Ile Asn Arg Leu Ser Asp Tyr Asp Val Asp His Ile
        835                 840                 845
Val Pro Gln Ser Phe Leu Lys Asp Asp Ser Ile Asp Asn Lys Val Leu
    850                 855                 860
Thr Arg Ser Asp Lys Asn Arg Gly Lys Ser Asp Asn Val Pro Ser Glu
865                 870                 875                 880
Glu Val Val Lys Lys Met Lys Asn Tyr Trp Arg Gln Leu Leu Asn Ala
                885                 890                 895
Lys Leu Ile Thr Gln Arg Lys Phe Asp Asn Leu Thr Lys Ala Glu Arg
```

-continued

```
                900                 905                 910
Gly Gly Leu Ser Glu Leu Asp Lys Ala Gly Phe Ile Lys Arg Gln Leu
            915                 920                 925

Val Glu Thr Arg Gln Ile Thr Lys His Val Ala Gln Ile Leu Asp Ser
        930                 935                 940

Arg Met Asn Thr Lys Tyr Asp Glu Asn Asp Lys Leu Ile Arg Glu Val
945                 950                 955                 960

Lys Val Ile Thr Leu Lys Ser Lys Leu Val Ser Asp Phe Arg Lys Asp
                965                 970                 975

Phe Gln Phe Tyr Lys Val Arg Glu Ile Asn Asn Tyr His His Ala His
            980                 985                 990

Asp Ala Tyr Leu Asn Ala Val Val Gly Thr Ala Leu Ile Lys Lys Tyr
            995                 1000                1005

Pro Lys Leu Glu Ser Glu Phe Val Tyr Gly Asp Tyr Lys Val Tyr
        1010                1015                1020

Asp Val Arg Lys Met Ile Ala Lys Ser Glu Gln Glu Ile Gly Lys
        1025                1030                1035

Ala Thr Ala Lys Tyr Phe Phe Tyr Ser Asn Ile Met Asn Phe Phe
        1040                1045                1050

Lys Thr Glu Ile Thr Leu Ala Asn Gly Glu Ile Arg Lys Arg Pro
        1055                1060                1065

Leu Ile Glu Thr Asn Gly Glu Thr Gly Glu Ile Val Trp Asp Lys
        1070                1075                1080

Gly Arg Asp Phe Ala Thr Val Arg Lys Val Leu Ser Met Pro Gln
        1085                1090                1095

Val Asn Ile Val Lys Lys Thr Glu Val Gln Thr Gly Gly Phe Ser
        1100                1105                1110

Lys Glu Ser Ile Leu Pro Lys Arg Asn Ser Asp Lys Leu Ile Ala
        1115                1120                1125

Arg Lys Lys Asp Trp Asp Pro Lys Lys Tyr Gly Gly Phe Asp Ser
        1130                1135                1140

Pro Thr Val Ala Tyr Ser Val Leu Val Val Ala Lys Val Glu Lys
        1145                1150                1155

Gly Lys Ser Lys Lys Leu Lys Ser Val Lys Glu Leu Leu Gly Ile
        1160                1165                1170

Thr Ile Met Glu Arg Ser Ser Phe Glu Lys Asn Pro Ile Asp Phe
        1175                1180                1185

Leu Glu Ala Lys Gly Tyr Lys Glu Val Lys Lys Asp Leu Ile Ile
        1190                1195                1200

Lys Leu Pro Lys Tyr Ser Leu Phe Glu Leu Glu Asn Gly Arg Lys
        1205                1210                1215

Arg Met Leu Ala Ser Ala Gly Glu Leu Gln Lys Gly Asn Glu Leu
        1220                1225                1230

Ala Leu Pro Ser Lys Tyr Val Asn Phe Leu Tyr Leu Ala Ser His
        1235                1240                1245

Tyr Glu Lys Leu Lys Gly Ser Pro Glu Asp Asn Glu Gln Lys Gln
        1250                1255                1260

Leu Phe Val Glu Gln His Lys His Tyr Leu Asp Glu Ile Ile Glu
        1265                1270                1275

Gln Ile Ser Glu Phe Ser Lys Arg Val Ile Leu Ala Asp Ala Asn
        1280                1285                1290

Leu Asp Lys Val Leu Ser Ala Tyr Asn Lys His Arg Asp Lys Pro
        1295                1300                1305
```

Ile Arg Glu Gln Ala Glu Asn Ile Ile His Leu Phe Thr Leu Thr
1310                1315                1320

Asn Leu Gly Ala Pro Ala Ala Phe Lys Tyr Phe Asp Thr Thr Ile
    1325                1330                1335

Asp Arg Lys Arg Tyr Thr Ser Thr Lys Glu Val Leu Asp Ala Thr
    1340                1345                1350

Leu Ile His Gln Ser Ile Thr Gly Leu Tyr Glu Thr Arg Ile Asp
    1355                1360                1365

Leu Ser Gln Leu Gly Gly Asp Lys Arg Pro Ala Ala Thr Lys Lys
    1370                1375                1380

Ala Gly Gln Ala Lys Lys Lys Gly Gly Gly Ser Gly Gly
    1385                1390                1395

Gly Gly Ser Gly Gly Gly Ser Glu Gln Ala Pro Glu Asp Gln
    1400                1405                1410

Gly Pro Gln Arg Glu Pro His Asn Glu Trp Thr Leu Glu Leu Leu
    1415                1420                1425

Glu Glu Leu Lys Asn Glu Ala Val Arg His Phe Pro Arg Ile Trp
    1430                1435                1440

Leu His Gly Leu Gly Gln His Ile Tyr Glu Thr Tyr Gly Asp Thr
    1445                1450                1455

Trp Ala Gly Val Glu Ala Ile Ile Arg Ile Leu Gln Gln Leu Leu
    1460                1465                1470

Phe Ile His Phe Arg Ile Gly Cys Arg His Ser Arg Ile Gly Val
    1475                1480                1485

Thr Arg Gln Arg Arg Ala Arg Asn Gly Ala Ser Arg Ser
    1490                1495                1500

<210> SEQ ID NO 16
<211> LENGTH: 4557
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atgacagacc ccagagaaag ggtaccgcca ggaaacagtg gagaagagac cattggagag      60
gccttcgagt ggctagagag gaccatagaa gccttaaaca gggaggcagt gaaccatctg     120
ccccgagagc tcattttcca ggtgtggcaa aggtcctgga gatattggca tgatgaacaa     180
gggatgtcag caagctacac aaagtataga tatttgtgcc taatgcaaaa agctatattt     240
acacatttca agagagggtg cacttgctgg ggggaggaca tgggccggga aggattggaa     300
gaccaaggac ctcccccctcc tccccctcca ggtctagtcg gtggaggtgg aagtggagga     360
ggcggctcag gtggaggtgg ttccgacaag cccaagaaaa gcggaaagt gaagtacagc      420 atcggcctgg acatcggcac caactctgtg gctgggccg tgatcaccga cgagtacaag      480
gtgcccagca gaaaattcaa ggtgctgggc aacaccgaca ggcacagcat caagaagaac     540
ctgatcggcg ccctgctgtt cgacagcggc gaaacagccg aggccaccag actgaagaga     600
accgccagaa gaagatacac caggcggaag aacaggatct gctatctgca agatcttc      660 agcaacgaga tggccaaggt ggacgacagc ttcttccaca gactggaaga gtccttcctg     720
gtggaagagg acaagaagca cgagagacac cccatcttcg gcaacatcgt ggacgaggtg     780
gcctaccacg agaagtaccc caccatctac cacctgagaa agaaactggt ggacagcacc     840

```
gacaaggccg acctgagact gatctacctg gccctggccc acatgatcaa gttcagaggc    900
cacttcctga tcgagggcga cctgaacccc gacaacagcg acgtggacaa gctgttcatc    960
cagctggtgc agacctacaa ccagctgttc gaggaaaacc ccatcaacgc cagcggcgtg   1020
gacgccaagg ctatcctgtc tgccagactg agcaagagcg aaggctggga aaatctgatc   1080
gcccagctgc ccggcgagaa gaagaacggc ctgttcggca acctgattgc cctgagcctg   1140
ggcctgaccc ccaacttcaa gagcaacttc gacctggccg aggatgccaa actgcagctg   1200
agcaaggaca cctacgacga cgacctggac aacctgctgg cccagatcgg cgaccagtac   1260
gccgacctgt cctggccgc caagaacctg tctgacgcca cctgctgag cgacatcctg    1320
agagtgaaca ccgagatcac caaggccccc ctgagcgcct ctatgatcaa gagatacgac   1380
gagcaccacc aggacctgac cctgctgaaa gctctcgtgc ggcagcagct gcctgagaag   1440
tacaaagaaa tcttcttcga ccagagcaag aacggctacg ccggctacat cgatggcggc   1500
gctagccagg aagagttcta caagttcatc aagcccatcc tggaaaagat ggacggcacc   1560
gaggaactgc tcgtgaagct gaacagagag gacctgctga aaagcagag aaccttcgac   1620
aacggcagca tcccccacca gatccacctg ggagagctgc acgctatcct gagaaggcag   1680
gaagattttt acccattcct gaaggacaac cgggaaaaga tcgagaagat cctgaccttc   1740
aggatcccct actacgtggg ccccctggcc agaggcaaca gcagattcgc ctggatgacc   1800
agaaagagcg aggaaaccat cacccccctgg aacttcgagg aagtggtgga caagggcgcc   1860
agcgcccaga gcttcatcga gagaatgaca aacttcgata agaacctgcc caacgagaag   1920
gtgctgccca gcacagcct gctgtacgag tacttcaccg tgtacaacga gctgaccaaa   1980
gtgaaatacg tgaccgaggg aatgagaaag cccgccttcc tgagcggcga gcagaaaaag   2040
gccatcgtgg acctgctgtt caagaccaac agaaaagtga ccgtgaagca gctgaaagag   2100
gactacttca gaaaatcga gtgcttcgac tccgtggaaa tctccggcgt ggaagataga   2160
ttcaacgcct ccctgggcac ataccacgat ctgctgaaaa ttatcaagga caaggacttc   2220
ctggataacg aagagaacga ggacattctg gaagatatcg tgctgaccct gacactgttt   2280
gaggaccgcg agatgatcga ggaaaggctg aaaacctacg ctcacctgtt cgacgacaaa   2340
gtgatgaagc agctgaagag aaggcggtac accggctggg gcaggctgag cagaaagctg   2400
atcaacggca tcagagacaa gcagagcggc aagacaatcc tggatttcct gaagtccgac   2460
ggcttcgcca accggaactt catgcagctg atccacgacg acagcctgac attcaaagag   2520
gacatccaga aagcccaggt gtccggccag ggcgactctc tgcacgagca tatcgctaac   2580
ctggccggca gccccgctat caagaagggc atcctgcaga cagtgaaggt ggtggacgag   2640
ctcgtgaaag tgatgggcag acacaagccc gagaacatcg tgatcgagat ggctagagag   2700
aaccagacca cccagaaggg acagaagaac tcccgcgaga ggatgaagag aatcgaagag   2760
ggcatcaaag agctgggcag ccagatcctg aaagaacacc ccgtggaaaa cacccagctg   2820
cagaacgaga agctgtacct gtactacctg cagaatggcc gggatatgta cgtggaccag   2880
gaactggaca tcaacagact gtccgactac gatgtggacc atatcgtgcc tcagagcttt   2940
ctgaaggaca actccatcga taacaaagtg ctgactcgga cgacaagaa cagaggcaag   3000
agcgacaacg tgccctccga gaggtcgtg aagaagatga gaactactg gcgacagctg   3060
ctgaacgcca agctgattac ccagaggaag ttcgataacc tgaccaaggc cgagagaggc   3120
ggcctgagcg agctggataa ggccggcttc atcaagaggc agctggtgga aaccagacag   3180
atcacaaagc acgtggcaca gatcctggac tcccggatga acactaagta cgacgaaaac   3240
```

```
gataagctga tccgggaagt gaaagtgatc accctgaagt ccaagctggt gtccgatttc    3300
cggaaggatt tccagtttta caaagtgcgc gagatcaaca actaccacca cgcccacgac    3360
gcctacctga acgccgtcgt gggaaccgcc ctgatcaaaa agtaccctaa gctggaaagc    3420
gagttcgtgt acggcgacta caaggtgtac gacgtgcgga agatgatcgc caagagcgag    3480
caggaaatcg gcaaggctac cgccaagtac ttcttctaca gcaacatcat gaactttttc    3540
aagaccgaaa tcaccctggc caacggcgag atcagaaagc ccctctgat cgagacaaac     3600 ggcgaaaccg gggagatcgt gtgggataag ggcagagact cgccacagt gcgaaggtg     3660 ctgagcatgc cccaagtgaa tatcgtgaaa aagaccgagg tgcagacagg cggcttcagc    3720
aaagagtcta tcctgcccaa gaggaacagc gacaagctga tcgccagaaa gaaggactgg    3780 gacccccaaga agtacggcgg cttcgacagc cctaccgtgg cctactctgt gctggtggtg    3840
gctaaggtgg aaaagggcaa gtccaagaaa ctgaagagtg tgaaagagct gctggggatc    3900
accatcatgg aaagaagcag ctttgagaag aaccctatcg actttctgga agccaagggc    3960
tacaaagaag tgaaaaagga cctgatcatc aagctgccta agtactccct gttcgagctg    4020
gaaaacggca aaagagaat gctggcctct gccggcgaac tgcagaaggg aaacgagctg     4080
gccctgccta gcaaatatgt gaacttcctg tacctggcct cccactatga agctgaag     4140 ggcagccctg aggacaacga acagaaacag ctgtttgtgg aacagcataa gcactacctg    4200
gacgagatca tcgagcagat cagcgagttc tccaagagag tgatcctggc cgacgccaat    4260
ctggacaagg tgctgtctgc ctacaacaag cacagggaca gcctatcag agagcaggcc     4320 gagaatatca tccacctgtt caccctgaca aacctgggcg ctcctgccgc cttcaagtac    4380
tttgacacca ccatcgaccg gaagaggtac accagcacca agaggtgct ggacgccacc     4440 ctgatccacc agagcatcac cggcctgtac gagacaagaa tcgacctgtc tcagctggga    4500
ggcgacaaga gacctgccgc cactaagaag gccggacagg ccaaaaagaa gaagtga       4557
```

<210> SEQ ID NO 17
<211> LENGTH: 1518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Met Thr Asp Pro Arg Glu Arg Val Pro Pro Gly Asn Ser Gly Glu Glu
1               5                   10                  15

Thr Ile Gly Glu Ala Phe Glu Trp Leu Glu Arg Thr Ile Glu Ala Leu
            20                  25                  30

Asn Arg Glu Ala Val Asn His Leu Pro Arg Glu Leu Ile Phe Gln Val
        35                  40                  45

Trp Gln Arg Ser Trp Arg Tyr Trp His Asp Glu Gln Gly Met Ser Ala
    50                  55                  60

Ser Tyr Thr Lys Tyr Arg Tyr Leu Cys Leu Met Gln Lys Ala Ile Phe
65                  70                  75                  80

Thr His Phe Lys Arg Gly Cys Thr Cys Trp Gly Glu Asp Met Gly Arg
                85                  90                  95

Glu Gly Leu Glu Asp Gln Gly Pro Pro Pro Pro Pro Gly Leu
            100                 105                 110

Val Gly Gly Gly Ser Gly Gly Gly Ser Gly Gly Gly Ser
        115                 120                 125
```

```
Asp Lys Pro Lys Lys Lys Arg Lys Val Lys Tyr Ser Ile Gly Leu Asp
    130                 135                 140

Ile Gly Thr Asn Ser Val Gly Trp Ala Val Ile Thr Asp Glu Tyr Lys
145                 150                 155                 160

Val Pro Ser Lys Lys Phe Lys Val Leu Gly Asn Thr Asp Arg His Ser
                165                 170                 175

Ile Lys Lys Asn Leu Ile Gly Ala Leu Leu Phe Asp Ser Gly Glu Thr
            180                 185                 190

Ala Glu Ala Thr Arg Leu Lys Arg Thr Ala Arg Arg Tyr Thr Arg
        195                 200                 205

Arg Lys Asn Arg Ile Cys Tyr Leu Gln Glu Ile Phe Ser Asn Glu Met
    210                 215                 220

Ala Lys Val Asp Asp Ser Phe Phe His Arg Leu Glu Glu Ser Phe Leu
225                 230                 235                 240

Val Glu Glu Asp Lys Lys His Glu Arg His Pro Ile Phe Gly Asn Ile
                245                 250                 255

Val Asp Glu Val Ala Tyr His Glu Lys Tyr Pro Thr Ile Tyr His Leu
                260                 265                 270

Arg Lys Lys Leu Val Asp Ser Thr Asp Lys Ala Asp Leu Arg Leu Ile
            275                 280                 285

Tyr Leu Ala Leu Ala His Met Ile Lys Phe Arg Gly His Phe Leu Ile
290                 295                 300

Glu Gly Asp Leu Asn Pro Asp Asn Ser Asp Val Asp Lys Leu Phe Ile
305                 310                 315                 320

Gln Leu Val Gln Thr Tyr Asn Gln Leu Phe Glu Glu Asn Pro Ile Asn
                325                 330                 335

Ala Ser Gly Val Asp Ala Lys Ala Ile Leu Ser Ala Arg Leu Ser Lys
                340                 345                 350

Ser Arg Arg Leu Glu Asn Leu Ile Ala Gln Leu Pro Gly Glu Lys Lys
            355                 360                 365

Asn Gly Leu Phe Gly Asn Leu Ile Ala Leu Ser Leu Gly Leu Thr Pro
370                 375                 380

Asn Phe Lys Ser Asn Phe Asp Leu Ala Glu Asp Ala Lys Leu Gln Leu
385                 390                 395                 400

Ser Lys Asp Thr Tyr Asp Asp Asp Leu Asp Asn Leu Leu Ala Gln Ile
                405                 410                 415

Gly Asp Gln Tyr Ala Asp Leu Phe Leu Ala Ala Lys Asn Leu Ser Asp
                420                 425                 430

Ala Ile Leu Leu Ser Asp Ile Leu Arg Val Asn Thr Glu Ile Thr Lys
            435                 440                 445

Ala Pro Leu Ser Ala Ser Met Ile Lys Arg Tyr Asp Glu His His Gln
450                 455                 460

Asp Leu Thr Leu Leu Lys Ala Leu Val Arg Gln Gln Leu Pro Glu Lys
465                 470                 475                 480

Tyr Lys Glu Ile Phe Phe Asp Gln Ser Lys Asn Gly Tyr Ala Gly Tyr
                485                 490                 495

Ile Asp Gly Gly Ala Ser Gln Glu Glu Phe Tyr Lys Phe Ile Lys Pro
                500                 505                 510

Ile Leu Glu Lys Met Asp Gly Thr Glu Glu Leu Leu Val Lys Leu Asn
            515                 520                 525

Arg Glu Asp Leu Leu Arg Lys Gln Arg Thr Phe Asp Asn Gly Ser Ile
530                 535                 540
```

```
Pro His Gln Ile His Leu Gly Glu Leu His Ala Ile Leu Arg Arg Gln
545                 550                 555                 560

Glu Asp Phe Tyr Pro Phe Leu Lys Asp Asn Arg Glu Lys Ile Glu Lys
                565                 570                 575

Ile Leu Thr Phe Arg Ile Pro Tyr Tyr Val Gly Pro Leu Ala Arg Gly
            580                 585                 590

Asn Ser Arg Phe Ala Trp Met Thr Arg Lys Ser Glu Glu Thr Ile Thr
        595                 600                 605

Pro Trp Asn Phe Glu Glu Val Val Asp Lys Gly Ala Ser Ala Gln Ser
    610                 615                 620

Phe Ile Glu Arg Met Thr Asn Phe Asp Lys Asn Leu Pro Asn Glu Lys
625                 630                 635                 640

Val Leu Pro Lys His Ser Leu Leu Tyr Glu Tyr Phe Thr Val Tyr Asn
                645                 650                 655

Glu Leu Thr Lys Val Lys Tyr Val Thr Glu Gly Met Arg Lys Pro Ala
                660                 665                 670

Phe Leu Ser Gly Glu Gln Lys Lys Ala Ile Val Asp Leu Leu Phe Lys
            675                 680                 685

Thr Asn Arg Lys Val Thr Val Lys Gln Leu Lys Glu Asp Tyr Phe Lys
        690                 695                 700

Lys Ile Glu Cys Phe Asp Ser Val Glu Ile Ser Gly Val Glu Asp Arg
705                 710                 715                 720

Phe Asn Ala Ser Leu Gly Thr Tyr His Asp Leu Leu Lys Ile Ile Lys
                725                 730                 735

Asp Lys Asp Phe Leu Asp Asn Glu Glu Asn Glu Asp Ile Leu Glu Asp
                740                 745                 750

Ile Val Leu Thr Leu Thr Leu Phe Glu Asp Arg Glu Met Ile Glu Glu
            755                 760                 765

Arg Leu Lys Thr Tyr Ala His Leu Phe Asp Asp Lys Val Met Lys Gln
        770                 775                 780

Leu Lys Arg Arg Arg Tyr Thr Gly Trp Gly Arg Leu Ser Arg Lys Leu
785                 790                 795                 800

Ile Asn Gly Ile Arg Asp Lys Gln Ser Gly Lys Thr Ile Leu Asp Phe
                805                 810                 815

Leu Lys Ser Asp Gly Phe Ala Asn Arg Asn Phe Met Gln Leu Ile His
                820                 825                 830

Asp Asp Ser Leu Thr Phe Lys Glu Asp Ile Gln Lys Ala Gln Val Ser
        835                 840                 845

Gly Gln Gly Asp Ser Leu His Glu His Ile Ala Asn Leu Ala Gly Ser
    850                 855                 860

Pro Ala Ile Lys Lys Gly Ile Leu Gln Thr Val Lys Val Val Asp Glu
865                 870                 875                 880

Leu Val Lys Val Met Gly Arg His Lys Pro Glu Asn Ile Val Ile Glu
                885                 890                 895

Met Ala Arg Glu Asn Gln Thr Thr Gln Lys Gly Gln Lys Asn Ser Arg
                900                 905                 910

Glu Arg Met Lys Arg Ile Glu Glu Gly Ile Lys Glu Leu Gly Ser Gln
            915                 920                 925

Ile Leu Lys Glu His Pro Val Glu Asn Thr Gln Leu Gln Asn Glu Lys
        930                 935                 940

Leu Tyr Leu Tyr Tyr Leu Gln Asn Gly Arg Asp Met Tyr Val Asp Gln
945                 950                 955                 960

Glu Leu Asp Ile Asn Arg Leu Ser Asp Tyr Asp Val Asp His Ile Val
```

-continued

```
              965                 970                 975
Pro Gln Ser Phe Leu Lys Asp Asp Ser Ile Asp Asn Lys Val Leu Thr
              980                 985                 990
Arg Ser Asp Lys Asn Arg Gly Lys Ser Asp Asn Val Pro Ser Glu Glu
              995                1000                1005
Val Val Lys Lys Met Lys Asn Tyr Trp Arg Gln Leu Leu Asn Ala
             1010                1015                1020
Lys Leu Ile Thr Gln Arg Lys Phe Asp Asn Leu Thr Lys Ala Glu
             1025                1030                1035
Arg Gly Gly Leu Ser Glu Leu Asp Lys Ala Gly Phe Ile Lys Arg
             1040                1045                1050
Gln Leu Val Glu Thr Arg Gln Ile Thr Lys His Val Ala Gln Ile
             1055                1060                1065
Leu Asp Ser Arg Met Asn Thr Lys Tyr Asp Glu Asn Asp Lys Leu
             1070                1075                1080
Ile Arg Glu Val Lys Val Ile Thr Leu Lys Ser Lys Leu Val Ser
             1085                1090                1095
Asp Phe Arg Lys Asp Phe Gln Phe Tyr Lys Val Arg Glu Ile Asn
             1100                1105                1110
Asn Tyr His His Ala His Asp Ala Tyr Leu Asn Ala Val Val Gly
             1115                1120                1125
Thr Ala Leu Ile Lys Lys Tyr Pro Lys Leu Glu Ser Glu Phe Val
             1130                1135                1140
Tyr Gly Asp Tyr Lys Val Tyr Asp Val Arg Lys Met Ile Ala Lys
             1145                1150                1155
Ser Glu Gln Glu Ile Gly Lys Ala Thr Ala Lys Tyr Phe Phe Tyr
             1160                1165                1170
Ser Asn Ile Met Asn Phe Phe Lys Thr Glu Ile Thr Leu Ala Asn
             1175                1180                1185
Gly Glu Ile Arg Lys Arg Pro Leu Ile Glu Thr Asn Gly Glu Thr
             1190                1195                1200
Gly Glu Ile Val Trp Asp Lys Gly Arg Asp Phe Ala Thr Val Arg
             1205                1210                1215
Lys Val Leu Ser Met Pro Gln Val Asn Ile Val Lys Lys Thr Glu
             1220                1225                1230
Val Gln Thr Gly Gly Phe Ser Lys Glu Ser Ile Leu Pro Lys Arg
             1235                1240                1245
Asn Ser Asp Lys Leu Ile Ala Arg Lys Lys Asp Trp Asp Pro Lys
             1250                1255                1260
Lys Tyr Gly Gly Phe Asp Ser Pro Thr Val Ala Tyr Ser Val Leu
             1265                1270                1275
Val Val Ala Lys Val Glu Lys Gly Lys Ser Lys Lys Leu Lys Ser
             1280                1285                1290
Val Lys Glu Leu Leu Gly Ile Thr Ile Met Glu Arg Ser Ser Phe
             1295                1300                1305
Glu Lys Asn Pro Ile Asp Phe Leu Glu Ala Lys Gly Tyr Lys Glu
             1310                1315                1320
Val Lys Lys Asp Leu Ile Ile Lys Leu Pro Lys Tyr Ser Leu Phe
             1325                1330                1335
Glu Leu Glu Asn Gly Arg Lys Arg Met Leu Ala Ser Ala Gly Glu
             1340                1345                1350
Leu Gln Lys Gly Asn Glu Leu Ala Leu Pro Ser Lys Tyr Val Asn
             1355                1360                1365
```

| | | | | | | | | | | | |
|---|---|---|---|---|---|---|---|---|---|---|---|
|Phe|Leu|Tyr|Leu|Ala|Ser|His|Tyr|Glu|Lys|Leu|Lys|Gly|Ser|Pro|
| | | |1370| | | |1375| | | |1380|

```
Phe Leu Tyr Leu Ala Ser His Tyr Glu Lys Leu Lys Gly Ser Pro
        1370                1375               1380

Glu Asp Asn Glu Gln Lys Gln Leu Phe Val Glu Gln His Lys His
    1385                1390                1395

Tyr Leu Asp Glu Ile Ile Glu Gln Ile Ser Glu Phe Ser Lys Arg
    1400                1405                1410

Val Ile Leu Ala Asp Ala Asn Leu Asp Lys Val Leu Ser Ala Tyr
    1415                1420                1425

Asn Lys His Arg Asp Lys Pro Ile Arg Glu Gln Ala Glu Asn Ile
    1430                1435                1440

Ile His Leu Phe Thr Leu Thr Asn Leu Gly Ala Pro Ala Ala Phe
    1445                1450                1455

Lys Tyr Phe Asp Thr Thr Ile Asp Arg Lys Arg Tyr Thr Ser Thr
    1460                1465                1470

Lys Glu Val Leu Asp Ala Thr Leu Ile His Gln Ser Ile Thr Gly
    1475                1480                1485

Leu Tyr Glu Thr Arg Ile Asp Leu Ser Gln Leu Gly Gly Asp Lys
    1490                1495                1500

Arg Pro Ala Ala Thr Lys Lys Ala Gly Gln Ala Lys Lys Lys Lys
    1505                1510                1515

<210> SEQ ID NO 18
<211> LENGTH: 4557
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atggacaagc ccagaaaaaa gcggaaagtg aagtacagca tcggcctgga catcggcacc      60
aactctgtgg ctgggccgt gatcaccgac gagtacaagg tgcccagcaa gaaattcaag     120
gtgctgggca acaccgacag gcacagcatc aagaagaacc tgatcggcgc cctgctgttc     180
gacagcggcg aaacagccga ggccaccaga ctgaagagaa ccgccagaag aagatacacc     240
aggcggaaga caggatctg ctatctgcaa gagatcttca gcaacgagat ggccaaggtg      300
gacgacagct tcttccacag actggaagag tccttcctgg tggaagagga caagaagcac     360
gagagacacc ccatcttcgg caacatcgtg gacgaggtgg cctaccacga aagtaccccc     420
accatctacc acctgagaaa gaaactggtg gacagcaccg acaaggccga cctgagactg     480
atctacctgg ccctggccca catgatcaag ttcagaggcc acttcctgat cgagggcgac     540
ctgaaccccg acaacagcga cgtggacaag ctgttcatcc agctggtgca gacctacaac     600
cagctgttcg aggaaaaccc catcaacgcc agcggcgtgg acgccaaggc tatcctgtct     660
gccagactga gcaagagcag aaggctggaa aatctgatcg cccagctgcc cggcgagaag     720
aagaacggcc tgttcggcaa cctgattgcc ctgagcctgg gcctgacccc aacttcaag      780 agcaacttcg acctggccga ggatgccaaa ctgcagctga gcaaggacac ctacgacgac     840
gacctggaca acctgctggc ccagatcggc gaccagtacg ccgacctgtt cctggccgcc     900
aagaacctgt ctgacgccat cctgctgagc gacatcctga gtgtgaacac cgagatcacc     960 aaggccccc tgagcgcctc tatgatcaag agatacgacg agcaccacca ggacctgacc    1020
ctgctgaaag ctctcgtgcg gcagcagctg cctgagaagt acaaagaaat cttcttcgac    1080
cagagcaaga acggctacgc cggctacatc gatggcggcg ctagccagga agagttctac    1140
```

```
aagttcatca agcccatcct ggaaaagatg gacggcaccg aggaactgct cgtgaagctg   1200
aacagagagg acctgctgag aaagcagaga accttcgaca acggcagcat cccccaccag   1260
atccacctgg gagagctgca cgctatcctg agaaggcagg aagattttta cccattcctg   1320
aaggacaacc gggaaaagat cgagaagatc ctgaccttca ggatcccta ctacgtgggc   1380 cccctggcca gaggcaacag cagattcgcc tggatgacca gaaagagcga ggaaaccatc   1440
accccctgga acttcgagga gtggtggac aagggcgcca gcgcccagag cttcatcgag   1500
agaatgacaa acttcgataa gaacctgccc aacgagaagg tgctgcccaa gcacagcctg   1560
ctgtacgagt acttcaccgt gtacaacgag ctgaccaaag tgaaatacgt gaccgaggga   1620
atgagaaagc ccgccttcct gagcggcgag cagaaaaagg ccatcgtgga cctgctgttc   1680
aagaccaaca gaaaagtgac cgtgaagcag ctgaaagagg actacttcaa gaaaatcgag   1740
tgcttcgact ccgtggaaat ctccggcgtg gaagatagat caacgcctc cctgggcaca   1800 taccacgatc tgctgaaaat tatcaaggac aaggacttcc tggataacga gagaacgag   1860 gacattctgg aagatatcgt gctgaccctg acactgtttg aggaccgcga tgatcgag   1920 gaaaggctga aaacctacgc tcacctgttc gacgacaaag tgatgaagca gctgaagaga   1980
aggcggtaca ccggctgggg caggctgagc agaaagctga tcaacggcat cagagacaag   2040
cagagcggca gacaatcct ggatttcctg aagtccgacg gcttcgccaa ccggaacttc   2100
atgcagctga tccacgacga cagcctgaca ttcaaagagg acatccagaa agcccaggtg   2160
tccggccagg gcgactctct gcacgagcat atcgctaacc tggccggcag ccccgctatc   2220
aagaagggca tcctgcagac agtgaaggtg gtggacgagc tcgtgaaagt gatgggcaga   2280
cacaagcccg agaacatcgt gatcgagatg gctagagaga accagaccac ccagaaggga   2340
cagaagaact cccgcgagag gatgaagaga atcgaagagg gcatcaaaga gctgggcagc   2400
cagatcctga agaacacccc cgtggaaaac acccagctgc agaacgagaa gctgtacctg   2460
tactacctgc agaatggccg ggatatgtac gtggaccagg aactggacat caacagactg   2520
tccgactacg atgtggacca tatcgtgcct cagagctttc tgaaggacga ctccatcgat   2580
aacaaagtgc tgactcggag cgacaagaac agaggcaaga gcgacaacgt gccctccgaa   2640
gaggtcgtga agaagatgaa gaactactgg cgacagctgc tgaacgccaa gctgattacc   2700
cagaggaagt tcgataacct gaccaaggcc gagagaggcg gcctgagcga gctggataag   2760
gccggcttca tcaagaggca gctggtggaa accagacaga tcacaaagca cgtggcacag   2820
atcctggact cccggatgaa cactaagtac gacgaaaacg ataagctgat ccgggaagtg   2880
aaagtgatca ccctgaagtc caagctggtg tccgatttcc ggaaggattt ccagttttac   2940
aaagtgcgcg agatcaacaa ctaccaccac gcccacgacg cctacctgaa cgccgtcgtg   3000
ggaaccgccc tgatcaaaaa gtaccctaag ctggaaagcg agttcgtgta cggcgactac   3060
aaggtgtacg acgtgcggaa gatgatcgcc aagagcgagc aggaaatcgg caaggctacc   3120
gccaagtact tcttctacag caacatcatg aacttttttca agaccgaaat caccctggcc   3180
aacggcgaga tcagaaagcg ccctctgatc gagacaaacg gcgaaaccgg ggagatcgtg   3240
tgggataagg gcagagactt cgccacagtg cgaaaggtgc tgagcatgcc ccaagtgaat   3300
atcgtgaaaa agaccgaggt gcagacaggc ggcttcagca agagtctat cctgcccaag   3360 aggaacagcg acaagctgat cgccagaaag aaggactggg accccaagaa gtacggcggc   3420
ttcgacagcc ctaccgtggc ctactctgtg ctggtggtgg ctaaggtgga aaagggcaag   3480
```

```
tccaagaaac tgaagagtgt gaaagagctg ctggggatca ccatcatgga agaagcagc      3540 tttgagaaga accctatcga ctttctggaa gccaagggct acaaagaagt gaaaaaggac     3600
ctgatcatca agctgcctaa gtactccctg ttcgagctgg aaaacggcag aaagagaatg    3660
ctggcctctg ccggcgaact gcagaaggga acgagctgg ccctgcctag caaatatgtg     3720
aacttcctgt acctggcctc ccactatgag aagctgaagg gcagccctga ggacaacgaa    3780
cagaaacagc tgtttgtgga acagcataag cactacctgg acgagatcat cgagcagatc    3840
agcgagttct ccaagagagt gatcctggcc gacgccaatc tggacaaggt gctgtctgcc    3900
tacaacaagc acagggacaa gcctatcaga gagcaggccg agaatatcat ccacctgttc    3960
accctgacaa acctgggcgc tcctgccgcc ttcaagtact ttgacaccac catcgaccgg    4020
aagaggtaca ccagcaccaa agaggtgctg acgccaccc tgatccacca gagcatcacc     4080
ggcctgtacg agacaagaat cgacctgtct cagctgggag cgacaagag acctgccgcc     4140 actaagaagg ccggacaggc caaaaagaag aagggtggag gtggaagtgg aggaggcggc    4200
tcaggtggag gtggttccac agaccccaga gaaagggtac cgccaggaaa cagtggagaa    4260
gagaccattg gagaggcctt cgagtggcta gagaggacca tagaagcctt aaacagggag    4320
gcagtgaacc atctgccccg agagctcatt ttccaggtgt ggcaaaggtc ctggagatat    4380
tggcatgatg aacaagggat gtcagcaagc tacacaaagt atagatattt gtgcctaatg    4440
caaaaagcta tatttacaca tttcaagaga gggtgcactt gctgggggga ggacatgggc    4500
cgggaaggat tggaagacca aggacctccc cctcctcccc ctccaggtct agtctaa       4557
```

<210> SEQ ID NO 19
<211> LENGTH: 1518
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 19

```
Met Asp Lys Pro Lys Lys Arg Lys Val Lys Tyr Ser Ile Gly Leu
1               5                   10                  15

Asp Ile Gly Thr Asn Ser Val Gly Trp Ala Val Ile Thr Asp Glu Tyr
                20                  25                  30

Lys Val Pro Ser Lys Lys Phe Lys Val Leu Gly Asn Thr Asp Arg His
                35                  40                  45

Ser Ile Lys Lys Asn Leu Ile Gly Ala Leu Leu Phe Asp Ser Gly Glu
        50                  55                  60

Thr Ala Glu Ala Thr Arg Leu Lys Arg Thr Ala Arg Arg Arg Tyr Thr
65                  70                  75                  80

Arg Arg Lys Asn Arg Ile Cys Tyr Leu Gln Glu Ile Phe Ser Asn Glu
                85                  90                  95

Met Ala Lys Val Asp Asp Ser Phe Phe His Arg Leu Glu Glu Ser Phe
                100                 105                 110

Leu Val Glu Glu Asp Lys Lys His Glu Arg His Pro Ile Phe Gly Asn
        115                 120                 125

Ile Val Asp Glu Val Ala Tyr His Glu Lys Tyr Pro Thr Ile Tyr His
    130                 135                 140

Leu Arg Lys Lys Leu Val Asp Ser Thr Asp Lys Ala Asp Leu Arg Leu
145                 150                 155                 160

Ile Tyr Leu Ala Leu Ala His Met Ile Lys Phe Arg Gly His Phe Leu
                165                 170                 175
```

```
Ile Glu Gly Asp Leu Asn Pro Asp Asn Ser Asp Val Asp Lys Leu Phe
            180                 185                 190

Ile Gln Leu Val Gln Thr Tyr Asn Gln Leu Phe Glu Glu Asn Pro Ile
            195                 200                 205

Asn Ala Ser Gly Val Asp Ala Lys Ala Ile Leu Ser Ala Arg Leu Ser
        210                 215                 220

Lys Ser Arg Arg Leu Glu Asn Leu Ile Ala Gln Leu Pro Gly Glu Lys
225                 230                 235                 240

Lys Asn Gly Leu Phe Gly Asn Leu Ile Ala Leu Ser Leu Gly Leu Thr
                245                 250                 255

Pro Asn Phe Lys Ser Asn Phe Asp Leu Ala Glu Asp Ala Lys Leu Gln
            260                 265                 270

Leu Ser Lys Asp Thr Tyr Asp Asp Leu Asp Asn Leu Leu Ala Gln
            275                 280                 285

Ile Gly Asp Gln Tyr Ala Asp Leu Phe Leu Ala Ala Lys Asn Leu Ser
        290                 295                 300

Asp Ala Ile Leu Leu Ser Asp Ile Leu Arg Val Asn Thr Glu Ile Thr
305                 310                 315                 320

Lys Ala Pro Leu Ser Ala Ser Met Ile Lys Arg Tyr Asp Glu His His
                325                 330                 335

Gln Asp Leu Thr Leu Leu Lys Ala Leu Val Arg Gln Gln Leu Pro Glu
            340                 345                 350

Lys Tyr Lys Glu Ile Phe Phe Asp Gln Ser Lys Asn Gly Tyr Ala Gly
            355                 360                 365

Tyr Ile Asp Gly Gly Ala Ser Gln Glu Glu Phe Tyr Lys Phe Ile Lys
        370                 375                 380

Pro Ile Leu Glu Lys Met Asp Gly Thr Glu Glu Leu Leu Val Lys Leu
385                 390                 395                 400

Asn Arg Glu Asp Leu Leu Arg Lys Gln Arg Thr Phe Asp Asn Gly Ser
                405                 410                 415

Ile Pro His Gln Ile His Leu Gly Glu Leu His Ala Ile Leu Arg Arg
            420                 425                 430

Gln Glu Asp Phe Tyr Pro Phe Leu Lys Asp Asn Arg Glu Lys Ile Glu
            435                 440                 445

Lys Ile Leu Thr Phe Arg Ile Pro Tyr Tyr Val Gly Pro Leu Ala Arg
450                 455                 460

Gly Asn Ser Arg Phe Ala Trp Met Thr Arg Lys Ser Glu Glu Thr Ile
465                 470                 475                 480

Thr Pro Trp Asn Phe Glu Glu Val Val Asp Lys Gly Ala Ser Ala Gln
                485                 490                 495

Ser Phe Ile Glu Arg Met Thr Asn Phe Asp Lys Asn Leu Pro Asn Glu
            500                 505                 510

Lys Val Leu Pro Lys His Ser Leu Leu Tyr Glu Tyr Phe Thr Val Tyr
            515                 520                 525

Asn Glu Leu Thr Lys Val Lys Tyr Val Thr Glu Gly Met Arg Lys Pro
            530                 535                 540

Ala Phe Leu Ser Gly Glu Gln Lys Lys Ala Ile Val Asp Leu Leu Phe
545                 550                 555                 560

Lys Thr Asn Arg Lys Val Thr Val Lys Gln Leu Lys Glu Asp Tyr Phe
                565                 570                 575

Lys Lys Ile Glu Cys Phe Asp Ser Val Glu Ile Ser Gly Val Glu Asp
            580                 585                 590
```

-continued

```
Arg Phe Asn Ala Ser Leu Gly Thr Tyr His Asp Leu Leu Lys Ile Ile
            595                 600                 605

Lys Asp Lys Asp Phe Leu Asp Asn Glu Glu Asn Glu Asp Ile Leu Glu
    610                 615                 620

Asp Ile Val Leu Thr Leu Thr Leu Phe Glu Asp Arg Glu Met Ile Glu
625                 630                 635                 640

Glu Arg Leu Lys Thr Tyr Ala His Leu Phe Asp Asp Lys Val Met Lys
                645                 650                 655

Gln Leu Lys Arg Arg Arg Tyr Thr Gly Trp Gly Arg Leu Ser Arg Lys
            660                 665                 670

Leu Ile Asn Gly Ile Arg Asp Lys Gln Ser Gly Lys Thr Ile Leu Asp
        675                 680                 685

Phe Leu Lys Ser Asp Gly Phe Ala Asn Arg Asn Phe Met Gln Leu Ile
    690                 695                 700

His Asp Asp Ser Leu Thr Phe Lys Glu Asp Ile Gln Lys Ala Gln Val
705                 710                 715                 720

Ser Gly Gln Gly Asp Ser Leu His Glu His Ile Ala Asn Leu Ala Gly
                725                 730                 735

Ser Pro Ala Ile Lys Lys Gly Ile Leu Gln Thr Val Lys Val Val Asp
            740                 745                 750

Glu Leu Val Lys Val Met Gly Arg His Lys Pro Glu Asn Ile Val Ile
        755                 760                 765

Glu Met Ala Arg Glu Asn Gln Thr Thr Gln Lys Gly Gln Lys Asn Ser
    770                 775                 780

Arg Glu Arg Met Lys Arg Ile Glu Glu Gly Ile Lys Glu Leu Gly Ser
785                 790                 795                 800

Gln Ile Leu Lys Glu His Pro Val Glu Asn Thr Gln Leu Gln Asn Glu
                805                 810                 815

Lys Leu Tyr Leu Tyr Tyr Leu Gln Asn Gly Arg Asp Met Tyr Val Asp
            820                 825                 830

Gln Glu Leu Asp Ile Asn Arg Leu Ser Asp Tyr Asp Val Asp His Ile
        835                 840                 845

Val Pro Gln Ser Phe Leu Lys Asp Asp Ser Ile Asp Asn Lys Val Leu
    850                 855                 860

Thr Arg Ser Asp Lys Asn Arg Gly Lys Ser Asp Asn Val Pro Ser Glu
865                 870                 875                 880

Glu Val Val Lys Lys Met Lys Asn Tyr Trp Arg Gln Leu Leu Asn Ala
                885                 890                 895

Lys Leu Ile Thr Gln Arg Lys Phe Asp Asn Leu Thr Lys Ala Glu Arg
            900                 905                 910

Gly Gly Leu Ser Glu Leu Asp Lys Ala Gly Phe Ile Lys Arg Gln Leu
        915                 920                 925

Val Glu Thr Arg Gln Ile Thr Lys His Val Ala Gln Ile Leu Asp Ser
    930                 935                 940

Arg Met Asn Thr Lys Tyr Asp Glu Asn Asp Lys Leu Ile Arg Glu Val
945                 950                 955                 960

Lys Val Ile Thr Leu Lys Ser Lys Leu Val Ser Asp Phe Arg Lys Asp
                965                 970                 975

Phe Gln Phe Tyr Lys Val Arg Glu Ile Asn Asn Tyr His His Ala His
            980                 985                 990

Asp Ala Tyr Leu Asn Ala Val Val Gly Thr Ala Leu Ile Lys Lys Tyr
        995                 1000                1005

Pro Lys Leu Glu Ser Glu Phe Val Tyr Gly Asp Tyr Lys Val Tyr
```

```
              1010                1015                1020

Asp Val Arg Lys Met Ile Ala Lys Ser Glu Gln Glu Ile Gly Lys
              1025                1030                1035

Ala Thr Ala Lys Tyr Phe Phe Tyr Ser Asn Ile Met Asn Phe Phe
              1040                1045                1050

Lys Thr Glu Ile Thr Leu Ala Asn Gly Glu Ile Arg Lys Arg Pro
              1055                1060                1065

Leu Ile Glu Thr Asn Gly Glu Thr Gly Glu Ile Val Trp Asp Lys
              1070                1075                1080

Gly Arg Asp Phe Ala Thr Val Arg Lys Val Leu Ser Met Pro Gln
              1085                1090                1095

Val Asn Ile Val Lys Lys Thr Glu Val Gln Thr Gly Gly Phe Ser
              1100                1105                1110

Lys Glu Ser Ile Leu Pro Lys Arg Asn Ser Asp Lys Leu Ile Ala
              1115                1120                1125

Arg Lys Lys Asp Trp Asp Pro Lys Lys Tyr Gly Gly Phe Asp Ser
              1130                1135                1140

Pro Thr Val Ala Tyr Ser Val Leu Val Val Ala Lys Val Glu Lys
              1145                1150                1155

Gly Lys Ser Lys Lys Leu Lys Ser Val Lys Glu Leu Leu Gly Ile
              1160                1165                1170

Thr Ile Met Glu Arg Ser Ser Phe Glu Lys Asn Pro Ile Asp Phe
              1175                1180                1185

Leu Glu Ala Lys Gly Tyr Lys Glu Val Lys Lys Asp Leu Ile Ile
              1190                1195                1200

Lys Leu Pro Lys Tyr Ser Leu Phe Glu Leu Glu Asn Gly Arg Lys
              1205                1210                1215

Arg Met Leu Ala Ser Ala Gly Glu Leu Gln Lys Gly Asn Glu Leu
              1220                1225                1230

Ala Leu Pro Ser Lys Tyr Val Asn Phe Leu Tyr Leu Ala Ser His
              1235                1240                1245

Tyr Glu Lys Leu Lys Gly Ser Pro Glu Asp Asn Glu Gln Lys Gln
              1250                1255                1260

Leu Phe Val Glu Gln His Lys His Tyr Leu Asp Glu Ile Ile Glu
              1265                1270                1275

Gln Ile Ser Glu Phe Ser Lys Arg Val Ile Leu Ala Asp Ala Asn
              1280                1285                1290

Leu Asp Lys Val Leu Ser Ala Tyr Asn Lys His Arg Asp Lys Pro
              1295                1300                1305

Ile Arg Glu Gln Ala Glu Asn Ile Ile His Leu Phe Thr Leu Thr
              1310                1315                1320

Asn Leu Gly Ala Pro Ala Ala Phe Lys Tyr Phe Asp Thr Thr Ile
              1325                1330                1335

Asp Arg Lys Arg Tyr Thr Ser Thr Lys Glu Val Leu Asp Ala Thr
              1340                1345                1350

Leu Ile His Gln Ser Ile Thr Gly Leu Tyr Glu Thr Arg Ile Asp
              1355                1360                1365

Leu Ser Gln Leu Gly Gly Asp Lys Arg Pro Ala Ala Thr Lys Lys
              1370                1375                1380

Ala Gly Gln Ala Lys Lys Lys Lys Gly Gly Gly Ser Gly Gly
              1385                1390                1395

Gly Gly Ser Gly Gly Gly Ser Thr Asp Pro Arg Glu Arg Val
              1400                1405                1410
```

Pro Pro Gly Asn Ser Gly Glu Glu Thr Ile Gly Glu Ala Phe Glu
    1415                 1420                1425

Trp Leu Glu Arg Thr Ile Glu Ala Leu Asn Arg Glu Ala Val Asn
    1430                 1435                1440

His Leu Pro Arg Glu Leu Ile Phe Gln Val Trp Gln Arg Ser Trp
    1445                 1450                1455

Arg Tyr Trp His Asp Glu Gln Gly Met Ser Ala Ser Tyr Thr Lys
    1460                 1465                1470

Tyr Arg Tyr Leu Cys Leu Met Gln Lys Ala Ile Phe Thr His Phe
    1475                 1480                1485

Lys Arg Gly Cys Thr Cys Trp Gly Glu Asp Met Gly Arg Glu Gly
    1490                 1495                1500

Leu Glu Asp Gln Gly Pro Pro Pro Pro Pro Pro Gly Leu Val
    1505                 1510                1515

<210> SEQ ID NO 20
<211> LENGTH: 4713
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atggttaatc cgaccgtttt ttttgatatc gcagttgatg gcgaaccgtt gggcagggtt      60
tccttcgagc tcttcgccga taaagtgccg aaaaccgcag aaaactttcg cgcgctcagt     120
acgggtgaaa aggggtttgg ttacaaaggg agctgttttc atcgaatcat tcctggtttc     180
atgtgtcagg gcggagattt cacccgacat aacgggactg gcgggaagag tatatatgga     240
gagaagttcg aggatgagaa ctttatactg aaacacaccg acccggaat tttgagtatg      300 gcaaatgcag gcctaacac caatggctcc cagttcttta tttgtacggc caagacagag      360
tggctcgacg ggaagcacgt tgtgttcgga aaggtcaaag aaggtatgaa tatagtagag     420
gcgatggaac ggtttggctc acgcaatggc aagacatcca aaaaaatcac aatagctgac     480
tgtggccaat tggagggtgg aggtggaagt ggaggaggcg gctcaggtgg aggtggttcc     540
gacaagccca gaaaaaagcg gaaagtgaag tacagcatcg gcctggacat cggcaccaac     600
tctgtgggct gggccgtgat caccgacgag tacaaggtgc ccagcaagaa attcaaggtg     660
ctgggcaaca ccgacaggca cagcatcaag aagaacctga tcggcgccct gctgttcgac     720
agcggcgaaa cagccgaggc caccagactg aagagaaccg ccagaagaag atacaccagg     780
cggaagaaca ggatctgcta tctgcaagag atcttcagca acgagatggc caaggtggac     840
gacagcttct tccacagact ggaagagtcc ttcctggtgg aagaggacaa gaagcacgag     900
agacacccca tcttcggcaa catcgtggac gaggtggcct accacgagaa gtaccccacc     960
atctaccacc tgagaaagaa actggtggac agcaccgaca ggccgacct gagactgatc    1020 tacctggccc tggcccacat gatcaagttc agaggccact tcctgatcga gggcgacctg    1080
aaccccgaca cagcgacgt ggacaagctt tcatccagc tggtgcagac ctacaaccag    1140
ctgttcgagg aaaaccccat caacgccagc ggcgtggacg ccaaggctat cctgtctgcc    1200
agactgagca gagcagaag gctggaaaat ctgatcgccc agctgccgg cgagaagaag    1260 aacggcctgt tcggcaacct gattgccctg agctgggcc tgaccccaa cttcaagagc    1320 aacttcgacc tggccgagga tgccaaactg cagctgagca aggacaccta cgacgacgac    1380

```
ctggacaacc tgctggccca gatcggcgac cagtacgccg acctgttcct ggccgccaag    1440
aacctgtctg acgccatcct gctgagcgac atcctgagag tgaacaccga gatcaccaag    1500 gccccctga gcgcctctat gatcaagaga tacgacgagc accaccagga cctgaccctg    1560
ctgaaagctc tcgtgcggca gcagctgcct gagaagtaca agaaatctt cttcgaccag    1620 agcaagaacg gctacgccgg ctacatcgat ggcggcgcta gccaggaaga gttctacaag    1680
ttcatcaagc ccatcctgga aaagatggac ggcaccgagg aactgctcgt gaagctgaac    1740
agagaggacc tgctgagaaa gcagagaacc ttcgacaacg gcagcatccc ccaccagatc    1800
cacctgggag agctgcacgc tatcctgaga aggcaggaag attttttaccc attcctgaag    1860 gacaaccggg aaaagatcga aagatcctg accttcagga tccctacta cgtgggcccc    1920 ctggccagag gcaacagcag attcgcctgg atgaccagaa agagcgagga aaccatcacc    1980
ccctggaact tcgaggaagt ggtggacaag ggcgccagcg cccagagctt catcgagaga    2040
atgacaaact tcgataagaa cctgcccaac gagaaggtgc tgcccaagca cagcctgctg    2100
tacgagtact tcaccgtgta caacgagctg accaaagtga aatacgtgac cgagggaatg    2160
agaaagcccg ccttcctgag cggcgagcag aaaaaggcca tcgtggacct gctgttcaag    2220
accaacagaa aagtgaccgt gaagcagctg aaagaggact acttcaagaa aatcgagtgc    2280
ttcgactccg tggaaatctc cggcgtggaa gatagattca acgcctccct gggcacatac    2340
cacgatctgc tgaaaattat caaggacaag gacttcctgg ataacgaaga gaacgaggac    2400
attctggaag atatcgtgct gaccctgaca ctgtttgagg accgcgagat gatcgaggaa    2460
aggctgaaaa cctacgctca cctgttcgac gacaaagtga tgaagcagct gaagagaagg    2520
cggtacaccg gctggggcag gctgagcaga aagctgatca acggcatcag agacaagcag    2580
agcggcaaga caatcctgga tttcctgaag tccgacggct tcgccaaccg gaacttcatg    2640
cagctgatcc acgacgacag cctgacattc aaagaggaca tccagaaagc ccaggtgtcc    2700
ggccagggcg actctctgca cgagcatatc gctaacctgg ccggcagccc cgctatcaag    2760
aagggcatcc tgcagacagt gaaggtggtg gacgagctcg tgaaagtgat gggcagacac    2820
aagcccgaga acatcgtgat cgagatggct agagagaacc agaccaccca gaagggacag    2880
aagaactccc gcgagaggat gaagagaatc gaagagggca tcaaagagct gggcagccag    2940
atcctgaaag aacaccccgt ggaaaacacc cagctgcaga acgagaagct gtacctgtac    3000
tacctgcaga atggccggga tatgtacgtg gaccaggaac tggacatcaa cagactgtcc    3060
gactacgatg tggaccatat cgtgcctcag agctttctga aggacgactc catcgataac    3120
aaagtgctga ctcggagcga caagaacaga ggcaagagcg acaacgtgcc ctccgaagag    3180
gtcgtgaaga agatgaagaa ctactggcga cagctgctga acgccaagct gattacccag    3240
aggaagttcg ataacctgac caaggccgag agaggcggcc tgagcgagct ggataaggcc    3300
ggcttcatca gaggcagct ggtggaaacc agacagatca aaagcacgt ggcacagatc    3360 ctggactccc ggatgaacac taagtacgac gaaaacgata agctgatccg ggaagtgaaa    3420
gtgatcaccc tgaagtccaa gctggtgtcc gatttccgga aggatttcca gttttacaaa    3480
gtgcgcgaga tcaacaacta ccaccacgcc cacgacgcct acctgaacgc cgtcgtggga    3540
accgccctga tcaaaaagta ccctaagctg gaaagcgagt tcgtgtacgg cgactacaag    3600
gtgtacgacg tgcggaagat gatcgccaag agcgagcagg aaatcggcaa ggctaccgcc    3660
aagtacttct tctacagcaa catcatgaac ttttttcaaga ccgaaatcac cctggccaac    3720
ggcgagatca gaaagcgccc tctgatcgag acaaacggcg aaaccgggga gatcgtgtgg    3780
```

-continued

```
gataagggca gagacttcgc cacagtgcga aaggtgctga gcatgcccca agtgaatatc   3840
gtgaaaaaga ccgaggtgca gacaggcggc ttcagcaaag agtctatcct gcccaagagg   3900
aacagcgaca agctgatcgc cagaaagaag gactgggacc ccaagaagta cggcggcttc   3960
gacagcccta ccgtggccta ctctgtgctg gtggtggcta aggtgaaaaa gggcaagtcc   4020
aagaaactga gagtgtgaa agagctgctg gggatcacca tcatggaaag aagcagcttt   4080
gagaagaacc ctatcgactt tctggaagcc aagggctaca agaagtgaa aaaggacctg   4140 atcatcaagc tgcctaagta ctccctgttc gagctggaaa acggcagaaa gagaatgctg   4200
gcctctgccg gcgaactgca gaagggaaac gagctggccc tgcctagcaa atatgtgaac   4260
ttcctgtacc tggcctccca ctatgagaag ctgaagggca gccctgagga caacgaacag   4320
aaacagctgt ttgtggaaca gcataagcac tacctggacg agatcatcga gcagatcagc   4380
gagttctcca agagagtgat cctggccgac gccaatctgg acaaggtgct gtctgcctac   4440
aacaagcaca gggacaagcc tatcagagag caggccgaga atatcatcca cctgttcacc   4500
ctgacaaacc tgggcgctcc tgccgccttc aagtactttg acaccaccat cgaccggaag   4560
aggtacacca gcaccaaaga ggtgctggac gccacctga tccaccagag catcaccggc   4620
ctgtacgaga caagaatcga cctgtctcag ctgggaggcg acaagagacc tgccgccact   4680
aagaaggccg acaggccaa aaagaagaag tga                                4713
```

<210> SEQ ID NO 21
<211> LENGTH: 1570
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30

Ala Glu Asn Phe Arg Ala Leu Ser Thr Gly Glu Lys Gly Phe Gly Tyr
        35                  40                  45

Lys Gly Ser Cys Phe His Arg Ile Ile Pro Gly Phe Met Cys Gln Gly
    50                  55                  60

Gly Asp Phe Thr Arg His Asn Gly Thr Gly Lys Ser Ile Tyr Gly
65                  70                  75                  80

Glu Lys Phe Glu Asp Glu Asn Phe Ile Leu Lys His Thr Gly Pro Gly
                85                  90                  95

Ile Leu Ser Met Ala Asn Ala Gly Pro Asn Thr Asn Gly Ser Gln Phe
            100                 105                 110

Phe Ile Cys Thr Ala Lys Thr Glu Trp Leu Asp Gly Lys His Val Val
        115                 120                 125

Phe Gly Lys Val Lys Glu Gly Met Asn Ile Val Glu Ala Met Glu Arg
    130                 135                 140

Phe Gly Ser Arg Asn Gly Lys Thr Ser Lys Lys Ile Thr Ile Ala Asp
145                 150                 155                 160

Cys Gly Gln Leu Glu Gly Gly Gly Ser Gly Gly Gly Ser Gly
                165                 170                 175

Gly Gly Gly Ser Asp Lys Pro Lys Lys Lys Arg Lys Val Lys Tyr Ser
            180                 185                 190
```

-continued

Ile Gly Leu Asp Ile Gly Thr Asn Ser Val Gly Trp Ala Val Ile Thr
        195                 200                 205

Asp Glu Tyr Lys Val Pro Ser Lys Lys Phe Lys Val Leu Gly Asn Thr
    210                 215                 220

Asp Arg His Ser Ile Lys Lys Asn Leu Ile Gly Ala Leu Leu Phe Asp
225                 230                 235                 240

Ser Gly Glu Thr Ala Glu Ala Thr Arg Leu Lys Arg Thr Ala Arg Arg
                245                 250                 255

Arg Tyr Thr Arg Arg Lys Asn Arg Ile Cys Tyr Leu Gln Glu Ile Phe
            260                 265                 270

Ser Asn Glu Met Ala Lys Val Asp Asp Ser Phe Phe His Arg Leu Glu
        275                 280                 285

Glu Ser Phe Leu Val Glu Glu Asp Lys Lys His Glu Arg His Pro Ile
    290                 295                 300

Phe Gly Asn Ile Val Asp Glu Val Ala Tyr His Glu Lys Tyr Pro Thr
305                 310                 315                 320

Ile Tyr His Leu Arg Lys Lys Leu Val Asp Ser Thr Asp Lys Ala Asp
                325                 330                 335

Leu Arg Leu Ile Tyr Leu Ala Leu Ala His Met Ile Lys Phe Arg Gly
            340                 345                 350

His Phe Leu Ile Glu Gly Asp Leu Asn Pro Asp Asn Ser Asp Val Asp
        355                 360                 365

Lys Leu Phe Ile Gln Leu Val Gln Thr Tyr Asn Gln Leu Phe Glu Glu
    370                 375                 380

Asn Pro Ile Asn Ala Ser Gly Val Asp Ala Lys Ala Ile Leu Ser Ala
385                 390                 395                 400

Arg Leu Ser Lys Ser Arg Arg Leu Glu Asn Leu Ile Ala Gln Leu Pro
                405                 410                 415

Gly Glu Lys Lys Asn Gly Leu Phe Gly Asn Leu Ile Ala Leu Ser Leu
            420                 425                 430

Gly Leu Thr Pro Asn Phe Lys Ser Asn Phe Asp Leu Ala Glu Asp Ala
        435                 440                 445

Lys Leu Gln Leu Ser Lys Asp Thr Tyr Asp Asp Leu Asp Asn Leu
    450                 455                 460

Leu Ala Gln Ile Gly Asp Gln Tyr Ala Asp Leu Phe Leu Ala Ala Lys
465                 470                 475                 480

Asn Leu Ser Asp Ala Ile Leu Leu Ser Asp Ile Leu Arg Val Asn Thr
                485                 490                 495

Glu Ile Thr Lys Ala Pro Leu Ser Ala Ser Met Ile Lys Arg Tyr Asp
            500                 505                 510

Glu His His Gln Asp Leu Thr Leu Leu Lys Ala Leu Val Arg Gln Gln
        515                 520                 525

Leu Pro Glu Lys Tyr Lys Glu Ile Phe Phe Asp Gln Ser Lys Asn Gly
    530                 535                 540

Tyr Ala Gly Tyr Ile Asp Gly Gly Ala Ser Gln Glu Glu Phe Tyr Lys
545                 550                 555                 560

Phe Ile Lys Pro Ile Leu Glu Lys Met Asp Gly Thr Glu Glu Leu Leu
                565                 570                 575

Val Lys Leu Asn Arg Glu Asp Leu Leu Arg Lys Gln Arg Thr Phe Asp
            580                 585                 590

Asn Gly Ser Ile Pro His Gln Ile His Leu Gly Glu Leu His Ala Ile
        595                 600                 605

```
Leu Arg Arg Gln Glu Asp Phe Tyr Pro Phe Leu Lys Asp Asn Arg Glu
610                 615                 620

Lys Ile Glu Lys Ile Leu Thr Phe Arg Ile Pro Tyr Tyr Val Gly Pro
625                 630                 635                 640

Leu Ala Arg Gly Asn Ser Arg Phe Ala Trp Met Thr Arg Lys Ser Glu
                645                 650                 655

Glu Thr Ile Thr Pro Trp Asn Phe Glu Glu Val Val Asp Lys Gly Ala
                660                 665                 670

Ser Ala Gln Ser Phe Ile Glu Arg Met Thr Asn Phe Asp Lys Asn Leu
                675                 680                 685

Pro Asn Glu Lys Val Leu Pro Lys His Ser Leu Leu Tyr Glu Tyr Phe
690                 695                 700

Thr Val Tyr Asn Glu Leu Thr Lys Val Lys Tyr Val Thr Glu Gly Met
705                 710                 715                 720

Arg Lys Pro Ala Phe Leu Ser Gly Glu Gln Lys Lys Ala Ile Val Asp
                725                 730                 735

Leu Leu Phe Lys Thr Asn Arg Lys Val Thr Val Lys Gln Leu Lys Glu
                740                 745                 750

Asp Tyr Phe Lys Lys Ile Glu Cys Phe Asp Ser Val Glu Ile Ser Gly
                755                 760                 765

Val Glu Asp Arg Phe Asn Ala Ser Leu Gly Thr Tyr His Asp Leu Leu
770                 775                 780

Lys Ile Ile Lys Asp Lys Asp Phe Leu Asp Asn Glu Glu Asn Glu Asp
785                 790                 795                 800

Ile Leu Glu Asp Ile Val Leu Thr Leu Thr Leu Phe Glu Asp Arg Glu
                805                 810                 815

Met Ile Glu Glu Arg Leu Lys Thr Tyr Ala His Leu Phe Asp Asp Lys
                820                 825                 830

Val Met Lys Gln Leu Lys Arg Arg Tyr Thr Gly Trp Gly Arg Leu
835                 840                 845

Ser Arg Lys Leu Ile Asn Gly Ile Arg Asp Lys Gln Ser Gly Lys Thr
850                 855                 860

Ile Leu Asp Phe Leu Lys Ser Asp Gly Phe Ala Asn Arg Asn Phe Met
865                 870                 875                 880

Gln Leu Ile His Asp Asp Ser Leu Thr Phe Lys Glu Asp Ile Gln Lys
                885                 890                 895

Ala Gln Val Ser Gly Gln Gly Asp Ser Leu His Glu His Ile Ala Asn
                900                 905                 910

Leu Ala Gly Ser Pro Ala Ile Lys Lys Gly Ile Leu Gln Thr Val Lys
                915                 920                 925

Val Val Asp Glu Leu Val Lys Val Met Gly Arg His Lys Pro Glu Asn
930                 935                 940

Ile Val Ile Glu Met Ala Arg Glu Asn Gln Thr Thr Gln Lys Gly Gln
945                 950                 955                 960

Lys Asn Ser Arg Glu Arg Met Lys Arg Ile Glu Glu Gly Ile Lys Glu
                965                 970                 975

Leu Gly Ser Gln Ile Leu Lys Glu His Pro Val Glu Asn Thr Gln Leu
                980                 985                 990

Gln Asn Glu Lys Leu Tyr Leu Tyr Tyr Leu Gln Asn Gly Arg Asp Met
                995                 1000                1005

Tyr Val Asp Gln Glu Leu Asp Ile Asn Arg Leu Ser Asp Tyr Asp
        1010                1015                1020

Val Asp His Ile Val Pro Gln Ser Phe Leu Lys Asp Asp Ser Ile
```

```
              1025                1030                1035

Asp Asn Lys Val Leu Thr Arg Ser Asp Lys Asn Arg Gly Lys Ser
         1040                1045                1050

Asp Asn Val Pro Ser Glu Glu Val Val Lys Lys Met Lys Asn Tyr
         1055                1060                1065

Trp Arg Gln Leu Leu Asn Ala Lys Leu Ile Thr Gln Arg Lys Phe
         1070                1075                1080

Asp Asn Leu Thr Lys Ala Glu Arg Gly Gly Leu Ser Glu Leu Asp
         1085                1090                1095

Lys Ala Gly Phe Ile Lys Arg Gln Leu Val Glu Thr Arg Gln Ile
         1100                1105                1110

Thr Lys His Val Ala Gln Ile Leu Asp Ser Arg Met Asn Thr Lys
         1115                1120                1125

Tyr Asp Glu Asn Asp Lys Leu Ile Arg Glu Val Lys Val Ile Thr
         1130                1135                1140

Leu Lys Ser Lys Leu Val Ser Asp Phe Arg Lys Asp Phe Gln Phe
         1145                1150                1155

Tyr Lys Val Arg Glu Ile Asn Asn Tyr His His Ala His Asp Ala
         1160                1165                1170

Tyr Leu Asn Ala Val Val Gly Thr Ala Leu Ile Lys Lys Tyr Pro
         1175                1180                1185

Lys Leu Glu Ser Glu Phe Val Tyr Gly Asp Tyr Lys Val Tyr Asp
         1190                1195                1200

Val Arg Lys Met Ile Ala Lys Ser Glu Gln Glu Ile Gly Lys Ala
         1205                1210                1215

Thr Ala Lys Tyr Phe Phe Tyr Ser Asn Ile Met Asn Phe Phe Lys
         1220                1225                1230

Thr Glu Ile Thr Leu Ala Asn Gly Glu Ile Arg Lys Arg Pro Leu
         1235                1240                1245

Ile Glu Thr Asn Gly Glu Thr Gly Glu Ile Val Trp Asp Lys Gly
         1250                1255                1260

Arg Asp Phe Ala Thr Val Arg Lys Val Leu Ser Met Pro Gln Val
         1265                1270                1275

Asn Ile Val Lys Lys Thr Glu Val Gln Thr Gly Gly Phe Ser Lys
         1280                1285                1290

Glu Ser Ile Leu Pro Lys Arg Asn Ser Asp Lys Leu Ile Ala Arg
         1295                1300                1305

Lys Lys Asp Trp Asp Pro Lys Lys Tyr Gly Gly Phe Asp Ser Pro
         1310                1315                1320

Thr Val Ala Tyr Ser Val Leu Val Val Ala Lys Val Glu Lys Gly
         1325                1330                1335

Lys Ser Lys Lys Leu Lys Ser Val Lys Glu Leu Leu Gly Ile Thr
         1340                1345                1350

Ile Met Glu Arg Ser Ser Phe Glu Lys Asn Pro Ile Asp Phe Leu
         1355                1360                1365

Glu Ala Lys Gly Tyr Lys Glu Val Lys Lys Asp Leu Ile Ile Lys
         1370                1375                1380

Leu Pro Lys Tyr Ser Leu Phe Glu Leu Glu Asn Gly Arg Lys Arg
         1385                1390                1395

Met Leu Ala Ser Ala Gly Glu Leu Gln Lys Gly Asn Glu Leu Ala
         1400                1405                1410

Leu Pro Ser Lys Tyr Val Asn Phe Leu Tyr Leu Ala Ser His Tyr
         1415                1420                1425
```

| | | | | | | | | | | |
|---|---|---|---|---|---|---|---|---|---|---|
|Glu|Lys|Leu|Lys|Gly|Ser|Pro|Glu|Asp|Asn|Glu|Gln|Lys|Gln|Leu|
| |1430| | | |1435| | | |1440| |

Phe Val Glu Gln His Lys His Tyr Leu Asp Glu Ile Ile Glu Gln
    1445            1450            1455

Ile Ser Glu Phe Ser Lys Arg Val Ile Leu Ala Asp Ala Asn Leu
    1460            1465            1470

Asp Lys Val Leu Ser Ala Tyr Asn Lys His Arg Asp Lys Pro Ile
    1475            1480            1485

Arg Glu Gln Ala Glu Asn Ile Ile His Leu Phe Thr Leu Thr Asn
    1490            1495            1500

Leu Gly Ala Pro Ala Ala Phe Lys Tyr Phe Asp Thr Thr Ile Asp
    1505            1510            1515

Arg Lys Arg Tyr Thr Ser Thr Lys Glu Val Leu Asp Ala Thr Leu
    1520            1525            1530

Ile His Gln Ser Ile Thr Gly Leu Tyr Glu Thr Arg Ile Asp Leu
    1535            1540            1545

Ser Gln Leu Gly Gly Asp Lys Arg Pro Ala Ala Thr Lys Lys Ala
    1550            1555            1560

Gly Gln Ala Lys Lys Lys Lys
    1565            1570

<210> SEQ ID NO 22
<211> LENGTH: 4716
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
atggacaagc ccaagaaaaa gcggaaagtg aagtacagca tcggcctgga catcggcacc      60
aactctgtgg ctgggccgt gatcaccgac gagtacaagg tgcccagcaa gaaattcaag     120
gtgctgggca acaccgacag gcacagcatc aagaagaacc tgatcggcgc cctgctgttc     180
gacagcggcg aaacagccga ggccaccaga ctgaagagaa ccgccagaag aagatacacc     240
aggcggaaga acaggatctg ctatctgcaa gagatcttca gcaacgagat ggccaaggtg     300
gacgacagct tcttccacag actggaagag tccttcctgg tggaagagga caagaagcac     360
gagagacacc ccatcttcgg caacatcgtg gacgaggtgg cctaccacga agtaccccc     420
accatctacc acctgagaaa gaaactggtg gacagcaccg acaaggccga cctgagactg     480
atctacctgg ccctggccca catgatcaag ttcagaggcc acttcctgat cgagggcgac     540
ctgaaccccg acaacagcga cgtggacaag ctgttcatcc agctggtgca gacctacaac     600
cagctgttcg aggaaaaccc catcaacgcc agcggcgtgg acgccaaggc tatcctgtct     660
gccagactga gcaagagcag aaggctggaa aatctgatcg cccagctgcc cggcgagaag     720
aagaacggcc tgttcggcaa cctgattgcc ctgagcctgg gcctgacccc caacttcaag     780
agcaacttcg acctggccga ggatgccaaa ctgcagctga gcaaggacac ctacgacgac     840
gacctggaca acctgctggc ccagatcggc gaccagtacg ccgacctgtt cctggccgcc     900
aagaacctgt ctgacgccat cctgctgagc gacatcctga gtgaacac cgagatcacc     960
aaggccccc tgagcgcctc tatgatcaag agatacgacg agcaccacca ggacctgacc    1020
ctgctgaaag ctctcgtgcg gcagcagctg cctgagaagt acaaagaaat cttcttcgac    1080
cagagcaaga acggctacgc cggctacatc gatggcggcg ctagccagga agagttctac    1140
```

```
aagttcatca agcccatcct ggaaaagatg gacggcaccg aggaactgct cgtgaagctg   1200
aacagagagg acctgctgag aaagcagaga accttcgaca acggcagcat cccccaccag   1260
atccacctgg gagagctgca cgctatcctg agaaggcagg aagattttta cccattcctg   1320
aaggacaacc gggaaaagat cgagaagatc ctgaccttca ggatccccta ctacgtgggc   1380
cccctggcca gaggcaacag cagattcgcc tggatgacca gaaagagcga ggaaaccatc   1440
accccctgga acttcgagga gtggtggac aagggcgcca gcgcccagag cttcatcgag   1500
agaatgacaa acttcgataa gaacctgccc aacgagaagg tgctgcccaa gcacagcctg   1560
ctgtacgagt acttcaccgt gtacaacgag ctgaccaaag tgaaatacgt gaccgaggga   1620
atgagaaagc ccgccttcct gagcggcgag cagaaaaagg ccatcgtgga cctgctgttc   1680
aagaccaaca gaaaagtgac cgtgaagcag ctgaaagagg actacttcaa gaaaatcgag   1740
tgcttcgact ccgtggaaat ctccggcgtg gaagatagat caacgcctc cctgggcaca   1800 taccacgatc tgctgaaaat tatcaaggac aaggacttcc tggataacga agagaacgag   1860
gacattctgg aagatatcgt gctgaccctg acactgtttg aggaccgcga tgatcgag   1920 gaaaggctga aaacctacgc tcacctgttc gacgacaaag tgatgaagca gctgaagaga   1980
aggcggtaca ccggctgggg caggctgagc agaaagctga tcaacggcat cagagacaag   2040
cagagcggca gacaatcct ggatttcctg aagtccgacg gcttcgccaa ccggaacttc   2100
atgcagctga tccacgacga cagcctgaca ttcaaagagg acatccagaa agcccaggtg   2160
tccggccagg gcgactctct gcacgagcat atcgctaacc tggccggcag ccccgctatc   2220
aagaagggca tcctgcagac agtgaaggtg gtggacgagc tcgtgaaagt gatgggcaga   2280
cacaagcccg agaacatcgt gatcgagatg gctagagaga accagaccac ccagaaggga   2340
cagaagaact cccgcgagag gatgaagaga atcgaagagg gcatcaaaga gctgggcagc   2400
cagatcctga agaacacccc cgtggaaaac acccagctgc agaacgagaa gctgtacctg   2460
tactacctgc agaatggccg ggatatgtac gtggaccagg aactggacat caacagactg   2520
tccgactacg atgtggacca tatcgtgcct cagagctttc tgaaggacga ctccatcgat   2580
aacaaagtgc tgactcggag cgacaagaac agaggcaaga gcgacaacgt gccctccgaa   2640
gaggtcgtga agaagatgaa gaactactgg cgacagctgc tgaacgccaa gctgattacc   2700
cagaggaagt tcgataacct gaccaaggcc gagagaggcg gcctgagcga gctggataag   2760
gccggcttca tcaagaggca gctggtggaa accagacaga tcacaaagca cgtggcacag   2820
atcctggact cccggatgaa cactaagtac gacgaaaacg ataagctgat ccgggaagtg   2880
aaagtgatca ccctgaagtc caagctggtg tccgatttcc ggaaggattt ccagttttac   2940
aaagtgcgcg agatcaacaa ctaccaccac gcccacgacg cctacctgaa cgccgtcgtg   3000
ggaaccgccc tgatcaaaaa gtaccctaag ctggaaagcg agttcgtgta cggcgactac   3060
aaggtgtacg acgtgcggaa gatgatcgcc aagagcgagc aggaaatcgg caaggctacc   3120
gccaagtact tcttctacag caacatcatg aactttttca gaccgaaat caccctggcc   3180 aacggcgaga tcagaaagcg ccctctgatc gagacaaacg gcgaaaccgg ggagatcgtg   3240
tgggataagg gcagagactt cgccacagtg cgaaaggtgc tgagcatgcc ccaagtgaat   3300
atcgtgaaaa agaccgaggt gcagacaggc ggcttcagca agagtctat cctgcccaag   3360 aggaacagcg acaagctgat cgccagaaag aaggactggg accccaagaa gtacggcggc   3420
ttcgacagcc ctaccgtggc ctactctgtg ctggtggtgg ctaaggtgga aaagggcaag   3480
```

```
tccaagaaac tgaagagtgt gaaagagctg ctggggatca ccatcatgga agaagcagc      3540 tttgagaaga accctatcga ctttctggaa gccaagggct acaaagaagt gaaaaaggac      3600
ctgatcatca agctgcctaa gtactccctg ttcgagctgg aaaacggcag aaagagaatg      3660
ctggcctctg ccggcgaact gcagaaggga acgagctgg ccctgcctag caaatatgtg       3720
aacttcctgt acctggcctc ccactatgag aagctgaagg gcagccctga ggacaacgaa      3780
cagaaacagc tgtttgtgga acagcataag cactacctgg acgagatcat cgagcagatc      3840
agcgagttct ccaagagagt gatcctggcc gacgccaatc tggacaaggt gctgtctgcc      3900
tacaacaagc acagggacaa gcctatcaga gagcaggccg agaatatcat ccacctgttc      3960
accctgacaa acctgggcgc tcctgccgcc ttcaagtact tgacaccac catcgaccgg       4020 aagaggtaca ccagcaccaa agaggtgctg acgccaccc tgatccacca gagcatcacc       4080
ggcctgtacg agacaagaat cgacctgtct cagctgggag gcgacaagag acctgccgcc      4140
actaagaagg ccggacaggc caaaaagaag aagggtggag gtggaagtgg aggaggcggc      4200
tcaggtggag gtggttccat ggttaatccg accgtttttt ttgatatcgc agttgatggc      4260
gaaccgttgg gcagggtttc cttcgagctc ttcgccgata agtgccgaa aaccgcagaa       4320 aactttcgcg cgctcagtac gggtgaaaag gggtttggtt acaaagggag ctgttttcat      4380
cgaatcattc ctggtttcat gtgtcagggc ggagatttca cccgacataa cgggactggc      4440
gggaagagta tatatggaga gaagttcgag gatgagaact ttatactgaa acacaccgga      4500
cccggaattt tgagtatggc aaatgcaggg cctaacacca atggctccca gttctttatt      4560
tgtacggcca agacagagtg gctcgacggg aagcacgttg tgttcggaaa ggtcaaagaa      4620
ggtatgaata tagtagaggc gatggaacgg tttggctcac gcaatggcaa gacatccaaa      4680
aaaatcacaa tagctgactg tggccaattg gagtaa                                4716
```

<210> SEQ ID NO 23
<211> LENGTH: 1570
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Met Asp Lys Pro Lys Lys Arg Lys Val Lys Tyr Ser Ile Gly Leu
1               5                   10                  15

Asp Ile Gly Thr Asn Ser Val Gly Trp Ala Val Ile Thr Asp Glu Tyr
                20                  25                  30

Lys Val Pro Ser Lys Lys Phe Lys Val Leu Gly Asn Thr Asp Arg His
            35                  40                  45

Ser Ile Lys Lys Asn Leu Ile Gly Ala Leu Leu Phe Asp Ser Gly Glu
        50                  55                  60

Thr Ala Glu Ala Thr Arg Leu Lys Arg Thr Ala Arg Arg Arg Tyr Thr
65                  70                  75                  80

Arg Arg Lys Asn Arg Ile Cys Tyr Leu Gln Glu Ile Phe Ser Asn Glu
                85                  90                  95

Met Ala Lys Val Asp Asp Ser Phe Phe His Arg Leu Glu Glu Ser Phe
            100                 105                 110

Leu Val Glu Glu Asp Lys Lys His Glu Arg His Pro Ile Phe Gly Asn
        115                 120                 125

Ile Val Asp Glu Val Ala Tyr His Glu Lys Tyr Pro Thr Ile Tyr His
        130                 135                 140
```

```
Leu Arg Lys Lys Leu Val Asp Ser Thr Asp Lys Ala Asp Leu Arg Leu
145                 150                 155                 160

Ile Tyr Leu Ala Leu Ala His Met Ile Lys Phe Arg Gly His Phe Leu
            165                 170                 175

Ile Glu Gly Asp Leu Asn Pro Asp Asn Ser Asp Val Asp Lys Leu Phe
        180                 185                 190

Ile Gln Leu Val Gln Thr Tyr Asn Gln Leu Phe Glu Glu Asn Pro Ile
    195                 200                 205

Asn Ala Ser Gly Val Asp Ala Lys Ala Ile Leu Ser Ala Arg Leu Ser
210                 215                 220

Lys Ser Arg Arg Leu Glu Asn Leu Ile Ala Gln Leu Pro Gly Glu Lys
225                 230                 235                 240

Lys Asn Gly Leu Phe Gly Asn Leu Ile Ala Leu Ser Leu Gly Leu Thr
                245                 250                 255

Pro Asn Phe Lys Ser Asn Phe Asp Leu Ala Glu Asp Ala Lys Leu Gln
            260                 265                 270

Leu Ser Lys Asp Thr Tyr Asp Asp Leu Asp Asn Leu Leu Ala Gln
        275                 280                 285

Ile Gly Asp Gln Tyr Ala Asp Leu Phe Leu Ala Ala Lys Asn Leu Ser
    290                 295                 300

Asp Ala Ile Leu Leu Ser Asp Ile Leu Arg Val Asn Thr Glu Ile Thr
305                 310                 315                 320

Lys Ala Pro Leu Ser Ala Ser Met Ile Lys Arg Tyr Asp Glu His His
                325                 330                 335

Gln Asp Leu Thr Leu Leu Lys Ala Leu Val Arg Gln Gln Leu Pro Glu
            340                 345                 350

Lys Tyr Lys Glu Ile Phe Phe Asp Gln Ser Lys Asn Gly Tyr Ala Gly
        355                 360                 365

Tyr Ile Asp Gly Gly Ala Ser Gln Glu Glu Phe Tyr Lys Phe Ile Lys
    370                 375                 380

Pro Ile Leu Glu Lys Met Asp Gly Thr Glu Glu Leu Leu Val Lys Leu
385                 390                 395                 400

Asn Arg Glu Asp Leu Leu Arg Lys Gln Arg Thr Phe Asp Asn Gly Ser
                405                 410                 415

Ile Pro His Gln Ile His Leu Gly Glu Leu His Ala Ile Leu Arg Arg
            420                 425                 430

Gln Glu Asp Phe Tyr Pro Phe Leu Lys Asp Asn Arg Glu Lys Ile Glu
        435                 440                 445

Lys Ile Leu Thr Phe Arg Ile Pro Tyr Tyr Val Gly Pro Leu Ala Arg
    450                 455                 460

Gly Asn Ser Arg Phe Ala Trp Met Thr Arg Lys Ser Glu Glu Thr Ile
465                 470                 475                 480

Thr Pro Trp Asn Phe Glu Glu Val Val Asp Lys Gly Ala Ser Ala Gln
                485                 490                 495

Ser Phe Ile Glu Arg Met Thr Asn Phe Asp Lys Asn Leu Pro Asn Glu
            500                 505                 510

Lys Val Leu Pro Lys His Ser Leu Leu Tyr Glu Tyr Phe Thr Val Tyr
        515                 520                 525

Asn Glu Leu Thr Lys Val Lys Tyr Val Thr Glu Gly Met Arg Lys Pro
    530                 535                 540

Ala Phe Leu Ser Gly Glu Gln Lys Lys Ala Ile Val Asp Leu Leu Phe
545                 550                 555                 560
```

```
Lys Thr Asn Arg Lys Val Thr Val Lys Gln Leu Lys Glu Asp Tyr Phe
            565                 570                 575
Lys Lys Ile Glu Cys Phe Asp Ser Val Glu Ile Ser Gly Val Glu Asp
        580                 585                 590
Arg Phe Asn Ala Ser Leu Gly Thr Tyr His Asp Leu Leu Lys Ile Ile
            595                 600                 605
Lys Asp Lys Asp Phe Leu Asp Asn Glu Glu Asn Glu Asp Ile Leu Glu
        610                 615                 620
Asp Ile Val Leu Thr Leu Thr Leu Phe Glu Asp Arg Glu Met Ile Glu
625                 630                 635                 640
Glu Arg Leu Lys Thr Tyr Ala His Leu Phe Asp Asp Lys Val Met Lys
                645                 650                 655
Gln Leu Lys Arg Arg Arg Tyr Thr Gly Trp Gly Arg Leu Ser Arg Lys
            660                 665                 670
Leu Ile Asn Gly Ile Arg Asp Lys Gln Ser Gly Lys Thr Ile Leu Asp
        675                 680                 685
Phe Leu Lys Ser Asp Gly Phe Ala Asn Arg Asn Phe Met Gln Leu Ile
    690                 695                 700
His Asp Asp Ser Leu Thr Phe Lys Glu Asp Ile Gln Lys Ala Gln Val
705                 710                 715                 720
Ser Gly Gln Gly Asp Ser Leu His Glu His Ile Ala Asn Leu Ala Gly
                725                 730                 735
Ser Pro Ala Ile Lys Lys Gly Ile Leu Gln Thr Val Lys Val Val Asp
            740                 745                 750
Glu Leu Val Lys Val Met Gly Arg His Lys Pro Glu Asn Ile Val Ile
        755                 760                 765
Glu Met Ala Arg Glu Asn Gln Thr Thr Gln Lys Gly Gln Lys Asn Ser
770                 775                 780
Arg Glu Arg Met Lys Arg Ile Glu Glu Gly Ile Lys Glu Leu Gly Ser
785                 790                 795                 800
Gln Ile Leu Lys Glu His Pro Val Glu Asn Thr Gln Leu Gln Asn Glu
                805                 810                 815
Lys Leu Tyr Leu Tyr Tyr Leu Gln Asn Gly Arg Asp Met Tyr Val Asp
            820                 825                 830
Gln Glu Leu Asp Ile Asn Arg Leu Ser Asp Tyr Asp Val Asp His Ile
        835                 840                 845
Val Pro Gln Ser Phe Leu Lys Asp Asp Ser Ile Asp Asn Lys Val Leu
        850                 855                 860
Thr Arg Ser Asp Lys Asn Arg Gly Lys Ser Asp Asn Val Pro Ser Glu
865                 870                 875                 880
Glu Val Val Lys Lys Met Lys Asn Tyr Trp Arg Gln Leu Leu Asn Ala
                885                 890                 895
Lys Leu Ile Thr Gln Arg Lys Phe Asp Asn Leu Thr Lys Ala Glu Arg
            900                 905                 910
Gly Gly Leu Ser Glu Leu Asp Lys Ala Gly Phe Ile Lys Arg Gln Leu
        915                 920                 925
Val Glu Thr Arg Gln Ile Thr Lys His Val Ala Gln Ile Leu Asp Ser
    930                 935                 940
Arg Met Asn Thr Lys Tyr Asp Glu Asn Asp Lys Leu Ile Arg Glu Val
945                 950                 955                 960
Lys Val Ile Thr Leu Lys Ser Lys Leu Val Ser Asp Phe Arg Lys Asp
                965                 970                 975
Phe Gln Phe Tyr Lys Val Arg Glu Ile Asn Asn Tyr His His Ala His
```

-continued

```
            980             985             990
Asp Ala Tyr Leu Asn Ala Val Val Gly Thr Ala Leu Ile Lys Lys Tyr
                995             1000            1005
Pro Lys Leu Glu Ser Glu Phe Val Tyr Gly Asp Tyr Lys Val Tyr
     1010            1015            1020
Asp Val Arg Lys Met Ile Ala Lys Ser Glu Gln Glu Ile Gly Lys
     1025            1030            1035
Ala Thr Ala Lys Tyr Phe Phe Tyr Ser Asn Ile Met Asn Phe Phe
     1040            1045            1050
Lys Thr Glu Ile Thr Leu Ala Asn Gly Glu Ile Arg Lys Arg Pro
     1055            1060            1065
Leu Ile Glu Thr Asn Gly Glu Thr Gly Glu Ile Val Trp Asp Lys
     1070            1075            1080
Gly Arg Asp Phe Ala Thr Val Arg Lys Val Leu Ser Met Pro Gln
     1085            1090            1095
Val Asn Ile Val Lys Lys Thr Glu Val Gln Thr Gly Gly Phe Ser
     1100            1105            1110
Lys Glu Ser Ile Leu Pro Lys Arg Asn Ser Asp Lys Leu Ile Ala
     1115            1120            1125
Arg Lys Lys Asp Trp Asp Pro Lys Lys Tyr Gly Gly Phe Asp Ser
     1130            1135            1140
Pro Thr Val Ala Tyr Ser Val Leu Val Val Ala Lys Val Glu Lys
     1145            1150            1155
Gly Lys Ser Lys Lys Leu Lys Ser Val Lys Glu Leu Leu Gly Ile
     1160            1165            1170
Thr Ile Met Glu Arg Ser Ser Phe Glu Lys Asn Pro Ile Asp Phe
     1175            1180            1185
Leu Glu Ala Lys Gly Tyr Lys Glu Val Lys Lys Asp Leu Ile Ile
     1190            1195            1200
Lys Leu Pro Lys Tyr Ser Leu Phe Glu Leu Glu Asn Gly Arg Lys
     1205            1210            1215
Arg Met Leu Ala Ser Ala Gly Glu Leu Gln Lys Gly Asn Glu Leu
     1220            1225            1230
Ala Leu Pro Ser Lys Tyr Val Asn Phe Leu Tyr Leu Ala Ser His
     1235            1240            1245
Tyr Glu Lys Leu Lys Gly Ser Pro Glu Asp Asn Glu Gln Lys Gln
     1250            1255            1260
Leu Phe Val Glu Gln His Lys His Tyr Leu Asp Glu Ile Ile Glu
     1265            1270            1275
Gln Ile Ser Glu Phe Ser Lys Arg Val Ile Leu Ala Asp Ala Asn
     1280            1285            1290
Leu Asp Lys Val Leu Ser Ala Tyr Asn Lys His Arg Asp Lys Pro
     1295            1300            1305
Ile Arg Glu Gln Ala Glu Asn Ile Ile His Leu Phe Thr Leu Thr
     1310            1315            1320
Asn Leu Gly Ala Pro Ala Ala Phe Lys Tyr Phe Asp Thr Thr Ile
     1325            1330            1335
Asp Arg Lys Arg Tyr Thr Ser Thr Lys Glu Val Leu Asp Ala Thr
     1340            1345            1350
Leu Ile His Gln Ser Ile Thr Gly Leu Tyr Glu Thr Arg Ile Asp
     1355            1360            1365
Leu Ser Gln Leu Gly Gly Asp Lys Arg Pro Ala Ala Thr Lys Lys
     1370            1375            1380
```

-continued

Ala Gly Gln Ala Lys Lys Lys Gly Gly Gly Ser Gly Gly
1385                 1390                1395

Gly Gly Ser Gly Gly Gly Ser Val Asn Pro Thr Val Phe Phe
1400             1405                1410

Asp Ile Ala Val Asp Gly Glu Pro Leu Gly Arg Val Ser Phe Glu
1415             1420                1425

Leu Phe Ala Asp Lys Val Pro Lys Thr Ala Glu Asn Phe Arg Ala
1430             1435                1440

Leu Ser Thr Gly Glu Lys Gly Phe Gly Tyr Lys Gly Ser Cys Phe
1445             1450                1455

His Arg Ile Ile Pro Gly Phe Met Cys Gln Gly Gly Asp Phe Thr
1460             1465                1470

Arg His Asn Gly Thr Gly Gly Lys Ser Ile Tyr Gly Glu Lys Phe
1475             1480                1485

Glu Asp Glu Asn Phe Ile Leu Lys His Thr Gly Pro Gly Ile Leu
1490             1495                1500

Ser Met Ala Asn Ala Gly Pro Asn Thr Asn Gly Ser Gln Phe Phe
1505             1510                1515

Ile Cys Thr Ala Lys Thr Glu Trp Leu Asp Gly Lys His Val Val
1520             1525                1530

Phe Gly Lys Val Lys Glu Gly Met Asn Ile Val Glu Ala Met Glu
1535             1540                1545

Arg Phe Gly Ser Arg Asn Gly Lys Thr Ser Lys Lys Ile Thr Ile
1550             1555                1560

Ala Asp Cys Gly Gln Leu Glu
1565             1570

<210> SEQ ID NO 24
<211> LENGTH: 9
<212> TYPE: PRT
<213> ORGANISM: Unknown
<220> FEATURE:
<223> OTHER INFORMATION: Description of Unknown:
      LAGLIDADG family peptide motif sequence

<400> SEQUENCE: 24

Leu Ala Gly Leu Ile Asp Ala Asp Gly
1               5

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(21)
<223> OTHER INFORMATION: a, c, t, g, unknown or other

<400> SEQUENCE: 25
gnnnnnnnnn nnnnnnnnnn ngg                                              23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (1)..(21)
<223> OTHER INFORMATION: a, c, t, g, unknown or other

<400> SEQUENCE: 26
nnnnnnnnnn nnnnnnnnnn ngg                                              23

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(23)
<223> OTHER INFORMATION: a, c, t, g, unknown or other

<400> SEQUENCE: 27
ggnnnnnnnn nnnnnnnnnn nnngg                                            25

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(21)
<223> OTHER INFORMATION: a, c, t, g, unknown or other

<400> SEQUENCE: 28
gnnnnnnnnn nnnnnnnnnn ngg                                              23

<210> SEQ ID NO 29
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t, g, unknown or other

<400> SEQUENCE: 29
nnnnnnnnnn ngg                                                         13

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(23)
<223> OTHER INFORMATION: a, c, t, g, unknown or other

<400> SEQUENCE: 30
ggnnnnnnnn nnnnnnnnnn nnngg                                            25

<210> SEQ ID NO 31
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
atcacaaacc agttaaccgg                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tttcagacga gccgacccgg                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tgtgtgtcat agcgatgtcg                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aacaggtacc ctatcctcac                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggcccggacc tagtctctct                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tcgtggttgc atgcgcactg                                              20

<210> SEQ ID NO 37
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gggaacccac agcatactcc                                                    20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gaatcatgca cggctacccc                                                    20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
tgctcctatg gggaggcgcg                                                    20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
actgagatca atgaccccga                                                    20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gggtcgcccg gaacctctac                                                    20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cttggataac attgataccc                                                    20

<210> SEQ ID NO 43
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 43
ggggcagagc ccttatatca                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tcgctcacat taatccctag                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tgtgggcctt tgctgatcac                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
aatctatgat cctatggcct                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tgccaatagc agtgacttga                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gggaagaatg ggctattgtc                                              20

<210> SEQ ID NO 49
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 49
ggttgtttgt gctgatgacg                                                   20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ccgtcctagg ccttctacgt                                                   20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gtactgggga atcggtggtc                                                   20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cacgcactcc aaatttatcc                                                   20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ctaagtgtgt atcagtacat                                                   20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tgccctgcac aataagcgca                                                   20

<210> SEQ ID NO 55
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 55
actcattgaa acgttatggc                                                   20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
agtaagggtg gattaaattc                                                   20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gccatctaga ttcatgtaac                                                   20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gactagaaat gttctgcacc                                                   20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gggcgaggag ctgttcaccg                                                   20

<210> SEQ ID NO 60
<211> LENGTH: 9198
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
tggaagggct aattcactcc caaagaagac aagatatcct tgatctgtgg atctaccaca        60
cacaaggcta cttccctgat tagcagaact acacaccagg gccagggqtc agatatccac       120 tgacctttgg atggtgctac aagctagtac cagttgagcc agataaggta gaagaggcca       180
ataaaggaga gaacaccagc ttgttacacc ctgtgagcct gcatgggatg gatgacccgg       240
agagagaagt gttagagtgg aggtttgaca gccgcctagc atttcatcac gtggcccgag       300
```

```
agctgcatcc ggagtacttc aagaactgct gatatcgagc ttgctacaag ggactttccg      360
ctggggactt tccagggagg cgtggcctgg gcgggactgg ggagtggcga gccctcagat      420
cctgcatata agcagctgct ttttgcctgt actgggtctc tctggttaga ccagatctga      480
gcctgggagc tctctggcta actagggaac ccactgctta agcctcaata agcttgcct       540
tgagtgcttc aagtagtgtg tgcccgtctg ttgtgtgact ctggtaacta gagatccctc      600
agaccctttt agtcagtgtg gaaaatctct agcagtggcg cccgaacagg gacttgaaag      660
cgaaagggaa accagaggag ctctctcgac gcaggactcg gcttgctgaa gcgcgcacgg      720
caagaggcga gggcggcga ctggtgagta cgccaaaaat tttgactagc ggaggctaga       780
aggagagaga tgggtgcgag agcgtcagta ttaagcgggg gagaattaga tcgcgatggg      840
aaaaaattcg gttaaggcca gggggaaaga aaaaatataa attaaaacat atagtatggg      900
caagcaggga gctagaacga ttcgcagtta atcctggcct gttagaaaca tcagaaggct      960
gtagacaaat actgggacag ctacaaccat cccttcagac aggatcagaa gaacttagat     1020
cattatataa tacagtagca accctctatt gtgtgcatca aaggatagag ataaaagaca     1080
ccaaggaagc tttagacaag atagaggaag agcaaaacaa aagtaagacc accgcacagc     1140
aagcggccgg ccgctgatct tcagacctgg aggaggagat atgagggaca attggagaag     1200
tgaattatat aaatataaag tagtaaaaat tgaaccatta ggagtagcac ccaccaaggc     1260
aaagagaaga gtggtgcaga gagaaaaaag agcagtggga ataggagctt tgttccttgg     1320
gttcttggga gcagcaggaa gcactatggg cgcagcgtca atgacgctga cggtacaggc     1380
cagacaatta ttgtctggta tagtgcagca gcagaacaat ttgctgaggg ctattgaggc     1440
gcaacagcat ctgttgcaac tcacagtctg gggcatcaag cagctccagg caagaatcct     1500
ggctgtggaa agatacctaa aggatcaaca gctcctgggg atttggggtt gctctggaaa     1560
actcatttgc accactgctg tgccttggaa tgctagttgg agtaataaat ctctggaaca     1620
gatttggaat cacacgacct ggatggagtg ggacagagaa attaacaatt acacaagctt     1680
aatacactcc ttaattgaag aatcgcaaaa ccagcaagaa aagaatgaac aagaattatt     1740
ggaattagat aaatgggcaa gtttgtggaa ttggtttaac ataacaaatt ggctgtggta     1800
tataaaatta ttcataatga tagtaggagg cttggtaggt ttaagaatag ttttgctgt      1860
actttctata gtgaatagag ttaggcaggg atattcacca ttatcgtttc agacccacct     1920
cccaaccccg aggggacccg acaggcccga aggaatagaa gaagaaggtg gagagagaga     1980
cagagacaga tccattcgat tagtgaacgg atctcgacgg tatcgccttt aaaagaaaag     2040
gggggattgg ggggtacagt gcaggggaaa gaatagtaga cataatagca acagacatac     2100
aaactaaaga attacaaaaa caaattacaa aaattcaaaa ttttcgggtt tattacaggg     2160
acagcagaga tccagttttg tacaaaggtc gggcaggaag agggcctatt tcccatgatt     2220
ccttcatatt tgcatatacg atacaaggct gttagagaga taattagaat taatttgact     2280
gtaaacacaa agatattagt acaaaatacg tgacgtagaa agtaataatt tcttgggtag     2340
tttgcagttt taaaattatg ttttaaaatg gactatcata tgcttaccgt aacttgaaag     2400
tatttcgatt tcttggcttt atatatcttg tggaaaggac gaaacaccgg gcgaggagct     2460
gttcaccggt tttagagcta gaaatagcaa gttaaaataa ggctagtccg ttatcaactt     2520
gaaaaagtgg caccgagtcg gtgctttttt tatcgatgag taattcatac aaaaggactc     2580
gccccctgcct tggggaatcc cagggaccgt cgttaaactc ccactaacgt agaacccaga     2640
```

```
gatcgctgcg ttcccgcccc ctcacccgcc cgctctcgtc atcactgagg tggagaagag    2700
catgcgtgag gctccggtgc ccgtcagtgg gcagagcgca catcgcccac agtccccgag    2760
aagttggggg gaggggtcgg caattgaacc ggtgcctaga aaggtggcg  cggggtaaac    2820
tgggaaagtg atgtcgtgta ctggctccgc ctttttcccg agggtggggg agaaccgtat    2880
ataagtgcag tagtcgccgt gaacgttctt tttcgcaacg ggtttgccgc cagaacacag    2940
gtaagtgccg tgtgtggttc ccgcgggcct ggcctcttta cgggttatgg cccttgcgtg    3000
ccttgaatta cttccacgcc cctggctgca gtacgtgatt cttgatcccg agcttcgggt    3060
tggaagtggg tgggagagtt cgaggccttg cgcttaagga gcccttcgc  ctcgtgcttg    3120
agttgaggcc tggcttgggc gctggggccg ccgcgtgcga atctggtggc accttcgcgc    3180
ctgtctcgct gctttcgata agtctctagc catttaaaat ttttgatgac ctgctgcgac    3240
gctttttttc tggcaagata gtcttgtaaa tgcgggccaa gatctgcaca ctggtatttc    3300
ggttttggg  gccgcgggcg cgacggggcc ccgtgcgtcc cagcgcacat gttcggcgag    3360
gcggggcctg cgagcgcggc caccgagaat cggacggggg tagtctcaag ctggccggcc    3420
tgctctggtg cctggcctcg cgccgccgtg tatcgccccg ccctgggcgg caaggctggc    3480
ccggtcggca ccagttgcgt gagcggaaag atggccgctt cccggccctg ctgcaggag    3540
ctcaaaatgg aggacgcggc gctcgggaga gcgggcgggt gagtcaccca cacaaaggaa    3600
aagggccttt ccgtcctcag ccgtcgcttc atgtgactcc acggagtacc gggcgccgtc    3660
caggcacctc gattagttct cgagcttttg gagtacgtcg tctttaggtt gggggagg     3720
gttttatgcg atggagtttc cccacactga gtgggtggag actgaagtta ggccagcttg    3780
gcacttgatg taattctcct tggaatttgc ccttttgag  tttggatctt ggttcattct    3840
caagcctcag acagtggttc aaagtttttt tcttccattt caggtgtcgt gaggatctat    3900
ttccggtgaa ttcctcgaga ctagttctag agcggccgcg gatcccgccc ctctccctcc    3960
ccccccccta cgttactgg  ccgaagccgc ttggaataag gccggtgtgc gtttgtctat    4020
atgttatttt ccaccatatt gccgtctttt ggcaatgtga gggcccggaa acctggccct    4080
gtcttcttga cgagcattcc tagggtgtct tcccctctcg ccaaaggaat gcaaggtctg    4140
ttgaatgtcg tgaaggaagc agttcctctg gaagcttctt gaagacaaac aacgtctgta    4200
gcgacccttt gcaggcagcg gaaccccca  cctggcgaca ggtgcctctg cggccaaaag    4260
ccacgtgtat aagatacacc tgcaaaggcg gcacaacccc agtgccacgt tgtgagttgg    4320
atagttgtgg aaagagtcaa atggctctcc tcaagcgtat tcaacaaggg gctgaaggat    4380
gcccagaagg taccccattg tatgggatct gatctggggc ctcggtgcac atgctttaca    4440
tgtgtttagt cgaggttaaa aaacgtctca ggcccccga  accacgggga cgtggttttc    4500
ctttgaaaaa cacgatgata agcttgccac aacccacaag gagacgacct tccatgaccg    4560
agtacaagcc cacggtgcgc ctcgccaccc gcgacgacgt ccccgggcc  gtacgcaccc    4620
tcgccgccgc gttcgccgac tacccgcca  cgcgccacac cgtcgacccg gaccgccaca    4680
tcgagcgggt caccgagctg caagaactct tcctcacgcg cgtcgggctc gacatcggca    4740
aggtgtgggt cgcggacgac ggcgccgcgg tggcggtctg gaccacgccg gagagcgtcg    4800
aagcgggggc ggtgttcgcc gagatcggcc cgcgcatggc cgagttgagc ggttcccggc    4860
tggccgcgca gcaacagatg gaaggcctcc tggcgccgca ccggcccaag agcccgcgt    4920
ggttcctggc caccgtcggc gtctcgcccg accaccaggg caagggtctg gcagcgccc    4980
tcgtgctccc cggagtggag gcggccgagc gcgccggggt gcccgccttc ctggagacct    5040
```

```
ccgcgcccg  caacctcccc  ttctacgagc  ggctcggctt  caccgtcacc  gccgacgtcg    5100
aggtgcccga  aggaccgcgc  acctggtgca  tgacccgcaa  gcccggtgcc  tagacgcgtc    5160
tggaacaatc  aacctctgga  ttacaaaatt  tgtgaaagat  tgactggtat  tcttaactat    5220
gttgctcctt  ttacgctatg  tggatacgct  gctttaatgc  ctttgtatca  tgctattgct    5280
tcccgtatgg  ctttcatttt  ctcctccttg  tataaatcct  ggttgctgtc  tctttatgag    5340
gagttgtggc  ccgttgtcag  gcaacgtggc  gtggtgtgca  ctgtgtttgc  tgacgcaacc    5400
cccactggtt  ggggcattgc  caccacctgt  cagctccttt  ccgggacttt  cgctttcccc    5460
ctccctattg  ccacggcgga  actcatcgcc  gcctgccttg  cccgctgctg  acaggggct    5520 cggctgttgg  gcactgacaa  ttccgtggtg  ttgtcgggga  agctgacgtc  ctttccatgg    5580
ctgctcgcct  gtgttgccac  ctggattctg  cgcgggacgt  ccttctgcta  cgtcccttcg    5640
gccctcaatc  cagcggacct  tccttcccgc  ggcctgctgc  cggctctgcg  gcctcttccg    5700
cgtcttcgcc  ttcgccctca  gacgagtcgg  atctccctt  gggccgcctc  cccgcctgga    5760
attaattctg  cagtcgagac  ctagaaaaac  atggagcaat  cacaagtagc  aatacagcag    5820
ctaccaatgc  tgattgtgcc  tggctagaag  cacaagagga  ggaggaggtg  ggttttccag    5880
tcacacctca  ggtacccttta  agaccaatga  cttacaaggc  agctgtagat  cttagccact    5940
ttttaaaaga  aaagaggga  ctggaagggc  taattcactc  ccaacgaaga  caagatatcc    6000
ttgatctgtg  gatctaccac  acacaaggct  acttccctga  ttagcagaac  tacacaccag    6060
ggccaggggt  cagatatcca  ctgacctttg  gatggtgcta  caagctagta  ccagttgagc    6120
cagataaggt  agaagaggcc  aataaaggag  agaacaccag  cttgttacac  cctgtgagcc    6180
tgcatgggat  ggatgacccg  gagagagaag  tgttagagtg  gaggtttgac  agccgcctag    6240
catttcatca  cgtggcccga  gagctgcatc  cggagtactt  caagaactgc  tgatatcgag    6300
cttgctacaa  gggactttcc  gctgggact  ttccagggag  gcgtggcctg  ggcgggactg    6360
gggagtggcg  agccctcaga  tcctgcatat  aagcagctgc  tttttgcctg  tactgggtct    6420
ctctggttag  accagatctg  agcctgggag  ctctctggct  aactagggaa  cccactgctt    6480
aagcctcaat  aaagcttgcc  ttgagtgctt  caagtagtgt  gtgcccgtct  gttgtgtgac    6540
tctggtaact  agagatccct  cagacccttt  tagtcagtgt  ggaaaatctc  tagcagtagt    6600
agttcatgtc  atcttattat  tcagtattta  taacttgcaa  agaaatgaat  atcagagagt    6660
gagaggcctt  gacattgcta  gcgtttaccg  tcgacctcta  gctagagctt  ggcgtaatca    6720
tggtcatagc  tgtttcctgt  gtgaaattgt  tatccgctca  caattccaca  caacatacga    6780
gccggaagca  taaagtgtaa  agcctggggt  gcctaatgag  tgagctaact  cacattaatt    6840
gcgttgcgct  cactgcccgc  tttccagtcg  ggaaacctgt  cgtgccagct  gcattaatga    6900
atcggccaac  gcgcgggag  aggcggtttg  cgtattgggc  gctcttccgc  ttcctcgctc    6960
actgactcgc  tgcgctcggt  cgttcggctg  cggcgagcgg  tatcagctca  ctcaaaggcg    7020
gtaatacggt  tatccacaga  atcaggggat  aacgcaggaa  agaacatgtg  agcaaaaggc    7080
cagcaaaagg  ccaggaaccg  taaaaaggcc  gcgttgctgg  cgtttttcca  taggctccgc    7140 cccctgacg  agcatcacaa  aaatcgacgc  tcaagtcaga  ggtggcgaaa  cccgacagga    7200
ctataaagat  accaggcgtt  tcccctgga  agctccctcg  tgcgctctcc  tgttccgacc    7260
ctgccgctta  ccggatacct  gtccgccttt  ctcccttcgg  gaagcgtggc  gctttctcat    7320
agctcacgct  gtaggtatct  cagttcggtg  taggtcgttc  gctccaagct  gggctgtgtg    7380
```

```
cacgaacccc ccgttcagcc cgaccgctgc gccttatccg gtaactatcg tcttgagtcc    7440
aacccggtaa gacacgactt atcgccactg gcagcagcca ctggtaacag gattagcaga    7500
gcgaggtatg taggcggtgc tacagagttc ttgaagtggt ggcctaacta cggctacact    7560
agaagaacag tatttggtat ctgcgctctg ctgaagccag ttaccttcgg aaaaagagtt    7620
ggtagctctt gatccggcaa acaaaccacc gctggtagcg gtggtttttt tgtttgcaag    7680
cagcagatta cgcgcagaaa aaaggatct caagaagatc ctttgatctt ttctacgggg     7740
tctgacgctc agtggaacga aaactcacgt taagggattt tggtcatgag attatcaaaa    7800
aggatcttca cctagatcct tttaaattaa aaatgaagtt ttaaatcaat ctaaagtata    7860
tatgagtaaa cttggtctga cagttaccaa tgcttaatca gtgaggcacc tatctcagcg    7920
atctgtctat ttcgttcatc catagttgcc tgactccccg tcgtgtagat aactacgata    7980
cgggagggct taccatctgg ccccagtgct gcaatgatac cgcgagaccc acgctcaccg    8040
gctccagatt tatcagcaat aaaccagcca gccggaaggg ccgagcgcag aagtggtcct    8100
gcaactttat ccgcctccat ccagtctatt aattgttgcc gggaagctag agtaagtagt    8160
tcgccagtta atagtttgcg caacgttgtt gccattgcta caggcatcgt ggtgtcacgc    8220
tcgtcgtttg gtatggcttc attcagctcc ggttcccaac gatcaaggcg agttacatga    8280
tcccccatgt tgtgcaaaaa agcggttagc tccttcggtc ctccgatcgt tgtcagaagt    8340
aagttggccg cagtgttatc actcatggtt atggcagcac tgcataattc tcttactgtc    8400
atgccatccg taagatgctt ttctgtgact ggtgagtact caaccaagtc attctgagaa    8460
tagtgtatgc ggcgaccgag ttgctcttgc ccggcgtcaa tacgggataa taccgcgcca    8520
catagcagaa ctttaaaagt gctcatcatt ggaaaacgtt cttcggggcg aaaactctca    8580
aggatcttac cgctgttgag atccagttcg atgtaaccca ctcgtgcacc caactgatct    8640
tcagcatctt ttactttcac cagcgtttct gggtgagcaa aaacaggaag gcaaaatgcc    8700
gcaaaaaagg gaataagggc gacacggaaa tgttgaatac tcatactctt cctttttcaa    8760
tattattgaa gcatttatca gggttattgt ctcatgagcg gatacatatt tgaatgtatt    8820
tagaaaaata aacaaatagg ggttccgcgc acatttcccc gaaaagtgcc acctgacgtc    8880
gacggatcgg gagatcaact tgtttattgc agcttataat ggttacaaat aaagcaatag    8940
catcacaaat ttcacaaata aagcatttt ttcactgcat tctagttgtg gtttgtccaa     9000
actcatcaat gtatcttatc atgtctggat caactggata actcaagcta accaaaatca    9060
tcccaaactt cccaccccat acctattac cactgccaat tacctgtggt ttcatttact     9120
ctaaacctgt gattcctctg aattattttc attttaaaga aattgtattt gttaaatatg    9180
tactacaaac ttagtagt                                                 9198
```

<210> SEQ ID NO 61
<211> LENGTH: 10661
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 61

```
aagcttatac tcgagctcta gattgggaac ccgggtctct cgaattcgcc accatggtta     60
atccgaccgt tttttttgat atcgcagttg atggcgaacc gttgggcagg gtttccttcg    120
agctcttcgc cgataaagtg ccgaaaaccg cagaaaactt tcgcgcgctc agtacgggtg    180
```

-continued

```
aaaagggatt tggttacaaa gggagctgtt ttcatcgaat cattcctggt ttcatgtgtc    240
agggcggaga tttcacccga cataacggga ctggcgggaa gagtatatat ggagagaagt    300
tcgaggatga gaactttata ctgaaacaca ccggacccgg aattttgagt atggcaaatg    360
cagggcctaa caccaatggc tcccagttct ttatttgtac ggccaagaca gagtggctcg    420
acgggaagca cgttgtgttc ggaaaggtca agaaggtat gaatatagta gaggcgatgg    480
aacggtttgg ctcacgcaat ggcaagacat ccaaaaaaat cacaatagct gactgtggcc    540
aattggaggg tggaggtgga agtggaggag gcggctcagg tggaggtggt tccgacaagc    600
ccaagaaaaa gcggaaagtg aagtacagca tcggcctgga catcggcacc aactctgtgg    660
gctgggccgt gatcaccgac gagtacaagg tgcccagcaa gaaattcaag gtgctgggca    720
acaccgacag gcacagcatc aagaagaacc tgatcggcgc cctgctgttc gacagcggcg    780
aaacagccga ggccaccaga ctgaagagaa ccgcagaag aagatacacc aggcggaaga    840
acaggatctg ctatctgcaa gagatcttca gcaacgagat ggccaaggtg acgacagct    900 tcttccacag actggaagag tccttcctgg tggaagagga caagaagcac gagagacacc    960
ccatcttcgg caacatcgtg gacgaggtgg cctaccacga gaagtacccc accatctacc   1020
acctgagaaa gaaactggtg gacagcaccg acaaggccga cctgagactg atctacctgg   1080
ccctggccca catgatcaag ttcagaggcc acttcctgat cgagggcgac ctgaaccccg   1140
acaacgacga cgtggacaag ctgttcatcc agctggtgca gacctacaac cagctgttcg   1200
aggaaaaccc catcaacgcc agcggcgtgg acgccaaggc tatcctgtct gccagactga   1260
gcaagagcag aaggctggaa aatctgatcg cccagctgcc cggcgagaag aagaacggcc   1320
tgttcggcaa cctgattgcc ctgagcctgg gcctgacccc caacttcaag agcaacttcg   1380
acctggccga ggatgccaaa ctgcagctga gcaaggacac ctacgacgac gacctggaca   1440
acctgctggc ccagatcggc gaccagtacg ccgacctgtt cctggccgcc aagaacctgt   1500
ctgacgccat cctgctgagc gacatcctga gagtgaacac cgagatcacc aaggcccccc   1560
tgagcgcctc tatgatcaag agatacgacg agcaccacca ggacctgacc ctgctgaaag   1620
ctctcgtgcg gcagcagctg cctgagaagt acaaagaaat cttcttcgac cagagcaaga   1680
acggctacgc cggctacatc gatggcggcg ctagccagga agagttctac aagttcatca   1740
agcccatcct ggaaaagatg gacggcaccg aggaactgct cgtgaagctg aacagagagg   1800
acctgctgag aaagcagaga accttcgaca acggcagcat ccccaccag atccacctgg   1860 gagagctgca cgctatcctg agaaggcagg aagattttta cccattcctg aaggacaacc   1920
gggaaaagat cgagaagatc ctgaccttca ggatcccta ctacgtgggc ccctggcca   1980 gaggcaacag cagattcgcc tggatgacca aaagagcga ggaaccatc accccctgga   2040 acttcgagga agtggtggac aagggcgcca gcgcccagag cttcatcgag agaatgacaa   2100
acttcgataa gaacctgccc aacgagaagg tgctgcccaa gcacagcctg ctgtacgagt   2160
acttcaccgt gtacaacgag ctgaccaaag tgaaatacgt gaccgaggga atgagaaagc   2220
ccgccttcct gagcggcgag cagaaaaagg ccatcgtgga cctgctgttc aagaccaaca   2280
gaaaagtgac cgtgaagcag ctgaaagagg actacttcaa gaaaatcgag tgcttcgact   2340
ccgtggaaat ctccggcgtg gaagatagat tcaacgcctc cctgggcaca taccacgatc   2400
tgctgaaaat tatcaaggac aaggacttcc tggataacga agagaacgag gacattctgg   2460
aagatatcgt gctgaccctg acactgtttg aggaccgcga tgatgatcgag gaaaggctga   2520 aaacctacgc tcacctgttc gacgacaaag tgatgaagca gctgaagaga aggcggtaca   2580
```

```
ccggctgggg caggctgagc agaaagctga tcaacggcat cagagacaag cagagcggca    2640
agacaatcct ggatttcctg aagtccgacg gcttcgccaa ccggaacttc atgcagctga    2700
tccacgacga cagcctgaca ttcaaagagg acatccagaa agcccaggtg tccggccagg    2760
gcgactctct gcacgagcat atcgctaacc tggccggcag ccccgctatc aagaagggca    2820
tcctgcagac agtgaaggtg gtggacgagc tcgtgaaagt gatgggcaga cacaagcccg    2880
agaacatcgt gatcgagatg gctagagaga accagaccac ccagaaggga cagaagaact    2940
cccgcgagag gatgaagaga atcgaagagg gcatcaaaga gctgggcagc cagatcctga    3000
aagaacaccc cgtggaaaac acccagctgc agaacgagaa gctgtacctg tactacctgc    3060
agaatggccg ggatatgtac gtggaccagg aactggacat caacagactg tccgactacg    3120
atgtggacca tatcgtgcct cagagctttc tgaaggacga ctccatcgat aacaaagtgc    3180
tgactcggag cgacaagaac agaggcaaga gcgacaacgt gccctccgaa gaggtcgtga    3240
agaagatgaa gaactactgg cgacagctgc tgaacgccaa gctgattacc cagaggaagt    3300
tcgataacct gaccaaggcc gagagaggcg gcctgagcga gctggataag gccggcttca    3360
tcaagaggca gctggtggaa accagacaga tcacaaagca cgtggcacag atcctggact    3420
cccggatgaa cactaagtac gacgaaaacg ataagctgat ccgggaagtg aaagtgatca    3480
ccctgaagtc caagctggtg tccgatttcc ggaaggattt ccagttttac aaagtgcgcg    3540
agatcaacaa ctaccaccac gcccacgacg cctacctgaa cgccgtcgtg ggaaccgccc    3600
tgatcaaaaa gtaccctaag ctggaaagcg agttcgtgta cggcgactac aaggtgtacg    3660
acgtgcggaa gatgatcgcc aagagcgagc aggaaatcgg caaggctacc gccaagtact    3720
tcttctacag caacatcatg aacttttttca gaccgaaat cacccctggcc aacggcgaga    3780 tcagaaagcg ccctctgatc gagacaaacg gcgaaaccgg ggagatcgtg tgggataagg    3840
gcagagactt cgccacagtg cgaaaggtgc tgagcatgcc ccaagtgaat atcgtgaaaa    3900
agaccgaggt gcagacaggc ggcttcagca agagtctat cctgcccaag aggaacagcg    3960
acaagctgat cgccagaaag aaggactggg accccaagaa gtacggcggc ttcgacagcc    4020
ctaccgtggc ctactctgtg ctggtggtgg ctaaggtgga aaagggcaag tccaagaaac    4080
tgaagagtgt gaaagagctg ctggggatca ccatcatgga agaagcagc tttgagaaga    4140 accctatcga ctttctggaa gccaagggct acaaagaagt gaaaaaggac ctgatcatca    4200
agctgcctaa gtactccctg ttcgagctgg aaaacggcag aaagagaatg ctggcctctg    4260
ccggcgaact gcagaaggga aacgagctgg ccctgcctag caaatatgtg aacttcctgt    4320
acctggcctc ccactatgag aagctgaagg gcagccctga ggacaacgaa cagaaacagc    4380
tgtttgtgga acagcataag cactacctgg acgagatcat cgagcagatc agcgagttct    4440
ccaagagagt gatcctggcc gacgccaatc tggacaaggt gctgtctgcc tacaacaagc    4500
acagggacaa gcctatcaga gagcaggccg agaatatcat ccacctgttc accctgacaa    4560
acctgggcgc tcctgccgcc ttcaagtact ttgacaccac catcgaccgg aagaggtaca    4620
ccagcaccaa agaggtgctg gacgccaccc tgatccacca gagcatcacc ggcctgtacg    4680
agacaagaat cgacctgtct cagctgggag gcgacagag acctgccgcc actaagaagg    4740
ccggacaggc caaaaagaag aagtgagcgg ccgctaatca gccataccac atttgtagag    4800
gttttacttg cttttaaaaaa cctcccacac ctccccctga acctgaaaca taaaatgaat    4860
gcaattgttg ttgttaactt gtttattgca gcttataatg gttacaaata aagcaatagc    4920
```

```
atcacaaatt tcacaaataa agcattttt tcactgcatt ctagttgtgg tttgtccaaa    4980
ctcatcaatg tatcttatca tgtctaccgg tagggcccct ctcttcatgt gagcaaaagg    5040
ccagcaaaag gccaggaacc gtaaaaaggc gcgttgctg gcgttttcc ataggctccg      5100
cccccctgac gagcatcaca aaaatcgacg ctcaagtcag aggtggcgaa acccgacagg    5160
actataaaga taccaggcgt ttccccctgg aagctccctc gtgcgctctc ctgttccgac    5220
cctgccgctt accggatacc tgtccgcctt tctcccttcg ggaagcgtgg cgctttctca    5280
atgctcacgc tgtaggtatc tcagttcggt gtaggtcgtt cgctccaagc tgggctgtgt    5340
gcacgaaccc cccgttcagc ccgaccgctg cgccttatcc ggtaactatc gtcttgagtc    5400
caacccggta agacacgact tatcgccact ggcagcagcc actggtaaca ggattagcag    5460
agcgaggtat gtaggcggtg ctacagagtt cttgaagtgg tggcctaact acggctacac    5520
tagaaggaca gtatttggta tctgcgctct gctgaagcca gttaccttcg aaaaagagt     5580
tggtagctct tgatccggca aacaaaccac cgctggtagc ggtggttttt tgtttgcaa     5640
gcagcagatt acgcgcagaa aaaaggatc tcaagaagat cctttgatct tttctacggg     5700
gtctgacgct cagtggaacg aaaactcacg ttaagggatt ttggtcatgg gcgcgcctca    5760
tactcctgca ggcatgagat tatcaaaaag gatcttcacc tagatccttt taaattaaaa    5820
atgaagtttt aaatcaatct aaagtatata tgagtaaact tggtctgaca gttaccaatg    5880
cttaatcagt gaggcaccta tctcagcgat ctgtctattt cgttcatcca tagttgcctg    5940
actccccgtc gtgtagataa ctacgatacg ggagggctta ccatctggcc ccagtgctgc    6000
aatgataccg cgagacccac gctcaccggc tccagattta tcagcaataa accagccagc    6060
cggaagggcc gagcgcagaa gtggtcctgc aactttatcc gcctccatcc agtctattaa    6120
ttgttgccgg gaagctagag taagtagttc gccagttaat agtttgcgca acgttgttgc    6180
cattgctaca ggcatcgtgg tgtcacgctc gtcgtttggt atggcttcat tcagctccgg    6240
ttcccaacga tcaaggcgag ttacatgatc ccccatgttg tgcaaaaaag cggttagctc    6300
cttcggtcct ccgatcgttg tcagaagtaa gttggccgca gtgttatcac tcatggttat    6360
ggcagcactg cataattctc ttactgtcat gccatccgta agatgctttt ctgtgactgg    6420
tgagtactca accaagtcat tctgagaata gtgtatgcgg cgaccgagtt gctcttgccc    6480
ggcgtcaata cgggataata ccgcgccaca tagcagaact ttaaaagtgc tcatcattgg    6540
aaaacgttct cggggcgaaa actctcaag gatcttaccg ctgttgagat ccagttcgat    6600
gtaacccact cgtgcaccca actgatcttc agcatctttt actttcacca gcgtttctgg    6660
gtgagcaaaa acaggaaggc aaaatgccgc aaaaaaggga ataagggcga cacggaaatg    6720
ttgaatactc atactcttcc tttttcaata ttattgaagc atttatcagg gttattgtct    6780
catgagcgga tacatatttg aatgtattta gaaaaataaa caaatagggg ttccgcgcac    6840
atttccccga aaagtgccac ctgacgtcag gtaccaagcc taggcctcca aaaaagcctc    6900
ctcactactt ctggaatagc tcagaggcag aggcggcctc ggcctctgca taaataaaaa    6960
aaattagtca gccatggggc ggagaatggg cggaactggg cggagttagg ggcgggatgg    7020
gcggagttag gggcgggact atggttgctg actaattgag atgcatgctt tgcatacttc    7080
tgcctgctgg ggagcctggg gactttccac acctggttgc tgactaattg agatgcatgc    7140
tttgcatact tctgcctgct ggggagcctg gggactttcc acaccggatc caccatggga    7200
tcggccattg aacaagatgg attgcacgca ggttctccgg ccgcttgggt ggagaggcta    7260
ttcggctatg actgggcaca acagacaatc ggctgctctg atgccgccgt gttccggctg    7320
```

```
tcagcgcagg ggcgcccggt tcttttgtc aagaccgacc tgtccggtgc cctgaatgaa    7380
ctgcaggacg aggcagcgcg gctatcgtgg ctggccacga cgggcgttcc ttgcgcagct    7440
gtgctcgacg ttgtcactga agcgggaagg gactggctgc tattgggcga agtgccgggg    7500
caggatctcc tgtcatctca ccttgctcct gccgagaaag tatccatcat ggctgatgca    7560
atgcggcggc tgcatacgct tgatccggct acctgcccat tcgaccacca agcgaaacat    7620
cgcatcgagc gagcacgtac tcggatggaa gccggtcttg tcgatcagga tgatctggac    7680
gaagagcatc aggggctcgc gccagccgaa ctgttcgcca ggctcaaggc gcgcatgccc    7740
gacggcgatg atctcgtcgt gacccatggc gatgcctgct tgccgaatat catggtggaa    7800
aatggccgct tttctggatt catcgactgt ggccggctgg gtgtggcgga ccgctatcag    7860
gacatagcgt tggctacccg tgatattgct gaagagcttg gcggcgaatg ggctgaccgc    7920
ttcctcgtgc tttacggtat cgccgctccc gattcgcagc gcatcgcctt ctatcgcctt    7980
cttgacgagt tcttctgaac gcgtgctgta agtctgcaga aattgatgat ctattaaaca    8040
ataaagatgt ccactaaaat ggaagttttt cctgtcatac tttgttaaga agggtgagaa    8100
cagagtacct acattttgaa tggaaggatt ggagctacgg gggtggggt ggggtgggat    8160
tagataaatg cctgctcttt actgaaggct ctttactatt gctttatgat aatgtttcat    8220
agttggatat cataatttaa acaagcaaaa ccaaattaag ggccagctca ttcctcccac    8280
tcatgatcta tggatctata gatctctcgt gcagctgggg ctctagggg tatccccacg    8340
cgccctgtag cggcgcatta agcgcggcgg gtgtggtggt tacgcgcagc gtgaccgcta    8400
cacttgccag cgccctagcg cccgctcctt tcgctttctt cccttccttt ctcgccacgt    8460
tcgccggctt tccccgtcaa gctctaaatc ggggctccc tttagggttc cgatttagtg    8520
ctttacggca cctcgacccc aaaaaacttg attagggtga tggttcacgt agtgggccat    8580
cgccctgata cacggttttt cgccctttga cgttggagtc cacgttcttt aatagtggac    8640
tcttgttcca aactggaaca acactcaacc ctatctcggt ctattctttt gatttataag    8700
ggattttgcc gatttcggcc tattggttaa aaaatgagct gatttaacaa aaatttaacg    8760
cgaattaatt ctgtggaatg tgtgtcagtt agtcgcgagg cctccgcgcc gggttttggc    8820
gcctcccgcg ggcgcccccc tcctcacggc gagcgctgcc acgtcagacg aagggcgcag    8880
cgagcgtcct gatccttccg cccggacgct caggacagcg gcccgctgct cataagactc    8940
ggccttagaa ccccagtatc agcagaagga cattttagga cgggacttgg gtgactctag    9000
ggcactggtt ttctttccag agagcggaac aggcgaggaa aagtagtccc ttctcggcga    9060
ttctgcggag ggatctccgt ggggcggtga acgccgatga ttatataagg acgcgccggg    9120
tgtggcacag ctagttccgt cgcagccggg atttgggtcg cggttcttgt ttgtggatcg    9180
ctgtgatcgt cacttggtga gtagcgggct gctgggctgg ccggggcttt cgtggccgcc    9240
gggccgctcg gtgggacgga agcgtgtgga gagaccgcca agggctgtag tctgggtccg    9300
cgagcaaggt tgccctgaac tgggggttgg ggggagcgca gcaaaatggc ggctgttccc    9360
gagtcttgaa tggaagacgc ttgtgaggcg ggctgtgagg tcgttgaaac aaggtggggg    9420
gcatggtggg cggcaagaac ccaaggtctt gaggccttcg ctaatgcggg aaagctctta    9480
ttcgggtgag atgggctggg gcaccatctg gggaccctga cgtgaagttt gtcactgact    9540
ggagaactcg gtttgtcgtc tgttgcgggg cggcagtta tggcggtgcc gttgggcagt    9600
gcacccgtac ctttgggagc gcgcgccctc gtcgtgtcgt gacgtcaccc gttctgttgg    9660
```

```
cttataatgc agggtggggc cacctgccgg taggtgtgcg gtaggctttt ctccgtcgca    9720
ggacgcaggg ttcgggccta gggtaggctc tcctgaatcg acaggcgccg gacctctggt    9780
gaggggaggg ataagtgagg cgtcagtttc tttggtcggt tttatgtacc tatcttctta    9840
agtagctgaa gctccggttt tgaactatgc gctcggggtt ggcgagtgtg ttttgtgaag    9900
ttttttaggc acctttgaa atgtaatcat ttgggtcaat atgtaatttt cagtgttaga     9960
ctagtaaatt gtccgctaaa ttctggccgt ttttggcttt tttgttagac gtcgaccgat   10020
cctgagaact tcagggtgag tttggggacc cttgattgtt ctttcttttt cgctattgta   10080
aaattcatgt tatatggagg gggcaaagtt ttcagggtgt tgtttagaat gggaagatgt   10140
cccttgtatc accatggacc ctcatgataa ttttgtttct ttcactttct actctgttga   10200
caaccattgt ctcctcttat tttcttttca ttttctgtaa cttttcgtt aactttagc     10260
ttgcatttgt aacgaatttt taaattcact tttgtttatt tgtcagattg taagtacttt   10320
ctctaatcac tttttttca aggcaatcag ggtatattat attgtacttc agcacagttt    10380
tagagaacaa ttgttataat taaatgataa ggtagaatat ttctgcatat aaattctggc   10440
tggcgtggaa atattcttat tggtagaaac aactcaccc tggtcatcat cctgcctttc    10500
tctttatggt tacaatgata tacactgttt gagatgagga taaaatactc tgagtccaaa   10560
ccgggcccct ctgctaacca tgttcatgcc ttcttctttt tcctacagct cctgggcaac   10620
gtgctggttg ttgtgctgtc tcatcatttt ggcaaagaat t                       10661
```

<210> SEQ ID NO 62
<211> LENGTH: 10417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
aagcttatac tcgagctcta gaatggacaa gcccaagaaa aagcggaaag tgaagtacag     60
catcggcctg gacatcggca ccaactctgt gggctgggcc gtgatcaccg acgagtacaa    120
ggtgcccagc aagaaattca aggtgctggg caacaccgac aggcacagca tcaagaagaa    180
cctgatcggc gccctgctgt tcgacagcgg cgaaacagcc gaggccacca gactgaagag    240
aaccgccaga gaagatacca ggcggaagaa caggatc tgctatctgc aagagatctt       300
cagcaacgag atggccaagg tggacgacag cttcttccac agactggaag agtccttcct   360
ggtggaaagc gacaagaagc acgagagaca ccccatcttc ggcaacatcg tggacgaggt   420
ggcctaccac gagaagtacc ccaccatcta ccacctgaga aagaaactgg tggacagcac   480
cgacaaggcc gacctgagac tgatctacct ggccctggcc cacatgatca gttcagagg    540
ccacttcctg atcgagggcg acctgaaccc cgacaacagc gacgtggaca gctgttcat    600
ccagctggtg cagacctaca accagctgtt cgaggaaaac cccatcaacg ccagcggcgt   660
ggacgccaag gctatcctgt ctgccagact gagcaagagc agaaggctgg aaaatctgat   720
cgcccagctg cccggcgaga gaagaacgg cctgttcggc aacctgattg ccctgagcct    780
gggcctgacc cccaacttca gagcaacttc gacctggcc gaggatgcca aactgcagct    840
gagcaaggac acctacgacg acgacctgga caacctgctg gcccagatcg gcgaccagta    900
cgccgacctg ttcctggccg ccaagaacct gtctgacgcc atcctgctga gcgacatcct    960
gagagtgaac accgagatca ccaaggcccc cctgagcgcc tctatgatca agagatacga   1020
```

-continued

```
cgagcaccac caggacctga ccctgctgaa agctctcgtg cggcagcagc tgcctgagaa    1080
gtacaaagaa atcttcttcg accagagcaa gaacggctac gccggctaca tcgatggcgg    1140
cgctagccag gaagagttct acaagttcat caagcccatc ctggaaaaga tggacggcac    1200
cgaggaactg ctcgtgaagc tgaacagaga ggacctgctg agaaagcaga gaacttcga    1260 caacggcagc atcccccacc agatccacct gggagagctg cacgctatcc tgagaaggca    1320
ggaagatttt tacccattcc tgaaggacaa ccgggaaaag atcgagaaga tcctgacctt    1380
caggatcccc tactacgtgg gcccctggc cagaggcaac agcagattcg cctggatgac    1440
cagaaagagc gaggaaacca tcaccccctg gaacttcgag gaagtggtgg acaagggcgc    1500
cagcgcccag agcttcatcg agagaatgac aaacttcgat aagaacctgc caacgagaa    1560 ggtgctgccc aagcacagcc tgctgtacga gtacttcacc gtgtacaacg agctgaccaa    1620
agtgaaatac gtgaccgagg aatgagaaa gcccgccttc ctgagcggcg agcagaaaaa    1680
ggccatcgtg gacctgctgt tcaagaccaa cagaaagtg accgtgaagc agctgaaaga    1740
ggactacttc aagaaaatcg agtgcttcga ctccgtggaa atctccggcg tggaagatag    1800
attcaacgcc tccctgggca cataccacga tctgctgaaa attatcaagg acaaggactt    1860
cctggataac gaagagaacg aggacattct ggaagatatc gtgctgaccc tgacactgtt    1920
tgaggaccgc gagatgatcg aggaaaggct gaaaacctac gctcacctgt tcgacgacaa    1980
agtgatgaag cagctgaaga aaggcggta caccggctgg ggcaggctga gcagaaagct    2040
gatcaacggc atcagagaca agcagagcgg caagacaatc ctggatttcc tgaagtccga    2100
cggcttcgcc aaccggaact tcatgcagct gatccacgac gacagcctga cattcaaaga    2160
ggacatccag aaagcccagg tgtccggcca gggcgactct ctgcacgagc atatcgctaa    2220
cctggccgga agcccccgcta tcaagaaggg catcctgcag acagtgaagg tggtggacga    2280
gctcgtgaaa gtgatgggca gacacaagcc cgagaacatc gtgatcgaga tggctagaga    2340
gaaccagacc acccagaagg gacagaagaa ctcccgcgag aggatgaaga aatcgaaga    2400 gggcatcaaa gagctgggca gccagatcct gaaagaacac cccgtggaaa cacccagct    2460 gcagaacgag aagctgtacc tgtactacct gcagaatggc cgggatatgt acgtggacca    2520
ggaactggac atcaacagac tgtccgacta cgatgtggac catatcgtgc ctcagagctt    2580
tctgaaggac gactccatcg ataacaaagt gctgactcgg agcgacaaga acagaggcaa    2640
gagcgacaac gtgccctccg aagaggtcgt gaagaagatg aagaactact ggcgacagct    2700
gctgaacgcc aagctgatta cccagaggaa gttcgataac ctgaccaagg ccgagagagg    2760
cggcctgagc gagctggata aggccggctt catcaagagg cagctggtgg aaaccagaca    2820
gatcacaaag cacgtggcac agatcctgga ctcccggatg aacactaagt acgacgaaaa    2880
cgataagctg atccgggaag tgaaagtgat caccctgaag tccaagctgg tgtccgattt    2940
ccggaaggat ttccagtttt acaaagtgcg cgagatcaac aactaccacc acgcccacga    3000
cgcctacctg aacgccgtcg tgggaaccgc cctgatcaaa aagtaccca agctggaaag    3060 cgagttcgtg tacggcgact acaaggtgta cgacgtgcgg aagatgatcg ccaagagcga    3120
gcaggaaatc ggcaaggcta ccgccaagta cttcttctac agcaacatca tgaactttt    3180 caagaccgaa atcacccctgg ccaacggcga gatcagaaag cgccctctga tcgagacaaa    3240
cggcgaaacc ggggagatcg tgtgggataa gggcagagac ttcgccacag tgcgaaggt    3300 gctgagcatg ccccaagtga atatcgtgaa aaagaccgag gtgcagacag gcggcttcag    3360
caaagagtct atcctgcccca agaggaacag cgacaagctg atcgccagaa agaaggactg    3420
```

-continued

```
ggaccccaag aagtacggcg gcttcgacag ccctaccgtg gcctactctg tgctggtggt    3480
ggctaaggtg gaaagggca agtccaagaa actgaagagt gtgaaagagc tgctggggat    3540
caccatcatg gaaagaagca gctttgagaa gaaccctatc gactttctgg aagccaaggg    3600
ctacaaagaa gtgaaaaagg acctgatcat caagctgcct aagtactccc tgttcgagct    3660
ggaaaacggc agaaagagaa tgctggcctc tgccggcgaa ctgcagaagg gaaacgagct    3720
ggccctgcct agcaaatatg tgaacttcct gtacctggcc tcccactatg agaagctgaa    3780
gggcagccct gaggacaacg aacagaaaca gctgtttgtg gaacagcata gcactacct    3840 ggacgagatc atcgagcaga tcagcgagtt ctccaagaga gtgatcctgg ccgacgccaa    3900
tctggacaag gtgctgtctg cctacaacaa gcacagggac aagcctatca gagagcaggc    3960
cgagaatatc atccacctgt tcaccctgac aaacctgggc gctcctgccg ccttcaagta    4020 cttttgacacc accatcgacc ggaagaggta caccagcacc aaagaggtgc tggacgccac    4080
cctgatccac cagagcatca ccggcctgta cgagacaaga atcgacctgt ctcagctggg    4140
aggcgacaag agacctgccg ccactaagaa ggccggacag gccaaaaaga gaagggagg    4200 tggaggttca ggtgggggtg ggtcaggagg aggtggttca gaacaagccc cagaagacca    4260
agggccacag agggagccac acaatgaatg gacactagag cttttagagg agcttaagaa    4320
tgaagctgtt agacattttc ctaggatttg gctccatggc ttagggcaac atatctatga    4380
aacttatggg gatacttggg caggagtgga agccataata agaattctgc aacaactgct    4440
gtttatccat tttcagaatt gggtgtcgac atagcagaat aggcgttact cgacagagga    4500
gagcaagaaa tggagccagt aggcggccgc taatcagcca taccacattt gtagaggttt    4560
tacttgcttt aaaaaacctc ccacacctcc ccctgaacct gaaacataaa atgaatgcaa    4620
ttgttgttgt taacttgttt attgcagctt ataatggtta caaataaagc aatagcatca    4680
caaatttcac aaataaagca ttttttttcac tgcattctag ttgtggtttg tccaaactca    4740
tcaatgtatc ttatcatgtc taccggtagg gcccctctct tcatgtgagc aaaaggccag    4800
caaaaggcca ggaaccgtaa aaaggccgcg ttgctggcgt ttttccatag gctccgcccc    4860
cctgacgagc atcacaaaaa tcgacgctca agtcagaggt ggcgaaaccc gacaggacta    4920
taaagatacc aggcgtttcc ccctggaagc tccctcgtgc gctctcctgt tccgaccctg    4980
ccgcttaccg gatacctgtc cgcctttctc ccttcgggaa gcgtggcgct ttctcaatgc    5040
tcacgctgta ggtatctcag ttcggtgtag tcgttcgct ccaagctggg ctgtgtgcac    5100 gaacccccg ttcagcccga ccgctgcgcc ttatccggta actatcgtct tgagtccaac    5160
ccggtaagac acgacttatc gccactggca gcagccactg gtaacaggat tagcagagcg    5220
aggtatgtag gcggtgctac agagttcttg aagtggtggc ctaactacgg ctacactaga    5280
aggacagtat ttggtatctg cgctctgctg aagccagtta ccttcggaaa aagagttggt    5340
agctcttgat ccggcaaaca aaccaccgct ggtagcggtg gttttttgt ttgcaagcag    5400 cagattacgc gcagaaaaaa aggatctcaa gaagatcctt tgatcttttc tacgggtct    5460 gacgctcagt ggaacgaaaa ctcacgttaa gggattttgg tcatgggcgc gcctcatact    5520
cctgcaggca tgagattatc aaaaaggatc ttcacctaga tccttttaaa ttaaaaatga    5580
agttttaaat caatctaaag tatatatgag taaacttggt ctgacagtta ccaatgctta    5640
atcagtgagg cacctatctc agcgatctgt ctatttcgtt catccatagt tgcctgactc    5700
cccgtcgtgt agataactac gatacgggag ggcttaccat ctggccccag tgctgcaatg    5760
```

```
ataccgcgag acccacgctc accggctcca gatttatcag caataaacca gccagccgga    5820
agggccgagc gcagaagtgg tcctgcaact ttatccgcct ccatccagtc tattaattgt    5880
tgccgggaag ctagagtaag tagttcgcca gttaatagtt tgcgcaacgt tgttgccatt    5940
gctacaggca tcgtggtgtc acgctcgtcg tttggtatgg cttcattcag ctccggttcc    6000
caacgatcaa ggcgagttac atgatccccc atgttgtgca aaaaagcggt tagctccttc    6060
ggtcctccga tcgttgtcag aagtaagttg gccgcagtgt tatcactcat ggttatggca    6120
gcactgcata attctcttac tgtcatgcca tccgtaagat gcttttctgt gactggtgag    6180
tactcaacca agtcattctg agaatagtgt atgcggcgac cgagttgctc ttgcccggcg    6240
tcaatacggg ataataccgc gccacatagc agaactttaa aagtgctcat cattggaaaa    6300
cgttcttcgg ggcgaaaact ctcaaggatc ttaccgctgt tgagatccag ttcgatgtaa    6360
cccactcgtg cacccaactg atcttcagca tcttttactt tcaccagcgt ttctgggtga    6420
gcaaaaacag gaaggcaaaa tgccgcaaaa aagggaataa gggcgacacg gaaatgttga    6480
atactcatac tcttcctttt tcaatattat tgaagcattt atcagggtta ttgtctcatg    6540
agcggataca tatttgaatg tatttagaaa aataaacaaa tagggggttcc gcgcacattt    6600
ccccgaaaag tgccacctga cgtcaggtac caagcctagg cctccaaaaa agcctcctca    6660
ctacttctgg aatagctcag aggcagaggc ggcctcggcc tctgcataaa taaaaaaaat    6720
tagtcagcca tggggcggag aatgggcgga actgggcgga gttaggggcg ggatgggcgg    6780
agttaggggc gggactatgg ttgctgacta attgagatgc atgctttgca tacttctgcc    6840
tgctggggag cctggggact ttccacacct ggttgctgac taattgagat gcatgctttg    6900
catacttctg cctgctgggg agcctgggga cttttcacac cggatccacc atgggatcgg    6960
ccattgaaca agatggattg cacgcaggtt ctccggccgc ttgggtggag aggctattcg    7020
gctatgactg ggcacaacag acaatcggct gctctgatgc cgccgtgttc cggctgtcag    7080
cgcaggggcg cccggttctt tttgtcaaga ccgacctgtc cggtgccctg aatgaactgc    7140
aggacgaggc agcgcggcta tcgtggctgg ccacgacggg cgttccttgc gcagctgtgc    7200
tcgacgttgt cactgaagcg ggaagggact ggctgctatt gggcgaagtg ccggggcagg    7260
atctcctgtc atctcacctt gctcctgccg agaaagtatc catcatggct gatgcaatgc    7320
ggcggctgca tacgcttgat ccggctacct gcccattcga ccaccaagcg aaacatcgca    7380
tcgagcgagc acgtactcgg atggaagccg gtcttgtcga tcaggatgat ctggacgaag    7440
agcatcaggg gctcgcgcca gccgaactgt tcgccaggct caaggcgcgc atgcccgacg    7500
gcgatgatct cgtcgtgacc catggcgatg cctgcttgcc gaatatcatg gtggaaaatg    7560
gccgcttttc tggattcatc gactgtggcc ggctgggtgt ggcggaccgc tatcaggaca    7620
tagcgttggc tacccgtgat attgctgaag agcttggcgg cgaatgggct gaccgcttcc    7680
tcgtgcttta cggtatcgcc gctcccgatt cgcagcgcat cgccttctat cgccttcttg    7740
acgagttctt ctgaacgcgt gctgtaagtc tgcagaaatt gatgatctat taacaataa    7800
agatgtccac taaaatggaa gtttttcctg tcatactttg ttaagaaggg tgagaacaga    7860
gtacctacat tttgaatgga aggattggag ctacgggggt ggggggtgggg tgggattaga    7920
taaatgcctg ctctttactg aaggctcttt actattgctt tatgataatg tttcatagtt    7980
ggatatcata atttaaacaa gcaaaaccaa attaagggcc agctcattcc tcccactcat    8040
gatctatgga tctatagatc tctcgtgcag ctggggctct aggggggtatc cccacgcgcc    8100
ctgtagcggc gcattaagcg cggcgggtgt ggtggttacg cgcagcgtga ccgctacact    8160
```

```
tgccagcgcc ctagcgcccg ctcctttcgc tttcttccct tcctttctcg ccacgttcgc    8220
cggctttccc cgtcaagctc taaatcgggg gctcccttta gggttccgat ttagtgcttt    8280
acggcacctc gaccccaaaa aacttgatta gggtgatggt tcacgtagtg ggccatcgcc    8340
ctgatagacg gttttcgcc ctttgacgtt ggagtccacg ttctttaata gtggactctt    8400
gttccaaact ggaacaacac tcaaccctat ctcggtctat tcttttgatt tataagggat    8460
tttgccgatt tcggcctatt ggttaaaaaa tgagctgatt taacaaaaat ttaacgcgaa    8520
ttaattctgt ggaatgtgtg tcagttagtc gcgaggcctc cgcgccgggt tttggcgcct    8580
cccgcgggcg ccccctcct cacgcgagc gctgccacgt cagacgaagg gcgcagcgag     8640
cgtcctgatc cttccgcccg gacgctcagg acagcggccc gctgctcata agactcggcc    8700 ttagaaccc agtatcagca gaaggacatt ttaggacggg acttgggtga ctctagggca     8760
ctggttttct ttccagagag cggaacaggc gaggaaaagt agtcccttct cggcgattct    8820
gcggagggat ctccgtgggg cggtgaacgc cgatgattat ataaggacgc gccgggtgtg    8880
gcacagctag ttccgtcgca gccgggattt gggtcgcggt tcttgtttgt ggatcgctgt    8940
gatcgtcact tggtgagtag cgggctgctg ggctggccgg ggctttcgtg gccgccgggc    9000
cgctcggtgg gacggaagcg tgtggagaga ccgccaaggg ctgtagtctg ggtccgcgag    9060
caaggttgcc ctgaactggg ggttgggggg agcgcagcaa aatggcggct gttcccgagt    9120
cttgaatgga agacgcttgt gaggcgggct gtgaggtcgt tgaaacaagg tgggggcat    9180 ggtgggcggc aagaacccaa ggtcttgagg ccttcgctaa tgcgggaaag ctcttattcg    9240
ggtgagatgg gctggggcac catctgggga ccctgacgtg aagtttgtca ctgactggag    9300
aactcggttt gtcgtctgtt gcgggggcgg cagttatggc ggtgccgttg ggcagtgcac    9360
ccgtaccttt gggagcgcgc gccctcgtcg tgtcgtgacg tcacccgttc tgttggctta    9420
taatgcaggg tgggggccacc tgccggtagg tgtgcggtag gcttttctcc gtcgcaggac    9480
gcagggttcg ggcctagggt aggctctcct gaatcgacag gcgccggacc tctggtgagg    9540
ggagggataa gtgaggcgtc agtttctttg gtcggtttta tgtacctatc ttcttaagta    9600
gctgaagctc cggttttgaa ctatgcgctc ggggttggcg agtgtgtttt gtgaagtttt    9660
ttaggcacct tttgaaatgt aatcatttgg gtcaatatgt aattttcagt gttagactag    9720
taaattgtcc gctaaattct ggccgttttt ggcttttttg ttagacgtcg accgatcctg    9780
agaacttcag ggtgagtttg gggacccttg attgttcttt cttttcgct attgtaaaat    9840 tcatgttata tggaggggc aaagttttca gggtgttgtt tagaatggga agatgtccct    9900
tgtatcacca tggaccctca tgataatttt gtttctttca ctttctactc tgttgacaac    9960
cattgtctcc tcttatttc tttcatttt ctgtaacttt tcgttaaac tttagcttgc     10020 atttgtaacg aattttaaa ttcactttg tttatttgtc agattgtaag tactttctct    10080
aatcactttt ttttcaaggc aatcagggta tattatattg tacttcagca cagttttaga    10140
gaacaattgt tataattaaa tgataaggta gaatatttct gcatataaat tctggctggc    10200
gtggaaatat tcttattggt agaaacaact acaccctggt catcatcctg cctttctctt    10260
tatggttaca atgatataca ctgtttgaga tgaggataaa atactctgag tccaaaccgg    10320
gcccctctgc taaccatgtt catgccttct tcttttcct acagctcctg ggcaacgtgc    10380
tggttgttgt gctgtctcat catttggca aagaatt                              10417
```

<210> SEQ ID NO 63

```
<211> LENGTH: 9539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
tggaagggct aattcactcc caaagaagac aagatatcct tgatctgtgg atctaccaca      60
cacaaggcta cttccctgat tagcagaact acacaccagg gccagggggtc agatatccac     120
tgacctttgg atggtgctac aagctagtac cagttgagcc agataaggta gaagaggcca     180
ataaaggaga gaacaccagc ttgttacacc ctgtgagcct gcatgggatg gatgacccgg     240
agagagaagt gttagagtgg aggtttgaca gccgcctagc atttcatcac gtggcccgag     300
agctgcatcc ggagtacttc aagaactgct gatatcgagc ttgctacaag gactttccg      360
ctggggactt tccagggagg cgtggcctgg gcgggactgg ggagtggcga gccctcagat     420
cctgcatata agcagctgct ttttgcctgt actgggtctc tctggttaga ccagatctga     480
gcctgggagc tctctggcta actagggaac ccactgctta agcctcaata aagcttgcct     540
tgagtgcttc aagtagtgtg tgcccgtctg ttgtgtgact ctggtaacta gagatccctc     600
agacccttt agtcagtgtg gaaaatctct agcagtggcg cccgaacagg gacttgaaag     660
cgaaagggaa accagaggag ctctctcgac gcaggactcg gcttgctgaa gcgcgcacgg     720
caagaggcga ggggcggcga ctggtgagta cgccaaaaat tttgactagc ggaggctaga     780
aggagagaga tgggtgcgag agcgtcagta ttaagcgggg gagaattaga tcgcgatggg     840
aaaaaattcg gttaaggcca gggggaaaga aaaaatataa attaaaacat atagtatggg     900
caagcaggga gctagaacga ttcgcagtta atcctggcct gttagaaaca tcagaaggct     960
gtagacaaat actgggacag ctacaaccat cccttcagac aggatcagaa gaacttagat    1020
cattatataa tacagtagca accctctatt gtgtgcatca aaggatagag ataaaagaca    1080
ccaaggaagc tttagacaag atagaggaag agcaaaacaa aagtaagacc accgcacagc    1140
aagcggccgg ccgctgatct tcagacctgg aggaggagat atgagggaca attggagaag    1200
tgaattatat aaatataaag tagtaaaaat tgaaccatta ggagtagcac ccaccaaggc    1260
aaagagaaga gtggtgcaga gagaaaaaag agcagtggga ataggagctt tgttccttgg    1320
gttcttggga gcagcaggaa gcactatggg cgcagcgtca atgacgctga cggtacaggc    1380
cagacaatta ttgtctggta tagtgcagca gcagaacaat ttgctgaggg ctattgaggc    1440
gcaacagcat ctgttgcaac tcacagtctg gggcatcaag cagctccagg caagaatcct    1500
ggctgtggaa agatacctaa aggatcaaca gctcctgggg atttggggtt gctctggaaa    1560
actcatttgc accactgctg tgccttggaa tgctagttgg agtaataaat ctctggaaca    1620
gatttggaat cacacgacct ggatggagtg ggacagagaa attaacaatt acacaagctt    1680
aatacactcc ttaattgaag aatcgcaaaa ccagcaagaa aagaatgaac aagaattatt    1740
ggaattagat aaatgggcaa gtttgtggaa ttggtttaac ataacaaatt ggctgtggta    1800
tataaaatta ttcataatga tagtaggagg cttggtaggt ttaagaatag ttttttgctgt    1860
actttctata gtgaatagag ttaggcaggg atattcacca ttatcgtttc agacccacct    1920
cccaaccccg aggggacccg acaggcccga aggaatagaa gaagaaggtg gagagagaga    1980
cagagacaga tccattcgat tagtgaacgg atctcgacgg tatcgccttt aaaagaaaag    2040
gggggattgg gggggtacagt gcaggggaaa gaatagtaga cataatagca acagacatac    2100
```

-continued

```
aaactaaaga attacaaaaa caaattacaa aaattcaaaa ttttcgggtt tattacaggg    2160
acagcagaga tccagtttat cgatgagtaa ttcatacaaa aggactcgcc cctgccttgg    2220
ggaatcccag ggaccgtcgt taaactccca ctaacgtaga acccagagat cgctgcgttc    2280 ccgcccctc  acccgcccgc tctcgtcatc actgaggtgg agaagagcat gcgtgaggct    2340
ccggtgcccg tcagtgggca gagcgcacat cgcccacagt ccccgagaag ttgggggag    2400 gggtcggcaa ttgaaccggt gcctagagaa ggtggcgcgg ggtaaactgg gaaagtgatg    2460
tcgtgtactg gctccgcctt tttcccgagg gtgggggaga accgtatata agtgcagtag    2520
tcgccgtgaa cgttcttttt cgcaacgggt ttgccgccag aacacaggta agtgccgtgt    2580
gtggttcccg cgggcctggc ctctttacgg gttatggccc ttgcgtgcct tgaattactt    2640
ccacgcccct ggctgcagta cgtgattctt gatcccgagc ttcgggttgg aagtgggtgg    2700
gagagttcga ggccttgcgc ttaaggagcc ccttcgcctc gtgcttgagt tgaggcctgg    2760
cttgggcgct ggggccgccg cgtgcgaatc tggtggcacc ttcgcgcctg tctcgctgct    2820
ttcgataagt ctctagccat ttaaaatttt tgatgacctg ctgcgacgct tttttctgg    2880 caagatagtc ttgtaaatgc gggccaagat ctgcacactg gtatttcggt ttttggggcc    2940
gcgggcggcg acgggcccg  tgcgtcccag cgcacatgtt cggcgaggcg gggcctgcga    3000
gcgcggccac cgagaatcgg acggggtag  tctcaagctg gccggcctgc tctggtgcct    3060
ggcctcgcgc cgccgtgtat cgcccgcc  tgggcggcaa ggctggccg  gtcggcacca    3120 gttgcgtgag cggaaagatg gccgcttccc ggccctgctg cagggagctc aaaatggagg    3180
acgcggcgct cgggagagcg ggcgggtgag tcacccacac aaaggaaaag gccttttccg    3240
tcctcagccg tcgcttcatg tgactccacg gagtaccggg cgccgtccag gcacctcgat    3300
tagttctcga gcttttggag tacgtcgtct ttaggttggg gggagggtt  ttatgcgatg    3360 gagtttcccc acactgagtg ggtggagact gaagttaggc cagcttggca cttgatgtaa    3420
ttctccttgg aatttgccct ttttgagttt ggatcttggt tcattctcaa gcctcagaca    3480
gtggttcaaa gttttttttct tccatttcag gtgtcgtgag gatctatttc cggtgaattc    3540
ctcgagacta gtatggtgag caagggcgag gagctgttca ccggggtggt gcccatcctg    3600
gtcgagctgg acggcgacgt aaacggccac aagttcagcg tgtccggcga gggcgagggc    3660
gatgccacct acggcaagct gaccctgaag ttcatctgca ccaccggcaa gctgcccgtg    3720
ccctggccca ccctcgtgac caccctgacc tacggcgtgc agtgcttcag ccgctacccc    3780
gaccacatga gcagcacga  cttcttcaag tccgccatgc ccgaaggcta cgtccaggag    3840
cgcaccatct tcttcaagga cgacggcaac tacaagaccc gcgccgaggt gaagttcgag    3900
ggcgacaccc tggtgaaccg catcgagctg aagggcatcg acttcaagga ggacggcaac    3960
atcctggggc acaagctgga gtacaactac aacagccaca cgtctatat  catggccgac    4020 aagcagaaga acggcatcaa ggtgaacttc aagatccgcc acaacatcga ggacggcagc    4080
gtgcagctcg ccgaccacta ccagcagaac acccccatcg gcgacggccc cgtgctgctg    4140
cccgacaacc actacctgag cacccagtcc gccctgagca agacccccaa cgagaagcgc    4200
gatcacatgg tcctgctgga gttcgtgacc gccgccggga tcactctcgg catggacgag    4260
ctgtacaagt aagcggccgc ggatcccgcc cctctccctc ccccccccct aacgttactg    4320
gccgaagccg cttggaataa ggccggtgtg cgtttgtcta tatgttattt tccaccatat    4380
tgccgtcttt tggcaatgtg agggcccgga acctggccc  tgtcttcttg acgagcattc    4440 ctagggggtct ttcccctctc gccaaaggaa tgcaaggtct gttgaatgtc gtgaaggaag    4500
```

```
cagttcctct ggaagcttct tgaagacaaa caacgtctgt agcgacccct tgcaggcagc   4560 ggaaccccccc  acctggcgac aggtgcctct gcggccaaaa gccacgtgta taagatacac   4620
ctgcaaaggc ggcacaaccc cagtgccacg ttgtgagttg gatagttgtg gaaagagtca   4680
aatggctctc ctcaagcgta ttcaacaagg ggctgaagga tgcccagaag gtaccccatt   4740
gtatgggatc tgatctgggg cctcggtgca catgctttac atgtgtttag tcgaggttaa   4800
aaaaacgtct aggccccccg aaccacgggg acgtggtttt cctttgaaaa acacgatgat   4860
aagcttgcca caacccacaa ggagacgacc ttccatgacc gagtacaagc ccacggtgcg   4920
cctcgccacc cgcgacgacg tccccgggc cgtacgcacc ctcgccgccg cgttcgccga   4980
ctaccccgcc acgcgccaca ccgtcgaccc ggaccgccac atcgagcggg tcaccgagct   5040
gcaagaactc ttcctcacgc gcgtcgggct cgacatcggc aaggtgtggg tcgcggacga   5100
cggcgccgcg gtggcggtct ggaccacgcc ggagagcgtc gaagcggggg cggtgttcgc   5160
cgagatcggc ccgcgcatgg ccgagttgag cggttcccgg ctggccgcgc agcaacagat   5220
ggaaggcctc ctggcgccgc accggcccaa ggagcccgcg tggttcctgg ccaccgtcgg   5280
cgtctcgccc gaccaccagg gcaagggtct gggcagcgcc gtcgtgctcc ccggagtgga   5340
ggcggccgag cgcgccgggg tgcccgcctt cctggagacc tccgcgcccc gcaacctccc   5400
cttctacgag cggctcggct tcaccgtcac cgccgacgtc gaggtgcccg aaggaccgcg   5460
cacctggtgc atgacccgca gcccggtgc ctagacgcgt ctggaacaat caacctctgg   5520
attacaaaat ttgtgaaaga ttgactggta ttcttaacta tgttgctcct tttacgctat   5580
gtggatacgc tgctttaatg cctttgtatc atgctattgc ttcccgtatg gctttcattt   5640
tctcctcctt gtataaatcc tggttgctgt ctctttatga ggagttgtgg cccgttgtca   5700
ggcaacgtgg cgtggtgtgc actgtgtttg ctgacgcaac ccccactggt tggggcattg   5760
ccaccacctg tcagctcctt tccgggactt tcgctttccc cctccctatt gccacggcgg   5820
aactcatcgc cgcctgcctt gcccgctgct ggacaggggc tcggctgttg ggcactgaca   5880
attccgtggt gttgtcgggg aagctgacgt ccttttccatg gctgctcgcc tgtgttgcca   5940
cctggattct gcgcgggacg tccttctgct acgtcccttc ggccctcaat ccagcggacc   6000
ttccttcccg cggcctgctg ccggctctgc ggcctcttcc gcgtcttcgc cttcgccctc   6060
agacgagtcg gatctcccctt tgggccgcct ccccgcctgg aattaattct gcagtcgaga   6120
cctagaaaaa catggagcaa tcacaagtag caatacagca gctaccaatg ctgattgtgc   6180
ctggctagaa gcacaagagg aggaggaggt gggttttcca gtcacacctc aggtacccttt   6240 aagaccaatg acttacaagg cagctgtaga tcttagccac ttttaaaag aaaagagggg   6300 actgaagggg ctaattcact cccaacgaag acaagatatc cttgatctgt ggatctacca   6360
cacacaaggc tacttccctg attagcagaa ctacacacca gggccagggg tcagatatcc   6420
actgaccttt ggatggtgct acaagctagt accagttgag ccagataagg tagaagaggc   6480
caataaagga gagaacacca gcttgttaca ccctgtgagc ctgcatggga tggatgaccc   6540
ggagagagaa gtgttagagt ggaggtttga cagccgccta gcatttcatc acgtggcccg   6600
agagctgcat ccggagtact tcaagaactg ctgatatcga gcttgctaca agggactttc   6660
cgctggggac tttccaggga ggcgtggcct gggcgggact ggggagtggc gagccctcag   6720
atcctgcata taagcagctg cttttttgcct gtactgggtc tctctggtta gaccagatct   6780
gagcctggga gctctctggc taactaggga acccactgct taagcctcaa taaagcttgc   6840
```

```
cttgagtgct tcaagtagtg tgtgcccgtc tgttgtgtga ctctggtaac tagagatccc    6900
tcagacccTt ttagtcagtg tggaaaatct ctagcagtag tagttcatgt catcttatta    6960
ttcagtattt ataacttgca aagaaatgaa tatcagagag tgagaggcct tgacattgct    7020
agcgtttacc gtcgacctct agctagagct tggcgtaatc atggtcatag ctgtttcctg    7080
tgtgaaattg ttatccgctc acaattccac acaacatacg agccgaagc ataaagtgta     7140 aagcctgggg tgcctaatga gtgagctaac tcacattaat tgcgttgcgc tcactgcccg    7200
ctttccagtc gggaaacctg tcgtgccagc tgcattaatg aatcggccaa cgcgcgggga    7260
gaggcggttt gcgtattggg cgctcttccg cttcctcgct cactgactcg ctgcgctcgg    7320
tcgttcggct gcggcgagcg gtatcagctc actcaaaggc ggtaatacgg ttatccacag    7380
aatcagggga taacgcagga aagaacatgt gagcaaaagg ccagcaaaag gccaggaacc    7440
gtaaaaaggc cgcgttgctg gcgttttttcc ataggctccg cccccctgac gagcatcaca    7500
aaaatcgacg ctcaagtcag aggtggcgaa acccgacagg actataaaga taccaggcgt    7560
ttccccctgg aagctccctc gtgcgctctc ctgttccgac cctgccgctt accggatacc    7620
tgtccgcctt tctcccttcg ggaagcgtgg cgctttctca tagctcacgc tgtaggtatc    7680
tcagttcggt gtaggtcgtt cgctccaagc tgggctgtgt gcacgaaccc cccgttcagc    7740
ccgaccgctg cgccttatcc ggtaactatc gtcttgagtc caacccggta agacacgact    7800
tatcgccact ggcagcagcc actggtaaca ggattagcag agcgaggtat gtaggcggtg    7860
ctacagagtt cttgaagtgg tggcctaact acggctacac tagaagaaca gtatttggta    7920
tctgcgctct gctgaagcca gttaccttcg gaaaaagagt tggtagctct tgatccggca    7980
aacaaaccac cgctggtagc ggtggttttt tgtttgcaa gcagcagatt acgcgcagaa     8040
aaaaaggatc tcaagaagat cctttgatct tttctacggg gtctgacgct cagtggaacg    8100
aaaactcacg ttaagggatt ttggtcatga gattatcaaa aaggatcttc acctagatcc    8160
ttttaaatta aaaatgaagt tttaaatcaa tctaaagtat atatgagtaa acttggtctg    8220
acagttacca atgcttaatc agtgaggcac ctatctcagc gatctgtcta tttcgttcat    8280
ccatagttgc ctgactcccc gtcgtgtaga taactacgat acgggagggc ttaccatctg    8340
gccccagtgc tgcaatgata ccgcgagacc cacgctcacc ggctccagat ttatcagcaa    8400
taaaccagcc agccggaagg gccgagcgca gaagtggtcc tgcaacttta tccgcctcca    8460
tccagtctat taattgttgc cgggaagcta gagtaagtag ttcgccagtt aatagtttgc    8520
gcaacgttgt tgccattgct acaggcatcg tggtgtcacg ctcgtcgttt ggtatggctt    8580
cattcagctc cggttcccaa cgatcaaggc gagttacatg atccccatg ttgtgcaaaa     8640 aagcggttag ctccttcggt cctccgatcg ttgtcagaag taagttggcc gcagtgttat    8700
cactcatggt tatggcagca ctgcataatt ctcttactgt catgccatcc gtaagatgct    8760
tttctgtgac tggtgagtac tcaaccaagt cattctgaga atagtgtatg cggcgaccga    8820
gttgctcttg cccggcgtca atacgggata ataccgcgcc acatagcaga actttaaaag    8880
tgctcatcat tggaaaacgt tcttcggggc gaaaactctc aaggatctta ccgctgttga    8940
gatccagttc gatgtaaccc actcgtgcac ccaactgatc ttcagcatct tttactttca    9000
ccagcgtttc tgggtgagca aaaacaggaa ggcaaaatgc cgcaaaaaag gaataagggg    9060
cgacacggaa atgttgaata ctcatactct tcctttttca atattattga agcatttatc    9120
agggttattg tctcatgagc ggatacatat ttgaatgtat ttagaaaaat aaacaaatag    9180
gggttccgcg cacatttccc cgaaaagtgc cacctgacgt cgacggatcg ggagatcaac    9240
```

-continued

| | |
|---|---|
| ttgtttattg cagcttataa tggttacaaa taaagcaata gcatcacaaa tttcacaaat | 9300 |
| aaagcattt tttcactgca ttctagttgt ggtttgtcca aactcatcaa tgtatcttat | 9360 |
| catgtctgga tcaactggat aactcaagct aaccaaaatc atcccaaact tcccacccca | 9420 |
| taccctatta ccactgccaa ttacctgtgg tttcatttac tctaaacctg tgattcctct | 9480 |
| gaattatttt cattttaaag aaattgtatt tgttaaatat gtactacaaa cttagtagt | 9539 |

<210> SEQ ID NO 64
<211> LENGTH: 10098
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64

| | |
|---|---|
| aagcttatac tcgagactag tgccaccatg gacaagccca agaaaaagcg gaaagtgaag | 60 |
| tacagcatcg gcctggacat cggcaccaac tctgtgggct gggccgtgat caccgacgag | 120 |
| tacaaggtgc ccagcaagaa attcaaggtg ctgggcaaca ccgacaggca cagcatcaag | 180 |
| aagaacctga tcggcgccct gctgttcgac agcggcgaaa cagccgaggc caccagactg | 240 |
| aagagaaccg ccagaagaag atacaccagg cggaagaaca ggatctgcta tctgcaagag | 300 |
| atcttcagca acgagatggc caaggtggac gacagcttct tccacagact ggaagagtcc | 360 |
| ttcctggtgg aagaggacaa gaagcacgag agacacccca tcttcggcaa catcgtggac | 420 |
| gaggtggcct accacgagaa gtaccccacc atctaccacc tgagaaagaa actggtggac | 480 |
| agcaccgaca aggccgacct gagactgatc tacctggccc tggcccacat gatcaagttc | 540 |
| agaggccact tcctgatcga gggcgacctg aaccccgaca cagcgacgt ggacaagctg | 600 |
| ttcatccagc tggtgcagac ctacaaccag ctgttcgagg aaaaccccat caacgccagc | 660 |
| ggcgtggacg ccaaggctat cctgtctgcc agactgagca gagcagaag gctgaaaat | 720 |
| ctgatcgccc agctgcccgg cgagaagaag aacggcctgt tcggcaacct gattgccctg | 780 |
| agcctgggcc tgacccccaa cttcaagagc aacttcgacc tggccgagga tgccaaactg | 840 |
| cagctgagca aggacaccta cgacgacgac ctggacaacc tgctggccca gatcggcgac | 900 |
| cagtacgccg acctgttcct ggccgccaag aacctgtctg acgccatcct gctgagcgac | 960 |
| atcctgagag tgaacaccga gatcaccaag gccccctga gcgcctctat gatcaagaga | 1020 |
| tacgacgagc accaccagga cctgaccctg ctgaaagctc tcgtgcggca gcagctgcct | 1080 |
| gagaagtaca aagaaatctt cttcgaccag agcaagaacg gctacgccgg ctacatcgat | 1140 |
| ggcggcgcta gcaggaaga gttctacaag ttcatcaagc catcctgga aaagatggac | 1200 |
| ggcaccgagg aactgctcgt gaagctgaac agagaggacc tgctgagaaa gcagagaacc | 1260 |
| ttcgacaacg gcagcatccc ccaccagatc caccctggag agctgcacgc tatcctgaga | 1320 |
| aggcaggaag atttttaccc attcctgaag gacaaccggg aaaagatcga aagatcctg | 1380 |
| accttcagga tccctactac cgtgggcccc ctggccagag caacagcag attcgcctgg | 1440 |
| atgaccagaa agagcgagga aaccatcacc ccctggaact tcgaggaagt ggtggacaag | 1500 |
| ggcgccagcg cccagagctt catcgagaga atgacaaact tcgataagaa cctgcccaac | 1560 |
| gagaaggtgc tgcccaagca cagcctgctg tacgagtact tcaccgtgta caacgagctg | 1620 |
| accaaagtga atacgtgac cgagggaatg agaaagcccg ccttcctgag cggcgagcag | 1680 |
| aaaaaggcca tcgtggacct gctgttcaag accaacagaa agtgaccgt gaagcagctg | 1740 |

```
aaagaggact acttcaagaa aatcgagtgc ttcgactccg tggaaatctc cggcgtggaa   1800
gatagattca acgcctccct gggcacatac cacgatctgc tgaaaattat caaggacaag   1860
gacttcctgg ataacgaaga gaacgaggac attctggaag atatcgtgct gaccctgaca   1920 ctgttttgagg accgcgagat gatcgaggaa aggctgaaaa cctacgctca cctgttcgac   1980
gacaaagtga tgaagcagct gaagagaagg cggtacaccg ctggggcag gctgagcaga   2040 aagctgatca acggcatcag agacaagcag agcggcaaga caatcctgga tttcctgaag   2100
tccgacggct tcgccaaccg gaacttcatg cagctgatcc acgacgacag cctgacattc   2160
aaagaggaca tccagaaagc ccaggtgtcc ggccagggcg actctctgca cgagcatatc   2220
gctaacctgg ccggcagccc cgctatcaag aagggcatcc tgcagacagt gaaggtggtg   2280
gacgagctcg tgaaagtgat gggcagacac aagcccgaga acatcgtgat cgagatggct   2340
agagagaacc agaccaccca aagggacag aagaactccc gcgagaggat gaagagaatc   2400
gaagagggca tcaaagagct gggcagccag atcctgaaag aacacccgt ggaaaacacc   2460 cagctgcaga acgagaagct gtacctgtac tacctgcaga atggccggga tatgtacgtg   2520
gaccaggaac tggacatcaa cagactgtcc gactacgatg tggaccatat cgtgcctcag   2580
agctttctga aggacgactc catcgataac aaagtgctga ctcggagcga caagaacaga   2640
ggcaagagcg acaacgtgcc ctccgaagag gtcgtgaaga gatgaagaa ctactggcga   2700 cagctgctga acgccaagct gattacccag aggaagttcg ataacctgac caaggccgag   2760
agaggcggcc tgagcgagct ggataaggcc ggcttcatca gaggcagct ggtgaaaacc   2820 agacagatca caaagcacgt ggcacagatc ctggactccc ggatgaacac taagtacgac   2880
gaaaacgata gctgatccg ggaagtgaaa gtgatcaccc tgaagtccaa gctggtgtcc   2940
gatttccgga aggatttcca gttttacaaa gtgcgcgaga tcaacaacta ccaccacgcc   3000
cacgacgcct acctgaacgc cgtcgtggga accgccctga tcaaaagta ccctaagctg   3060 gaaagcgagt tcgtgtacgg cgactacaag gtgtacgacg tgcggaagat gatcgccaag   3120
agcgagcagg aaatcggcaa ggctaccgcc aagtacttct tctacagcaa catcatgaac   3180
tttttcaaga ccgaaatcac cctggccaac ggcgagatca gaaagcgccc tctgatcgag   3240
acaaacggcg aaaccgggga gatcgtgtgg gataagggca gagacttcgc cacagtgcga   3300
aaggtgctga gcatgcccca agtgaatatc gtgaaaaaga ccgaggtgca gacaggcggc   3360
ttcagcaaag agtctatcct gcccaagagg aacagcgaca agctgatcgc cagaaagaag   3420
gactgggacc ccaagaagta cggcggcttc gacagcccta ccgtggccta ctctgtgctg   3480
gtggtggcta aggtggaaaa gggcaagtcc aagaaactga gagtgtgaa agagctgctg   3540 gggatcacca tcatggaaag aagcagcttt gagaagaacc ctatcgactt tctggaagcc   3600
aagggctaca aagaagtgaa aaaggacctg atcatcaagc tgcctaagta ctccctgttc   3660
gagctggaaa acggcagaaa gagaatgctg gcctctgccg cgaactgca aagggaaac   3720 gagctggccc tgcctagcaa atatgtgaac ttcctgtacc tggcctccca ctatgagaag   3780
ctgaagggca gccctgagga caacgaacag aaacagctgt tgtggaaca gcataagcac   3840 tacctggacg agatcatcga gcagatcagc gagttctcca agagagtgat cctggccgac   3900
gccaatctgg acaaggtgct gtctgcctac aacaagcaca gggacaagcc tatcagagag   3960
caggccgaga atatcatcca cctgttcacc ctgacaaacc tgggcgctcc tgccgccttc   4020
aagtactttg acaccaccat cgaccggaag aggtacacca gcaccaaaga ggtgctggac   4080
```

-continued

```
gccaccctga tccaccagag catcaccggc ctgtacgaga caagaatcga cctgtctcag    4140
ctggaggcg  acaagagacc tgccgccact aagaaggccg acaggccaa  aaagaagaag    4200
tgagcggccg ctaatcagcc ataccacatt tgtagaggtt ttacttgctt taaaaaacct    4260
cccacacctc cccctgaacc tgaaacataa aatgaatgca attgttgttg ttaacttgtt    4320
tattgcagct tataatggtt acaaataaag caatagcatc acaaatttca caaataaagc    4380
attttttca  ctgcattcta gttgtggttt gtccaaactc atcaatgtat cttatcatgt    4440
ctaccggtag ggcccctctc ttcatgtgag caaaaggcca gcaaaggcc  aggaaccgta    4500
aaaaggccgc gttgctggcg ttttttccata ggctccgccc ccctgacgag catcacaaaa    4560
atcgacgctc aagtcagagg tggcgaaacc cgacaggact ataaagatac caggcgtttc    4620
cccctggaag ctccctcgtg cgctctcctg ttccgaccct gccgcttacc ggatacctgt    4680
ccgcctttct cccttcggga agcgtggcgc tttctcaatg ctcacgctgt aggtatctca    4740
gttcggtgta ggtcgttcgc tccaagctgg gctgtgtgca cgaaccccc  gttcagcccg    4800
accgctgcgc cttatccggt aactatcgtc ttgagtccaa cccggtaaga cacgacttat    4860
cgccactggc agcagccact ggtaacagga ttagcagagc gaggtatgta ggcggtgcta    4920
cagagttctt gaagtggtgg cctaactacg gctacactag aaggacagta tttggtatct    4980
gcgctctgct gaagccagtt accttcggaa aaagagttgg tagctcttga tccggcaaac    5040
aaaccaccgc tggtagcggt ggttttttg  tttgcaagca gcagattacg cgcagaaaaa    5100
aaggatctca agaagatcct ttgatctttt ctacggggtc tgacgctcag tggaacgaaa    5160
actcacgtta agggattttg gtcatgggcg cgcctcatac tcctgcaggc atgagattat    5220
caaaaaggat cttcacctag atcctttaa  attaaaaatg aagttttaaa tcaatctaaa    5280
gtatatatga gtaaacttgg tctgacagtt accaatgctt aatcagtgag gcacctatct    5340
cagcgatctg tctatttcgt tcatccatag ttgcctgact ccccgtcgtg tagataacta    5400
cgatacggga gggcttacca tctggcccca gtgctgcaat gataccgcga gacccacgct    5460
caccggctcc agatttatca gcaataaacc agccagccgg aagggccgag cgcagaagtg    5520
gtcctgcaac tttatccgcc tccatccagt ctattaattg ttgccgggaa gctagagtaa    5580
gtagttcgcc agttaatagt ttgcgcaacg ttgttgccat tgctacaggc atcgtggtgt    5640
cacgctcgtc gtttggtatg gcttcattca gctccggttc ccaacgatca aggcgagtta    5700
catgatcccc catgttgtgc aaaaaagcgg ttagctcctt cggtcctccg atcgttgtca    5760
gaagtaagtt ggccgcagtg ttatcactca tggttatggc agcactgcat aattctctta    5820
ctgtcatgcc atccgtaaga tgcttttctg tgactggtga gtactcaacc aagtcattct    5880
gagaatagtg tatgcggcga ccgagttgct cttgcccggc gtcaatacgg gataataccg    5940
cgccacatag cagaacttta aaagtgctca tcattggaaa acgttcttcg ggcgaaaac    6000
tctcaaggat cttaccgctg ttgagatcca gttcgatgta acccactcgt gcacccaact    6060
gatcttcagc atcttttact ttcaccagcg tttctgggtg agcaaaaaca ggaaggcaaa    6120
atgccgcaaa aaagggaata agggcgacac ggaaatgttg aatactcata ctcttccttt    6180
ttcaatatta ttgaagcatt tatcagggtt attgtctcat gagcggatac atatttgaat    6240
gtatttagaa aaataaacaa ataggggttc cgcgcacatt tccccgaaaa gtgccacctg    6300
acgtcaggta ccaagcctag gcctccaaaa aagcctcctc actacttctg gaatagctca    6360
gaggcagagg cggcctcggc ctctgcataa ataaaaaaaa ttagtcagcc atggggcgga    6420
gaatgggcgg aactgggcgg agttaggggc gggatgggcg gagttagggg cgggactatg    6480
```

-continued

```
gttgctgact aattgagatg catgctttgc atacttctgc ctgctggga gcctggggac    6540
tttccacacc tggttgctga ctaattgaga tgcatgcttt gcatacttct gcctgctggg    6600
gagcctgggg actttccaca ccggatccac catgggatcg gccattgaac aagatggatt    6660
gcacgcaggt tctccggccg cttggtgga gaggctattc ggctatgact gggcacaaca    6720
gacaatcggc tgctctgatg ccgccgtgtt ccggctgtca gcgcaggggc gcccggttct    6780
ttttgtcaag accgacctgt ccggtgccct gaatgaactg caggacgagg cagcgcggct    6840
atcgtggctg gccacgacgg gcgttccttg cgcagctgtg ctcgacgttg tcactgaagc    6900
gggaagggac tggctgctat tgggcgaagt gccggggcag gatctcctgt catctcacct    6960
tgctcctgcc gagaaagtat ccatcatggc tgatgcaatg cggcggctgc atacgcttga    7020
tccggctacc tgcccattcg accaccaagc gaaacatcgc atcgagcgag cacgtactcg    7080
gatggaagcc ggtcttgtcg atcaggatga tctggacgaa gagcatcagg gctcgcgcc    7140
agccgaactg ttcgccaggc tcaaggcgcg catgcccgac ggcgatgatc tcgtcgtgac    7200
ccatggcgat gcctgcttgc cgaatatcat ggtggaaaat ggccgctttt ctggattcat    7260
cgactgtggc cggctgggtg tggcggaccg ctatcaggac atagcgttgg ctacccgtga    7320
tattgctgaa gagcttggcg gcgaatgggc tgaccgcttc ctcgtgcttt acggtatcgc    7380
cgctcccgat tcgcagcgca tcgccttcta tcgccttctt gacgagttct tctgaacgcg    7440
tgctgtaagt ctgcagaaat tgatgatcta ttaaacaata aagatgtcca ctaaaatgga    7500
agttttttcct gtcatacttt gttaagaagg gtgagaacag agtacctaca ttttgaatgg    7560
aaggattgga gctacggggg tgggggtggg gtgggattag ataaatgcct gctctttact    7620
gaaggctctt tactattgct ttatgataat gtttcatagt tggatatcat aatttaaaca    7680
agcaaaacca aattaagggc cagctcattc ctcccactca tgatctatgg atctatagat    7740
ctctcgtgca gctggggctc taggggtat ccccacgcgc cctgtagcgg cgcattaagc    7800
gcggcgggtg tggtggttac gcgcagcgtg accgctacac ttgccagcgc cctagcgccc    7860
gctcctttcg ctttcttccc ttcctttctc gccacgttcg ccggctttcc ccgtcaagct    7920
ctaaatcggg ggctcccttt agggttccga tttagtgctt tacggcacct cgaccccaaa    7980
aaacttgatt agggtgatgg ttcacgtagt gggccatcgc cctgatagac ggttttttcgc    8040
cctttgacgt tggagtccac gttctttaat agtggactct tgttccaaac tggaacaaca    8100
ctcaaccccta tctcggtcta ttcttttgat ttataaggga ttttgccgat ttcggcctat    8160
tggttaaaaa atgagctgat ttaacaaaaa tttaacgcga attaattctg tggaatgtgt    8220
gtcagttagt cgcgaggcct ccgcgccggg ttttggcgcc tcccgcgggc gcccccctcc    8280
tcacggcgag cgctgccacg tcagacgaag gcgcagcga gcgtcctgat ccttccgccc    8340
ggacgctcag gacagcggcc cgctgctcat aagactcggc cttagaaccc cagtatcagc    8400
agaaggacat tttaggacgg gacttgggtg actctagggc actggttttc tttccagaga    8460
gcggaacagg cgaggaaaag tagtcccttc tcggcgattc tgcggaggga tctccgtggg    8520
gcggtgaacg ccgatgatta taaggacg cgccgggtgt ggcacagcta gttccgtcgc    8580
agccgggatt tgggtcgcgg ttcttgtttg tggatcgctg tgatcgtcac ttggtgagta    8640
gcgggctgct gggctggccg gggctttcgt ggccgccggg ccgctcggtg gacggaagc    8700
gtgtggagag accgccaagg gctgtagtct gggtccgcga gcaaggttgc cctgaactgg    8760
gggttggggg gagcgcagca aaatggcggc tgttcccgag tcttgaatgg aagacgcttg    8820
```

```
tgaggcgggc tgtgaggtcg ttgaaacaag gtgggggca tggtgggcgg caagaaccca    8880
aggtcttgag gccttcgcta atgcgggaaa gctcttattc gggtgagatg ggctggggca    8940
ccatctgggg accctgacgt gaagtttgtc actgactgga gaactcggtt tgtcgtctgt    9000 tgcggggcg gcagttatgg cggtgccgtt gggcagtgca cccgtacctt tgggagcgcg     9060
cgccctcgtc gtgtcgtgac gtcacccgtt ctgttggctt ataatgcagg gtggggccac    9120
ctgccggtag gtgtgcggta ggcttttctc cgtcgcagga cgcagggttc gggcctaggg    9180
taggctctcc tgaatcgaca ggcgccggac ctctggtgag gggagggata agtgaggcgt    9240
cagtttcttt ggtcggtttt atgtacctat cttcttaagt agctgaagct ccggttttga    9300
actatgcgct cggggttggc gagtgtgttt tgtgaagttt tttaggcacc tttgaaatg     9360 taatcatttg ggtcaatatg taattttcag tgttagacta gtaaattgtc cgctaaattc    9420
tggccgtttt tggctttttt gttagacgtc gaccgatcct gagaacttca gggtgagttt    9480 ggggacccctt gattgttctt tcttttttcgc tattgtaaaa ttcatgttat atggaggggg   9540
caaagttttc agggtgttgt ttagaatggg aagatgtccc ttgtatcacc atggaccctc    9600
atgataattt tgtttctttc acttctact ctgttgacaa ccattgtctc ctcttatttt    9660
cttttcattt tctgtaactt tttcgttaaa ctttagcttg catttgtaac gaattttaa    9720 attcactttt gtttatttgt cagattgtaa gtactttctc taatcacttt tttttcaagg   9780
caatcagggt atattatatt gtacttcagc acagttttag agaacaattg ttataattaa    9840
atgataaggt agaatatttc tgcatataaa ttctggctgg cgtggaaata ttcttattgg   9900
tagaaacaac tacacccctgg tcatcatcct gcctttctct ttatggttac aatgatatac   9960
actgtttgag atgaggataa aatactctga gtccaaaccg ggcccctctg ctaaccatgt   10020
tcatgccttc ttcttttttcc tacagctcct gggcaacgtg ctggttgttg tgctgtctca  10080
tcattttggc aaagaatt                                                  10098

<210> SEQ ID NO 65
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gcccggatag ctcagtcggt agagcatcag acttttaatc tgagggtcca gggttcaagt    60
ccctgttcgg gcg                                                       73

<210> SEQ ID NO 66
<211> LENGTH: 10435
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
aagcttatac tcgagctcta gattgggaac ccgggtctct cgaattcctc gaggccgggc    60
gcggtggcgc gtgcctgtag tcccagctac tcgggaggct gaggctggag gatcgcttga   120
gtccaggagt tctgggctgt agtgcgctat gccgatcggg tgtccgcact aagttcggca   180
tcaatatggt gacctcccgg gagcggggga ccaccaggtt gcctaaggag gggtgaaccg   240
gcccaggtcg gaaacggagc aggtcaaaac tcccgtgctg atcagtagtg ggatcgcgcc   300
```

```
tgtgaatagc cactgcactc cagcctgggc aacatagcga gacccgtct ctactagtgc     360 caccatggac aagcccaaga aaaagcggaa agtgaagtac agcatcggcc tggacatcgg     420
caccaactct gtgggctggg ccgtgatcac cgacgagtac aaggtgccca gcaagaaatt     480
caaggtgctg ggcaacaccg acaggcacag catcaagaag aacctgatcg gcgccctgct     540
gttcgacagc ggcgaaacag ccgaggccac cagactgaag agaaccgcca gaagaagata     600
caccaggcgg aagaacagga tctgctatct gcaagagatc ttcagcaacg agatggccaa     660
ggtggacgac agcttcttcc acagactgga agagtccttc ctggtggaag aggacaagaa     720
gcacgagaga cacccccatct tcggcaacat cgtggacgag gtggcctacc acgagaagta     780
ccccaccatc taccacctga aaagaaact ggtggacagc accgacaagg ccgacctgag     840
actgatctac ctggccctgg cccacatgat caagttcaga ggccacttcc tgatcgaggg     900
cgacctgaac cccgacaaca gcgacgtgga caagctgttc atccagctgg tgcagaccta     960
caaccagctg ttcgaggaaa acccccatcaa cgccagcggc gtggacgcca aggctatcct    1020
gtctgccaga ctgagcaaga gcagaaggct ggaaaatctg atcgcccagc tgcccggcga    1080
gaagaagaac ggcctgttcg gcaacctgat tgccctgagc ctgggcctga cccccaactt    1140
caagagcaac ttcgacctgg ccgaggatgc caaactgcag ctgagcaagg acacctacga    1200
cgacgacctg gacaacctgc tggcccagat cggcgaccag tacgccgacc tgttcctggc    1260
cgccaagaac ctgtctgacg ccatcctgct gagcgacatc ctgagagtga acaccgagat    1320
caccaaggcc cccctgagcg cctctatgat caagagatac gacgagcacc accaggacct    1380
gaccctgctg aaagctctcg tgcggcagca gctgcctgag aagtacaaag aaatcttctt    1440
cgaccagagc aagaacggct acgccggcta catcgatggc ggcgctagcc aggaagagtt    1500
ctacaagttc atcaagccca tcctggaaaa gatggacggc accgaggaac tgctcgtgaa    1560
gctgaacaga gaggacctgc tgagaaagca gagaaccttc gacaacggca gcatcccccca    1620 ccagatccac ctgggagagc tgcacgctat cctgagaagg caggaagatt tttacccatt    1680
cctgaaggac aaccgggaaa gatcgagaa gatcctgacc ttcaggatcc cctactacgt    1740 gggcccctg gccagaggca acagcagatt cgcctggatg accagaaaga gcgaggaaac    1800
catcaccccc tggaacttcg aggaagtggt ggacaagggc gccagcgccc agagcttcat    1860
cgagagaatg acaaacttcg ataagaacct gcccaacgaa aaggtgctgc ccaagcacag    1920
cctgctgtac gagtacttca ccgtgtacaa cgagctgacc aaagtgaaat acgtgaccga    1980
gggaatgaga aagcccgcct tcctgagcgg cgagcagaaa aaggccatcg tggacctgct    2040
gttcaagacc aacagaaaag tgaccgtgaa gcagctgaaa gaggactact tcaagaaaat    2100
cgagtgcttc gactccgtgg aaatctccgg cgtggaagat agattcaacg cctccctggg    2160
cacataccac gatctgctga aaattatcaa ggacaaggac ttcctggata cgaagagaa    2220 cgaggacatt ctggaagata tcgtgctgac cctgacactg tttgaggacc gcgagatgat    2280
cgaggaaagg ctgaaaacct acgctcacct gttcgacgac aaagtgatga agcagctgaa    2340
gagaaggcgg tacaccggct ggggcaggct gagcagaaag ctgatcaacg gcatcagaga    2400
caagcagagc ggcaagacaa tcctggattt cctgaagtcc gacggcttcg ccaaccggaa    2460
cttcatgcag ctgatccacg acgacagcct gacattcaaa gaggacatcc agaaagccca    2520
ggtgtccggc caggcgact ctctgcacga gcatatcgct aacctggccg gcagccccgc    2580
tatcaagaag ggcatcctgc agacagtgaa ggtggtggac gagctcgtga aagtgatggg    2640
```

```
cagacacaag cccgagaaca tcgtgatcga gatggctaga gagaaccaga ccacccagaa    2700
gggacagaag aactcccgcg agaggatgaa gagaatcgaa gagggcatca aagagctggg    2760
cagccagatc ctgaaagaac accccgtgga aaacacccag ctgcagaacg agaagctgta    2820
cctgtactac ctgcagaatg gccgggatat gtacgtggac caggaactgg acatcaacag    2880
actgtccgac tacgatgtgg accatatcgt gcctcagagc tttctgaagg acgactccat    2940
cgataacaaa gtgctgactc ggagcgacaa gaacagaggc aagagcgaca acgtgccctc    3000
cgaagaggtc gtgaagaaga tgaagaacta ctggcgacag ctgctgaacg ccaagctgat    3060
tacccgagag aagttcgata acctgaccaa ggccgagaga ggcggcctga gcagctggag    3120
taaggccggc ttcatcaaga ggcagctggt ggaaaccaga cagatcacaa agcacgtggc    3180
acagatcctg gactcccgga tgaacactaa gtacgacgaa aacgataagc tgatccggga    3240
agtgaaagtg atcaccctga agtccaagct ggtgtccgat tccggaaggg atttccagtt    3300
ttacaaagtg cgcgagatca acaactacca ccacgcccac gacgcctacc tgaacgccgt    3360
cgtgggaacc gccctgatca aaaagtaccc taagctggaa agcgagttcg tgtacggcga    3420
ctacaaggtg tacgacgtgc ggaagatgat cgccaagagc gagcaggaaa tcggcaaggc    3480
taccgccaag tacttcttct acagcaacat catgaacttt ttcaagaccg aaatcaccct    3540
ggccaacggc gagatcagaa agcgccctct gatcgagaca aacggcgaaa ccggggagat    3600
cgtgtgggat aagggcagag acttcgccac agtgcgaaag gtgctgagca tgccccaagt    3660
gaatatcgtg aaaaagaccg aggtgcagac aggcggcttc agcaaagagt ctatcctgcc    3720
caagaggaac agcgacaagc tgatcgccag aaagaaggac tgggacccca agaagtacgg    3780
cggcttcgac agccctaccg tggcctactc tgtgctggtg gtggctaagg tggaaaaggg    3840
caagtccaag aaactgaaga gtgtgaaaga gctgctgggg atcaccatca tggaaagaag    3900
cagctttgag aagaacccta tcgactttct ggaagccaag ggctacaaag aagtgaaaaa    3960
ggacctgatc atcaagctgc ctaagtactc cctgttcgag ctggaaaacg gcagaaagag    4020
aatgctggcc tctgccggcg aactgcagaa gggaaacgag ctggcccctg ctagcaaata    4080
tgtgaacttc ctgtacctgg cctcccacta tgagaagctg aagggcagcc ctgaggacaa    4140
cgaacagaaa cagctgtttg tggaacagca taagcactac ctggacgaga tcatcgagca    4200
gatcagcgag ttctccaaga gagtgatcct ggccgacgcc aatctggaca aggtgctgtc    4260
tgcctacaac aagcacaggg acaagcctat cagagagcag gccgagaata tcatccacct    4320
gttcaccctg acaaacctgg gcgctcctgc cgccttcaag tactttgaca ccaccatcga    4380
ccggaagagg tacaccagca ccaaagaggt gctggacgcc accctgatcc accagagcat    4440
caccggcctg tacgagacaa gaatcgacct gtctcagctg ggaggcgaca gagacctgc     4500
cgccactaag aaggccggac aggccaaaaa gaagaagtga gcggccgcta atcagccata    4560
ccacatttgt agaggtttta cttgctttaa aaaacctccc acacctcccc ctgaacctga    4620
aacataaaat gaatgcaatt gttgttgtta acttgtttat tgcagcttat aatggttaca    4680
aataaagcaa tagcatcaca aatttcacaa ataaagcatt ttttcactg  cattctagtt    4740
gtggtttgtc caaactcatc aatgtatctt atcatgtcta ccgtagggc  ccctctcttc    4800
atgtgagcaa aaggccagca aaaggccagg aaccgtaaaa aggccgcgtt gctggcgttt    4860
ttccataggc tccgcccccc tgacgagcat cacaaaaatc gacgctcaag tcagaggtgg    4920
cgaaacccga caggactata aagataccag gcgtttcccc ctggaagctc cctcgtgcgc    4980
tctcctgttc cgaccctgcc gcttaccgga tacctgtccg cctttctccc ttcgggaagc    5040
```

```
gtggcgcttt ctcaatgctc acgctgtagg tatctcagtt cggtgtaggt cgttcgctcc    5100
aagctgggct gtgtgcacga acccccgtt cagcccgacc gctgcgcctt atccggtaac     5160
tatcgtcttg agtccaaccc ggtaagacac gacttatcgc cactggcagc agccactggt    5220
aacaggatta gcagagcgag gtatgtaggc ggtgctacag agttcttgaa gtggtggcct    5280
aactacggct acactagaag gacagtattt ggtatctgcg ctctgctgaa gccagttacc    5340
ttcggaaaaa gagttggtag ctcttgatcc ggcaaacaaa ccaccgctgg tagcggtggt    5400 tttttgttt gcaagcagca gattacgcgc agaaaaaag gatctcaaga agatcctttg     5460 atctttcta cggggtctga cgctcagtgg aacgaaaact cacgttaagg gattttggtc     5520
atgggcgcgc ctcatactcc tgcaggcatg agattatcaa aaaggatctt cacctagatc    5580
cttttaaatt aaaaatgaag ttttaaatca atctaaagta tatatgagta aacttggtct    5640
gacagttacc aatgcttaat cagtgaggca cctatctcag cgatctgtct atttcgttca    5700
tccatagttg cctgactccc cgtcgtgtag ataactacga tacgggaggg cttaccatct    5760
ggccccagtg ctgcaatgat accgcgagac ccacgctcac cggctccaga tttatcagca    5820
ataaaccagc cagccggaag ggccgagcgc agaagtggtc ctgcaacttt atccgcctcc    5880
atccagtcta ttaattgttg ccgggaagct agagtaagta gttcgccagt taatagtttg    5940
cgcaacgttg ttgccattgc tacaggcatc gtggtgtcac gctcgtcgtt tggtatggct    6000
tcattcagct ccggttccca acgatcaagg cgagttacat gatccccat gttgtgcaaa      6060 aaagcggtta gctccttcgg tcctccgatc gttgtcagaa gtaagttggc cgcagtgtta    6120
tcactcatgg ttatggcagc actgcataat tctcttactg tcatgccatc cgtaagatgc    6180
ttttctgtga ctggtgagta ctcaaccaag tcattctgag aatagtgtat gcggcgaccg    6240
agttgctctt gcccggcgtc aatacgggat aataccgcgc cacatagcag aactttaaaa    6300
gtgctcatca ttggaaaacg ttcttcgggg cgaaaactct caaggatctt accgctgttg    6360
agatccagtt cgatgtaacc cactcgtgca cccaactgat cttcagcatc ttttactttc    6420
accagcgttt ctgggtgagc aaaaacagga aggcaaaatg ccgcaaaaaa gggaataagg    6480
gcgacacgga aatgttgaat actcatactc ttcctttttc aatattattg aagcatttat    6540
cagggttatt gtctcatgag cggatacata tttgaatgta tttagaaaaa taaacaaata    6600
ggggttccgc gcacatttcc ccgaaaagtg ccacctgacg tcaggtacca agcctaggcc    6660
tccaaaaaag cctcctcact acttctggaa tagctcagag gcagaggcgg cctcggcctc    6720
tgcataaata aaaaaaatta gtcagccatg gggcggagaa tgggcggaac tgggcggagt    6780
taggggcggg atgggcggag ttaggggcgg gactatggtt gctgactaat tgagatgcat    6840
gctttgcata cttctgcctg ctggggagcc tggggacttt ccacacctgg ttgctgacta    6900
attgagatgc atgctttgca tacttctgcc tgctggggag cctggggact tccacaccg     6960 gatccaccat gggatcggcc attgaacaag atggattgca cgcaggttct ccggccgctt    7020
gggtggagag gctattcggc tatgactggg cacaacagac aatcggctgc tctgatgccg    7080
ccgtgttccg gctgtcagcg caggggcgcc cggttctttt tgtcaagacc gacctgtccg    7140
gtgccctgaa tgaactgcag gacgaggcag cgcggctatc gtggctggcc acgacgggcg    7200
ttccttgcgc agctgtgctc gacgttgtca ctgaagcggg aagggactgg ctgctattgg    7260
gcgaagtgcc ggggcaggat ctcctgtcat ctcaccttgc tcctgccgag aaagtatcca    7320
tcatggctga tgcaatgcgg cggctgcata cgcttgatcc ggctacctgc ccattcgacc    7380
```

```
accaagcgaa acatcgcatc gagcgagcac gtactcggat ggaagccggt cttgtcgatc    7440
aggatgatct ggacgaagag catcaggggc tcgcgccagc cgaactgttc gccaggctca    7500
aggcgcgcat gcccgacggc gatgatctcg tcgtgaccca tggcgatgcc tgcttgccga    7560
atatcatggt ggaaaatggc cgcttttctg gattcatcga ctgtggccgg ctgggtgtgg    7620
cggaccgcta tcaggacata gcgttggcta cccgtgatat tgctgaagag cttggcggcg    7680
aatgggctga ccgcttcctc gtgctttacg gtatcgccgc tcccgattcg cagcgcatcg    7740
ccttctatcg ccttcttgac gagttcttct gaacgcgtgc tgtaagtctg cagaaattga    7800
tgatctatta aacaataaag atgtccacta aaatggaagt ttttcctgtc atactttgtt    7860
aagaagggtg agaacagagt acctacattt tgaatggaag gattggagct acggggtggg    7920
gggtggggtg ggattagata aatgcctgct ctttactgaa ggctctttac tattgcttta    7980
tgataatgtt tcatagttgg atatcataat ttaaacaagc aaaaccaaat taagggccag    8040
ctcattcctc ccactcatga tctatggatc tatagatctc tcgtgcagct ggggctctag    8100
ggggtatccc cacgcgccct gtagcggcgc attaagcgcg gcgggtgtgg tggttacgcg    8160
cagcgtgacc gctacacttg ccagcgccct agcgcccgct cctttcgctt tcttcccttc    8220
cttttctcgc acgttcgccg gctttccccg tcaagctcta aatcggggc  tccctttagg    8280 gttccgattt agtgctttac ggcacctcga ccccaaaaaa cttgattagg gtgatggttc    8340
acgtagtggg ccatcgccct gatagacggt ttttcgccct tgacgttgg  agtccacgtt    8400 ctttaatagt ggactcttgt tccaaactgg aacaacactc aaccctatct cggtctattc    8460
ttttgattta taagggattt tgccgatttc ggcctattgg ttaaaaaatg agctgattta    8520
acaaaatttt aacgcgaatt aattctgtgg aatgtgtgtc agttagtcgc gaggcctccg    8580
cgccgggttt ggcgcctcc  cgcgggcgcc cccctcctca cggcgagcgc tgccacgtca    8640
gacgaagggc gcagcgagcg tcctgatcct tccgcccgga cgctcaggac agcggcccgc    8700
tgctcataag actcggcctt agaacccccag tatcagcaga aggacatttt aggacgggac    8760
ttgggtgact ctagggcact ggttttcttt ccagagagcg gaacaggcga ggaaaagtag    8820
tcccttctcg gcgattctgc ggagggatct ccgtggggcg gtgaacgccg atgattatat    8880
aaggacgcgc cgggtgtggc acagctagtt ccgtcgcagc cgggatttgg gtcgcggttc    8940
ttgtttgtgg atcgctgtga tcgtcacttg gtgagtagcg ggctgctggg ctggccgggg    9000 cttttcgtggc cgccgggccg ctcggtggga cggaagcgtg tggagagacc gccaagggct    9060
gtagtctggg tccgcgagca aggttgccct gaactggggg ttgggggag  cgcagcaaaa    9120 tggcggctgt tcccgagtct tgaatggaag acgcttgtga ggcgggctgt gaggtcgttg    9180
aaacaaggtg gggggcatgg tgggcggcaa gaacccaagg tcttgaggcc ttcgctaatg    9240
cgggaaagct cttattcggg tgagatgggc tgggggcacca tctgggacc  ctgacgtgaa    9300 gtttgtcact gactggagaa ctcggttttgt cgtctgttgc gggggcggca gttatgcgg    9360 tgccgttggg cagtgcaccc gtacctttgg gagcgcgcgc cctcgtcgtg tcgtgacgtc    9420
acccgttctg ttggcttata atgcagggtg gggccacctg ccggtaggtg tgcggtaggc    9480
ttttctccgt cgcaggacgc agggttcggg cctaggtag  gctctcctga atcgacaggc    9540 gccggaacctc tggtgagggg aggataagt  gaggcgtcag tttctttggt cggttttatg    9600
tacctatctt cttaagtagc tgaagctccg gttttgaact atgcgctcgg ggttggcgag    9660
tgtgttttgt gaagtttttt aggcaccttt tgaaatgtaa tcatttgggt caatatgtaa    9720
ttttcagtgt tagactagta aattgtccgc taaattctgg ccgttttttgg cttttttgtt    9780
```

```
agacgtcgac cgatcctgag aacttcaggg tgagtttggg gacccttgat tgttctttct    9840
ttttcgctat tgtaaaattc atgttatatg gagggggcaa agttttcagg gtgttgttta    9900
gaatgggaag atgtcccttg tatcaccatg gaccctcatg ataattttgt ttctttcact    9960
ttctactctg ttgacaacca ttgtctcctc ttattttctt ttcattttct gtaacttttt   10020
cgttaaactt tagcttgcat ttgtaacgaa ttttaaatt cacttttgtt tatttgtcag    10080
attgtaagta ctttctctaa tcactttttt ttcaaggcaa tcagggtata ttatattgta   10140
cttcagcaca gttttagaga acaattgtta taattaaatg ataaggtaga atatttctgc   10200
atataaattc tggctggcgt ggaaatattc ttattggtag aaacaactac accctggtca   10260
tcatcctgcc tttctcttta tggttacaat gatatacact gtttgagatg aggataaaat   10320
actctgagtc caaaccgggc ccctctgcta accatgttca tgccttcttc tttttcctac   10380
agctcctggg caacgtgctg gttgttgtgc tgtctcatca ttttggcaaa gaatt         10435
```

<210> SEQ ID NO 67
<211> LENGTH: 10441
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
aagcttatac tcgagctcta gattgggaac ccgggtctct cgaattcctc gagactagtg      60
ccaccatgga caagcccaag aaaaagcgga agtgaagta cagcatcggc ctggacatcg     120
gcaccaactc tgtgggctgg gccgtgatca ccgacgagta caaggtgccc agcaagaaat     180
tcaaggtgct gggcaacacc gacaggcaca gcatcaagaa gaacctgatc ggcgccctgc     240
tgttcgacag cggcgaaaca gccgaggcca ccagactgaa gagaaccgcc agaagaagat     300
acaccaggcg gaagaacagg atctgctatc tgcaagagat cttcagcaac gagatggcca     360
aggtggacga cagcttcttc cacagactgg aagagtcctt cctggtggaa gaggacaaga     420
agcacgagag acaccccatc ttcggcaaca tcgtggacga ggtggcctac cacgagaagt     480
accccaccat ctaccacctg agaaagaaac tggtggacag caccgacaag gccgacctga     540
gactgatcta cctggccctg gcccacatga tcaagttcag aggccacttc ctgatcgagg     600
gcgacctgaa ccccgacaac agcgacgtgg acaagctgtt catccagctg gtgcagacct     660
acaaccagct gttcgaggaa aaccccatca cgccagcgg cgtggacgcc aaggctatcc     720
tgtctgccag actgagcaag agcagaaggc tggaaaatct gatcgcccag ctgccggcg     780 agaagaagaa cggcctgttc ggcaacctga ttgccctgag cctgggcctg accccccaact     840 tcaagagcaa cttcgacctg gccgaggatg ccaaactgca gctgagcaag gacacctacg     900
acgacgacct ggacaacctg ctggcccaga tcggcgacca gtacgccgac ctgttcctgg     960
ccgccaagaa cctgtctgac gccatcctgc tgagcgacat cctgagagtg aacaccgaga    1020
tcaccaaggc cccctgagc gcctctatga tcaagagata cgacgagcac caccaggacc    1080
tgaccctgct gaaagctctc gtgcggcagc agctgcctga agtacaaa gaaatcttct    1140 tcgaccagag caagaacggc tacgccggct acatcgatgg cggcgctagc caggaagagt    1200
tctacaagtt catcaagccc atcctggaaa agatggacgg caccgaggaa ctgctcgtga    1260
agctgaacag agaggacctg ctgagaaagc agagaacctt cgacaacggc agcatccccc    1320
accagatcca cctgggagag ctgcacgcta tcctgagaag gcaggaagat ttttacccat    1380
```

```
tcctgaagga caaccgggaa aagatcgaga agatcctgac cttcaggatc ccctactacg    1440
tgggccccct ggccagaggc aacagcagat tcgcctggat gaccagaaag agcgaggaaa    1500
ccatcacccc ctggaacttc gaggaagtgg tggacaaggg cgccagcgcc cagagcttca    1560
tcgagagaat gacaaacttc gataagaacc tgcccaacga gaaggtgctg cccaagcaca    1620
gcctgctgta cgagtacttc accgtgtaca acgagctgac caaagtgaaa tacgtgaccg    1680
agggaatgag aaagcccgcc ttcctgagcg gcgagcagaa aaaggccatc gtggacctgc    1740
tgttcaagac caacagaaaa gtgaccgtga agcagctgaa agaggactac ttcaagaaaa    1800
tcgagtgctt cgactccgtg gaaatctccg gcgtggaaga tagattcaac gcctccctgg    1860
gcacatacca cgatctgctg aaaattatca aggacaagga cttcctggat aacgaagaga    1920
acgaggacat tctggaagat atcgtgctga ccctgacact gtttgaggac cgcgagatga    1980
tcgaggaaag gctgaaaacc tacgctcacc tgttcgacga caaagtgatg aagcagctga    2040
agagaaggcg gtacaccggc tggggcaggc tgagcagaaa gctgatcaac ggcatcagag    2100
acaagcagag cggcaagaca atcctggatt tcctgaagtc cgacggcttc gccaaccgga    2160
acttcatgca gctgatccac gacgacagcc tgacattcaa agaggacatc cagaaagccc    2220
aggtgtccgg ccagggcgac tctctgcacg agcatatcgc taacctggcc ggcagccccg    2280
ctatcaagaa gggcatcctg cagacagtga aggtggtgga cgagctcgtg aaagtgatgg    2340
gcagacacaa gcccgagaac atcgtgatcg agatggctag agagaaccag accacccaga    2400
agggacagaa gaactcccgc gagaggatga agagaatcga gagggcatc aaagagctgg    2460
gcagccagat cctgaaagaa cacccgtgg aaaacaccca gctgcagaac gagaagctgt    2520
acctgtacta cctgcagaat ggccgggata tgtacgtgga ccaggaactg gacatcaaca    2580
gactgtccga ctacgatgtg gaccatatcg tgcctcagag ctttctgaag gacgactcca    2640
tcgataacaa agtgctgact cggagcgaca gaacagagg caagagcgac aacgtgccct    2700
ccgaagaggt cgtgaagaag atgaagaact actggcgaca gctgctgaac gccaagctga    2760
ttacccagag gaagttcgat aacctgacca aggccgagag aggcggcctg agcgagctgg    2820
ataaggccgg cttcatcaag aggcagctgg tggaaaccag acagatcaca aagcacgtgg    2880
cacagatcct ggactcccgg atgaacacta gtacgacga aaacgataag ctgatccggg    2940
aagtgaaagt gatcacctg aagtccaagc tggtgtccga tttccggaag gatttccagt    3000
tttacaaagt gcgcgagatc aacaactacc accacgccca cgacgcctac ctgaacgccg    3060
tcgtgggaac cgcccgatc aaaaagtacc ctaagctgga aagcgagttc gtgtacggcg    3120
actacaaggt gtacgacgtg cggaagatga tcgccaagag cgagcaggaa atcggcaagg    3180
ctaccgccaa gtacttcttc tacagcaaca tcatgaactt tttcaagacc gaaatcaccc    3240
tggccaacgg cgagatcaga aagcgccctc tgatcgagac aaacggcgaa accggggaga    3300
tcgtgtggga taagggcaga gacttcgcca cagtgcgaaa ggtgctgagc atgccccaag    3360
tgaatatcgt gaaaaagacc gaggtgcaga caggcggctt cagcaaagag tctatcctgc    3420
ccaagaggaa cagcgacaag ctgatcgcca gaaagaagga ctgggacccc aagaagtacg    3480
gcggcttcga cagccctacc gtggcctact ctgtgctggt ggtggctaag gtggaaaagg    3540
gcaagtccaa gaaactgaag agtgtgaaag agctgctggg gatcaccatc atggaaagaa    3600
gcagctttga gaagaaccct atcgactttc tggaagccaa gggctacaaa gaagtgaaaa    3660
aggacctgat catcaagctg cctaagtact ccctgttcga gctggaaaac ggcagaaaga    3720
```

```
gaatgctggc ctctgccggc gaactgcaga agggaaacga gctggccctg cctagcaaat   3780
atgtgaactt cctgtacctg gcctcccact atgagaagct gaagggcagc cctgaggaca   3840
acgaacagaa acagctgttt gtggaacagc ataagcacta cctggacgag atcatcgagc   3900
agatcagcga gttctccaag agagtgatcc tggccgacgc caatctggac aaggtgctgt   3960
ctgcctacaa caagcacagg gacaagccta tcagagagca ggccgagaat atcatccacc   4020 tgttcacccct gacaaacctg ggcgctcctg ccgccttcaa gtactttgac accaccatcg   4080
accggaagag gtacaccagc accaaagagg tgctggacgc caccctgatc caccagagca   4140
tcaccggcct gtacgagaca agaatcgacc tgtctcagct gggaggcgac aagagacctg   4200
ccgccactaa gaaggccgga caggccaaaa agaagaagtg atctagagcc gggcgcggtg   4260
gcgcgtgcct gtagtcccag ctactcggga ggctgaggct ggaggatcgc ttgagtccag   4320
gagttctggg ctgtagtgcg ctatgccgat cgggtgtccg cactaagttc ggcatcaata   4380
tggtgacctc ccgggagcgg gggaccacca ggttgcctaa ggaggggtga accggcccag   4440
gtcggaaacg gagcaggtca aaactcccgt gctgatcagt agtgggatcg cgcctgtgaa   4500
tagccactgc actccagcct gggcaacata gcgagacccc gtctctgcgg ccgctaatca   4560
gccataccac atttgtagag gttttacttg cttttaaaaa cctcccacac ctccccctga   4620
acctgaaaca taaatgaat gcaattgttg ttgttaactt gtttattgca gcttataatg   4680
gttacaaata aagcaatagc atcacaaatt tcacaaataa agcatttttt tcactgcatt   4740
ctagttgtgg tttgtccaaa ctcatcaatg tatcttatca tgtctaccgg tagggcccct   4800
ctcttcatgt gagcaaaagg ccagcaaaag gccaggaacc gtaaaaaggc cgcgttgctg   4860 gcgttttttcc ataggctccg ccccctgac gagcatcaca aaaatcgacg ctcaagtcag   4920
aggtggcgaa acccgacagg actataaaga taccaggcgt ttccccctgg aagctccctc   4980
gtgcgctctc ctgttccgac cctgccgctt accggatacc tgtccgcctt tctcccttcg   5040
ggaagcgtgg cgctttctca atgctcacgc tgtaggtatc tcagttcggt gtaggtcgtt   5100
cgctccaagc tgggctgtgt gcacgaaccc cccgttcagc ccgaccgctg cgccttatcc   5160
ggtaactatc gtcttgagtc aacccggta agacacgact tatcgccact ggcagcagcc   5220
actggtaaca ggattagcag agcgaggtat gtaggcggtg ctacagagtt cttgaagtgg   5280
tggcctaact acggctacac tagaaggaca gtatttggta tctgcgctct gctgaagcca   5340
gttaccttcg gaaaaagagt tggtagctct tgatccggca acaaaccac cgctggtagc   5400 ggtggttttt ttgtttgcaa gcagcagatt acgcgcagaa aaaaaggatc tcaagaagat   5460
cctttgatct tttctacggg gtctgacgct cagtggaacg aaaactcacg ttaagggatt   5520
ttggtcatgg gcgcgcctca tactcctgca ggcatgagat tatcaaaaag gatcttcacc   5580
tagatccttt taaattaaaa atgaagtttt aaatcaatct aaagtatata tgagtaaact   5640
tggtctgaca gttaccaatg cttaatcagt gaggcaccta tctcagcgat ctgtctattt   5700
cgttcatcca tagttgcctg actccccgtc gtgtagataa ctacgatacg ggagggctta   5760
ccatctggcc ccagtgctgc aatgataccg cgagacccac gctcaccggc tccagattta   5820
tcagcaataa accagccagc cggaagggcc gagcgcagaa gtggtcctgc aactttatcc   5880
gcctccatcc agtctattaa ttgttgccgg gaagctagag taagtagttc gccagttaat   5940
agtttgcgca acgttgttgc cattgctaca ggcatcgtgg tgtcacgctc gtcgtttggt   6000
atggcttcat tcagctccgg ttcccaacga tcaaggcgag ttacatgatc ccccatgttg   6060
tgcaaaaaag cggttagctc cttcggtcct ccgatcgttg tcagaagtaa gttggccgca   6120
```

```
gtgttatcac tcatggttat ggcagcactg cataattctc ttactgtcat gccatccgta    6180
agatgctttt ctgtgactgg tgagtactca accaagtcat tctgagaata gtgtatgcgg    6240
cgaccgagtt gctcttgccc ggcgtcaata cgggataata ccgcgccaca tagcagaact    6300
ttaaaagtgc tcatcattgg aaaacgttct cggggcgaaa actctcaag gatcttaccg     6360
ctgttgagat ccagttcgat gtaacccact cgtgcaccca actgatcttc agcatctttt    6420
actttcacca gcgtttctgg gtgagcaaaa acaggaaggc aaaatgccgc aaaaaaggga    6480
ataagggcga cacggaaatg ttgaatactc atactcttcc ttttttcaata ttattgaagc   6540
atttatcagg gttattgtct catgagcgga tacatatttg aatgtattta gaaaaataaa    6600
caaatagggg ttccgcgcac atttccccga aaagtgccac ctgacgtcag gtaccaagcc    6660
taggcctcca aaaagcctc ctcactactt ctggaatagc tcagaggcag aggcggcctc     6720
ggcctctgca taaataaaaa aaattagtca gccatggggc ggagaatggg cggaactggg    6780
cggagttagg ggcgggatgg gcggagttag gggcgggact atggttgctg actaattgag    6840
atgcatgctt tgcatacttc tgcctgctgg ggagcctggg actttccac acctggttgc     6900
tgactaattg agatgcatgc tttgcatact tctgcctgct ggggagcctg ggacttttcc    6960
acaccggatc caccatggga tcggccattg aacaagatgg attgcacgca ggttctccgg    7020
ccgcttgggt ggagaggcta ttcggctatg actgggcaca acagacaatc ggctgctctg    7080
atgccgccgt gttccggctg tcagcgcagg ggcgcccggt tctttttgtc aagaccgacc    7140
tgtccggtgc cctgaatgaa ctgcaggacg aggcagcgcg gctatcgtgg ctggccacga    7200
cgggcgttcc ttgcgcagct gtgctcgacg ttgtcactga agcgggaagg gactggctgc    7260
tattgggcga agtgccgggg caggatctcc tgtcatctca ccttgctcct gccgagaaag    7320
tatccatcat ggctgatgca atgcggcggc tgcatacgct tgatccggct acctgcccat    7380
tcgaccacca agcgaaacat cgcatcgagc gagcacgtac tcggatggaa gccggtcttg    7440
tcgatcagga tgatctggac gaagagcatc aggggctcgc gccagccgaa ctgttcgcca    7500
ggctcaaggc gcgcatgccc gacggcgatg atctcgtcgt gacccatggc gatgcctgct    7560
tgccgaatat catggtggaa aatggccgct tttctggatt catcgactgt ggccggctgg    7620
gtgtggcgga ccgctatcag gacatagcgt tggctacccg tgatattgct gaagagcttg    7680
gcggcgaatg ggctgaccgc ttcctcgtgc tttacggtat cgccgctccc gattcgcagc    7740
gcatcgcctt ctatcgcctt cttgacgagt tcttctgaac gcgtgctgta agtctgcaga    7800
aattgatgat ctattaaaca ataaagatgt ccactaaaat ggaagttttt cctgtcatac    7860
tttgttaaga agggtgagaa cagagtacct acatttgaa tggaaggatt ggagctacgg     7920
gggtgggggt gggtgggat tagataaatg cctgctcttt actgaaggct ctttactatt     7980
gctttatgat aatgtttcat agttggatat cataatttaa acaagcaaaa ccaaattaag    8040
ggccagctca ttcctcccac tcatgatcta tggatctata gatctctcgt gcagctgggg    8100
ctctaggggg tatccccacg cgccctgtag cggcgcatta agcgcggcgg gtgtggtggt    8160
tacgcgcagc gtgaccgcta cacttgccag cgccctagcg cccgctcctt tcgctttctt    8220
cccttccttt ctcgccacgt tcgccggctt tccccgtcaa gctctaaatc ggggggctccc   8280
tttagggttc cgatttagtg ctttacggca cctcgacccc aaaaaacttg attagggtga    8340
tggttcacgt agtgggccat cgccctgata gacggttttt cgccctttga cgttggagtc    8400
cacgttcttt aatagtggac tcttgttcca aactggaaca acactcaacc ctatctcggt    8460
```

```
ctattctttt gatttataag ggattttgcc gatttcggcc tattggttaa aaaatgagct    8520
gatttaacaa aaatttaacg cgaattaatt ctgtggaatg tgtgtcagtt agtcgcgagg    8580
cctccgcgcc gggttttggc gcctcccgcg ggcgccccc tcctcacggc gagcgctgcc     8640
acgtcagacg aagggcgcag cgagcgtcct gatccttccg cccggacgct caggacagcg    8700
gcccgctgct cataagactc ggccttagaa ccccagtatc agcagaagga cattttagga    8760
cgggacttgg gtgactctag gcactggtt ttctttccag agagcggaac aggcgaggaa     8820
aagtagtccc ttctcggcga ttctgcggag ggatctccgt ggggcggtga acgccgatga    8880
ttatataagg acgcgccggg tgtggcacag ctagttccgt cgcagccggg atttgggtcg    8940
cggttcttgt ttgtggatcg ctgtgatcgt cacttggtga gtagcgggct gctgggctgg    9000
ccggggcttt cgtggccgcc gggccgctcg gtgggacgga agcgtgtgga gagaccgcca    9060
agggctgtag tctgggtccg cgagcaaggt tgccctgaac tgggggttgg ggggagcgca    9120
gcaaaatggc ggctgttccc gagtcttgaa tggaagacgc ttgtgaggcg ggctgtgagg    9180
tcgttgaaac aaggtggggg gcatggtggg cggcaagaac ccaaggtctt gaggccttcg    9240
ctaatgcggg aaagctctta ttcgggtgag atgggctggg gcaccatctg ggaccctga    9300
cgtgaagttt gtcactgact ggagaactcg gtttgtcgtc tgttgcgggg gcggcagtta    9360
tggcggtgcc gttgggcagt gcacccgtac ctttgggagc gcgcgccctc gtcgtgtcgt    9420
gacgtcaccc gttctgttgg cttataatgc agggtggggc cacctgccgg taggtgtgcg    9480
gtaggctttt ctccgtcgca ggacgcaggg ttcgggccta gggtaggctc tcctgaatcg    9540
acaggcgccg gacctctggt gaggggaggg ataagtgagg cgtcagtttc tttggtcggt    9600
tttatgtacc tatcttctta agtagctgaa gctccggttt tgaactatgc gctcggggtt    9660
ggcgagtgtg ttttgtgaag ttttttaggc acctttgaa atgtaatcat ttgggtcaat     9720
atgtaatttt cagtgttaga ctagtaaatt gtccgctaaa ttctggccgt ttttggcttt    9780
tttgttagac gtcgaccgat cctgagaact tcagggtgag tttggggacc cttgattgtt    9840
cttttttttt cgctattgta aaattcatgt tatatggagg gggcaaagtt tcagggtgt     9900
tgtttagaat gggaagatgt cccttgtatc accatggacc ctcatgataa ttttgtttct    9960
ttcactttct actctgttga caaccattgt ctcctcttat tttcttttca ttttctgtaa   10020
cttttttcgtt aaactttagc ttgcatttgt aacgaatttt taaattcact tttgtttatt  10080
tgtcagattg taagtacttt ctctaatcac ttttttttca aggcaatcag ggtatattat   10140
attgtacttc agcacagttt tagagaacaa ttgttataat taaatgataa ggtagaatat   10200
ttctgcatat aaattctggc tggcgtggaa atattcttat tggtagaaac aactacaccc   10260
tggtcatcat cctgcctttc tctttatggt tacaatgata tacactgttt gagatgagga   10320
taaaatactc tgagtccaaa ccgggcccct ctgctaacca tgttcatgcc ttcttctttt   10380
tcctacagct cctgggcaac gtgctggttg ttgtgctgtc tcatcatttt ggcaaagaat   10440
t                                                                  10441
```

<210> SEQ ID NO 68
<211> LENGTH: 8825
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
tggaagggct aattcactcc caaagaagac aagatatcct tgatctgtgg atctaccaca    60
cacaaggcta cttccctgat tagcagaact acacaccagg gccagggtc agatatccac    120
tgacctttgg atggtgctac aagctagtac cagttgagcc agataaggta gaagaggcca   180
ataaaggaga gaacaccagc ttgttacacc ctgtgagcct gcatgggatg gatgacccgg   240
agagagaagt gttagagtgg aggtttgaca gccgcctagc atttcatcac gtggcccgag   300
agctgcatcc ggagtacttc aagaactgct gatatcgagc ttgctacaag gactttccg    360
ctggggactt tccagggagg cgtggcctgg gcgggactgg ggagtggcga gccctcagat   420
cctgcatata agcagctgct ttttgcctgt actgggtctc tctggttaga ccagatctga   480
gcctgggagc tctctggcta actagggaac ccactgctta agcctcaata aagcttgcct   540
tgagtgcttc aagtagtgtg tgcccgtctg ttgtgtgact ctggtaacta gagatccctc   600
agaccctttt agtcagtgtg gaaaatctct agcagtggcg cccgaacagg gacttgaaag   660
cgaaagggaa accagaggag ctctctcgac gcaggactcg gcttgctgaa gcgcgcacgg   720
caagaggcga ggggcggcga ctggtgagta cgccaaaaat tttgactagc ggaggctaga   780
aggagagaga tgggtgcgag agcgtcagta ttaagcgggg gagaattaga tcgcgatggg   840
aaaaaattcg gttaaggcca gggggaaaga aaaaatataa attaaaacat atagtatggg   900
caagcaggga gctagaacga ttcgcagtta atcctggcct gttagaaaca tcagaaggct   960
gtagacaaat actgggacag ctacaaccat cccttcagac aggatcagaa gaacttagat  1020
cattatataa tacagtagca accctctatt gtgtgcatca aaggatagag ataaaagaca  1080
ccaaggaagc tttagacaag atagaggaag agcaaaacaa aagtaagacc accgcacagc  1140
aagcggccgg ccgctgatct tcagacctgg aggaggagat atgagggaca attggagaag  1200
tgaattatat aaatataaag tagtaaaaat tgaaccatta ggagtagcac ccaccaaggc  1260
aaagagaaga gtggtgcaga gagaaaaaag agcagtggga ataggagctt tgttccttgg  1320
gttcttggga gcagcaggaa gcactatggg cgcagcgtca atgacgctga cggtacaggc  1380
cagacaatta ttgtctggta tagtgcagca gcagaacaat ttgctgaggg ctattgaggc  1440
gcaacagcat ctgttgcaac tcacagtctg ggcatcaag cagctccagg caagaatcct  1500
ggctgtggaa agatacctaa aggatcaaca gctcctgggg atttggggtt gctctggaaa  1560
actcatttgc accactgctg tgccttggaa tgctagttgg agtaataaat ctctggaaca  1620
gatttggaat cacacgacct ggatggagtg ggacagagaa attaacaatt acacaagctt  1680
aatacactcc ttaattgaag aatcgcaaaa ccagcaagaa aagaatgaac aagaattatt  1740
ggaattagat aaatgggcaa gtttgtggaa ttggtttaac ataacaaatt ggctgtggta  1800
tataaaatta ttcataatga tagtaggagg cttggtaggt ttaagaatag ttttgctgt   1860
actttctata gtgaatagag ttaggcaggg atattcacca ttatcgtttc agacccacct  1920
cccaaccccg aggggacccg acaggcccga aggaatagaa gaagaaggtg gagagagaga  1980
cagagacaga tccattcgat tagtgaacgg atctcgacgg tatcgccttt aaaagaaaag  2040
gggggattgg ggggtacagt gcaggggaaa gaatagtaga cataatagca acagacatac  2100
aaactaaaga attacaaaaa caaattacaa aaattcaaaa ttttcgggtt tattacaggg  2160
acagcagaga tccagtttat cgatgagtaa ttcatacaaa aggactcgcc cctgccttgg  2220
ggaatcccag ggaccgtcgt taaactccca ctaacgtaga acccagagat cgctgcgttc  2280
ccgccccctc acccgcccgc tctcgtcatc actgaggtgg agaagagcat gcgtgaggct  2340
ccggtgcccg tcagtgggca gagcgcacat cgcccacagt ccccgagaag ttgggggag   2400
```

```
gggtcggcaa ttgaaccggt gcctagagaa ggtggcgcgg ggtaaactgg gaaagtgatg   2460
tcgtgtactg gctccgcctt tttcccgagg gtgggggaga accgtatata agtgcagtag   2520
tcgccgtgaa cgttctttt cgcaacgggt ttgccgccag aacacaggta agtgccgtgt    2580
gtggttcccg cgggcctggc ctctttacgg gttatggccc ttgcgtgcct tgaattactt   2640
ccacgcccct ggctgcagta cgtgattctt gatcccgagc ttcgggttgg aagtgggtgg   2700
gagagttcga ggccttgcgc ttaaggagcc ccttcgcctc gtgcttgagt tgaggcctgg   2760
cttgggcgct ggggccgccg cgtgcgaatc tggtggcacc ttcgcgcctg tctcgctgct   2820
ttcgataagt ctctagccat ttaaaatttt tgatgacctg ctgcgacgct ttttttctgg   2880
caagatagtc ttgtaaatgc gggccaagat ctgcacactg gtatttcggt ttttggggcc   2940
gcgggcggcg acgggcccg tgcgtcccag cgcacatgtt cggcgaggcg gggcctgcga    3000
gcgcggccac cgagaatcgg acgggggtag tctcaagctg gccggcctgc tctggtgcct   3060
ggcctcgcgc cgccgtgtat cgccccgccc tgggcggcaa ggctggcccg gtcggcacca   3120
gttgcgtgag cggaaagatg gccgcttccc ggccctgctg cagggagctc aaaatggagg   3180
acgcggcgct cgggagagcg ggcgggtgag tcacccacac aaaggaaaag gccttttccg   3240
tcctcagccg tcgcttcatg tgactccacg gagtaccggg cgccgtccag gcacctcgat   3300
tagttctcga gcttttggag tacgtcgtct ttaggttggg gggagggggtt ttatgcgatg   3360 gagtttcccc acactgagtg ggtggagact gaagttaggc cagcttggca cttgatgtaa   3420
ttctccttgg aatttgccct ttttgagttt ggatcttggt tcattctcaa gcctcagaca   3480
gtggttcaaa gtttttttct tccatttcag gtgtcgtgag gatctatttc cggtgaattc   3540
ctcgagacta gttctagagc ggccgcggat cccgccctc tccctccccc ccccctaacg    3600
ttactggccg aagccgcttg gaataaggcc ggtgtgcgtt tgtctatatg ttattttcca   3660
ccatattgcc gtcttttggc aatgtgaggg cccggaaacc tggccctgtc ttcttgacga   3720
gcattcctag gggtctttcc cctctcgcca aaggaatgca aggtctgttg aatgtcgtga   3780
aggaagcagt tcctctggaa gcttcttgaa gacaaacaac gtctgtagcg acccttgca    3840 ggcagcggaa ccccccacct ggcgacaggt gcctctgcgg ccaaaagcca cgtgtataag   3900
atacacctgc aaaggcggca aaccccagt gccacgttgt gagttggata gttgtggaaa    3960
gagtcaaatg gctctcctca agcgtattca acaaggggct gaaggatgcc cagaaggtac   4020
cccattgtat gggatctgat ctggggcctc ggtgcacatg ctttacatgt gtttagtcga   4080
ggttaaaaaa acgtctaggc ccccgaacc acggggacgt ggttttcctt tgaaaaacac    4140
gatgataagc ttgccacaac ccacaaggag acgaccttcc atgaccgagt acaagcccac   4200
ggtgcgcctc gccacccgcg acgacgtccc ccgggccgta cgcaccctcg ccgccgcgtt   4260
cgccgactac cccgccacgc gccacaccgt cgacccggac cgccacatcg agcgggtcac   4320
cgagctgcaa gaactcttcc tcacgcgcgt cgggctcgac atcggcaagg tgtgggtcgc   4380
ggacgacggc gccgcggtgg cggtctggac cacgccggag agcgtcgaag cggggggcgt   4440
gttcgccgag atcggcccgc gcatggccga gttgagcggt tccggctgg ccgcgcagca    4500 acagatggaa ggcctcctgg cgccgcaccg gcccaaggag cccgcgtggt tcctggccac   4560
cgtcggcgtc tcgcccgacc accagggcaa gggtctgggc agcgccgtcg tgctccccgg   4620
agtggaggcg gccgagcgcg ccggggtgcc cgccttcctg gagacctccg cgcccgcaa    4680 cctccccttc tacgagcggc tcggcttcac cgtcaccgcc gacgtcgagg tgcccgaagg   4740
```

```
accgcgcacc tggtgcatga cccgcaagcc cggtgcctag acgcgtctgg aacaatcaac    4800
ctctggatta caaaatttgt gaaagattga ctggtattct taactatgtt gctccttta    4860
cgctatgtgg atacgctgct ttaatgcctt tgtatcatgc tattgcttcc cgtatggctt    4920
tcattttctc ctccttgtat aaatcctggt tgctgtctct ttatgaggag ttgtggcccg    4980
ttgtcaggca acgtggcgtg gtgtgcactg tgtttgctga cgcaacccc actggttggg    5040
gcattgccac cacctgtcag ctcctttccg ggactttcgc tttccccctc cctattgcca    5100
cggcggaact catcgccgcc tgccttgccc gctgctggac aggggctcgg ctgttgggca    5160
ctgacaattc cgtggtgttg tcggggaagc tgacgtcctt ccatggctg ctcgcctgtg    5220
ttgccacctg gattctgcgc gggacgtcct tctgctacgt cccttcggcc ctcaatccag    5280
cggaccttcc ttcccgcggc ctgctgccgg ctctgcggcc tcttccgcgt cttcgccttc    5340
gccctcagac gagtcggatc tccctttggg ccgcctcccc gcctggaatt aattctgcag    5400
tcgagaccta gaaaaacatg gagcaatcac aagtagcaat acagcagcta ccaatgctga    5460
ttgtgcctgg ctagaagcac aagaggagga ggaggtgggt tttccagtca cacctcaggt    5520
acctttaaga ccaatgactt acaaggcagc tgtagatctt agccacttt taaaagaaaa    5580
gaggggactg gaagggctaa ttcactccca acgaagacaa gatatccttg atctgtggat    5640
ctaccacaca caaggctact ccctgatta gcagaactac acaccagggc caggggtcag    5700
atatccactg acctttggat ggtgctacaa gctagtacca gttgagccag ataaggtaga    5760
agaggccaat aaaggagaga acaccagctt gttacaccct gtgagcctgc atgggatgga    5820
tgacccggag agagaagtgt tagagtggag gtttgacagc cgcctagcat tcatcacgt    5880
ggcccgagag ctgcatccgg agtacttcaa gaactgctga tatcgagctt gctacaaggg    5940
actttccgct ggggactttc cagggaggcg tggcctgggc gggactgggg agtggcgagc    6000
cctcagatcc tgcatataag cagctgcttt tgcctgtac tgggtctctc tggttagacc    6060
agatctgagc ctgggagctc tctggctaac taggaaccc actgcttaag cctcaataaa    6120
gcttgccttg agtgcttcaa gtagtgtgtg cccgtctgtt gtgtgactct ggtaactaga    6180
gatccctcag acccttttag tcagtgtgga aaatctctag cagtagtagt tcatgtcatc    6240
ttattattca gtatttataa cttgcaaaga atgaatatc agagagtgag aggccttgac    6300
attgctagcg tttaccgtcg acctctagct agagcttggc gtaatcatgg tcatagctgt    6360
ttcctgtgtg aaattgttat ccgctcacaa ttccacacaa catacgagcc ggaagcataa    6420
agtgtaaagc ctggggtgcc taatgagtga gctaactcac attaattgcg ttgcgctcac    6480
tgcccgcttt ccagtcggga aacctgtcgt gccagctgca ttaatgaatc ggccaacgcg    6540
cggggagagg cggtttgcgt attgggcgct cttccgcttc ctcgctcact gactcgctgc    6600
gctcggtcgt tcggctgcgg cgagcggtat cagctcactc aaaggcggta atacggttat    6660
ccacagaatc aggggataac gcaggaaaga acatgtgagc aaaaggccag caaaaggcca    6720
ggaaccgtaa aaaggccgcg ttgctggcgt ttttccatag gctccgcccc cctgacgagc    6780
atcacaaaaa tcgacgctca agtcagaggt ggcgaaaccc gacaggacta taaagatacc    6840
aggcgtttcc ccctggaagc tccctcgtgc gctctcctgt tccgaccctg ccgcttaccg    6900
gatacctgtc cgcctttctc ccttcgggaa gcgtggcgct ttctcatagc tcacgctgta    6960
ggtatctcag ttcggtgtag gtcgttcgct ccaagctggg ctgtgtgcac gaaccccccg    7020
ttcagcccga ccgctgcgcc ttatccggta actatcgtct tgagtccaac ccggtaagac    7080
acgacttatc gccactggca gcagccactg gtaacaggat tagcagagcg aggtatgtag    7140
```

```
gcggtgctac agagttcttg aagtggtggc ctaactacgg ctacactaga agaacagtat    7200
ttggtatctg cgctctgctg aagccagtta ccttcggaaa aagagttggt agctcttgat    7260
ccggcaaaca aaccaccgct ggtagcggtg gttttttttgt ttgcaagcag cagattacgc    7320
gcagaaaaaa aggatctcaa gaagatcctt tgatcttttc tacggggtct gacgctcagt    7380
ggaacgaaaa ctcacgttaa gggattttgg tcatgagatt atcaaaaagg atcttcacct    7440
agatcctttt aaattaaaaa tgaagtttta aatcaatcta agtatatat gagtaaactt    7500 ggtctgacag ttaccaatgc ttaatcagtg aggcacctat ctcagcgatc tgtctatttc    7560
gttcatccat agttgcctga ctccccgtcg tgtagataac tacgatacgg gagggcttac    7620
catctggccc cagtgctgca atgataccgc gagacccacg ctcaccggct ccagatttat    7680
cagcaataaa ccagccagcc ggaagggccg agcgcagaag tggtcctgca actttatccg    7740
cctccatcca gtctattaat tgttgccggg aagctagagt aagtagttcg ccagttaata    7800
gtttgcgcaa cgttgttgcc attgctacag gcatcgtggt gtcacgctcg tcgtttggta    7860
tggcttcatt cagctccggt tcccaacgat caaggcgagt tacatgatcc cccatgttgt    7920
gcaaaaaagc ggttagctcc ttcggtcctc cgatcgttgt cagaagtaag ttggccgcag    7980
tgttatcact catggttatg gcagcactgc ataattctct tactgtcatg ccatccgtaa    8040
gatgcttttc tgtgactggt gagtactcaa ccaagtcatt ctgagaatag tgtatgcggc    8100
gaccgagttg ctcttgcccg gcgtcaatac gggataatac cgcgccacat agcagaactt    8160
taaaagtgct catcattgga aaacgttctt cggggcgaaa actctcaagg atcttaccgc    8220
tgttgagatc cagttcgatg taacccactc gtgcacccaa ctgatcttca gcatctttta    8280
ctttcaccag cgtttctggg tgagcaaaaa caggaaggca aaatgccgca aaaaagggaa    8340
taagggcgac acggaaatgt tgaatactca tactcttcct ttttcaatat tattgaagca    8400
tttatcaggg ttattgtctc atgagcggat acatatttga atgtatttag aaaaataaac    8460
aaataggggt tccgcgcaca tttccccgaa aagtgccacc tgacgtcgac ggatcgggag    8520
atcaacttgt ttattgcagc ttataatggt tacaaataaa gcaatagcat cacaaatttc    8580
acaaataaag catttttttc actgcattct agttgtggtt tgtccaaact catcaatgta    8640
tcttatcatg tctggatcaa ctggataact caagctaacc aaaatcatcc caaacttccc    8700
accccatacc ctattaccac tgccaattac ctgtggtttc atttactcta aacctgtgat    8760
tcctctgaat tattttcatt ttaaagaaat tgtatttgtt aaatatgtac tacaaactta    8820
gtagt                                                               8825
```

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
gacaggcaca gcatcaagaa                                                  20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
ttctggcggt tctcttcagt                                                    20

<210> SEQ ID NO 71
<211> LENGTH: 10736
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (341)..(344)
<223> OTHER INFORMATION: a, c, t, g, unknown or other
<220> FEATURE:
<221> NAME/KEY: modified_base
<222> LOCATION: (4525)..(4528)
<223> OTHER INFORMATION: a, c, t, g, unknown or other

<400> SEQUENCE: 71

| | | | | | |
|---|---|---|---|---|---|
| catcatcaat | aatatacctt | attttggatt | gaagccaata | tgataatgag | ggggtggagt | 60 |
| ttgtgacgtg | gcgcggggcg | tgggaacggg | gcgggtgacg | tagtagtgtg | gcggaagtgt | 120 |
| gatgttgcaa | gtgtggcgga | acacatgtaa | gcgacgcatg | tggcaaaagt | gacgttttg | 180 |
| gtgtgcgccg | gtgtacacag | gaagtgacaa | ttttcgcgcg | gttttaggcg | gatgttgtag | 240 |
| taaatttggg | cgtaaccgag | taagatttgg | ccattttcgc | gggaaaactg | aataagagga | 300 |
| agtgaaatct | gaataatttt | gtgttactca | tagcgcgtaa | nnnntaatag | taatcaatta | 360 |
| cggggtcatt | agttcatagc | ccatatatgg | agttccgcgt | tacataactt | acggtaaatg | 420 |
| gcccgcctgg | ctgaccgccc | aacgacccc | gcccattgac | gtcaataatg | acgtatgttc | 480 |
| ccatagtaac | gccaataggg | actttccatt | gacgtcaatg | ggtggagtat | ttacggtaaa | 540 |
| ctgcccactt | ggcagtacat | caagtgtatc | atatgccaag | tacgcccct | attgacgtca | 600 |
| atgacggtaa | atggcccgcc | tggcattatg | cccagtacat | gaccttatgg | gactttccta | 660 |
| cttggcagta | catctacgta | ttagtcatcg | ctattaccat | ggtgatgcgg | ttttggcagt | 720 |
| acatcaatgg | gcgtggatag | cggtttgact | cacggggatt | tccaagtctc | cacccccattg | 780 |
| acgtcaatgg | gagtttgttt | tggcaccaaa | atcaacggga | ctttccaaaa | tgtcgtaaca | 840 |
| actccgcccc | attgacgcaa | atgggcggta | ggcgtgtacg | gtgggaggtc | tatataagca | 900 |
| gagctggttt | agtgaaccgt | cagatccgct | agagatctgg | taccgtcgac | gcggccgctc | 960 |
| gagaccatgg | tcgttttaca | acgtcgtgac | tgggaaaacc | ctggcgttac | ccaacttaat | 1020 |
| cgccttgcag | cacatccccc | tttcgccagc | tggcgtaata | gcgaagaggc | ccgcaccgat | 1080 |
| cgcccttccc | aacagttgcg | cagcctgaat | ggcgaatggc | gctttgcctg | gtttccggca | 1140 |
| ccagaagcgg | tgccggaaag | ctggctggag | tgcgatcttc | ctgaggccga | tactgtcgtc | 1200 |
| gtccctcaa | actggcagat | gcacggttac | gatgcgccca | tctacaccaa | cgtgacctat | 1260 |
| cccattacgg | tcaatccgcc | gtttgttccc | acggagaatc | cgacgggttg | ttactcgctc | 1320 |
| acatttaatg | ttgatgaaag | ctggctacag | gaaggccaga | cgcgaattat | ttttgatggc | 1380 |
| gttaactcgg | cgtttcatct | gtggtgcaac | gggcgctggg | tcggttacgg | ccaggacagt | 1440 |
| cgtttgccgt | ctgaatttga | cctgagcgca | tttttacgcg | ccggagaaaa | ccgcctcgcg | 1500 |
| gtgatggtgc | tgcgttggag | tgacggcagt | tatctggaag | atcaggatat | gtggcggatg | 1560 |
| agcggcattt | tccgtgacgt | ctcgttgctg | cataaaccga | ctacacaaat | cagcgatttc | 1620 |

```
catgttgcca ctcgctttaa tgatgatttc agccgcgctg tactggaggc tgaagttcag    1680
atgtgcggcg agttgcgtga ctacctacgg gtaacagttt ctttatggca gggtgaaacg    1740
caggtcgcca gcggcaccgc gcctttcggc ggtgaaatta tcgatgagcg tggtggttat    1800
gccgatcgcg tcacactacg tctgaacgtc gaaaacccga actgtggag cgccgaaatc    1860 ccgaatctct atcgtgcggt ggttgaactg cacaccgccg acggcacgct gattgaagca    1920
gaagcctgcg atgtcggttt ccgcgaggtg cggattgaaa atggtctgct gctgctgaac    1980
ggcaagccgt tgctgattcg aggcgttaac cgtcacgagc atcatcctct gcatggtcag    2040
gtcatggatg agcagacgat ggtgcaggat atcctgctga tgaagcagaa caactttaac    2100
gccgtgcgct gttcgcatta tccgaaccat ccgctgtggt acacgctgtg cgaccgctac    2160
ggcctgtatg tggtggatga agccaatatt gaaacccacg gcatggtgcc aatgaatcgt    2220
ctgaccgatg atccgcgctg gctaccggcg atgagcgaac gcgtaacgcg aatggtgcag    2280
cgcgatcgta atcacccgag tgtgatcatc tggtcgctgg ggaatgaatc aggccacggc    2340
gctaatcacg acgcgctgta tcgctggatc aaatctgtcg atccttcccg cccggtgcag    2400
tatgaaggcg cggagccga caccacggcc accgatatta tttgcccgat gtacgcgcgc    2460
gtggatgaag accagccctt cccggctgtg ccgaaatggt ccatcaaaaa atggcttcg    2520 ctacctggag agacgcgccc gctgatcctt tgcgaatacg cccacgcgat gggtaacagt    2580
cttggcggtt tcgctaaata ctggcaggcg tttcgtcagt atccccgttt acagggcggc    2640
ttcgtctggg actgggtgga tcagtcgctg attaaatatg atgaaaacgg caacccgtgg    2700
tcggcttacg gcggtgattt tggcgatacg ccgaacgatc gccagttctg tatgaacggt    2760
ctggtctttg ccgaccgcac gccgcatcca gcgctgacgg aagcaaaaca ccagcagcag    2820
tttttccagt tccgtttatc cgggcaaacc atcgaagtga ccagcgaata cctgttccgt    2880
catagcgata acgagctcct gcactggatg gtggcgctgg atggtaagcc gctggcaagc    2940
ggtgaagtgc ctctggatgt cgctccacaa ggtaaacagt tgattgaact gcctgaacta    3000
ccgcagccgg agagcgccgg gcaactctgg ctcacagtac gcgtagtgca accgaacgcg    3060
accgcatggt cagaagccgg gcacatcagc gcctggcagc agtggcgtct ggcggaaaac    3120
ctcagtgtga cgctccccgc cgcgtcccac gccatcccgc atctgaccac cagcgaaatg    3180 gattttgca tcgagctggg taataagcgt tggcaattta accgccagtc aggctttctt    3240
tcacagatgt ggattggcga taaaaaacaa ctgctgacgc cgctgcgcga tcagttcacc    3300
cgtgcaccgc tggataacga cattggcgta agtgaagcga cccgcattga ccctaacgcc    3360
tgggtcgaac gctggaaggc ggcgggccat taccaggccg aagcagcgtt gttgcagtgc    3420
acggcagata cacttgctga tgcggtgctg attacgaccg ctcacgcgtg gcagcatcag    3480
gggaaaacct tatttatcag ccggaaaacc taccggattg atggtagtgg tcaaatggcg    3540
attaccgttg atgttgaagt ggcgagcgat acaccgcatc cggcgcggat tggcctgaac    3600
tgccagctgg cgcaggtagc agagcgggta aactggctcg gattagggcc gcaagaaaac    3660
tatcccgacc gccttactgc cgcctgtttt gaccgctggg atctgccatt gtcagacatg    3720
tataccccgt acgtcttccc gagcgaaaac ggtctgcgct gcgggacgcg cgaattgaat    3780
tatggcccac accagtggcg cggcgacttc cagttcaaca tcagccgcta cagtcaacag    3840
caactgatgg aaaccagcca tcgccatctg ctgcacgcgg aagaaggcac atggctgaat    3900
atcgacggtt ccatatgggg gattggtggc gacgactcct ggagcccgtc agtatcggcg    3960
gaattccagc tgagcgccgg tcgctaccat taccagttgg tctggtgtca aaataagga    4020
```

```
tcccgccect   ctecctcccc   ccccectaac   gttactggcc   gaagccgctt   ggaataaggc    4080
cggtgtgcgt   ttgtctatat   gttatttcc    accatattgc   cgtcttttgg   caatgtgagg    4140
gcccggaaac   ctggccctgt   cttcttgacg   agcattccta   ggggtctttc   cctctcgcc     4200 aaaggaatgc   aaggtctgtt   gaatgtcgtg   aaggaagcag   ttcctctgga   agcttctaga    4260
taagatatcc   gatccaccgg   atctagataa   ctgatcataa   tcagccatac   cacatttgta    4320
gaggttttac   ttgctttaaa   aaacctccca   cacctccccc   tgaacctgaa   acataaaatg    4380
aatgcaattg   ttgttgttaa   cttgtttatt   gcagcttata   atggttacaa   ataaagcaat    4440
agcatcacaa   atttcacaaa   taaagcattt   ttttcactgc   attctagttg   tggtttgtcc    4500
aaactcatca   atgtatctta   acgcnnnnta   agggtgggaa   agaatatata   aggtgggggt    4560
cttatgtagt   tttgtatctg   ttttgcagca   gccgccgccg   ccatgagcac   caactcgttt    4620
gatggaagca   ttgtgagctc   atatttgaca   acgcgcatgc   cccatgggc    cggggtgcgt    4680 cagaatgtga   tgggctccag   cattgatggt   cgccccgtcc   tgcccgcaaa   ctctactacc    4740
ttgacctacg   agaccgtgtc   tggaacgccg   ttggagactg   cagcctccgc   cgccgcttca    4800
gccgctgcag   ccaccgcccg   cgggattgtg   actgactttg   ctttcctgag   cccgcttgca    4860
agcagtgcag   cttcccgttc   atccgcccgc   gatgacaagt   tgacggctct   tttggcacaa    4920
ttggattctt   tgacccggga   acttaatgtc   gtttctcagc   agctgttgga   tctgcgccag    4980 caggttctg    ccctgaaggc   ttcctccct    cccaatgcgg   tttaaaacat   aaataaaaaa    5040
ccagactctg   tttggatttg   gatcaagcaa   gtgtcttgct   gtctttattt   aggggttttg    5100
cgcgcgcggt   aggcccggga   ccagcggtct   cggtcgttga   gggtcctgtg   tattttttcc    5160
aggacgtggt   aaaggtgact   ctggatgttc   agatacatgg   gcataagccc   gtctctgggg    5220
tggaggtagc   accactgcag   agcttcatgc   tgcggggtgg   tgttgtagat   gatccagtcg    5280
tagcaggagc   gctgggcgtg   gtgcctaaaa   atgtctttca   gtagcaagct   gattgccagg    5340
ggcaggccct   tggtgtaagt   gtttacaaag   cggttaagct   gggatgggtg   catacgtggg    5400
gatatgagat   gcatcttgga   ctgtattttt   aggttggcta   tgttcccagc   catatccctc    5460
cggggattca   tgttgtgcag   aaccaccagc   acagtgtatc   cggtgcactt   gggaaatttg    5520
tcatgtagct   tagaaggaaa   tgcgtggaag   aacttggaga   cgcccttgtg   acctccaaga    5580
ttttccatgc   attcgtccat   aatgatgca    atggcccac    gggcggcggc   ctgggcgaag    5640
atatttctgg   gatcactaac   gtcatagttg   tgttccagga   tgagatcgtc   ataggccatt    5700
tttacaaagc   gcgggcggag   ggtgccgac    tgcggtataa   tggttccatc   cggcccaggg    5760
gcgtagttac   cctcacagat   ttgcatttcc   cacgctttga   gttcagatgg   gggatcatg     5820 tctacctgcg   gggcgatgaa   gaaaacggtt   tccggggtag   gggagatcag   ctgggaagaa    5880
agcaggttcc   tgagcagctg   cgacttaccg   cagccggtgg   gcccgtaaat   cacacctatt    5940
accgggtgca   actggtagtt   aagagagctg   cagctgccgt   catccctgag   cagggggcc     6000 acttcgttaa   gcatgtccct   gactcgcatg   ttttccctga   ccaaatccgc   cagaaggcgc    6060
tcgccgccca   gcgatagcag   ttcttgcaag   gaagcaaagt   ttttcaacgg   tttgagaccg    6120
tccgccgtag   gcatgctttt   gagcgtttga   ccaagcagtt   ccaggcggtc   ccacagctcg    6180
gtcacctgct   ctacggcatc   tcgatccagc   atatctcctc   gtttcgcggg   ttggggcggc    6240
tttcgctgta   cggcagtagt   cggtgctcgt   ccagacgggc   cagggtcatg   tctttccacg    6300
ggcgcagggt   cctcgtcagc   gtagtctggg   tcacggtgaa   ggggtgcgct   ccgggctgcg    6360
```

```
cgctggccag ggtgcgcttg aggctggtcc tgctggtgct gaagcgctgc cggtcttcgc    6420
cctgcgcgtc ggccaggtag catttgacca tggtgtcata gtccagcccc tccgcggcgt    6480
ggcccttggc gcgcagcttg cccttggagg aggcgccgca cgaggggcag tgcagacttt    6540
tgagggcgta gagcttgggc gcgagaaata ccgattccgg ggagtaggca tccgcgccgc    6600
aggccccgca gacggtctcg cattccacga gccaggtgag ctctggccgt tcgggtcaa    6660
aaaccaggtt tcccccatgc tttttgatgc gtttcttacc tctggtttcc atgagcggt    6720
gtccacgctc ggtgacgaaa aggctgtccg tgtccccgta tacagacttg agagggagtt    6780
taaacgaatt caatagcttg ttgcatgggc ggcgatataa aatgcaaggt gctgctcaaa    6840
aaatcaggca aagcctcgcg caaaaaagaa agcacatcgt agtcatgctc atgcagataa    6900
aggcaggtaa gctccggaac caccacagaa aaagacacca tttttctctc aaacatgtct    6960
gcgggtttct gcataaacac aaaataaaat aacaaaaaaa catttaaaca ttagaagcct    7020
gtcttacaac aggaaaaaca acccttataa gcataagacg gactacggcc atgccggcgt    7080
gaccgtaaaa aaactggtca ccgtgattaa aaagcaccac cgacagctcc tcggtcatgt    7140
ccggagtcat aatgtaagac tcggtaaaca catcaggttg attcatcggt cagtgctaaa    7200
aagcgaccga aatagcccgg gggaatacat acccgcaggc gtagagacaa cattacagcc    7260
cccataggag gtataacaaa attaatagga gagaaaaaca cataaacacc tgaaaaaccc    7320
tcctgcctag gcaaaatagc accctcccgc tccagaacaa catacagcgc ttcacagcgg    7380
cagcctaaca gtcagcctta ccagtaaaaa agaaaaccta ttaaaaaaac accactcgac    7440
acggcaccag ctcaatcagt cacagtgtaa aaaagggcca agtgcagagc gagtatatat    7500
aggactaaaa aatgacgtaa cggttaaagt ccacaaaaaa cacccagaaa accgcacgcg    7560
aacctacgcc cagaaacgaa agccaaaaaa cccacaactt cctcaaatcg tcacttccgt    7620
tttcccacgt tacgtaactt cccattttaa gaaaactaca attcccaaca catacaagtt    7680
actccgcccct aaaacctacg tcacccgccc cgttccacg ccccgcgcca cgtcacaaac    7740
tccacccccct cattatcata ttggcttcaa tccaaaataa ggtatattat tgatgatgtt    7800
aattaacatg catggatcca tatgcggtgt gaaataccgc acagatgcgt aaggagaaaa    7860
taccgcatca ggcgctcttc cgcttcctcg ctcactgact cgctgcgctc ggtcgttcgg    7920
ctgcggcgag cggtatcagc tcactcaaag gcggtaatac ggttatccac agaatcaggg    7980
gataacgcag gaaagaacat gtgagcaaaa ggccagcaaa aggccaggaa ccgtaaaaag    8040
gccgcgttgc tggcgttttt ccataggctc cgcccccctg acgagcatca caaaaatcga    8100
cgctcaagtc agaggtggcg aaacccgaca ggactataaa gataccaggc gtttccccct    8160
ggaagctccc tcgtgcgctc tcctgttccg accctgccgc ttaccggata cctgtccgcc    8220
tttctccctt cgggaagcgt ggcgctttct catagctcac gctgtaggta tctcagttcg    8280
gtgtaggtcg ttcgctccaa gctgggctgt gtgcacgaac cccccgttca gcccgaccgc    8340
tgcgccttat ccggtaacta tcgtcttgag tccaacccgg taagacacga cttatcgcca    8400
ctggcagcag ccactggtaa caggattagc agagcgaggt atgtaggcgg tgctacagag    8460
ttcttgaagt ggtggcctaa ctacggctac actagaagga cagtatttgg tatctgcgct    8520
ctgctgaagc cagttacctt cggaaaaaga gttggtagct cttgatccgg caaacaaacc    8580
accgctggta gcggtggttt ttttgtttgc aagcagcaga ttacgcgcag aaaaaaagga    8640
tctcaagaag atcctttgat cttttctacg ggtctgacg ctcagtggaa cgaaaactca    8700
cgttaaggga ttttggtcat gagattatca aaaaggatct tcacctagat ccttttaaat    8760
```

```
taaaaatgaa gttttaaatc aatctaaagt atatatgagt aaacttggtc tgacagttac    8820
caatgcttaa tcagtgaggc acctatctca gcgatctgtc tatttcgttc atccatagtt    8880
gcctgactcc ccgtcgtgta gataactacg atacgggagg gcttaccatc tggccccagt    8940
gctgcaatga taccgcgaga cccacgctca ccggctccag atttatcagc aataaaccag    9000
ccagccggaa gggccgagcg cagaagtggt cctgcaactt tatccgcctc catccagtct    9060
attaattgtt gccgggaagc tagagtaagt agttcgccag ttaatagttt gcgcaacgtt    9120
gttgccattg ctgcagccat gagattatca aaaaggatct tcacctagat ccttttcacg    9180
tagaaagcca gtccgcagaa acggtgctga ccccggatga atgtcagcta ctgggctatc    9240
tggacaaggg aaaacgcaag cgcaaagaga agcaggtag cttgcagtgg gcttacatgg    9300
cgatagctag actgggcggt tttatggaca gcaagcgaac cggaattgcc agctggggcg    9360
ccctctggta aggttgggaa gccctgcaaa gtaaactgga tggctttctt gccgccaagg    9420
atctgatggc gcaggggatc aagctctgat caagagacag gatgaggatc gtttcgcatg    9480
attgaacaag atggattgca cgcaggttct ccggccgctt gggtggagag ctattcggc    9540 tatgactggg cacaacagac aatcggctgc tctgatgccg ccgtgttccg gctgtcagcg    9600
caggggcgcc cggttctttt tgtcaagacc gacctgtccg gtgccctgaa tgaactgcaa    9660
gacgaggcag cgcggctatc gtggctggcc acgacgggcg ttccttgcgc agctgtgctc    9720
gacgttgtca ctgaagcggg aagggactgg ctgctattgg gcgaagtgcc ggggcaggat    9780
ctcctgtcat ctcaccttgc tcctgccgag aaagtatcca tcatggctga tgcaatgcgg    9840
cggctgcata cgcttgatcc ggctacctgc ccattcgacc accaagcgaa acatcgcatc    9900
gagcgagcac gtactcggat ggaagccggt cttgtcgatc aggatgatct ggacgaagag    9960
catcaggggc tcgcgccagc cgaactgttc gccaggctca aggcgagcat gcccgacggc    10020
gaggatctcg tcgtgaccca tggcgatgcc tgcttgccga atatcatggt ggaaaatggc    10080
cgcttttctg gattcatcga ctgtggccgg ctgggtgtgg cggaccgcta tcaggacata    10140
gcgttggcta cccgtgatat tgctgaagag cttggcggcg aatgggctga ccgcttcctc    10200
gtgctttacg gtatcgccgc tcccgattcg cagcgcatcg ccttctatcg ccttcttgac    10260
gagttcttct gaattttgtt aaaattttg ttaaatcagc tcattttta accaataggc    10320 cgaaatcggc aacatccctt ataaatcaaa agaatagacc gcgatagggt tgagtgttgt    10380
tccagtttgg aacaagagtc cactattaaa gaacgtggac tccaacgtca aagggcgaaa    10440
aaccgtctat cagggcgatg gcccactacg tgaaccatca cccaaatcaa gttttttgcg    10500
gtcgaggtgc cgtaaagctc taaatcggaa ccctaaaggg agcccccgat ttagagcttg    10560
acggggaaag ccggcgaacg tggcgagaaa ggaagggaag aaagcgaaag gagcgggcgc    10620
tagggcgctg gcaagtgtag cggtcacgct gcgcgtaacc accacacccg cgcgcttaat    10680
gcgccgctac agggcgcgtc cattcgccat tcaggatcga attaattctt aattaa        10736
```

<210> SEQ ID NO 72
<211> LENGTH: 97
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 72

```
tcgcgtgggc gtattggcaa gttttagagc tagaaatagc aagttaaaat aaggctagtc    60
```
cgttatcaac ttgaaaaagt ggcaccgagt cggtgct                            97

<210> SEQ ID NO 73
<211> LENGTH: 2812
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

| | |
|---|---|
| aagcggtgcc ggaaagctgg ctggagtgcg atcttcctga ggccgatact gtcgtcgtcc | 60 |
| cctcaaactg gcagatgcac ggttacgatg cgcccatcta caccaacgtg acctatccca | 120 |
| ttacggtcaa tccgccgttt gttcccacgg agaatccgac gggttgttac tcgctcacat | 180 |
| ttaatgttga tgaaagctgg ctacaggaag gccagacgcg aattattttt gatggcgtta | 240 |
| actcggcgtt tcatctgtgg tgcaacgggc gctgggtcgg ttacggccag gacagtcgtt | 300 |
| tgccgtctga atttgacctg agcgcatttt tacgcgccgg agaaaaccgc ctcgcggtga | 360 |
| tggtgctgcg ttggagtgac ggcagttatc tggaagatca ggatatgtgg cggatgagcg | 420 |
| gcattttccg tgacgtctcg ttgctgcata aaccgactac acaaatcagc gatttccatg | 480 |
| ttgccactcg ctttaatgat gatttcagcc gcgctgtact ggaggctgaa gttcagatgt | 540 |
| gcggcgagtt gcgtgactac ctacgggtaa cagtttcttt atggcagggt gaaacgcagg | 600 |
| tcgccagcgg caccgcgcct ttcggcggtg aaattatcga tgagcgtggt ggttatgccg | 660 |
| atcgcgtcac actacgtctg aacgtcgaaa acccgaaact gtggagcgcc gaaatcccga | 720 |
| atctctatcg tgcggtggtt gaactgcaca ccgccgacgg cacgctgatt gaagcagaag | 780 |
| cctgcgatgt cggttttcgc gaggtgcgga ttgaaaatgg tctgctgctg ctgaacggca | 840 |
| agccgttgct gattcgaggc gttaaccgtc acgagcatca tcctctgcat ggtcaggtca | 900 |
| tggatgagca gacgatggtg caggatatcc tgctgatgaa gcagaacaac tttaacgccg | 960 |
| tgcgctgttc gcattatccg aaccatccgc tgtggtacac gctgtgcgac cgctacggcc | 1020 |
| tgtatgtggt ggatgaagcc aatattgaaa cccacggcat ggtgccaatg aatcgtctga | 1080 |
| ccgatgatcc gcgctggcta ccggcgatga gcgaacgcgt aacgcgaatg gtgcagcgcg | 1140 |
| atcgtaatca cccgagtgtg atcatctggt cgctggggaa tgaatcaggc cacggcgcta | 1200 |
| atcacgacgc gctgtatcgc tggatcaaat ctgtcgatcc ttcccgcccg gtgcagtatg | 1260 |
| aaggcggcgg agccgacacc acggccaccg atattatttg cccgatgtac gcgcgcgtgg | 1320 |
| atgaagacca gcccttcccg gctgtgccga atggtccat caaaaaatgg ctttcgctac | 1380 |
| ctggagagac gcgcccgctg attctttgcg aatacgccca cgcgatgggt aacagtcttg | 1440 |
| gcggtttcgc taaatactgg caggcgtttc gtcagtatcc ccgtttacag ggcggcttcg | 1500 |
| tctgggactg ggtggatcag tcgctgatta aatatgatga aaacggcaac ccgtggtcgg | 1560 |
| cttacggcgg tgattttggc gatacgccga acgatcgcca gttctgtatg aacggtctgg | 1620 |
| tctttgccga ccgcacgccg catccagcgc tgacggaagc aaaacaccag cagcagtttt | 1680 |
| tccagttccg tttatccggg caaaccatcg aagtgaccag cgaatacctg ttccgtcata | 1740 |
| gcgataacga gctcctgcac tggatggtgg cgctggatgg taagccgctg caagcggtg | 1800 |
| aagtgcctct ggatgtcgct ccacaaggta acagttgat tgaactgcct gaactaccgc | 1860 |
| agccggagag cgccgggcaa ctctggctca cagtacgcgt agtgcaaccg aacgcgaccg | 1920 |
| catggtcaga agccgggcac atcagcgcct ggcagcagtg gcgtctggcg gaaaacctca | 1980 |

-continued

```
gtgtgacgct ccccgccgcg tcccacgcca tcccgcatct gaccaccagc gaaatggatt    2040
tttgcatcga gctgggtaat aagcgttggc aatttaaccg ccagtcaggc tttctttcac    2100
agatgtggat tggcgataaa aaacaactgc tgacgccgct gcgcgatcag ttcacccgtg    2160
caccgctgga taacgacatt ggcgtaagtg aagcgacccg cattgaccct aacgcctggg    2220
tcgaacgctg gaaggcggcg ggccattacc aggccgaagc agcgttgttg cagtgcacgg    2280
cagatacact tgctgatgcg gtgctgatta cgaccgctca cgcgtggcag catcagggga    2340
aaaccttatt tatcagccgg aaaacctacc ggattgatgg tagtggtcaa atggcgatta    2400
ccgttgatgt tgaagtggcg agcgatacac cgcatccggc gcggattggc ctgaactgcc    2460
agctggcgca ggtagcagag cgggtaaact ggctcggatt agggccgcaa gaaaactatc    2520
ccgaccgcct tactgccgcc tgttttgacc gctgggatct gccattgtca gacatgtata    2580
ccccgtacgt cttcccgagc gaaaacggtc tgcgctgcgg gacgcgcgaa ttgaattatg    2640
gcccacacca gtggcgcggc gacttccagt tcaacatcag ccgctacagt caacagcaac    2700
tgatggaaac cagccatcgc catctgctgc acgcggaaga aggcacatgg ctgaatatcg    2760
acggtttcca tatggggatt ggtggcgacg actcctggag cccgtcagta tc            2812
```

<210> SEQ ID NO 74
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 74

```
cgacgcggcc gctcgag                                                     17
```

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 75

```
tgggcgtatt ggcaaaggat                                                  20
```

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 76

```
atcctttgcc aatacgccca                                                  20
```

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 77

-continued

```
cggatatctt atctagaagc tt                                              22

<210> SEQ ID NO 78
<211> LENGTH: 10690
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
tggaagggct aattcactcc caaagaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agataaggta gaagaggcca     180
ataaaggaga gaacaccagc ttgttacacc ctgtgagcct gcatgggatg gatgacccgg     240
agagagaagt gttagagtgg aggtttgaca gccgcctagc atttcatcac gtggcccgag     300
agctgcatcc ggagtacttc aagaactgct gatatcgagc ttgctacaag gactttccg      360 ctggggactt tccagggagg cgtggcctgg gcgggactgg ggagtggcga gccctcagat     420
cctgcatata agcagctgct ttttgcctgt actgggtctc tctggttaga ccagatctga     480
gcctgggagc tctctggcta actagggaac ccactgctta agcctcaata agcttgcct      540 tgagtgcttc aagtagtgtg tgcccgtctg ttgtgtgact ctggtaacta gagatccctc     600
agaccctttt agtcagtgtg gaaaatctct agcagtggcg cccgaacagg gacttgaaag     660
cgaaagggaa accagaggag ctctctcgac gcaggactcg gcttgctgaa gcgcgcacgg     720
caagaggcga gggcggcga ctggtgagta cgccaaaaat tttgactagc ggaggctaga     780
aggagagaga tgggtgcgag agcgtcagta ttaagcgggg gagaattaga tcgcgatggg     840
aaaaaattcg gttaaggcca ggggaaaga aaaaatataa attaaaacat atagtatggg     900
caagcaggga gctagaacga ttcgcagtta atcctggcct gttagaaaca tcagaaggct     960
gtagacaaat actgggacag ctacaaccat cccttcagac aggatcagaa gaacttagat    1020
cattatataa tacagtagca accctctatt gtgtgcatca aaggatagag ataaaagaca    1080
ccaaggaagc tttagacaag atagaggaag agcaaaacaa aagtaagacc accgcacagc    1140
aagcggccgg ccgctgatct tcagacctgg aggaggagat atgagggaca attggagaag    1200
tgaattatat aaatataaag tagtaaaaat tgaaccatta ggagtagcac ccaccaaggc    1260
aaagagaaga gtggtgcaga gagaaaaaag agcagtggga ataggagctt tgttccttgg    1320
gttcttggga gcagcaggaa gcactatggg cgcagcgtca atgacgctga cggtacaggc    1380
cagacaatta ttgtctggta tagtgcagca gcagaacaat ttgctgaggg ctattgaggc    1440
gcaacagcat ctgttgcaac tcacagtctg gggcatcaag cagctccagg caagaatcct    1500
ggctgtggaa agatacctaa aggatcaaca gctcctgggg atttggggt gctctggaaa     1560 actcatttgc accactgctg tgccttggaa tgctagttgg agtaataaat ctctggaaca    1620
gatttggaat cacacgacct ggatggagtg ggacagagaa attaacaatt acacaagctt    1680
aatacactcc ttaattgaag aatcgcaaaa ccagcaagaa aagaatgaac aagaattatt    1740
ggaattagat aaatgggcaa gtttgtgaa ttggtttaac ataacaaatt ggctgtggta     1800
tataaaatta ttcataatga tagtaggagg cttggtaggt ttaagaatag ttttgctgt     1860 actttctata gtgaatagag ttaggcaggg atattcacca ttatcgtttc agacccacct    1920
cccaaccccg aggggacccg acaggcccga aggaatagaa gaagaaggtg gagagagaga    1980
```

```
cagagacaga tccattcgat tagtgaacgg atctcgacgg tatcgccttt aaaagaaaag   2040
gggggattgg ggggtacagt gcaggggaaa gaatagtaga cataatagca acagacatac   2100
aaactaaaga attacaaaaa caaattacaa aaattcaaaa ttttcgggtt tattacaggg   2160
acagcagaga tccagttttg tacaaaaaag caggctttaa aggaaccaat tcagtcgact   2220
ggatccggta ccaaggtcgg gcaggaagag ggcctatttc ccatgattcc ttcatatttg   2280
catatacgat acaaggctgt tagagagata attagaatta atttgactgt aaacacaaag   2340
atattagtac aaaatacgtg acgtagaaag taataatttc ttgggtagtt tgcagtttta   2400
aaattatgtt ttaaaatgga ctatcatatg cttaccgtaa cttgaaagta tttcgatttc   2460
ttggctttat atatcttgtg gaaaggacga aacacctcgc gtgggcgtat tggcaagttt   2520
tagagctaga aatagcaagt taaaataagg ctagtccgtt atcaacttga aaaagtggca   2580
ccgagtcggt gctttttttg aattcaagcg gtgccggaaa gctggctgga gtgcgatctt   2640
cctgaggccg atactgtcgt cgtcccctca aactggcaga tgcacggtta cgatgcgccc   2700
atctacacca acgtgaccta tcccattacg gtcaatccgc cgtttgttcc cacgagaat   2760 ccgacgggtt gttactcgct cacatttaat gttgatgaaa gctggctaca ggaaggccag   2820
acgcgaatta tttttgatgg cgttaactcg gcgtttcatc tgtggtgcaa cgggcgctgg   2880
gtcggttacg gccaggacag tcgtttgccg tctgaatttg acctgagcgc attttttacgc   2940 gccgagaaa accgctcgc ggtgatggtg ctgcgttgga gtgacggcag ttatctggaa   3000
gatcaggata tgtggcggat gagcggcatt ttccgtgacg tctcgttgct gcataaaccg   3060
actacacaaa tcagcgattt ccatgttgcc actcgcttta atgatgattt cagccgcgct   3120
gtactggagg ctgaagttca gatgtgcggc gagttgcgtg actacctacg ggtaacagtt   3180
tctttatggc agggtgaaac gcaggtcgcc agcggcaccg cgccttttcgg cggtgaaatt   3240 atcgatgagc gtggtggtta tgccgatcgc gtcacactac gtctgaacgt cgaaaacccg   3300
aaactgtgga gcgccgaaat cccgaatctc tatcgtgcgg tggttgaact gcacaccgcc   3360
gacggcacgc tgattgaagc agaagcctgc gatgtcggtt tccgcgaggt gcggattgaa   3420
aatggtctgc tgctgctgaa cggcaagccg ttgctgattc gaggcgttaa ccgtcacgag   3480
catcatcctc tgcatggtca ggtcatggat gagcagacga tggtgcagga tatcctgctg   3540
atgaagcaga caactttaa cgccgtgcgc tgttcgcatt atccgaacca tccgctgtgg   3600
tacacgctgt gcgaccgcta cggcctgtat gtggtggatg aagccaatat tgaaacccac   3660
ggcatggtgc caatgaatcg tctgaccgat gatccgcgct ggctaccggc gatgagcgaa   3720
cgcgtaacgc gaatggtgca gcgcgatcgt aatcacccga gtgtgatcat ctggtcgctg   3780
gggaatgaat caggccacgg cgctaatcac acgcgctgt atcgctggat caaatctgtc   3840
gatccttccc gcccggtgca gtatgaaggc ggcggagccg acaccacggc caccgatatt   3900
atttgcccga tgtacgcgcg cgtggatgaa gaccagccct tcccggctgt gccgaaatgg   3960
tccatcaaaa aatggcttc gctacctgga gagacgcgcc cgctgattct ttgcgaatac   4020
gcccacgcga tgggtaacag tcttggcggt ttcgctaaat actggcaggc gtttcgtcag   4080 tatcccccgtt tacagggcgg cttcgtctgg gactgggtgg atcagtcgct gattaaatat   4140
gatgaaaacg gcaacccgtg gtcggcttac ggcggtgatt ttggcgatac gccgaacgat   4200
cgccagttct gtatgaacgg tctggtctt gccgaccgca cgccgcatcc agcgctgacg   4260
gaagcaaaac accagcagca gttttttccag ttccgtttat ccgggcaaac catcgaagtg   4320
accagcgaat acctgttccg tcatagcgat aacgagctcc tgcactggat ggtggcgctg   4380
```

-continued

```
gatggtaagc cgctggcaag cggtgaagtg cctctggatg tcgctccaca aggtaaacag    4440
ttgattgaac tgcctgaact accgcagccg gagagcgccg ggcaactctg gctcacagta    4500
cgcgtagtgc aaccgaacgc gaccgcatgg tcagaagccg ggcacatcag cgcctggcag    4560
cagtggcgtc tggcggaaaa cctcagtgtg acgctccccg ccgcgtccca cgccatcccg    4620
catctgacca ccagcgaaat ggattttgc atcgagctgg gtaataagcg ttggcaattt     4680
aaccgccagt caggctttct ttcacagatg tggattggcg ataaaaaaca actgctgacg    4740
ccgctgcgcg atcagttcac ccgtgcaccg ctggataacg acattggcgt aagtgaagcg    4800
acccgcattg accctaacgc ctgggtcgaa cgctggaagg cggcgggcca ttaccaggcc    4860
gaagcagcgt tgttgcagtg cacggcagat acacttgctg atgcggtgct gattacgacc    4920
gctcacgcgt ggcagcatca ggggaaaaac ttatttatca gccggaaaac ctaccggatt    4980
gatggtagtg gtcaaatggc gattaccgtt gatgttgaag tggcgagcga tacaccgcat    5040
ccggcgcgga ttggcctgaa ctgccagctg gcgcaggtag cagagcgggt aaactggctc    5100
ggattagggc cgcaagaaaa ctatcccgac cgccttactg ccgcctgttt tgaccgctgg    5160
gatctgccat tgtcagacat gtataccccg tacgtcttcc cgagcgaaaa cggtctgcgc    5220
tgcgggacgc gcgaattgaa ttatggccca caccagtggc gcggcgactt ccagttcaac    5280
atcagccgct acagtcaaca gcaactgatg gaaaccagcc atcgccatct gctgcacgcg    5340
gaagaaggca catggctgaa tatcgacggt ttccatatgg ggattggtgg cgacgactcc    5400
tggagcccgt cagtatctct agagcggccg cggatcccgc cctctccct cccccccccc    5460
taacgttact ggccgaagcc gcttggaata aggccggtgt gcgtttgtct atatgttatt    5520
ttccaccata ttgccgtctt ttggcaatgt gagggcccgg aaacctggcc ctgtcttctt    5580
gacgagcatt cctaggggtc tttcccctct cgccaaagga atgcaaggtc tgttgaatgt    5640
cgtgaaggaa gcagttcctc tggaagcttc ttgaagacaa acaacgtctg tagcgaccct    5700
ttgcaggcag cggaaccccc cacctggcga caggtgcctc tgcggccaaa agccacgtgt    5760
ataagataca cctgcaaagg cggcacaacc ccagtgccac gttgtgagtt ggatagttgt    5820
ggaaagagtc aaatggctct cctcaagcgt attcaacaag ggctgaagg atgcccagaa    5880
ggtaccccat tgtatgggat ctgatctggg gcctcggtgc acatgcttta catgtgttta    5940
gtcgaggtta aaaaaacgtc taggcccccc gaaccacggg gacgtggttt tcctttgaaa    6000
aacacgatga taagcttgcc acaacccaca aggagacgac cttccatgac cgagtacaag    6060
cccacggtgc gcctcgccac ccgcgacgac gtccccgggc cgtacgcac cctcgccgcc    6120
gcgttcgccg actaccccgc cacgcgccac accgtcgacc cggaccgcca catcgagcgg    6180
gtcaccgagc tgcaagaact cttcctcacg cgcgtcgggc tcgacatcgg caaggtgtgg    6240
gtcgcggacg acggcgccgc ggtggcggtc tggaccacgc cggagagcgt cgaagcgggg    6300
gcggtgttcg ccgagatcgg cccgcgcatg gccgagttga gcggttcccg gctggccgcg    6360
cagcaacaga tggaaggcct cctggcgccg caccggccca aggagcccgc gtggttcctg    6420
gccaccgtcg gcgtctcgcc cgaccaccag ggcaagggtc tgggcagcgc cgtcgtgctc    6480
cccgagtgg aggcggccga gcgcgccggg gtgcccgcct tcctggagac ctccgcgccc    6540
cgcaacctcc ccttctacga gcggctcggc ttcaccgtca ccgccgacgt cgaggtgccc    6600
gaaggaccgc gcacctggtg catgacccgc aagcccggtg cctagacgcg tctggaacaa    6660
tcaacctctg gattacaaaa tttgtgaaag attgactggt attcttaact atgttgctcc    6720
```

```
ttttacgcta tgtggatacg ctgctttaat gcctttgtat catgctattg cttcccgtat    6780
ggctttcatt ttctcctcct tgtataaatc ctggttgctg tctctttatg aggagttgtg    6840
gcccgttgtc aggcaacgtg gcgtggtgtg cactgtgttt gctgacgcaa ccccactgg     6900
ttggggcatt gccaccacct gtcagctcct ttccgggact ttcgctttcc cctccctat     6960
tgccacggcg gaactcatcg ccgcctgcct tgcccgctgc tggacagggg ctcggctgtt    7020
gggcactgac aattccgtgg tgttgtcggg gaagctgacg tcctttccat ggctgctcgc    7080
ctgtgttgcc acctggattc tgcgcgggac gtccttctgc tacgtccctt cggccctcaa    7140
tccagcggac cttccttccc gcggcctgct gccggctctg cggcctcttc cgcgtcttcg    7200
ccttcgccct cagacgagtc ggatctccct ttgggccgcc tccccgcctg gaattaattc    7260
tgcagtcgag acctgaaaaa acatggagca atcacaagta gcaatacagc agctaccaat    7320
gctgattgtg cctggctaga agcacaagag gaggaggagg tgggttttcc agtcacacct    7380
caggtacctt taagaccaat gacttacaag gcagctgtag atcttagcca ctttttaaaa    7440
gaaaagaggg gactggaagg gctaattcac tcccaacgaa gacaagatat ccttgatctg    7500
tggatctacc acacacaagg ctacttccct gattagcaga actacacacc agggccaggg    7560
gtcagatatc cactgacctt tggatggtgc tacaagctag taccagttga gccagataag    7620
gtagaagagg ccaataaagg agagaacacc agcttgttac accctgtgag cctgcatggg    7680
atggatgacc cggagagaga agtgttagag tggaggtttg acagccgcct agcatttcat    7740
cacgtggccc gagagctgca tccggagtac ttcaagaact gctgatatcg agcttgctac    7800
aagggacttt ccgctgggga ctttccaggg aggcgtggcc tgggcgggac tggggagtgg    7860
cgagccctca gatcctgcat ataagcagct gcttttgcc tgtactgggt ctctctggtt     7920
agaccagatc tgagcctggg agctctctgg ctaactaggg aacccactgc ttaagcctca    7980
ataaagcttg ccttgagtgc ttcaagtagt gtgtgcccgt ctgttgtgtg actctggtaa    8040
ctagagatcc ctcagaccct tttagtcagt gtggaaaatc tctagcagta gtagttcatg    8100
tcatcttatt attcagtatt tataacttgc aaagaaatga atatcagaga gtgagaggcc    8160
ttgacattgc tagcgtttac cgtcgacctc tagctagagc ttggcgtaat catggtcata    8220
gctgttcct gtgtgaaatt gttatccgct cacaattcca cacaacatac gagccggaag     8280
cataaagtgt aaagcctggg gtgcctaatg agtgagctaa ctcacattaa ttgcgttgcg    8340
ctcactgccc gctttccagt cgggaaacct gtcgtgccag ctgcattaat gaatcggcca    8400
acgcgcgggg agaggcggtt tgcgtattgg gcgctcttcc gcttcctcgc tcactgactc    8460
gctgcgctcg gtcgttcggc tgcggcgagc ggtatcagct cactcaaagg cggtaatacg    8520
gttatccaca gaatcagggg ataacgcagg aaagaacatg tgagcaaaag gccagcaaaa    8580
ggccaggaac cgtaaaaagg ccgcgttgct ggcgtttttc cataggctcc gcccccctga    8640
cgagcatcac aaaaatcgac gctcaagtca gaggtggcga aacccgacag gactataaag    8700
ataccaggcg tttccccctg gaagctccct cgtgcgctct cctgttccga ccctgccgct    8760
taccggatac ctgtccgcct ttctcccttc gggaagcgtg gcgctttctc atagctcacg    8820
ctgtaggtat ctcagttcgg tgtaggtcgt tcgctccaag ctgggctgtg tgcacgaacc    8880
ccccgttcag cccgaccgct gcgccttatc cggtaactat cgtcttgagt ccaacccggt    8940
aagacacgac ttatcgccac tggcagcagc cactggtaac aggattagca gagcgaggta    9000
tgtaggcggt gctacagagt tcttgaagtg gtggcctaac tacggctaca ctagaagaac    9060
agtatttggt atctgcgctc tgctgaagcc agttaccttc ggaaaaagag ttggtagctc    9120
```

```
ttgatccggc aaacaaacca ccgctggtag cggtggtttt tttgtttgca agcagcagat      9180
tacgcgcaga aaaaaggat ctcaagaaga tcctttgatc ttttctacgg ggtctgacgc       9240
tcagtggaac gaaaactcac gttaagggat tttggtcatg agattatcaa aaaggatctt      9300
cacctagatc cttttaaatt aaaaatgaag ttttaaatca atctaaagta tatatgagta     9360
aacttggtct gacagttacc aatgcttaat cagtgaggca cctatctcag cgatctgtct     9420
atttcgttca tccatagttg cctgactccc cgtcgtgtag ataactacga tacgggaggg    9480
cttaccatct ggccccagtg ctgcaatgat accgcgagac ccacgctcac cggctccaga    9540
tttatcagca ataaaccagc cagccggaag ggccgagcgc agaagtggtc ctgcaacttt    9600
atccgcctcc atccagtcta ttaattgttg ccgggaagct agagtaagta gttcgccagt    9660
taatagtttg cgcaacgttg ttgccattgc tacaggcatc gtggtgtcac gctcgtcgtt    9720
tggtatggct tcattcagct ccggttccca acgatcaagg cgagttacat gatccccat     9780 gttgtgcaaa aaagcggtta gctccttcgg tcctccgatc gttgtcagaa gtaagttggc    9840
cgcagtgtta tcactcatgg ttatggcagc actgcataat tctcttactg tcatgccatc    9900
cgtaagatgc ttttctgtga ctggtgagta ctcaaccaag tcattctgag aatagtgtat   9960
gcggcgaccg agttgctctt gcccggcgtc aatacgggat aataccgcgc cacatagcag    10020
aactttaaaa gtgctcatca ttggaaaacg ttcttcgggg cgaaaactct caaggatctt    10080
accgctgttg agatccagtt cgatgtaacc cactcgtgca cccaactgat cttcagcatc    10140
ttttactttc accagcgttt ctgggtgagc aaaaacagga aggcaaaatg ccgcaaaaaa    10200
gggaataagg gcgacacgga aatgttgaat actcatactc ttcctttttc aatattattg    10260
aagcatttat cagggttatt gtctcatgag cggatacata tttgaatgta tttagaaaaa    10320
taaacaaata ggggttccgc gcacatttcc ccgaaaagtg ccacctgacg tcgacggatc    10380
gggagatcaa cttgtttatt gcagcttata atggttacaa ataaagcaat agcatcacaa    10440
atttcacaaa taaagcattt ttttcactgc attctagttg tggtttgtcc aaactcatca    10500
atgtatctta tcatgtctgg atcaactgga taactcaagc taaccaaaat catcccaaac    10560
ttcccacccc atccctatt accactgcca attacctgtg gtttcattta ctctaaacct    10620
gtgattcctc tgaattattt tcattttaaa gaaattgtat ttgttaaata tgtactacaa    10680
acttagtagt                                                           10690
```

<210> SEQ ID NO 79
<211> LENGTH: 12570
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 79

```
tggaagggct aattcactcc caagaagac aagatatcct tgatctgtgg atctaccaca       60
cacaaggcta cttccctgat tagcagaact acacaccagg gccagggtc agatatccac       120 tgacctttgg atggtgctac aagctagtac cagttgagcc agataaggta gaagaggcca     180
ataaaggaga gaacaccagc ttgttacacc ctgtgagcct gcatgggatg gatgacccgg      240
agagagaagt gttagagtgg aggtttgaca gccgcctagc atttcatcac gtggcccgag     300
agctgcatcc ggagtacttc aagaactgct gatatcgagc ttgctacaag gactttccg     360 ctggggactt tccagggagg cgtggcctgg gcgggactgg ggagtggcga gccctcagat    420
```

```
cctgcatata agcagctgct ttttgcctgt actgggtctc tctggttaga ccagatctga      480
gcctgggagc tctctggcta actagggaac ccactgctta agcctcaata aagcttgcct      540
tgagtgcttc aagtagtgtg tgcccgtctg ttgtgtgact ctggtaacta gagatccctc      600 agacccttt t agtcagtgtg gaaaatctct agcagtggcg cccgaacagg gacttgaaag      660
cgaaagggaa accagaggag ctctctcgac gcaggactcg gcttgctgaa gcgcgcacgg      720
caagaggcga gggcggcga ctggtgagta cgccaaaaat tttgactagc ggaggctaga      780
aggagagaga tgggtgcgag agcgtcagta ttaagcgggg gagaattaga tcgcgatggg      840
aaaaaattcg gttaaggcca gggggaaaga aaaaatataa attaaaacat atagtatggg      900
caagcaggga gctagaacga ttcgcagtta atcctggcct gttagaaaca tcagaaggct      960
gtagacaaat actgggacag ctacaaccat cccttcagac aggatcagaa gaacttagat     1020
cattatataa tacagtagca accctctatt gtgtgcatca aaggatagag ataaaagaca     1080
ccaaggaagc tttagacaag atagaggaag agcaaaacaa aagtaagacc accgcacagc     1140
aagcggccgg ccgctgatct tcagacctgg aggaggagat atgagggaca attggagaag     1200
tgaattatat aaatataaag tagtaaaaat tgaaccatta ggagtagcac ccaccaaggc     1260
aaagagaaga gtggtgcaga gagaaaaaag agcagtggga ataggagctt tgttccttgg     1320
gttcttggga gcagcaggaa gcactatggg cgcagcgtca atgacgctga cggtacaggc     1380
cagacaatta ttgtctggta tagtgcagca gcagaacaat ttgctgaggg ctattgaggc     1440
gcaacagcat ctgttgcaac tcacagtctg gggcatcaag cagctccagg caagaatcct     1500
ggctgtggaa agatacctaa aggatcaaca gctcctgggg atttggggtt gctctggaaa     1560
actcatttgc accactgctg tgccttggaa tgctagttgg agtaataaat ctctggaaca     1620
gatttggaat cacacgacct ggatggagtg ggacagagaa attaacaatt acacaagctt     1680
aatacactcc ttaattgaag aatcgcaaaa ccagcaagaa aagaatgaac aagaattatt     1740
ggaattagat aaatgggcaa gtttgtggaa ttggtttaac ataacaaatt ggctgtggta     1800
tataaaatta ttcataatga tagtaggagg cttggtaggt ttaagaatag ttttgctgt     1860 actttctata gtgaatagag ttaggcaggg atattcacca ttatcgtttc agacccacct     1920
cccaaccccg aggggacccg acaggcccga aggaatagaa gaagaaggtg gagagagaga     1980
cagagacaga tccattcgat tagtgaacgg atctcgacgg tatcgccttt aaaagaaaag     2040
gggggattgg ggggtacagt gcaggggaaa gaatagtaga cataatagca acagacatac     2100
aaactaaaga attacaaaaa caaattacaa aaattcaaaa ttttcgggtt tattacaggg     2160
acagcagaga tccagtttat cgactggatc cggtaccaag gtcgggcagg aagagggcct     2220
atttcccatg attccttcat atttgcatat acgatacaag gctgttagag ataattag      2280 aattaatttg actgtaaaca caaagatatt agtacaaaat acgtgacgta gaaagtaata     2340
atttcttggg tagtttgcag ttttaaaatt atgttttaaa atggactatc atatgcttac     2400
cgtaacttga agtatttcg atttcttggc tttatatatc ttgtggaaag gacgaaacac     2460
cgagacgcct cccgtctcgt tttagagcta gaaatagcaa gttaaaataa ggctagtccg     2520
ttatcaactt gaaaaagtgg caccgagtcg gtgctttttt tctagaccca gctttcttgt     2580
acaaagttgg cattaacgcg tctggcctcg cgagtgtgac tagttattaa tagtaatcaa     2640
ttacggggtc attagttcat agcccatata tggagttccg cgttacataa cttacggtaa     2700
atggcccgcc tggctgaccg cccaacgacc cccgcccatt gacgtcaata atgacgtatg     2760
```

```
ttcccatagt aacgccaata gggactttcc attgacgtca atgggtggag tatttacggt    2820
aaactgccca cttggcagta catcaagtgt atcatatgcc aagtacgccc cctattgacg    2880
tcaatgacgg taaatggccc gcctggcatt atgcccagta catgacctta tgggactttc    2940
ctacttggca gtacatctac gtattagtca tcgctattac catggtcgag gtgagcccca    3000
cgttctgctt cactctcccc atctccccc cctccccacc cccaattttg tatttattta    3060
tttttttaatt attttgtgca gcgatggggg cggggggggg gggggggcgc gcgcaggcg    3120
ggcggggcg gggcgagggg cggggcgggg cgaggcggag aggtgcggcg gcagccaatc    3180
agagcggcgc gctccgaaag tttccttta tggcgaggcg gcggcggcgg cggccctata    3240
aaaagcgaag cgcgcggcgg gcggggagtc gctgcgacgc tgccttcgcc ccgtgccccg    3300
ctccgccgcc gcctcgcgcc gcccgccccg gctctgactg accgcgttac tcccacaggt    3360
gagcgggcgg gacggcccctt ctcctccggg ctgtaattag cgcttggttt aatgacggct    3420
tgtttctttt ctgtggctgc gtgaaagcct tgagggctc cgggagggcc ctttgtgcgg    3480
ggggagcggc tcgggggtg cgtgcgtgtg tgtgtgcgtg gggagcgccg cgtgcggctc    3540
cgcgctgccc ggcggctgtg agcgctgcgg gcgcggcgcg gggctttgtg cgctccgcag    3600
tgtgcgcgag gggagcgcgg ccgggggcgg tgccccgcgg tgcggggggg gctgcgaggg    3660
gaacaaaggc tgcgtgcggg gtgtgtgcgt gggggggtga gcaggggggtg tgggcgcgtc    3720
ggtcgggctg caaccccccc tgcaccccccc tccccgagtt gctgagcacg gcccggcttc    3780
gggtgcgggg ctccgtacgg ggcgtggcgc ggggctcgcc gtgccgggcg ggggtggcg    3840
gcaggtgggg gtgccgggcg gggcgggggcc gcctcgggcc ggggagggct cggggagggg    3900
gcgcggcggc ccccggagcg ccggcggctg tcgaggcgcg gcgagccgca gccattgcct    3960
tttatggtaa tcgtgcgaga gggcgcaggg acttcctttg tcccaaatct gtgcggagcc    4020
gaaatctggg aggcgccgcc gcacccccctc tagcgggcgc ggggcgaagc ggtgcggcgc    4080
cggcaggaag gaaatgggcg gggagggcct tcgtgcgtcg ccgcgccgcc gtccccttct    4140
ccctctccag cctcggggct gtccgcgggg ggacggctgc cttcgggggg gacggggcag    4200
ggcgggttc ggcttctggc gtgtgaccgg cggctctaga gcctctgcta accatgttca    4260
tgccttcttc ttttttcctac agctcctggg caacgtgctg gttattgtgc tgtctcatca    4320
ttttggcaaa gaattcgcta gggccaccat ggacaagccc aagaaaaagc ggaaagtgaa    4380
gtacagcatc ggcctggaca tcggcaccaa ctctgtgggc tgggccgtga tcaccgacga    4440
gtacaaggtg cccagcaaga aattcaaggt gctgggcaac accgacaggc acagcatcaa    4500
gaagaacctg atcggcgccc tgctgttcga cagcggcgaa acagccgagg ccaccagact    4560
gaagagaacc gccagaagaa gatacaccag gcggaagaac aggatctgct atctgcaaga    4620
gatcttcagc aacgagatgg ccaaggtgga cgacagcttc ttccacagac tggaagagtc    4680
cttcctggtg gaagaggaca agaagcacga gagacacccc atcttcggca acatcgtgga    4740
cgaggtggcc taccacgaga agtaccccac catctaccac ctgagaaaga aactggtgga    4800
cagcaccgac aaggccgacc tgagactgat ctacctggcc ctgcccacac tgatcaagtt    4860
cagaggccac ttcctgatcg agggcgacct gaacccccgac aacagcgacg tggacaagct    4920
gttcatccag ctggtgcaga cctacaacca gctgttcgag gaaaacccca tcaacgccag    4980
cggcgtggac gccaaggcta tcctgtctgc cagactgagc aagagcagaa ggctggaaaa    5040
tctgatcgcc cagctgcccg gcgagaagaa gaacggcctg ttcggcaacc tgattgccct    5100
gagcctgggc ctgacccccca acttcaagag caacttcgac ctggccgagg atgccaaact    5160
```

```
gcagctgagc aaggacacct acgacgacga cctggacaac ctgctggccc agatcggcga   5220
ccagtacgcc gacctgttcc tggccgccaa gaacctgtct gacgccatcc tgctgagcga   5280
catcctgaga gtgaacaccg agatcaccaa ggccccctg agcgcctcta tgatcaagag    5340
atacgacgag caccaccagg acctgaccct gctgaaagct ctcgtgcggc agcagctgcc   5400
tgagaagtac aaagaaatct tcttcgacca gagcaagaac ggctacgccg gctacatcga   5460
tggcggcgct agccaggaag agttctacaa gttcatcaag cccatcctgg aaaagatgga   5520
cggcaccgag gaactgctcg tgaagctgaa cagagaggac ctgctgagaa gcagagaac    5580
cttcgacaac ggcagcatcc cccaccagat ccacctggga gagctgcacg ctatcctgag   5640
aaggcaggaa gattttacc cattcctgaa ggacaaccgg aaaagatcg agaagatcct     5700
gaccttcagg atcccctact acgtgggccc cctggccaga ggcaacagca gattcgcctg   5760
gatgaccaga aagagcgagg aaaccatcac ccctggaac ttcgaggaag tggtggacaa    5820
gggcgccagc gcccagagct tcatcgagag aatgacaaac ttcgataaga acctgcccaa   5880
cgagaaggtg ctgcccaagc acagcctgct gtacgagtac ttcaccgtgt acaacgagct   5940
gaccaaagtg aaatacgtga ccgagggaat gagaaagccc gccttcctga gcggcgagca   6000
gaaaaaggcc atcgtggacc tgctgttcaa gaccaacaga aaagtgaccg tgaagcagct   6060
gaaagaggac tacttcaaga aaatcgagtg cttcgactcc gtggaaatct ccggcgtgga   6120
agatagattc aacgcctccc tgggcacata ccacgatctg ctgaaaatta tcaaggacaa   6180
ggacttcctg gataacgaag agaacgagga cattctggaa gatatcgtgc tgaccctgac   6240
actgtttgag gaccgcgaga tgatcgagga aaggctgaaa acctacgctc acctgttcga   6300
cgacaaagtg atgaagcagc tgaagagaag gcggtacacc ggctggggca ggctgagcag   6360
aaagctgatc aacggcatca gagacaagca gagcggcaag acaatcctgg atttcctgaa   6420
gtccgacggc ttcgccaacc ggaacttcat gcagctgatc cacgacgaca gcctgacatt   6480
caaagaggac atccagaaag cccaggtgtc cggccagggc gactctctgc acgagcatat   6540
cgctaacctg gccggcagcc ccgctatcaa gaagggcatc ctgcagacag tgaaggtggt   6600
ggacgagctc gtgaaagtga tgggcagaca caagcccgag aacatcgtga tcgagatggc   6660
tagagagaac cagaccaccc agaagggaca gaagaactcc cgcgagagga tgaagagaat   6720
cgaagagggc atcaaagagc tgggcagcca gatcctgaaa gaacacccg tggaaaacac   6780
ccagctgcag aacgagaagc tgtacctgta ctacctgcag aatggccggg atatgtacgt   6840
ggaccaggaa ctggacatca acagactgtc cgactacgat gtggaccata tcgtgcctca   6900
gagctttctg aaggacgact ccatcgataa caaagtgctg actcggagcg acaagaacag   6960
aggcaagagc gacaacgtgc cctccgaaga ggtcgtgaag aagatgaaga actactggcg   7020
acagctgctg aacgccaagc tgattaccca gaggaagttc gataacctga ccaaggccga   7080
gagaggcggc ctgagcgagc tggataaggc cggcttcatc aagaggcagc tggtggaaac   7140
cagacagatc acaaagcacg tggcacagat cctggactcc cggatgaaca ctaagtacga   7200
cgaaaacgat aagctgatcc gggaagtgaa agtgatcacc ctgaagtcca agctggtgtc   7260
cgatttccgg aaggatttcc agtttacaa agtgcgcgat atcaacaact accaccacgc   7320
ccacgacgcc tacctgaacg ccgtcgtggg aaccgccctg atcaaaaagt accctaagct   7380
ggaaagcgag ttcgtgtacg gcgactacaa ggtgtacgac gtgcgaagaa tgatcgccaa   7440
gagcgagcag gaaatcggca aggctaccgc caagtacttc ttctacagca acatcatgaa   7500
```

-continued

```
cttttttcaag accgaaatca ccctggccaa cggcgagatc agaaagcgcc ctctgatcga      7560
gacaaacggc gaaaccgggg agatcgtgtg ggataagggc agagacttcg ccacagtgcg      7620
aaaggtgctg agcatgcccc aagtgaatat cgtgaaaaag accgaggtgc agacaggcgg      7680
cttcagcaaa gagtctatcc tgcccaagag gaacagcgac aagctgatcg ccagaaagaa      7740
ggactgggac cccaagaagt acggcggctt cgacagccct accgtggcct actctgtgct      7800
ggtggtggct aaggtggaaa agggcaagtc caagaaactg aagagtgtga aagagctgct      7860
ggggatcacc atcatggaaa gaagcagctt tgagaagaac cctatcgact ttctggaagc      7920
caagggctac aaagaagtga aaaggacct gatcatcaag ctgcctaagt actccctgtt      7980
cgagctggaa acggcagaa agagaatgct ggcctctgcc ggcgaactgc agaagggaaa      8040
cgagctggcc ctgcctagca aatatgtgaa cttcctgtac ctggcctccc actatgagaa      8100
gctgaagggc agccctgagg acaacgaaca gaaacagctg tttgtggaac agcataagca      8160
ctacctggac gagatcatcg agcagatcag cgagttctcc aagagagtga tcctggccga      8220
cgccaatctg gacaaggtgc tgtctgccta caacaagcac agggacaagc ctatcagaga      8280
gcaggccgag aatatcatcc acctgttcac cctgacaaac ctgggcgctc ctgccgcctt      8340
caagtacttt gacaccacca tcgaccggaa gaggtacacc agcaccaaag aggtgctgga      8400
cgccaccctg atccaccaga gcatcaccgg cctgtacgag acaagaatcg acctgtctca      8460
gctgggaggc gacaagagac ctgccgccac taagaaggcc ggacaggcca aaaagaagaa      8520
gtgaggcgcg tctggaacaa tcaacctctg gattacaaaa tttgtgaaag attgactggt      8580
attcttaact atgttgctcc ttttacgcta tgtggatacg ctgctttaat gcctttgtat      8640
catgctattg cttcccgtat ggctttcatt ttctcctcct tgtataaatc ctggttgctg      8700
tctctttatg aggagttgtg gcccgttgtc aggcaacgtg gcgtggtgtg cactgtgttt      8760
gctgacgcaa cccccactgg ttggggcatt gccaccacct gtcagctcct ttccgggact      8820
ttcgctttcc ccctccctat tgccacgcg gaactcatcg ccgcctgcct tgcccgctgc      8880
tggacagggg ctcggctgtt gggcactgac aattccgtgg tgttgtcggg gaagctgacg      8940 tccttccat ggctgctcgc ctgtgttgcc acctggattc tgcgcgggac gtccttctgc      9000
tacgtccctt cggccctcaa tccagcggac cttccttccc gcggcctgct gccggctctg      9060
cggcctcttc cgcgtcttcg ccttcgccct cagacgagtc ggatctccct ttgggccgcc      9120
tccccgcctg gaattaattc tgcagtcgag acctagaaaa acatggagca atcacaagta      9180
gcaatacagc agctaccaat gctgattgtg cctggctaga agcacaagag gaggaggagg      9240
tgggttttcc agtcacacct caggtacctt taagaccaat gacttacaag gcagctgtag      9300
atcttagcca cttttttaaaa gaaaagaggg gactggaagg gctaattcac tcccaacgaa      9360
gacaagatat ccttgatctg tggatctacc acacacaagg ctacttccct gattagcaga      9420
actacacacc agggccaggg gtcagatatc cactgacctt tggatggtgc tacaagctag      9480
taccagttga gccagataag gtagaagagg ccaataaagg agaacacc agcttgttac      9540 accctgtgag cctgcatggg atggatgacc cggagagaga agtgttagag tggaggtttg      9600
acagccgcct agcatttcat cacgtggccc gagagctgca tccggagtac ttcaagaact      9660
gctgatatcg agcttgctac aagggacttt ccgctgggga ctttccaggg aggcgtggcc      9720
tgggcgggac tggggagtgg cgagccctca gatcctgcat ataagcagct gcttttgcc      9780 tgtactgggt ctctctggtt agaccagatc tgagcctggg agctctctgg ctaactaggg      9840
aacccactgc ttaagcctca ataaagcttg ccttgagtgc ttcaagtagt gtgtgcccgt      9900
```

```
ctgttgtgtg actctggtaa ctagagatcc ctcagaccct tttagtcagt gtggaaaatc   9960
tctagcagta gtagttcatg tcatcttatt attcagtatt tataacttgc aaagaaatga  10020
atatcagaga gtgagaggcc ttgacattgc tagcgtttac cgtcgacctc tagctagagc  10080
ttggcgtaat catggtcata gctgtttcct gtgtgaaatt gttatccgct cacaattcca  10140
cacaacatac gagccggaag cataaagtgt aaagcctggg gtgcctaatg agtgagctaa  10200
ctcacattaa ttgcgttgcg ctcactgccc gctttccagt cgggaaacct gtcgtgccag  10260
ctgcattaat gaatcggcca acgcgcgggg agaggcggtt tgcgtattgg gcgctcttcc  10320
gcttcctcgc tcactgactc gctgcgctcg tcgttcggc tgcggcgagc ggtatcagct  10380
cactcaaagg cggtaatacg gttatccaca gaatcagggg ataacgcagg aaagaacatg  10440
tgagcaaaag gccagcaaaa ggccaggaac cgtaaaaagg ccgcgttgct ggcgtttttc  10500
cataggctcc gcccccctga cgagcatcac aaaaatcgac gctcaagtca gaggtggcga  10560
aacccgacag gactataaag ataccaggcg tttccccctg gaagctccct cgtgcgctct  10620
cctgttccga ccctgccgct taccggatac ctgtccgcct ttctcccttc gggaagcgtg  10680
gcgctttctc atagctcacg ctgtaggtat ctcagttcgg tgtaggtcgt tcgctccaag  10740
ctgggctgtg tgcacgaacc ccccgttcag cccgaccgct gcgccttatc cggtaactat  10800
cgtcttgagt ccaacccggt aagacacgac ttatcgccac tggcagcagc cactggtaac  10860
aggattagca gagcgaggta tgtaggcggt gctacagagt tcttgaagtg gtggcctaac  10920
tacggctaca ctagaagaac agtatttggt atctgcgctc tgctgaagcc agttaccttc  10980
ggaaaaagag ttggtagctc ttgatccggc aaacaaacca ccgctggtag cggtggtttt  11040
tttgtttgca agcagcagat tacgcgcaga aaaaaaggat ctcaagaaga tcctttgatc  11100
ttttctacgg ggtctgacgc tcagtggaac gaaaactcac gttaagggat tttggtcatg  11160
agattatcaa aaaggatctt cacctagatc cttttaaatt aaaaatgaag ttttaaatca  11220
atctaaagta tatatgagta aacttggtct gacagttacc aatgcttaat cagtgaggca  11280
cctatctcag cgatctgtct atttcgttca tccatagttg cctgactccc cgtcgtgtag  11340
ataactacga tacgggaggg cttaccatct ggccccagtg ctgcaatgat accgcgagac  11400
ccacgctcac cggctccaga tttatcagca ataaaccagc cagccggaag ggccgagcgc  11460
agaagtggtc ctgcaacttt atccgcctcc atccagtcta ttaattgttg ccgggaagct  11520
agagtaagta gttcgccagt taatagtttg cgcaacgttg ttgccattgc tacaggcatc  11580
gtggtgtcac gctcgtcgtt tggtatggct tcattcagct ccggttccca acgatcaagg  11640
cgagttacat gatcccccat gttgtgcaaa aaagcggtta gctccttcgg tcctccgatc  11700
gttgtcagaa gtaagttggc cgcagtgtta tcactcatgg ttatggcagc actgcataat  11760
tctcttactg tcatgccatc cgtaagatgc ttttctgtga ctggtgagta ctcaaccaag  11820
tcattctgag aatagtgtat gcggcgaccg agttgctctt gcccggcgtc aatacggat   11880
aataccgcgc cacatagcag aactttaaaa gtgctcatca ttggaaaacg ttcttcgggg  11940
cgaaaactct caaggatctt accgctgttg agatccagtt cgatgtaacc cactcgtgca  12000
cccaactgat cttcagcatc ttttactttc accagcgttt ctgggtgagc aaaaacagga  12060
aggcaaaatg ccgcaaaaaa gggaataagg gcgacacgga aatgttgaat actcatactc  12120
ttcctttttc aatattattg aagcatttat cagggttatt gtctcatgag cggatacata  12180
tttgaatgta tttagaaaaa taaacaaata ggggttccgc gcacatttcc ccgaaaagtg  12240
```

```
ccacctgacg tcgacggatc gggagatcaa cttgtttatt gcagcttata atggttacaa    12300
ataaagcaat agcatcacaa atttcacaaa taaagcattt ttttcactgc attctagttg    12360
tggtttgtcc aaactcatca atgtatctta tcatgtctgg atcaactgga taactcaagc    12420
taaccaaaat catcccaaac ttcccacccc atccctatt accactgcca attacctgtg     12480
gtttcattta ctctaaacct gtgattcctc tgaattattt tcattttaaa gaaattgtat    12540
ttgttaaata tgtactacaa acttagtagt                                     12570

<210> SEQ ID NO 80
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
gcccggauag ucagucggu agagcaucag acuuuaauc ugagggucca ggguucaagu      60
cccuguucgg gcg                                                       73

<210> SEQ ID NO 81
<211> LENGTH: 301
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 81
gccgggcgcg guggcgcgug ccuguagucc cagcuacucg ggaggcugag gugggaggau     60
cgcuugagcc caggaguucu gggcuguagu gcgcuaugcc gaucggugu ccgcacuaag    120 uucggcauca auauggugac cucccgggag cgggggacca ccagguugcc uaaggagggg   180
ugaaccggcc caggucggaa acggagcagg ucaaaacucc cgucugauc aguagugga    240 ucgcgccugu gaauagccac ugcacuccag ccugugcaac auagcgagac cccgucucuu   300
u                                                                   301

<210> SEQ ID NO 82
<211> LENGTH: 301
<212> TYPE: RNA
<213> ORGANISM: Homo sapiens

<400> SEQUENCE: 82
gccgggcgcg guggcgcgug ccuguagucc cagcuacucg ggaggcugag gcuggaggau     60
cgcuugaguc caggaguucu gggcuguagu gcgcuaugcc gaucggugu ccgcacuaag    120 uucggcauca auauggugac cucccgggag cgggggacca ccagguugcc uaaggagggg   180
ugaaccggcc caggucggaa acggagcagg ucaaaacucc cgucugauc aguagugga    240 ucgcgccugu gaauagccac ugcacuccag ccugugcaac auagcgagac cccgucucuu   300
u                                                                   301

<210> SEQ ID NO 83
<211> LENGTH: 68
<212> TYPE: DNA
<213> ORGANISM: Homo sapiens
```

<400> SEQUENCE: 83
gccgggcgcg gtggcgcgtg cctgtagtcc cagctactcg ggaggctgag gctggaggat    60
cgcttgag                                                              68

<210> SEQ ID NO 84
<211> LENGTH: 151
<212> TYPE: DNA
<213> ORGANISM: Homo sapiens

<400> SEQUENCE: 84
cgatcgggtg tccgcactaa gttcggcatc aatatggtga cctcccggga gcggggacc     60 accaggttgc ctaaggaggg gtgaaccggc ccaggtcgga aacggagcag gtcaaaactc   120
ccgtgctgat cagtagtggg atcgcgcctg t                                   151

<210> SEQ ID NO 85
<211> LENGTH: 111
<212> TYPE: DNA
<213> ORGANISM: Homo sapiens

<400> SEQUENCE: 85
gttcggcatc aatatggtga cctcccggga gcggggacc accaggttgc ctaaggaggg     60
gtgaaccggc ccaggtcgga aacggagcag gtcaaaactc ccgtgctgat c             111

<210> SEQ ID NO 86
<211> LENGTH: 81
<212> TYPE: DNA
<213> ORGANISM: Homo sapiens

<400> SEQUENCE: 86
gccgggcgcg gtggcgcgtg cctgtagtcc cagctactcg ggaggctgag gctggaggat    60
cgcttgagtc caggagttct g                                              81

<210> SEQ ID NO 87
<211> LENGTH: 22
<212> TYPE: DNA
<213> ORGANISM: Homo sapiens

<400> SEQUENCE: 87
aacatagcga gaccccgtct ct                                             22

<210> SEQ ID NO 88
<211> LENGTH: 31
<212> TYPE: DNA
<213> ORGANISM: Homo sapiens

<400> SEQUENCE: 88
agcctgggca acatagcgag accccgtctc t                                   31

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Gly Gly Gly Ser Gly Gly Gly Gly Ser Gly Gly Gly Gly Ser
1               5                   10                  15

-continued

```
<210> SEQ ID NO 90
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 90
gtccaggagu uc                                                         12

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Ser Gly Gly Ser
1               5

<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Gly Gly Ser
1

<210> SEQ ID NO 93
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Gly Ser Gly
1

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Gly Ser Gly Gly
1               5

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 95

Gly Ser Gly Ser Gly
1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Ser Gly Gly Gly
1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Gly Ser Gly
1               5

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Ser Ser Ser Gly
1               5

<210> SEQ ID NO 99
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gcgasggggs ggggs                                                       15

<210> SEQ ID NO 100
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gggasggggs ggggs                                                       15

<210> SEQ ID NO 101
<211> LENGTH: 10
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 101 gggasggggs                                                              10

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Gly Gly Ser Gly Gly Gly Ser
1               5

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Gly Gly Ser Gly Gly Gly Ser Gly Gly Gly Ser
1               5                   10

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Gly Gly Gly Ser
1               5

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Gly Gly Gly Ser Gly Gly Gly Gly Ser
1               5                   10

<210> SEQ ID NO 106
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Gly Gly Gly Ser Gly Gly Gly Gly Ser Gly Gly Gly Gly Ser Gly
1               5                   10                  15

Gly Gly Gly Ser
```

```
<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Gly Gly Ser Gly Gly Ser
1               5

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Glu Phe Gly Asn Met
1               5

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Glu Phe Gly Gly Asn Met
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Glu Phe Gly Gly Asn Gly Gly Asn Met
1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Gly Ser Asn Met Ala Gly
1               5

<210> SEQ ID NO 112
<211> LENGTH: 12
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 112
gggggtggtt cc                                                         12

<210> SEQ ID NO 113
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ggtgggtctg gg                                                         12

<210> SEQ ID NO 114
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gggtccgggg gctcc                                                      15

<210> SEQ ID NO 115
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ggtgggagcg gtggt                                                      15

<210> SEQ ID NO 116
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ggcagcggaa gcgga                                                      15

<210> SEQ ID NO 117
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gggagtgggg gaggt                                                      15

<210> SEQ ID NO 118
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 118
ggtgggggaa gtgga                                                      15

<210> SEQ ID NO 119
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ggcagctcat ctggt                                                      15

<210> SEQ ID NO 120
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ggatgtggtg catctggagg gggaggctct gggggggtg gatct                      45

<210> SEQ ID NO 121
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gggtgtggtg ctagtggggg tggcggatca ggtggaggcg ggagc                     45

<210> SEQ ID NO 122
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gggggcggag gatctggggg aggggatca                                       30

<210> SEQ ID NO 123
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ggggggggcg cttcaggcgg aggtggaagt ggtggaggag gt                        42

<210> SEQ ID NO 124
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 124 ggaggggggag gttctggcgg cgggggatca ggaggcggtg ggagc            45

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125 ggtgggggg cgtcaggtgg aggcggaagt                              30

<210> SEQ ID NO 126
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ggcggcggag gttctggtgg gggtggcagt ggaggaggag gcagc            45

<210> SEQ ID NO 127
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ggaggtggag gtagtggcgg tggtgggtca gggggaggcg ggtccggtgg cggtgggagt    60

<210> SEQ ID NO 128
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ggtggcggta gt                                                12

<210> SEQ ID NO 129
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gggggatctg gt                                                12

<210> SEQ ID NO 130
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
```

```
ggcagtggcg gtagc                                                   15
```

<210> SEQ ID NO 131
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131

```
ggagggagtg gaggg                                                   15
```

<210> SEQ ID NO 132
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132

```
gggtctggct caggc                                                   15
```

<210> SEQ ID NO 133
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133

```
ggttctggcg gaggt                                                   15
```

<210> SEQ ID NO 134
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134

```
ggtggtggga gtgga                                                   15
```

<210> SEQ ID NO 135
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135

```
ggctcaagca gtgga                                                   15
```

<210> SEQ ID NO 136
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136

```
ggctgtgggg ctagtgggggg aggtggtagt ggtggtggcg gttcc            45

<210> SEQ ID NO 137
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ggatgtgggg cctcaggtgg gggtggcagc ggtggtggag ggtca            45

<210> SEQ ID NO 138
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ggtggcgggg gctctggtgg aggaggatct                              30

<210> SEQ ID NO 139
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ggaggcggcg cttctggggg cgggggtagt ggggggtggag gt               42

<210> SEQ ID NO 140
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ggtggaggtg gaagtggagg aggggggatca ggcggaggcg ggagc            45

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141 ggaggggggag cctctggcgg tggaggatca                             30

<210> SEQ ID NO 142
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gggggaggag gcagtggagg tgggggaagt ggtggagggg ggtct             45
```

<210> SEQ ID NO 143
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gggggtggag gatcaggagg cggtggttct gggggaggtg gatccggcgg gggtggtagt     60

<210> SEQ ID NO 144
<211> LENGTH: 4
<212> TYPE: PRT
<213> ORGANISM: Sindbis virus

<400> SEQUENCE: 144

Ser Leu Lys Gln
1

<210> SEQ ID NO 145
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ala Ala Ala Ala
1

<210> SEQ ID NO 146
<211> LENGTH: 36
<212> TYPE: DNA
<213> ORGANISM: Unknown
<220> FEATURE:
<223> OTHER INFORMATION: Description of Unknown:
      LacZ sequence
<220> FEATURE:
<221> NAME/KEY: CDS
<222> LOCATION: (1)..(36)

<400> SEQUENCE: 146 ctg atc ctt tgc gaa tac gcc cac gcg atg ggt aac                       36
Leu Ile Leu Cys Glu Tyr Ala His Ala Met Gly Asn
1               5                   10

<210> SEQ ID NO 147
<211> LENGTH: 12
<212> TYPE: PRT
<213> ORGANISM: Unknown
<220> FEATURE:
<223> OTHER INFORMATION: Description of Unknown:
      LacZ sequence

<400> SEQUENCE: 147

Leu Ile Leu Cys Glu Tyr Ala His Ala Met Gly Asn
1               5                   10

<210> SEQ ID NO 148
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: CDS
<222> LOCATION: (1)..(36)

<400> SEQUENCE: 148 ctg atc ctt tgc caa tac gcc cac gcg atg ggt aac         36
Leu Ile Leu Cys Gln Tyr Ala His Ala Met Gly Asn
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Leu Ile Leu Cys Gln Tyr Ala His Ala Met Gly Asn
1               5                   10

<210> SEQ ID NO 150
<211> LENGTH: 114
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 150
gccgggcgcg guggcgcgug ccuguagucc cagcuacucg ggaggcugag gcuggaggau      60
cgcuugaguc caggaguucu gagccugugc aacauagcga gaccccgucu cuuu          114

<210> SEQ ID NO 151
<211> LENGTH: 87
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gccgggcgcg guggcgcgug ccuguagucc cagcuacucg ggaggcugag gcuggaggau      60
cgcuugauag cgagaccccg ucucuuu                                         87

<210> SEQ ID NO 152
<211> LENGTH: 92
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
gccgggcgcg guggcgcgug ccuguagucc cagcuacucg ggaggcugag gcuggaggau      60
cgcuguggau caaagcgaga ccccgucucu uu                                   92

<210> SEQ ID NO 153
<211> LENGTH: 153
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 153
```

```
gaucgggugu ccgcacuaag uucggcauca auauggugac cucccgggag cgggggacca      60
ccagguugcc uaaggagggg ugaaccggcc caggucggaa acggagcagg ucaaaacucc     120
cgugcugauc aguaguggga ucgcgccugu uuu                                  153
```

<210> SEQ ID NO 154
<211> LENGTH: 114
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 154

```
guucggcauc aauaugguga ccucccggga gcgggggacc accagguugc cuaaggaggg      60
gugaaccggc ccaggucgga aacggagcag gucaaaacuc ccgugcugau cuuu           114
```

<210> SEQ ID NO 155
<211> LENGTH: 186
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 155

```
gccgggcgcg guggcgcgug ccuguagucc cagcuacucg ggaggcugag gcuggaggau      60
guucggcauc aauaugguga ccucccggga gcgggggacc accagguugc cuaaggaggg     120
gugaaccggc ccaggucgga aacggagcag gucaaaacuc ccgugcugau cagacccgu     180 cucuuu                                                                186
```

<210> SEQ ID NO 156
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156

```
gcccaggagu uc                                                          12
```

DELIVERY OF A GENE-EDITING SYSTEM WITH A SINGLE RETROVIRAL PARTICLE AND METHODS OF GENERATION AND USE

CROSS-REFERENCE TO RELATED APPLICATIONS

This application is a National Stage application of International Application No. PCT/US2018/049547, filed Sep. 5, 2018, which claims priority to U.S. Provisional Patent Application No. 62/554,500 filed Sep. 5, 2017, all of which is hereby incorporated by reference in their entirety.

SEQUENCE LISTING

The instant application contains a Sequence Listing which has been submitted electronically in ASCII format and is hereby incorporated by reference in its entirety. Said ASCII copy, created on Nov. 2, 2018, is named 250298_000061_SL.txt and is 337,425 bytes in size.

TECHNICAL FIELD

Described herein are retroviral particles for delivery of gene-editing molecules to a target cell.

BACKGROUND

The Clustered Regularly Interspaced Short Palindromic Repeats (CRISPR)/CRISPR-associated (Cas) system is a powerful genome editing technique allowing for a permanent disruption, deletion, repair, mutation, addition, alteration, or modification of a gene sequence at a target locus in a gene after a single administration. Current methods rely on two essential elements: a component for targeted DNA recognition (e.g., guide RNA) and a component for nuclease activity to induce a single or double strand break at the specific site in the genomic DNA (e.g., Cas9 nucleases). See Mout et al., (2017) *Bioconjugate Chem* 25:880-884. In instances where there is a repair or genetic alteration to be made, a repair template with the desired repair/mutation may be present. Id. One way to deliver the CRISPR/Cas system to the cell of interest is by using a viral packaging system. Virol genomes, however, are compact and there is typically no room for a Cas protein coding sequence together with the guide RNA and repair template in the same viral particle genome. For example, the size limit of a cargo gene in adeno-associated viral particles is ~4.7 kbp, while the size of SpCas9 by itself is ~4.3 kbp. Id. For lentiviral particles, the packaging limit is ~8.5 kbp—however, inserts larger than ~3 kbp are packaged less efficiently. See e.g., Komor et al., (2017) *Cell* 168:20-36. Thus, the existing delivery systems suffer from inefficiencies because the different CRISPR/Cas components are split into different delivery units (e.g., via two viral particles or via a viral particle and a lipid nanoparticle) or smaller Cas proteins would need to be used. Moreover, many of the current systems require the CRISPR genes to remain in the target cells once delivered, resulting in unwanted gene editing and potential immunogenic reactions due to the constitutive expression. See e.g., Mout et al., (2017) *ACS Nano* 11:2452-2458.

SUMMARY

As specified in the Background section, above, there is a need in the art for a single recombinant viral particle system and methods for generating such particles that allow for the efficient delivery of all components of a gene-editing system (e.g., the CRISPR/Cas system) required for gene modification at a target locus in a genome. The present invention addresses this and other needs by providing recombinant retroviral particles for delivery of gene-editing molecules to target cells. The retroviral particles described herein are capable of delivering together all components of a gene-editing system (e.g., the CRISPR/Cas system) required for gene modification in a target cell and for the treatment of various diseases.

In one aspect, the invention provides a recombinant RNA molecule comprising (i) a sequence of a gene-editing molecule mRNA, or a sequence of a functional fragment or derivative thereof, and (ii) at least one sequence of a coding or non-coding enrichment RNA, or a sequence of a functional fragment or derivative thereof, wherein the enrichment RNA, or functional fragment or derivative thereof, is capable of enhancing inclusion of the gene-editing molecule mRNA, or functional fragment or derivative thereof, into a retroviral particle. In some embodiments, the gene-editing molecule mRNA, or a fragment or derivative thereof, is codon optimized for expression in a eukaryotic cell (e.g., a non-human mammalian cell, a human cell, a rodent cell, a pluripotent cell, a one-cell stage embryo, a differentiated cell, or a combination thereof). In some embodiments, the sequence of the gene-editing molecule mRNA, or a sequence of a fragment or derivative thereof, and the sequence of the small RNA, or a sequence of a fragment or derivative thereof are separated by a linker sequence. In some embodiments, the gene-editing molecule is a Cas protein (e.g., Cpf1, CasX, CasY, C2C2, Cas1, Cas1B, Cas2, Cas3, Cas4, Cas5, Cas5e (CasD), Cash, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cu1966). In some embodiments, the Cas protein is a Cas9 protein (e.g., wild type Cas9, a Cas9 nickase, a dead Cas9 (dCas9), or a split Cas9). In some embodiments, the Cas9 protein is a *Streptococcus pyogenes* Cas9 protein or *Staphylococcus aureus* Cas9 protein. In some embodiments, the enrichment RNA is a small non-coding or coding RNA. In some embodiments, the small non-coding RNA is 7SL RNA, tRNA (including primer tRNAs), 5S rRNA, U1 snRNA, U2 snRNA, U6 snRNA, Y1 RNA, Y3 RNA, B1 RNA, VL30 RNA, 7SK RNA, Alu RNA, miRNA, snoRNA, or cytoplasmic vault ncRNA. In some embodiments, the small non-coding RNA is 7SL RNA. In some embodiments, the gene-editing molecule mRNA is Cas9 mRNA and the non-coding RNA is 7SL RNA. In some embodiments, the retroviral particle is a lentiviral particle.

In a related aspect, the invention provides nucleic acid molecules encoding the recombinant RNA molecules of the invention as well as vectors comprising the nucleic acid molecules, wherein the nucleic acid molecule encoding a recombinant RNA molecule is operably linked to a promoter.

In a further aspect, the invention provides host cells comprising the RNA molecules of the invention or the nucleic acid molecules encoding such RNA molecules or the vectors comprising the nucleic acid molecules.

In another aspect, the invention provides recombinant retroviral particles comprising the RNA molecules of the invention. In some embodiments, the retroviral particles are lentiviral particles. In some embodiments, the retroviral particles further comprise a nucleic acid molecule encoding one or more guide RNAs (gRNA) and/or a nucleic acid molecule comprising one or more sequences corresponding to one or more repair templates (RT). In some embodiments, the nucleic acid sequence(s) encoding the gRNA and the nucleic acid sequence(s) corresponding to the RT are located within the same nucleic acid molecule. In some embodiments, in addition to the sequence(s) encoding the gRNA and/or the sequence(s) corresponding to the RT, the nucleic acid molecule comprises one or more retroviral elements. In some embodiments, the retroviral particles are replication deficient.

In some embodiments, the retroviral particles further comprise a gene-editing molecule fusion protein. In some embodiments, the gene-editing molecule fusion protein comprises (i) a sequence of a gene-editing protein, or a sequence of a functional fragment or derivative thereof, and (ii) at least one sequence of an enrichment protein, or a sequence of a functional fragment or derivative thereof, wherein the enrichment protein, or functional fragment or derivative thereof, is capable of enhancing inclusion of the gene-editing protein, or functional fragment or derivative thereof, into the retroviral particle. In some embodiments, (i) the sequence of the gene-editing molecule, or a sequence of a fragment or derivative thereof, and (ii) the at least one sequence of the enrichment protein, or a sequence of a fragment or derivative thereof, are separated by a linker sequence (e.g., $(G_4S)_3$ (SEQ ID NO: 89)). In some embodiments, the gene-editing molecule is a Cas protein (e.g., Cpf1, CasX, CasY, C2C2, Cas1, Cas1B, Cas2, Cas3, Cas4, Cas5, Cas5e (CasD), Cash, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cu1966, or homologs or modified versions thereof). In some embodiments the Cas protein is a Cas9 protein (e.g., a wild type Cas9, a Cas9 nickase, a dead Cas9 (dCas9), or a split Cas9). In some embodiments, the Cas9 protein is a *Streptococcus pyogenes* Cas9 protein or *Staphylococcus aureus* Cas9 protein. In some embodiments, the enrichment protein is cyclophilin A (CypA) protein and/or a viral protein R (Vpr).

In another aspect, the invention provides a method of producing the retroviral particles of the invention, the method comprising culturing a packaging cell in conditions sufficient for the production of a plurality of retroviral particles, wherein the packaging cell comprises one or more plasmids comprising (i) one or more retroviral elements involved in the assembly of the retroviral particle, and (ii) at least one nucleic acid sequence encoding the RNA molecule of the invention. In some embodiments, the packaging cell further comprises a plasmid encoding one or more guide RNAs (gRNA) and/or comprising one or more sequences corresponding to one or more repair templates (RT). In some embodiments, the packaging cell comprises (a) GAG, (b) POL, and (c) TAT and/or REV retroviral (e.g., lentiviral) elements. In some embodiments, the method of producing the retroviral particles of the invention further comprises collecting the retroviral particles. In some embodiments, the method of producing the retroviral particles of the invention comprises one or more of the following steps: (a) clearing cell debris, (b) treating a supernatant containing the retroviral particles with DNase I and $MgCl_2$, (c) concentrating the retroviral particles, and (d) purifying the retroviral particles.

In a related embodiment, the invention provides the retroviral particle made by any of the above methods.

In another aspect, the invention provides pharmaceutical compositions comprising any of the retroviral particles of the invention and a pharmaceutically acceptable carrier or excipient.

In a further aspect, the invention provides pharmaceutical dosage forms comprising any of the retroviral particles of the invention.

In yet another aspect, the invention provides a method for modifying a genome of a target cell comprising introducing into the cell any of the retroviral particles of the invention. In some embodiments, the genome modification is a disruption, deletion, repair, mutation, addition, alteration, or modification of a gene.

In yet another aspect, the invention provides a method for modulating an activity of a gene in a target cell comprising introducing into the cell any of the retroviral particles of the invention. In some embodiments, the method inhibits, suppresses, down regulates, knocks down, knocks out, or silences the expression of a gene product. In some embodiments, the gene product is a protein or RNA.

In some embodiments of any of the above methods, the target cell is in a subject and the retroviral particle is administered to the subject.

In some embodiments of any of the above methods, the method further comprises harvesting the target cell from a subject prior to introducing the retroviral particle into the target cell, introducing the retroviral particle into the target cell ex vivo and returning the target cell to the subject.

In some embodiments of any of the above methods, the method further comprises introducing into the target cell one or more gRNA molecules (e.g., as a complex with proteins). In some embodiments, such separate introduction of gRNA molecules is conducted when retroviral particles comprise no gRNA. In some embodiments, retroviral particles comprise one or more gRNA and separately introduced gRNA provide additional gRNA molecules.

In a further aspect, the invention provides a method for treating a disease in a subject in need thereof, the method comprising administering to the subject a therapeutically effective amount of any of the retroviral particles of the invention or a pharmaceutical composition comprising such retroviral particles, wherein the retroviral particles target a cell in the subject.

In some embodiments of any of the above methods involving administration to the subject, the retroviral particle or the pharmaceutical composition is administered intravenously, subcutaneously, intramuscularly, transdermally, intranasally, orally, or mucosally.

In a further aspect, the invention provides a method for treating a disease in a subject in need thereof, the method comprising:
a. harvesting a target cell from the subject;
b. introducing into the target cell from step a) ex vivo a therapeutically effective amount of any of the retroviral particles of the invention or a pharmaceutical composition comprising such retroviral particles; and
c. returning the target cell from step b) to the subject.

BRIEF DESCRIPTION OF THE DRAWINGS

FIG. 1A shows recruiting the Cas9 fusion proteins or Cas9 mRNAs into lentiviral particles for transduction of functional Cas9 proteins into infected cells. The gRNA is contained in the retroviral genome. FIG. 1B shows 7SL RNA constructs, wherein 7SL RNA is fused before the start codon or after stop codon of Cas9 mRNA. FIG. 1C shows Cas9 protein constructs: cyclophilin A (CypA) fused to the N-terminus of Cas9 protein or viral protein R (Vpr) fused to the C-terminus of the Cas9 protein via a linker (e.g., $(G_4S)_3$ (SEQ ID NO: 89)).

FIG. 2 A-G show fluorescence-activated cell sorting (FACS) analysis evaluating expression upon infection of 293T pLVX EF1a eGFP IRES puro c12 cells with: (FIG. 2C) Cas9/GFP gRNA: a lentiviral particle carrying randomly packaged Cas9 proteins and mRNAs and gRNA.

FIG. 4 discloses SEQ ID NOS 146-149, respectively, in order of appearance.

FIG. 6A discloses SEQ ID NO: 81. FIG. 6B discloses SEQ ID NO: 150. FIG. 6C discloses SEQ ID NO: 151. FIG. 6D discloses SEQ ID NO: 152. FIG. 6E discloses SEQ ID NO: 153. FIG. 6F discloses SEQ ID NO: 154. FIG. 6G discloses SEQ ID NO: 155. FIG. 6H discloses SEQ ID NO: 156. FIG. 6I discloses SEQ ID NO: 90. The numbers in FIGS. 6A-6G represent established nomenclature for 7SL RNA helices and loops. See also Keene and Telesnitsky *J Virol.* 2012 August; 86(15): 7934-7942, incorporated by reference herein in its entirety for all purposes.

DETAILED DESCRIPTION

Figure 1A:
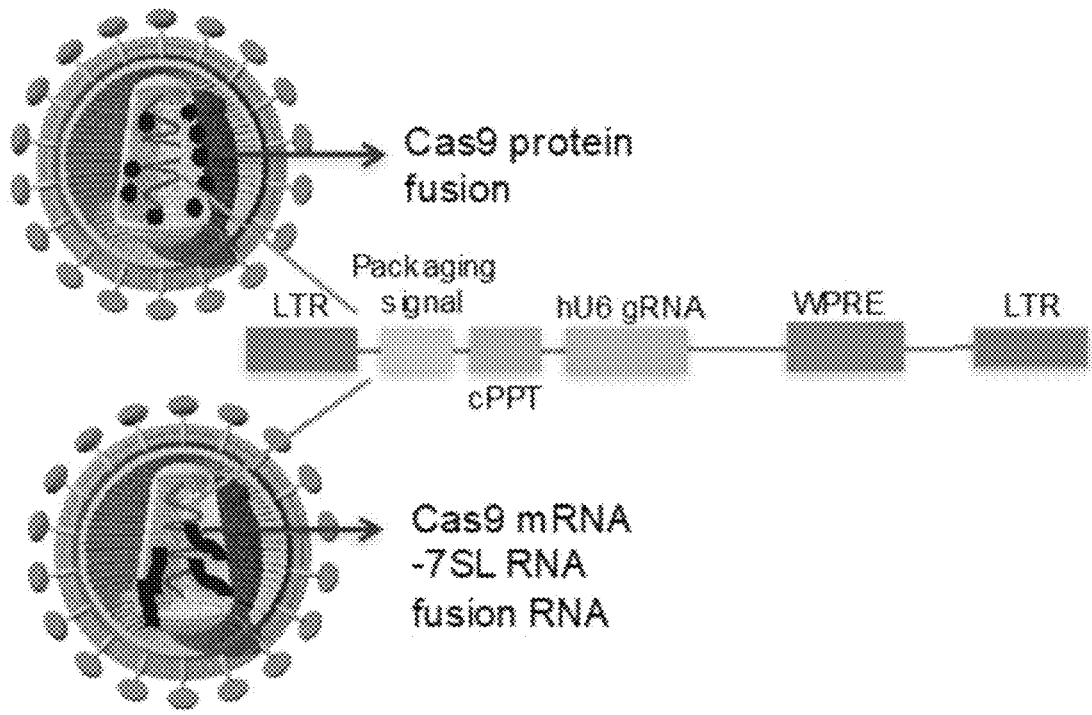
FIGS. 1A-C provide a schematic representation of concepts and four exemplary Cas9 constructs of the invention.
Figure 1B:
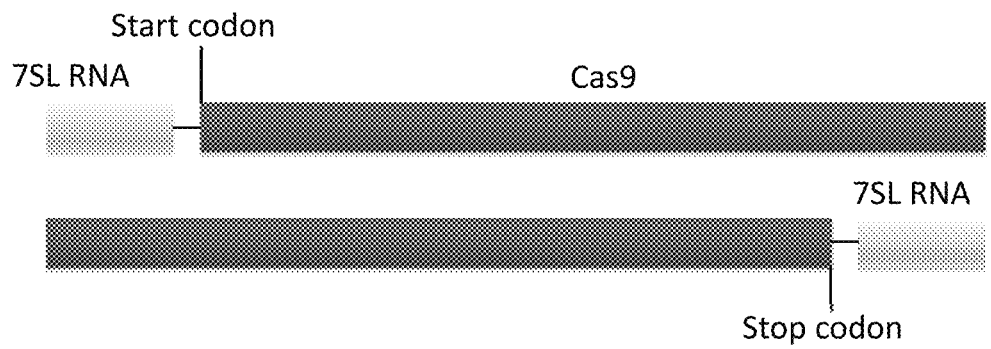
Figure 1C:
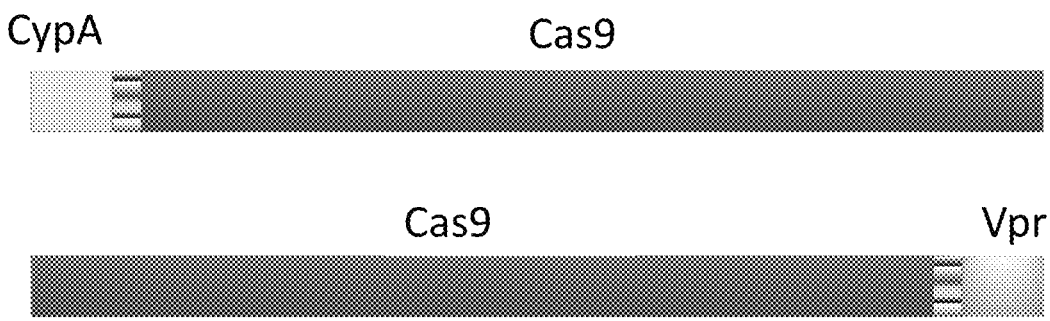

The present invention provides recombinant retroviral particles for the delivery of a gene-editing fusion molecule, and optionally a guide RNA (gRNA) and/or a repair template, in one retroviral particle. The retroviral particles described herein are capable of delivery of all components required for gene modification and/or modulating an activity of a gene in a target cell and are therefore useful for treatment of various diseases treatable by modification and/or modulating an activity of a gene.

I. Definitions

Unless defined otherwise, all technical and scientific terms used herein have the same meaning as commonly understood by one of ordinary skill in the art to which this invention belongs.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3 oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "wild type" includes entities having a structure and/or activity as found in a normal (as contrasted with mutant, diseased, altered, or so forth) state or context. Wild type genes and polypeptides often exist in multiple different forms (e.g., alleles).

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells (e.g., packaging cells) and/or target cells by replacing at least one codon of the native sequence with a codon that is more frequently or most frequently used in the genes of the host cells and/or target cells while maintaining the native amino acid sequence. For example, a nucleic acid encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host and/or target cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host and/or target are also available (see, e.g., Gene Forge).

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. As used herein, the term "promoter" encompasses enhancers. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). RNA Pol III promoters are frequently used to express small RNAs, such as small interfering RNA (siRNA)/short hairpin RNA (shRNA) and guide RNA sequences used in CRISPR-Cas9 systems. Examples of RNA Pol III promoters that can be used in the invention include, but are not limited to, the human U6 promoter, a rat U6 polymerase III promoter, or a mouse U6 polymerase III promoter, and the HI promoter, which are described in, for example Goomer and Kunkel, Nucl. Acids Res., 20 (18): 4903-4912 (1992), and Myslinski et al., Nucleic Acids Res., 29(12): 2502-9 (2001). Examples of promoters can be found, for example, in WO 2013/176772, herein incorporated by reference in its entirety for all purposes.

Examples of inducible promoters include, for example, chemically regulated promoters and physically-regulated promoters. Chemically regulated promoters include, for example, alcohol-regulated promoters (e.g., an alcohol dehydrogenase (alcA) gene promoter), tetracycline-regulated promoters (e.g., a tetracycline-responsive promoter, a tetracycline operator sequence (tetO), a tet-On promoter, or a tet-Off promoter), steroid regulated promoters (e.g., a rat glucocorticoid receptor, a promoter of an estrogen receptor, or a promoter of an ecdysone receptor), or metal-regulated promoters (e.g., a metalloprotein promoter). Physically regulated promoters include, for example temperature-regulated promoters (e.g., a heat shock promoter) and light-regulated promoters (e.g., a light-inducible promoter or a light-repressible promoter).

Tissue-specific promoters can be, for example, neuron-specific promoters, glia-specific promoters, muscle cell-specific promoters, heart cell-specific promoters, kidney cell-specific promoters, bone cell-specific promoters, endothelial cell-specific promoters, or immune cell-specific promoters (e.g., a B cell promoter or a T cell promoter).

Developmentally regulated promoters include, for example, promoters active only during an embryonic stage of development, or only in an adult cell.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

"Complementarity" or "complementary" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N.Y., 1989), herein incorporated by reference in its entirety for all purposes.

Hybridization requires that the two nucleic acids contain complementary sequences, although mismatches between bases are possible. The conditions appropriate for hybridization between two nucleic acids depend on the length of the nucleic acids and the degree of complementation, variables which are well known. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid/target locus to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid/target locus sequence to which they are targeted. For example, a gRNA in which 18 of 20 nucleotides are complementary to a target region, and would therefore specifically hybridize, would represent 90% complementarity. In this example, the remaining non-complementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs (Altschul et al. (1990) *J Mol. Biol.* 215:403-410; Zhang and Madden (1997) *Genome Res.* 7:649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The methods and compositions provided herein employ a variety of different components. Some components throughout the description can have active variants and fragments. Such components include, for example, Cas proteins, CRISPR RNAs, and guide RNAs. Biological activity for each of these components is described elsewhere herein. The term "functional" refers to the innate ability of a protein or nucleic acid (or a fragment or derivative thereof) to exhibit a biological activity or function. Such biological activities or functions can include, for example, the ability of a Cas protein, or functional fragment or derivative thereof, to bind to a guide RNA (gRNA), bind to a target DNA sequence, exhibit endonuclease activity, or to retain its ability to be incorporated into the retroviral particle. The biological functions of functional fragments or derivatives may be the same or may in fact be changed (e.g., with respect to their specificity or selectivity or efficacy) in comparison to the full-length wild type molecule or original counterpart, but with retention of the basic biological function of gene-editing.

The term "fragment" when referring to a protein means a protein that is shorter or has fewer amino acids than the full-length protein. A fragment can be, for example, an N-terminal fragment (i.e., removal of a portion of the C-terminal end of the protein), a C-terminal fragment (i.e., removal of a portion of the N-terminal end of the protein), or an internal fragment. The term "fragment" when referring to a nucleic acid means a nucleic acid that is shorter or has fewer nucleotides than the full-length nucleic acid. A fragment can be, for example, a 5' fragment (i.e., removal of a portion of the 3' end of the nucleic acid), a 3' fragment (i.e., removal of a portion of the 5' end of the protein), or an internal fragment.

The term "derivative" as used herein refers to a nucleic acid, peptide, or protein or a variant or analog thereof comprising one or more mutations and/or chemical modifications as compared to a corresponding full-length wild type nucleic acid, peptide or protein. Non-limiting examples of chemical modifications involving nucleic acids include, for example, modifications to the base moiety, sugar moiety, phosphate moiety, phosphate-sugar backbone, or a combination thereof.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

| | | | | | |
|---|---|---|---|---|---|
| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

The term "enriched" as used herein in relation to fusion gene-editing molecule RNA or protein of the invention indicates that the retroviral particle population comprises a higher number or higher percentage of gene-editing molecules than is found when the gene-editing molecule is not fused to an "enrichment" molecule (e.g., Vpr or CypA protein or 7SL RNA) or a fragment or derivative thereof. The "enrichment molecule" or fragment or derivative thereof is capable of effectively incorporating (i.e., enhancing inclusion of) the gene-editing molecule into a retroviral particle. In certain embodiments, the number of gene-editing fusion molecules incorporated into the retroviral particle is at least 1%, 2%, 3%, 4%, 5%, 7%, 10%, 15%, 20%, 30%, 40%, 50%, 60%, 70%, 80%, 90% or 95% higher than when compared to the same non-fused gene-editing molecule into the same type of retroviral particle.

The terms "retroviral element" or "retroviral component" are used herein to refer to retroviral genes (e.g., genes encoding polymerase or structural proteins) or other elements of the retroviral genome (e.g., packaging signals, regulatory elements, LTRs, etc.).

By "decreased" is intended any decrease in the level or activity of the gene/protein (e.g., encoded at the locus of interest). For example, a decrease in activity can comprise either (1) a statistically significant decrease in the overall level or activity of a given protein including, for example, a decreased level or activity of 0.5%, 1%, 5%, 10%, 20%, 30%, 40%, 50%, 60%, 70%, 80%, 90%, 100%, 120% or greater when compared to an appropriate control.

By "increased" is intended any increase in the level or activity of the gene/protein (e.g., encoded at the locus of interest). For example, an increase in activity can comprise either (1) a statistically significant increase in the overall level or activity of a given protein including, for example, an increased level or activity of 0.5%, 1%, 5%, 10%, 20%, 30%, 40%, 50%, 60%, 70%, 80%, 90%, 100%, 120% or greater when compared to an appropriate control.

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

An "individual" or "subject" or "animal" refers to humans, veterinary animals (e.g., cats, dogs, cows, horses, sheep, pigs, etc.) and experimental animal models of diseases (e.g., mice, rats). In a preferred embodiment, the subject is a human.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

In accordance with the disclosure herein, there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition. Cold Spring Harbor, NY: Cold Spring Harbor Laboratory Press, 1989 (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); Ausubel, F. M. et al. (eds.). Current Protocols in Molecular Biology. John Wiley & Sons, Inc., 1994. These techniques include site directed mutagenesis as described in Kunkel, Proc. Natl. Acad. Sci. USA 82: 488-492 (1985), U.S. Pat. No. 5,071,743, Fukuoka et al., Biochem. Biophys. Res. Commun. 263: 357-360 (1999); Kim and Maas, BioTech. 28: 196-198 (2000); Parikh and Guengerich, BioTech. 24: 428-431 (1998); Ray and Nickoloff, BioTech. 13: 342-346 (1992); Wang et al., BioTech. 19: 556-559 (1995); Wang and Malcolm, BioTech. 26: 680-682 (1999); Xu and Gong, BioTech. 26: 639-641 (1999), U.S. Pat. Nos. 5,789,166 and 5,932,419, Hogrefe, Strategies 14. 3: 74-75 (2001), U.S. Pat. Nos. 5,702,931, 5,780,270, and 6,242,222, Angag and Schutz, Biotech. 30: 486-488 (2001), Wang and Wilkinson, Biotech. 29: 976-978 (2000), Kang et al., Biotech. 20: 44-46 (1996), Ogel and McPherson, Protein Engineer. 5: 467-468 (1992), Kirsch and Joly, Nucl. Acids. Res. 26: 1848-1850 (1998), Rhem and Hancock, J. Bacteriol. 178: 3346-3349 (1996), Boles and Miogsa, Curr. Genet. 28: 197-198 (1995), Barrenttino et al., Nuc. Acids. Res. 22: 541-542 (1993), Tessier and Thomas, Meths. Molec. Biol. 57: 229-237, and Pons et al., Meth. Molec. Biol. 67: 209-218.

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

Singular forms "a", "an", and "the" include plural references unless the context clearly dictates otherwise. Thus, for example, a reference to "a method" includes one or more methods, and/or steps of the type described herein, and/or which will become apparent to those persons skilled in the art upon reading this disclosure.

II. Recombinant Retroviral Particles

In one aspect, described herein is a recombinant retroviral particle that is capable of introducing a gene-editing system (e.g., the CRISPR/Cas system) into a target cell, the recombinant retroviral particle comprising (i) a gene-editing fusion molecule and optionally (ii) a guide RNA (gRNA) and/or a repair template. In certain embodiments, the gene-editing molecule is a functional fragment or derivative thereof. In certain embodiments, the gene-editing fusion molecule is a recombinant RNA molecule. In certain embodiments, the recombinant RNA molecule is a fusion RNA molecule which comprises (i) a sequence of a gene-editing molecule mRNA, or a sequence of a functional fragment or derivative thereof, and (ii) at least one sequence of an enrichment coding or non-coding RNA (e.g., a small coding or non-coding RNA), or a sequence of a functional fragment or derivative thereof, wherein the enrichment RNA, or functional fragment or derivative thereof, is capable of enhancing inclusion of the gene-editing molecule mRNA, or functional fragment or derivative thereof, into a retroviral particle. In certain embodiments, the recombinant RNA molecule comprises one or more sequences of an enrichment coding or non-coding RNA, or functional fragment or derivative thereof. In certain embodiments, when there is more than one sequence of enrichment coding or non-coding RNA, or functional fragment or derivative thereof, each enrichment coding or non-coding RNA, or functional fragment or derivative thereof, is the same or different. In certain embodiments, the gene-editing fusion molecule is a recombinant protein molecule. In certain embodiments, the recombinant protein molecule is a fusion protein molecule which comprises (i) a sequence of a gene-editing protein, or a sequence of a functional fragment or derivative thereof, and (ii) at least one enrichment protein sequence, or a sequence of functional fragment or derivative thereof, wherein the enrichment protein, or functional fragment or derivative thereof, is capable of enhancing inclusion of the gene-editing protein, or functional fragment or derivative thereof, into a retroviral particle. In certain embodiments, the fusion protein molecule comprises one or more sequences of an enrichment protein, or functional fragment or derivative thereof. In certain embodiments, when there is more than one sequence of enrichment protein, or functional fragment or derivative thereof, each enrichment protein, or functional fragment or derivative thereof, is the same or different. In certain embodiments, the retroviral particle comprises both the fusion RNA molecule and the fusion protein molecule.

In certain embodiments, the recombinant retroviral particle comprises a sequence encoding gRNA. In certain embodiments, the recombinant retroviral particle comprises a sequence corresponding to a repair template (RT). In certain embodiments, the recombinant retroviral particle comprises both a sequence encoding gRNA and a sequence corresponding to a repair template (RT). In certain embodiments, upon introduction into a target cell of the recombinant retroviral particle, the sequence encoding the gRNA and/or the sequence corresponding to the repair template (RT) integrate into the cell genome. In certain embodiments, upon introduction into a target cell of the recombinant retroviral particle, the sequence encoding the gRNA and/or the sequence corresponding to the repair template (RT) do not integrate into the cell genome. In certain embodiments, the gRNA can comprise a single RNA molecule (single RNA polynucleotide). In certain embodiments, the gRNA can comprise two separate RNA molecules: an activator-RNA (e.g., tracrRNA) and a targeter-RNA (e.g., CRISPR RNA or crRNA).

In certain embodiments, the target cell for the retroviral particle is a eukaryotic cell, e.g., a mammalian cell (including, e.g., human, veterinary animal or rodent cell) or amphibian cell, avian cell, insect cell, and yeast.

The term "retroviral particle" as used herein refers to a recombinant retroviral particle generated in a packaging cell that is able to deliver a gene-editing fusion molecule, and optionally a guide RNA (gRNA) and/or a repair template into a suitable target cell. In one embodiment, the retroviral particles of the invention are replication deficient. In certain embodiments, the retroviral particle is a retroviral particle (e.g., a lentiviral particle). In some embodiments, the retroviral particle is lacking one or more of the wild type envelope proteins. In some embodiments, the retroviral particle is a pseudotyped particle. The term "pseudotyped" in connection with enveloped retroviral particles described herein refers to retroviral particles comprising in their lipid envelope molecules, e.g., proteins, glycoproteins, etc., which are mutated and/or heterologous compared to molecules typically found on the surface of the retrovirus from which the particles are derived, and which may affect, contribute to, direct, redirect and/or completely change the tropism of the retroviral particle in comparison to a reference wild type retrovirus from which the retroviral particle is derived. In some embodiments, a retroviral particle is pseudotyped such that it recognizes, binds and/or infects a target (ligand or cell) that is different to that of a reference wild type retrovirus from which the retroviral particle is derived. In some embodiments, a retroviral particle is pseudotyped such that it does not recognize, bind, and/or infect a target (ligand or cell) of the reference wild type retrovirus from which the retroviral particle is derived.

A "gene-editing molecule" is a molecule (e.g., a protein or mRNA encoding such protein) used for modifying a genomic locus of interest (i.e., target) in a cell (e.g., eukaryotic, mammalian, human, or non-human cell). Such modifications include, but are not limited to a disruption, deletion, repair, mutation, addition, alteration, or modification of a gene sequence at a target locus in a gene. Examples of gene-editing molecules include, but are not limited to, endonucleases. Endonucleases are enzymes that cleave the phosphodiester bond within a polynucleotide chain, but they only break internal phosphodiester bonds. Examples of gene-editing endonucleases useful in the compositions and methods of the present invention include, but are not limited to, zinc finger nucleases (ZFns), transcription activator-like effector nucleases (TALENs), meganucleases, restriction endonucleases, recombinases, and Clustered Regularly Interspersed Short Palindromic Repeats, (CRISPR)/CRISPR-associated (Cas) proteins.

A. Cas Fusion Molecule

The methods and compositions disclosed herein can utilize the Clustered Regularly Interspersed Short Palindromic Repeats (CRISPR)/CRISPR-associated (Cas) systems or components of such systems to modify a genome within a cell. CRISPR/Cas systems include transcripts and other elements involved in the expression of, or directing the activity of, Cas genes. A CRISPR/Cas system can be, for example, a type I, a type II, or a type III system. Alternatively, a CRISPR/Cas system can be a type V system (e.g., subtype V-A or subtype V-B). The methods and compositions disclosed herein can employ CRISPR/Cas systems by utilizing CRISPR complexes (comprising a guide RNA (gRNA) complexed with a Cas protein) for site-directed cleavage of nucleic acids.

CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together, employ a Cas protein that does not occur naturally, or employ a gRNA that does not occur naturally.

In one aspect, described herein are Cas fusion molecules to be delivered to a target cell. In certain aspects, the Cas portion of the Cas fusion molecule is a Cas molecule, or a functional fragment or derivative thereof.

In certain embodiments, the Cas fusion molecule is a recombinant RNA molecule. In certain embodiments, the recombinant RNA molecule is a Cas fusion RNA which comprises (i) a sequence of a Cas mRNA, or a sequence of a functional fragment or derivative thereof, and (ii) at least one sequence of a coding or non-coding RNA, or a sequence of a functional fragment or derivative thereof, wherein the coding or non-coding RNA, or functional fragment or derivative thereof is capable of enhancing inclusion of the Cas mRNA, or functional fragment or derivative thereof, into a retroviral particle. In certain embodiments, the Cas fusion RNA molecule comprises one or more sequences of an enrichment coding or non-coding RNA, or functional fragment or derivative thereof. In certain embodiments, when there is more than one sequence of enrichment coding or non-coding RNA, or functional fragment or derivative thereof, each enrichment coding or non-coding RNA, or functional fragment or derivative thereof, is the same or different. In certain embodiments, the coding or non-coding RNA is a small coding or non-coding RNA. The term "small RNA" as used herein refers to RNA molecules that are <350 nucleotides that can be coding or non-coding RNA molecules. The term "coding RNA" refers to a functional RNA molecule that can translate into a protein. The terms "non-coding RNA (ncRNA)", "non-protein-coding RNA (npcRNA)", "non-messenger RNA (nmRNA)", and "functional RNA (fRNA)" refer to a functional RNA molecule that is not translated into a protein. The nucleic acid sequence from which a non-coding RNA is transcribed is often called an RNA gene. Non-limiting examples of non-coding RNAs include, e.g., 7SL RNA, tRNAs (including primer tRNAs), 5S rRNA, U1 snRNA, U2 snRNA, U6 snRNA, Y1 RNA, Y3 RNA, B1 RNA, VL30 RNA, 7SK RNA, Alu RNA, miRNA, snoRNA, and cytoplasmic vault ncRNA. Small coding or non-coding RNA are discussed in greater detail below.

In certain embodiments, the Cas fusion molecule is a recombinant protein molecule. In certain embodiments, the recombinant protein molecule is a Cas fusion protein which comprises (i) a sequence of a Cas protein, or a sequence of a functional fragment or derivative thereof, and (ii) at least one enrichment protein sequence, or a sequence of a functional fragment or derivative thereof, wherein the enrichment protein, or functional fragment or derivative thereof, is capable of enhancing inclusion of the gene-editing protein, or functional fragment or derivative thereof, into the retroviral particle. In certain embodiments, the Cas fusion protein comprises one or more sequences of an enrichment protein, or functional fragment or derivative thereof. In certain embodiments, when there is more than one sequence of and enrichment protein, or functional fragment or derivative thereof, each enrichment protein, or functional fragment or derivative thereof, is the same or different. In one embodiment, the enrichment protein is cyclophilin A (CypA) protein or a viral protein R (Vpr). Additional enrichment proteins are discussed in greater detail below.

In certain embodiments, the retroviral particle comprises at least one Cas fusion RNA. In certain embodiments, the retroviral particle comprises at least one Cas fusion protein. In certain embodiments, the retroviral particle comprises at least one Cas fusion RNA and at least one Cas fusion protein.

The Cas fusion molecule, or functional fragment or derivative thereof, can be associated with a retroviral particle. The Cas fusion molecule, or functional fragment or derivative thereof, is "associated" with the retroviral particle if it is incorporated in, physically or chemically linked or bound to the retroviral particle, such that a complex between the Cas fusion molecule and retroviral particle is formed. The Cas fusion molecule can be associated with the retroviral particle using any suitable method for nucleic acid-nucleic acid, nucleic acid-protein, protein-protein linking, nucleic acid-virus, or protein-virus linking known in the art. In certain embodiments, the Cas fusion molecule is associated with a capsid protein of the retroviral particle. In certain embodiments, the Cas fusion molecule is associated with a nucleocapside domain of the retroviral particle. In other embodiments, the Cas fusion molecule can be packaged into the retroviral particle.

(i) Cas Molecule

"Cas molecules", "Cas proteins" or "Cas nucleases" useful in the compositions and methods of the invention generally comprise at least one RNA recognition or binding domain that can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus.

Examples of Cas proteins useful in the compositions and methods of the invention include Cas1, Cas1B, Cas2, Cas3, Cas4, Cas5, Cas5e (CasD), Cash, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from Cas9 from a type II CRISPR/Cas system. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitire-*

*ducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Neisseria meningitidis,* or *Campylobacter jejuni.* Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Comm.* 8:14500, herein incorporated by reference in its entirety for all purposes. SaCas9 is smaller than SpCas9, and CjCas9 is smaller than both SaCas9 and SpCas9.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida, Prevotella albensis,* Lachnospiraceae bacterium MC2017 1, *Butyrivibrio proteoclasticus,* Peregrinibacteria bacterium GW2011_GWA2_33_10, Parcubacteria bacterium GW2011_GWC2_44_17, *Smithella* sp. *SCADC, Acidaminococcus* sp. BV3L6, Lachnospiraceae bacterium MA2020, *Candidatus Methanoplasma termitum, Eubacterium eligens, Moraxella bovoculi* 237, *Leptospira inadai,* Lachnospiraceae bacterium ND2006, *Porphyromonas crevioricanis* 3, *Prevotella disiens,* and *Porphyromonas macacae.* Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity.

Assays for nick-inducing or double-strand-break-inducing activity are known and generally measure the overall activity and specificity of the Cas protein on DNA substrates containing the cleavage site.

One example of a modified Cas protein is the modified SpCas9-HF1 protein, which is a high-fidelity variant of *Streptococcus pyogenes* Cas9 harboring alterations (N497A/R661A/Q695A/Q926A) designed to reduce non-specific DNA contacts. See, e.g., Kleinstiver et al. (2016) *Nature* 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) *Science* 351(6268):84-88, herein incorporated by reference in its entirety for all purposes. Other SpCas9 variants include K855A and K810A/K1003A/R1060A.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or more of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break at a guide RNA recognition sequence within a double-stranded DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null or nuclease-inactive Cas protein, or a catalytically dead Cas protein (dCas)). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839), H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes. If all of the nuclease domains are deleted or mutated in a Cas protein (e.g., both of the nuclease domains are deleted or mutated in a Cas9 protein), the resulting Cas protein (e.g., Cas9) will have a reduced ability to cleave both strands of a double-stranded DNA (e.g., a nuclease-null or nuclease-inactive Cas protein). One specific example is a D10A/H840A *S. pyogenes* Cas9 double mutant or a corresponding double mutant in a Cas9 from another species when optimally aligned with *S. pyogenes* Cas9. Another specific example is a D10A/N863A *S. pyogenes* Cas9 double mutant or a corresponding double mutant in a Cas9 from another species when optimally aligned with *S. pyogenes* Cas9.

Examples of inactivating mutations in the catalytic domains of *Staphylococcus aureus* Cas9 proteins are also known. For example, the *Staphyloccocus aureus* Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes.

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), Lachnospiraceae bacterium ND2006 (LbCpf1), and *Moraxella bovoculi* 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas fusion proteins can also be tethered to labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10): 1328-1332; Goodman et al. (2009) *Chembiochem.* 10(9): 1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The labeled nucleic acid can be tethered to the C-terminus, the N-terminus, or to an internal region within the Cas protein. Preferably, the labeled nucleic acid is tethered to the C-terminus or the N-terminus of the Cas protein. Likewise, the Cas protein can be tethered to the 5' end, the 3' end, or to an internal region within the labeled nucleic acid. That is, the labeled nucleic acid can be tethered in any orientation and polarity. Preferably, the Cas protein is tethered to the 5' end or the 3' end of the labeled nucleic acid.

In some embodiments, the nucleic acids encoding the Cas proteins of the invention, or functional fragments or derivatives thereof, can be codon optimized for efficient translation into protein in a particular cell or organism. For example, the nucleic acid encoding a Cas protein, or functional fragment or derivative thereof, can be modified to substitute codons having a higher frequency of usage in a bacterial cell, a yeast cell, a human cell, a non-human cell, a mammalian cell, a rodent cell, a mouse cell, a rat cell, or any other host (e.g. packaging) and/or target cell of interest. When a fusion RNA encoding a Cas protein, or a functional fragment or derivative thereof, is introduced into the cell, the Cas protein, or functional fragment or derivative thereof, can be transiently or conditionally expressed in the cell.

(ii) Cas Fusion RNA

In one aspect, described herein is a recombinant RNA molecule that is capable of being translated into a gene-editing protein, or functional fragment or derivative thereof, in a target cell. In certain embodiments, the recombinant RNA molecule is a Cas fusion RNA that is capable of being translated into a Cas protein, or functional fragment or derivative thereof, in a target cell, the Cas fusion RNA, which comprises (i) a sequence of a Cas mRNA, or a sequence of a functional fragment or derivative thereof, and (ii) a sequence of at least one small coding or non-coding RNA, or a sequence of a functional fragment or derivative thereof, wherein the small coding or non-coding RNA, or functional fragment or derivative thereof, is capable of enhancing inclusion of the Cas mRNA, or functional fragment or derivative thereof, into a retroviral particle.

In certain embodiments, the Cas fusion RNA molecule comprises one or more sequences of an enrichment coding or non-coding RNA, or functional fragment or derivative thereof. In certain embodiments, the Cas fusion RNA comprises at least about 1, at least about 2, at least about 3, at least about 4, at least about 5, at least about 6, at least about 7, at least about 8, at least about 9, or at least about 10 sequences of a small coding or non-coding RNA, or a sequence of a functional fragment or derivative thereof. In certain embodiments, the Cas fusion RNA comprises multiple copies of the same sequence of the small coding or non-coding RNA, or a sequence of a functional fragment or derivative thereof. In certain embodiments, the Cas fusion RNA comprises different sequences of small coding or non-coding RNA, or sequences of functional fragments or derivatives thereof.

In certain embodiments, the Cas mRNA, or functional fragment or derivative thereof, is operably linked to at least one small coding or non-coding RNA molecule, or fragment or derivative thereof. In certain embodiments, the at least one sequence of small coding or non-coding RNA, or a sequence of a fragment or derivative thereof, is operably linked to the 5' end of the sequence of Cas mRNA, or a sequence of a functional fragment or derivative thereof. In certain embodiments, the at least one sequence of small coding or non-coding RNA, or a sequence of a fragment or derivative thereof, is fused before the start codon of Cas mRNA, or a sequence of a functional fragment or derivative thereof. In certain embodiments, the at least one sequence of small coding or non-coding RNA, or a sequence of a fragment or derivative thereof, is operably linked to the 3' end of the sequence of Cas mRNA, or a sequence of a functional fragment of derivative thereof. In certain embodiments, the at least one sequence of small coding or non-coding RNA, or a sequence of a fragment or derivative thereof, is fused after the stop codon of Cas mRNA, or a sequence of a functional fragment or derivative thereof. In certain embodiments, when there is more than one sequence of small coding or non-coding RNA, or a fragment or derivative thereof, at least one sequence of small coding or non-coding RNA, or a fragment or derivative thereof, is operably linked to the 5' end of the sequence of Cas mRNA, or a sequence of a functional fragment or derivative thereof and at least one sequence of small coding or non-coding RNA, or a fragment or derivative thereof, is operably linked to the 3' end of the sequence of Cas mRNA, or a sequence of a functional fragment or derivative thereof.

The Cas mRNA and small coding or non-coding RNA are linked such that there is no interruption of the initiation, elongation, and/or termination of the translation of the Cas mRNA in the target cell. The Cas mRNA, or functional fragment or derivative thereof, and small coding or non-coding RNA, or functional fragment or derivative thereof, are linked such that there is no interruption of the packaging of the small coding or non-coding RNA, or functional fragment or derivative thereof, into the retroviral particle. In certain embodiments, the enhancement of inclusion in to the retroviral particle can occur by interaction or binding of the small coding or non-coding RNA, or functional fragment or derivative thereof, to a component of the retroviral particle. In certain embodiments, the enhancement or inclusion into the retroviral particle can occur by interaction or binding of the small coding or non-coding RNA, or functional fragment or derivative thereof, to a nucleocapsid (NC) domain of the retroviral particle. In certain embodiments, the NC domain is the NC domain of a Gag molecule.

In certain embodiments, the sequence of Cas mRNA, or a sequence of a functional fragment or derivative thereof, and sequence of non-coding RNA, or a sequence of a functional fragment or derivative thereof, are separated by a linker. In certain embodiments, when there is more than one enrichment coding or non-coding RNA, or functional fragment or derivative thereof, each enrichment coding or non-coding RNA, or functional fragment or derivative thereof, can be separated by a linker. Suitable linkers used in the Cas fusion RNA can be of any of a number of suitable lengths, such as, e.g., from 1 to 200 nucleotides or even longer. In certain embodiments, the linker is not cleavable (e.g., by a restriction enzyme). In certain embodiments, the linker is cleavable. In certain embodiments, the linker is a selectively cleavable linker. A selectively cleavable linker is a linker that is cleaved under selected conditions, such as a photo-cleavable linker, a chemically cleavable linker and an enzymatically cleavable linker (i.e., a restriction endonuclease site or a ribonucleotide/RNase digestion). The stability of a nucleic acid-based biodegradable linker molecule can be modulated by using various chemistries, for example combinations of ribonucleotides, deoxyribonucleotides, and chemically-modified nucleotides, such as 2'-O-methyl, 2'-fluoro, 2'-amino, 2'-O-amino, 2'-C-allyl, 2'-O-allyl, and other 2'-modified or base modified nucleotides. The linker molecule can also comprise nucleic acid backbone, nucleic acid sugar, or nucleic acid base modifications.

The compositions and methods take advantage of the fact that small coding or non-coding RNA can be effectively incorporated ("enriched") from the packaging cell into the retroviral particle. As an example, retroviruses are ribonucleoprotein complexes produced by cells as orchestrated by genetic information contained in virion RNA. While the most abundant nucleic acid in a retroviral particle is its genomic RNA (>50% of the RNA mass), the remainder of the RNA in the retroviral particle is host (e.g., packaging cell) encoded. See Onafuwa-Nuga et al., (2006) RNA 12:542-546. One of the first host encoded RNA packaged into a retrovirus was a molecule with 7S sedimentation properties, identified as 7SL RNA. Id. 7SL is the non-coding RNA component of signal recognition particle (SRP), which is the ribonucleoprotein complex promoting co-translational protein transport into the endoplasmic reticulum. See Water and Blobel (1982) Nature 299:691-698 and Doudna and Batey (2004) Annu. Rev. Biochem. 74:3046-3057, both herein incorporated by reference in their entirety for all purposes. In fact, 7SL RNA is the most abundant non-viral derived RNA found in lentiviruses (Eckwahl et al., (2016) mBio 7:e02025-15) and it is 7SL RNA is found in higher copy number in HIV viral particles than its own viral genomic RNA (Onafuwa-Nuga et al., (2006) *RNA* 12:542-546). Such data indicates that 7SL RNA could be selectively enriched into retroviral particles, and it is possible that the 7SL RNAs are not passively included into budding particles, but are actively packaged via interactions with Gag molecules. See Tian et al., (2007) *Nucleic Acids Res.* 35:7288-7302, which is incorporated by reference in its entirety for all purposes. In addition to 7SL RNA, several other small coding or non-coding RNA molecules are known to be enriched into retroviral particles. Examples of such small coding or non-coding RNA useful in the compositions and methods of the present invention include, but are not limited to, tRNAs (including primer tRNAs, SEQ ID NO: GCCCGGATAGCTCAGTCGGTAGAGCATCA GACTTTTAATCTGAGGGTCCAGGGTTCAAGTCCCTGTTCGGGCG), 5S rRNA, U1 snRNA, U2 snRNA, U6 snRNA, Y1 RNA, Y3 RNA, B1 RNA, VL30 RNA, 7SK RNA, Alu RNA, miRNA, snoRNA, and cytoplasmic vault ncRNA. See Linial and Miller (1990) *Curr. Top. Microbiol. Immunol* 157:125-152; Berkowitz, et al., (1996) *Curr. Top. Microbiol. Immunol* 214:177-218; Giles et al., (2004) *RNA* 10:299-307; Onafuwa-Nuga et al., (2005) *J. Virol.* 79:13528-13537; Tian et al., (2007) *Nucleic Acids Res.* 35:7288-7302, each of which herein incorporated by reference in their entirety for all purposes. Enrichment into the retroviral particles can occur by any means. For example, Primer tRNAs are selectively enriched via an interaction with retroviral reverse transcriptase. See Levin and Seidman (1979) *J. Virol.* 29:328-335; Kleiman (2002) *IUBMB Life* 53:107-114, each of which are incorporated in their entirety for all purposes. tRNA(Lys$_3$) is also selected by forming a complex with the capsid domain of the Gag molecule. See Cen et al., (2002) *J. Virol.* 76:13111-13115, incorporated in its entirety for all purposes. At least some nascent RNAs (e.g., pre-tRNAs) are packaged as well. See Eckwahl et al., (2016) *mBio* 7:e02025-15, incorporated by reference in its entirety for all purposes.

In certain embodiments, the non-coding RNA can be, but is not limited to, 7SL RNA, tRNAs (including primer tRNAs), 5S rRNA, U1 snRNA, U2 snRNA, U6 snRNA, Y1 RNA, Y3 RNA, B1 RNA, VL30 RNA, 7SK RNA, Alu RNA, miRNA, snoRNA, cytoplasmic vault ncRNA, or a functional fragment or derivative thereof that is capable of enhancing inclusion of the Cas mRNA into a retroviral particle. In certain embodiments, primer tRNAs include, but are not limited to, tRNA(Trp), tRNA(Pro), tRNA(Lys$_{1,2}$), tRNA(Lys$_3$), tRNA(iMet), tRNA(Gln), tRNA(Leu), tRNA (Ser), tRNA(Asn), tRNA(Ile), and tRNA(Arg). In certain embodiments, the primer tRNA is tRNA(Lys$_3$). In certain embodiments, the non-coding RNA is 7SL RNA.

Figure 6A:
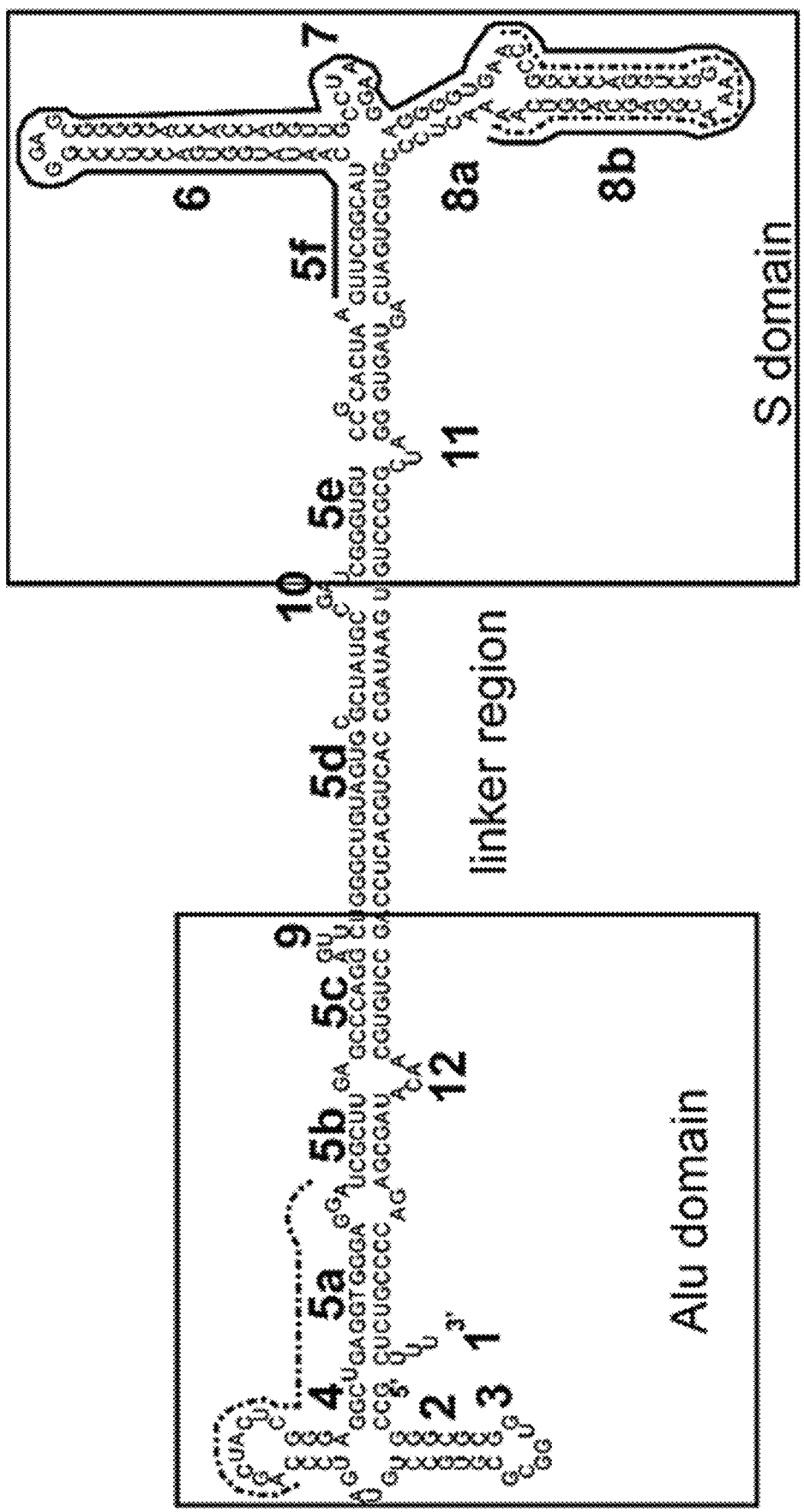
FIG. 6A shows the secondary structure of an exemplar 7SL RNA, including its Alu and S domains.
Figure 6B:
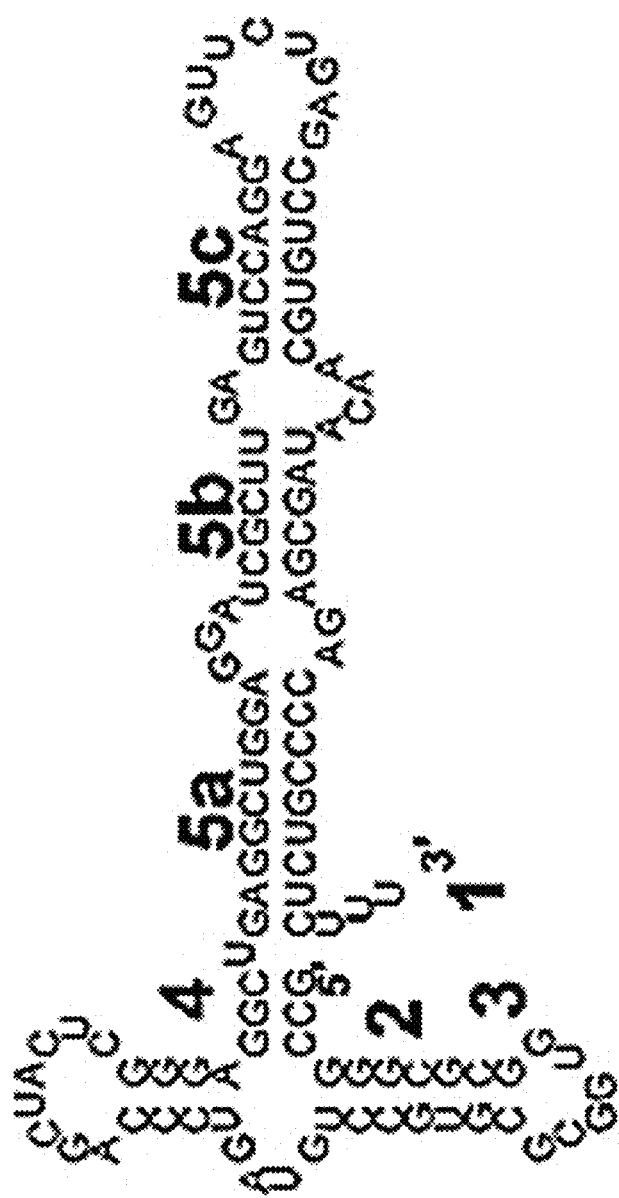
FIG. 6B shows an example of the Alu domain of a 7SL RNA.
Figure 6C:
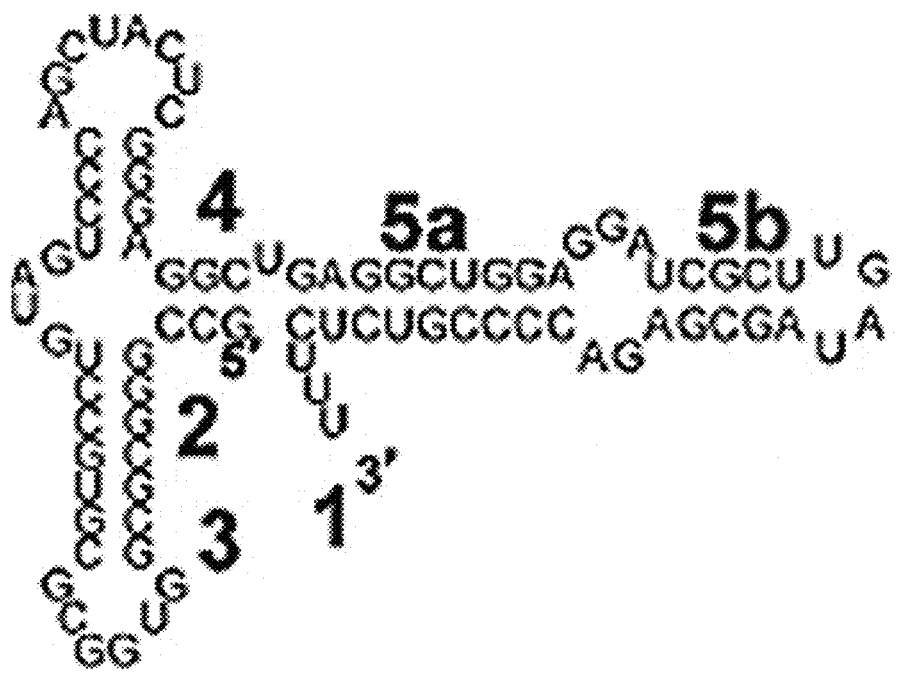
FIGS. 6C and 6D show non-limiting examples of fragments of the Alu domain of a 7SL RNA.
Figure 6D:
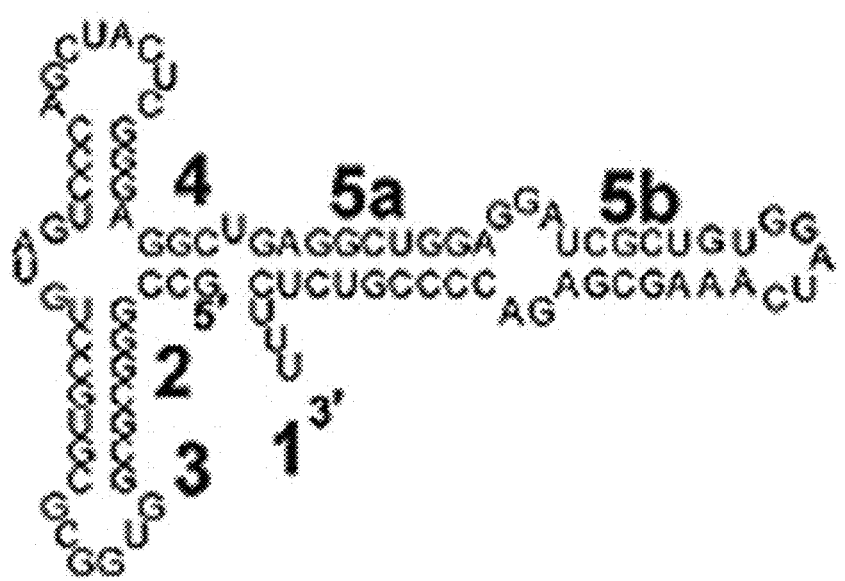
Figure 6E:
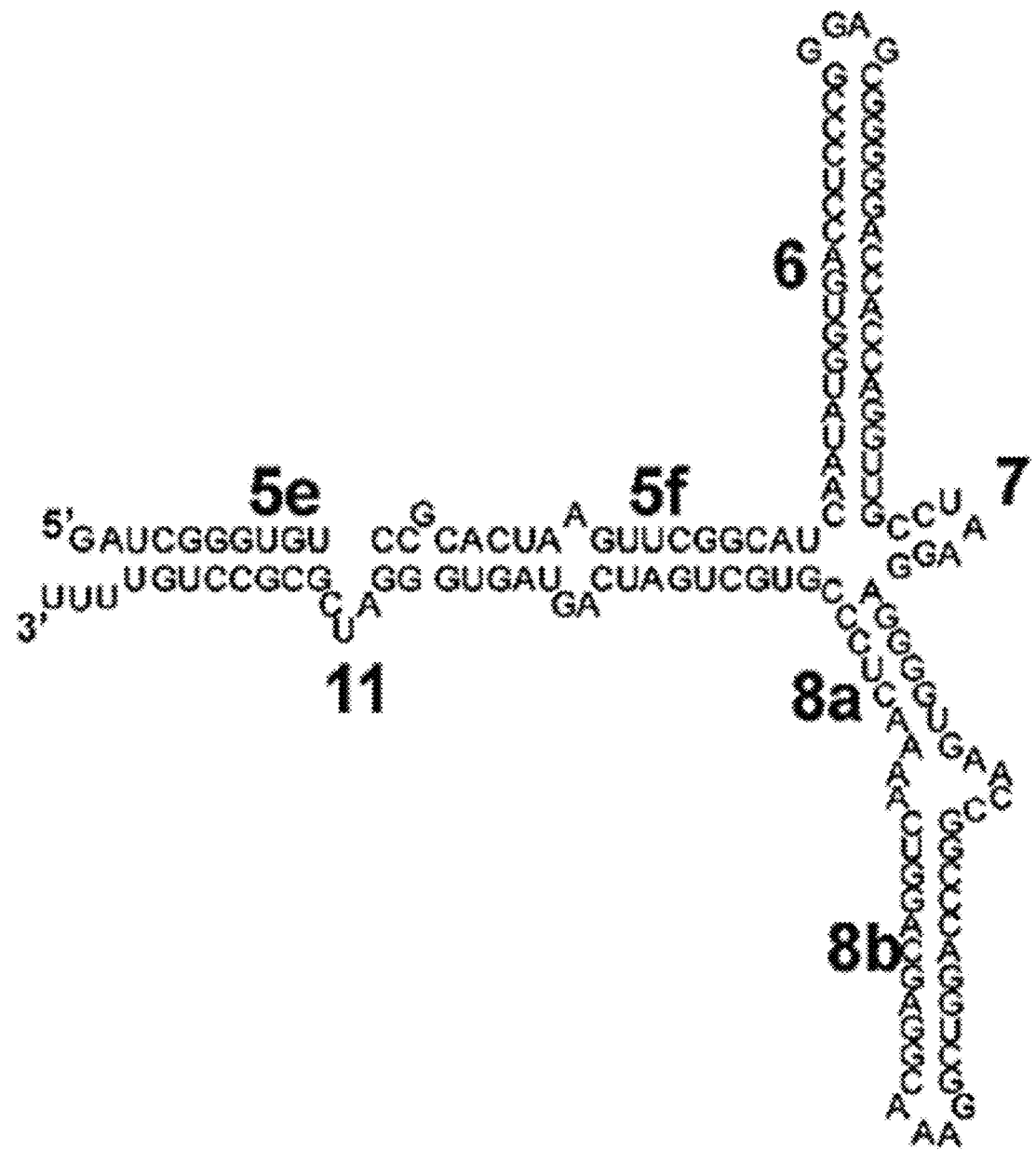
FIG. 6E shows the S domain of a 7SL RNA.
Figure 6F:
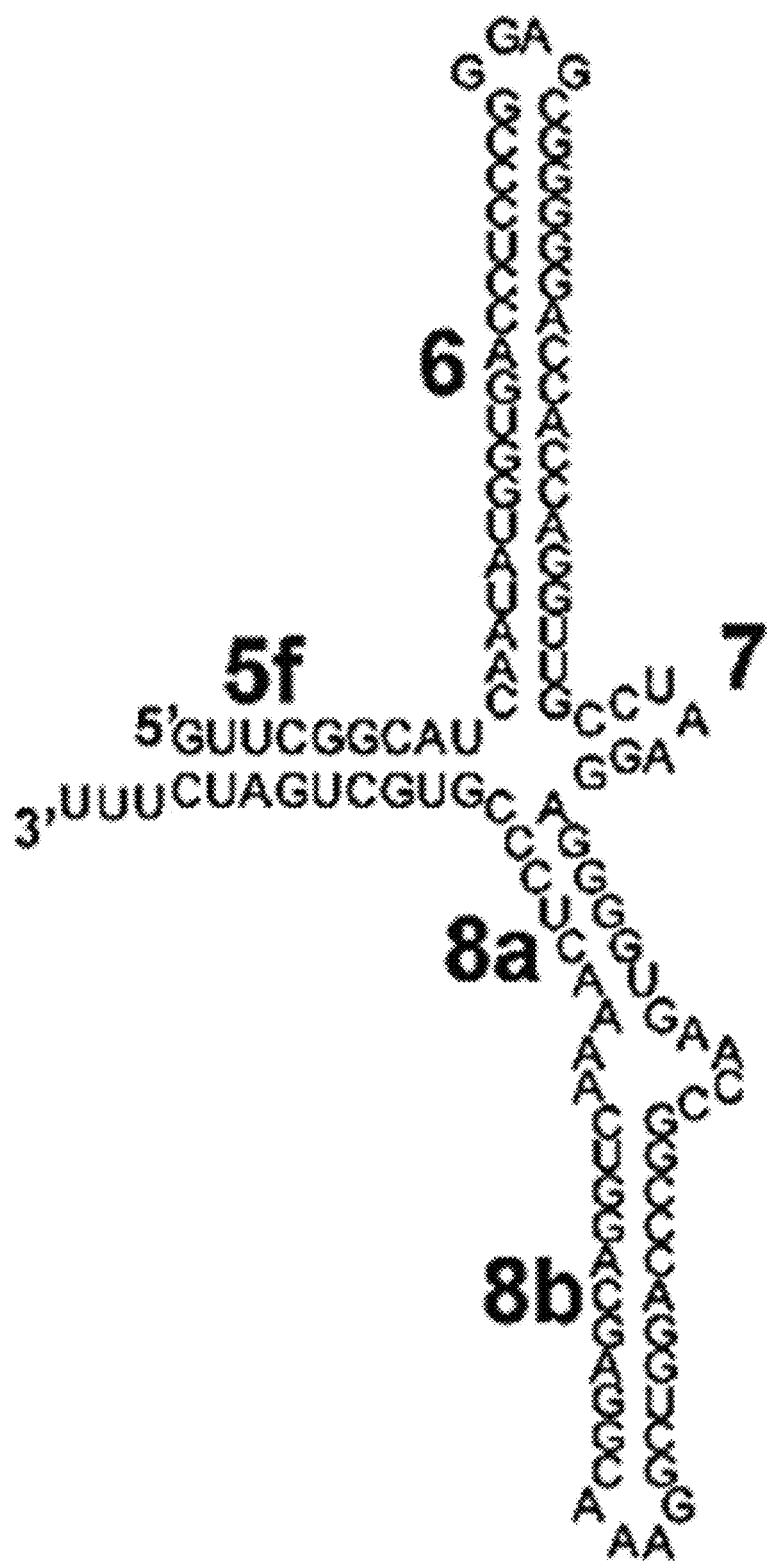
FIG. 6F shows a non-limiting example of a fragment of the S domain of a 7SL RNA.
Figures 6G, 6H, 6I:
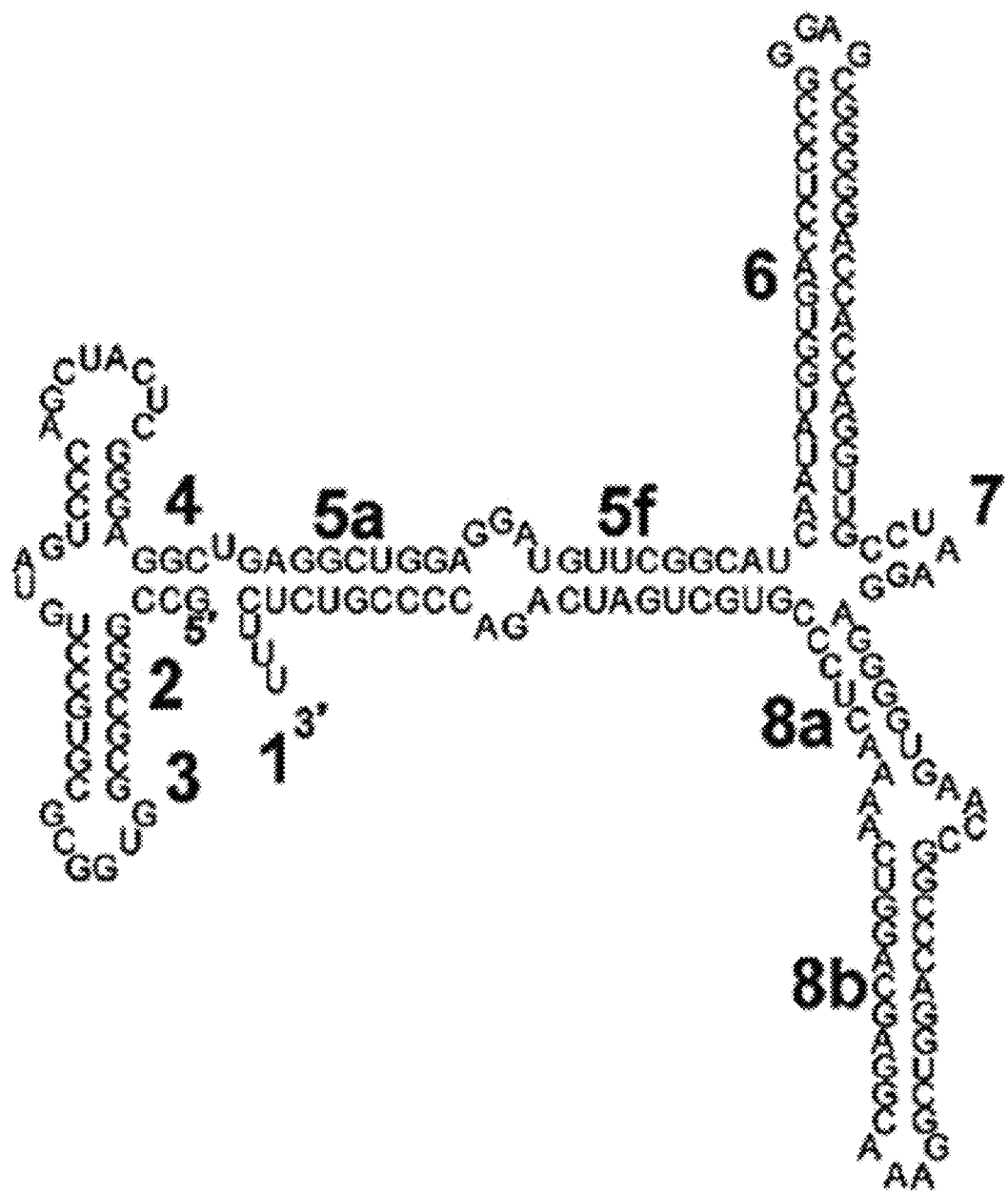
FIG. 6G shows a non-limiting example of a derivative of the S domain of a 7SL RNA.
FIGS. 6H and 6I show non-limiting examples of the 5c domain of a 7SL RNA.

In certain embodiments, the Cas fusion RNA molecule comprises (i) a sequence of Cas mRNA encoding a Cas protein, or functional fragment or derivative thereof, and (ii) at least one sequence of 7SL RNA, or a sequence of a functional fragment or derivative thereof, that is capable of enhancing inclusion of the Cas mRNA, or functional fragment or derivative thereof, into a retroviral particle. In certain embodiments, the 7SL RNA fragment or derivative comprises the 7SLrem domain (e.g., see below; SEQ ID NO: 85); the Alu domain (e.g., see below; SEQ ID NOs: 83&87 and 86&88; and FIG. 6B), or fragment or derivative thereof (e.g., FIGS. 6C and 6D); the S domain (e.g., see below; SEQ ID NO: 84; and FIG. 6E), or fragment or derivative thereof (e.g., FIGS. 6F and 6G); or a fragment or derivative of 7SL RNA or Alu domain comprising the 5c helix (See FIGS. 6A, 6B, 6H, and 6I). See e.g., Keene et al., (2010) *J. of Virology* 84:9070-9077 and Keene and Telesnitsky *J Virol.* 2012 August; 86(15): 7934-7942, both incorporated by reference in their entirety for all purposes. In certain embodiments, fragments or derivatives can encompass a 7SL RNA sequence, 7SLrem domain, Alu domain, S domain, or 5c helix with the same or similar secondary structure. In certain embodiments, exemplar fragments or derivatives of 7SL RNA sequence, 7SLrem domain, Alu domain, S domain, or 5c helix are those disclosed above and/or below or similar sequences with additional or fewer nucleotides. In certain embodiments, the additional or fewer nucleotides are those present in the 7SL RNA sequence. In certain embodiments, the additional nucleotides are not those that normally appear next in the 7SL RNA sequence. Both the Alu domain and the S domain are sufficient on their own to mediate packaging when expressed as separate truncations of 7SL. Inclusion of the 5c helix aids in packaging efficiency. See Keene (2012). In certain embodiments, the 7SL RNA, or fragment or derivative thereof, is able to interact or bind with an NC domain. In certain embodiments, the 7SL RNA, or fragment or derivative thereof, is able to interact or bind with a Gag molecule.

In certain embodiments, the Cas mRNA, or functional fragment or derivative thereof, is operably linked to at least one 7SL RNA, or fragment or derivative thereof. In certain embodiments, the at least one sequence of 7SL RNA, or the sequence of a functional fragment or derivative thereof, is operably linked to the 5' of the sequence of Cas mRNA, or a sequence of a functional fragment or derivative thereof. In certain embodiments, the at least one sequence encoding the 7SL RNA, or a sequence of fragment of derivative thereof, is fused before the start codon of the sequence encoding the Cas mRNA, or a sequence of a functional fragment or derivative thereof. In certain embodiments, the at least one sequence of 7SL RNA, or a sequence of functional fragment or derivative thereof, is operably linked to the 3' of the sequence of Cas mRNA, or a sequence of a functional fragment or derivative thereof. In certain embodiments, the at least one sequence encoding the 7SL RNA, or a sequence of fragment of derivative thereof, is fused after the stop codon of the sequence encoding the Cas mRNA or a sequence of a functional fragment or derivative thereof. In certain embodiments, when there is more than one sequence of 7SL RNA, or a fragment or derivative thereof, at least one sequence of 7SL RNA, or a fragment or derivative thereof, is operably linked to the 5' end of the sequence of Cas mRNA, or a sequence of a functional fragment or derivative thereof and at least one sequence of 7SL RNA, or a fragment or derivative thereof, is operably linked to the 3' end of the sequence of Cas mRNA, or a sequence of a functional fragment or derivative thereof.

In certain embodiments, the Cas fusion RNA comprises a linker between the Cas mRNA, or functional fragment or derivative thereof, and the 7SL RNA, or functional fragment or derivative thereof. The Cas mRNA, or functional fragment or derivative thereof, and 7SL RNA, or functional fragment or derivative thereof, are linked such that there is no interruption of the translation of the Cas mRNA into Cas protein, or functional fragment or derivative thereof, in the target cell. In certain embodiments, when there is more than one 7SL RNA, or functional fragment or derivative thereof, each 7SL RNA, or functional fragment or derivative thereof, can be separated by a linker. Suitable linkers are disclosed above.

In certain embodiments, the 7SL RNA is encoded by the nucleic acid sequence of SEQ ID NO: 1, SEQ ID NO: 81, or SEQ ID NO:82. In certain embodiments, the 7SL RNA fragment comprises the 7SLrem domain; or the Alu domain, or functional fragment or derivative thereof; the S domain, or functional fragment or derivative thereof or a fragment or derivative of 7SL RNA or Alu domain comprising the 5c helix. See e.g., FIGS. 6A-6I; SEQ ID NOs: 83&87 and 84-85; and Keene et al., (2010) 1 of Virology 84:9070-9077 and Keene and Telesnitsky *J Virol.* 2012 August; 86(15): 7934-7942, both incorporated by reference in their entirety for all purposes. In certain embodiments, the 7SL RNA fragment is encoded by one of the following nucleic acid sequences:

```
                                              (SEQ ID NO: 1)
GCCGGGCGCGGTGGCGCGTGCCTGTAGTCCCAGCTACTCGGGAGGCTGAGG

CTGGAGGATCGCTTGAGTCCAGGAGTTCTGGGCTGTAGTGCGCTATGCCGA

TCGGGTGTCCGCACTAAGTTCGGCATCAATATGGTGACCTCCCGGGAGCGG

GGGACCACCAGGTTGCCTAAGGAGGGGTGAACCGGCCCAGGTCGGAAACGG

AGCAGGTCAAAACTCCCGTGCTGATCAGTAGTGGGATCGCGCCTGTGAATA

GCCACTGCACTCCAGCCTGGGCAACATAGCGAGACCCCGTCTCT
```

(underlined is the sequence of the 7SLrem domain the sequences corresponding to the Alu domain are shown in bold; the sequence corresponding to the S domain is italicized).

In certain embodiments, the Cas mRNA, or functional fragment or derivative thereof, is operably linked to at least one tRNA(Lys$_3$), or fragment or derivative thereof. In certain embodiments, the at least one sequence of tRNA(Lys$_3$), or the sequence of a functional fragment or derivative thereof, is operably linked to the 5' of the sequence of Cas mRNA, or a sequence of a functional fragment or derivative thereof. In certain embodiments, the at least one sequence encoding the tRNA(Lys$_3$), or a sequence of fragment of derivative thereof, is fused before the start codon of the sequence encoding the Cas mRNA, or a sequence of a functional fragment or derivative thereof. In certain embodiments, the at least one sequence of tRNA(Lys$_3$), or a sequence of functional fragment or derivative thereof, is operably linked to the 3' of the sequence of Cas mRNA, or a sequence of a functional fragment or derivative thereof. In certain embodiments, the at least one sequence encoding the tRNA(Lys$_3$), or a sequence of fragment of derivative thereof, is fused after the stop codon of the sequence encoding the Cas mRNA or a sequence of a functional fragment or derivative thereof. In certain embodiments, when there is more than one sequence of tRNA(Lys$_3$), or a fragment or derivative thereof, at least one sequence of tRNA(Lys$_3$), or a fragment or derivative thereof, is operably linked to the 5' end of the sequence of Cas mRNA, or a sequence of a functional fragment or derivative thereof and at least one sequence of tRNA(Lys$_3$), or a fragment or derivative thereof, is operably linked to the 3' end of the sequence of Cas mRNA, or a sequence of a functional fragment or derivative thereof.

In certain embodiments, the Cas fusion RNA comprises a linker between the Cas mRNA, or functional fragment or derivative thereof, and the tRNA(Lys$_3$), or functional fragment or derivative thereof. The Cas mRNA, or functional fragment or derivative thereof, and tRNA(Lys$_3$), or functional fragment or derivative thereof, are linked such that there is no interruption of the translation of the Cas mRNA into Cas protein, or functional fragment or derivative thereof, in the target cell. In certain embodiments, when there is more than one tRNA(Lys$_3$), or functional fragment or derivative thereof, each tRNA(Lys$_3$), or functional fragment or derivative thereof, can be separated by a linker. Suitable linkers are disclosed above.

In certain embodiments, the tRNA(Lys$_3$) is encoded by the nucleic acid sequence of SEQ ID NO: 80.

In certain embodiments, the Cas molecule is a Cas9 molecule, or a functional fragment or derivative thereof. In certain embodiments, the Cas9 can be wild type Cas9, a Cas9 nickase, a dead Cas9 (dCas9) a split Cas9, and a Cas9 fusion protein. In certain embodiments, the Cas9 is a *Streptococcus pyogenes* or *Staphylococcus aureus* Cas9. In certain embodiments, the sequence of the Cas9 mRNA is codon optimized for expression in a eukaryotic cell. In certain embodiments, the Cas9 mRNA molecule is encoded by the nucleic acid sequence of SEQ ID NO: 2 (mouse codon optimized).

In certain embodiments, the Cas fusion RNA molecule comprises (i) a sequence of Cas9 mRNA encoding a Cas9 protein, or a sequence of a functional fragment or derivative thereof, and (ii) at least one sequence of 7SL RNA, or a sequence of a functional fragment or derivative thereof, that is capable of enhancing inclusion of the Cas9 mRNA, or functional fragment or derivative thereof, into a retroviral particle. In certain embodiments, the Cas9 mRNA, or functional fragment or derivative thereof, is operably linked to the at least one 7SL RNA molecule, or fragment or derivative thereof. In certain embodiments, the at least one sequence of 7SL RNA, or sequence of a functional fragment or derivative thereof, is operably linked to the 5' of the sequence of Cas9 mRNA, or a sequence of a functional fragment or derivative thereof. In certain embodiments, the at least one sequence encoding the 7SL RNA, or a sequence of fragment of derivative thereof, is fused before the start codon of the sequence encoding the Cas9 mRNA or a sequence of a functional fragment or derivative thereof. In certain embodiments, the at least one sequence of 7SL RNA, or a sequence of a functional fragment or derivative thereof, is operably linked to the 3' of the sequence of Cas9 mRNA, or a sequence of a functional fragment or derivative thereof. In certain embodiments, the at least one sequence encoding the 7SL RNA, or a sequence of a fragment of derivative thereof, is fused after the stop codon of the sequence encoding the Cas9 mRNA, or a sequence of a functional fragment or derivative thereof. In certain embodiments, when there is more than one sequence of 7SL RNA, or a fragment or derivative thereof, at least one sequence of 7SL RNA, or a fragment or derivative thereof, is operably linked to the 5' end and at least one sequence 7SL RNA, or a fragment or derivative thereof, 3' end of the sequence of Cas9 mRNA, or a sequence of a functional fragment or derivative thereof In certain embodiments, the Cas9 fusion RNA comprises a linker between the Cas9 mRNA, or functional fragment or derivative thereof, and the 7SL RNA, or functional fragment or derivative thereof. The Cas9 mRNA and 7SL RNA are linked such that there is no interruption of the initiation, elongation, and/or termination of the translation of the Cas9 mRNA in the target cell. In certain embodiments, when there is more than one 7SL RNA, or functional fragment or derivative thereof, each 7SL RNA, or functional fragment or derivative thereof, can be separated by a linker.

In certain embodiments, the Cas9 mRNA, or functional fragment or derivative thereof, is operably linked to at least one tRNA(Lys$_3$), or fragment or derivative thereof. In certain embodiments, the at least one sequence of tRNA(Lys$_3$), or the sequence of a functional fragment or derivative thereof, is operably linked to the 5' of the sequence of Cas9 mRNA, or a sequence of a functional fragment or derivative thereof. In certain embodiments, the at least one sequence encoding the tRNA(Lys$_3$), or a sequence of fragment of derivative thereof, is fused before the start codon of the sequence encoding the Cas9 mRNA, or a sequence of a functional fragment or derivative thereof. In certain embodiments, the at least one sequence of tRNA(Lys$_3$), or a sequence of functional fragment or derivative thereof, is operably linked to the 3' of the sequence of Cas9 mRNA, or a sequence of a functional fragment or derivative thereof. In certain embodiments, the at least one sequence encoding the tRNA(Lys$_3$), or a sequence of fragment of derivative thereof, is fused after the stop codon of the sequence encoding the Cas9 mRNA or a sequence of a functional fragment or derivative thereof. In certain embodiments, when there is more than one sequence of tRNA(Lys$_3$), or a fragment or derivative thereof, at least one sequence of tRNA(Lys$_3$), or a fragment or derivative thereof, is operably linked to the 5' end of the sequence of Cas9 mRNA, or a sequence of a functional fragment or derivative thereof and at least one sequence of tRNA(Lys$_3$), or a fragment or derivative thereof, is operably linked to the 3' end of the sequence of Cas9 mRNA, or a sequence of a functional fragment or derivative thereof.

In certain embodiments, the Cas9 fusion RNA comprises a linker between the Cas9 mRNA, or functional fragment or derivative thereof, and the tRNA(Lys$_3$), or functional fragment or derivative thereof. The Cas9 mRNA, or functional fragment or derivative thereof, and tRNA(Lys$_3$), or functional fragment or derivative thereof, are linked such that there is no interruption of the translation of the Cas9 mRNA into Cas9 protein, or functional fragment or derivative thereof, in the target cell. In certain embodiments, when there is more than one tRNA(Lys$_3$), or functional fragment or derivative thereof, each tRNA(Lys$_3$), or functional fragment or derivative thereof, can be separated by a linker. Suitable linkers are disclosed above.

In certain embodiments, the nucleic acid sequence encoding Cas9 fusion RNA is SEQ ID NO: 3 (i.e., the nucleic acid sequence encoding 7SL attached to the 5' end of the Cas9 mRNA before the start codon). In certain embodiments, the nucleic acid sequence encoding Cas9 fusion RNA is SEQ ID NO: 4 (i.e., the nucleic acid sequence encoding 7SL attached to the 3' end of the Cas9 mRNA after the stop codon).

The Cas fusion RNA can be produced using routine molecular biology techniques, such as those described in He et al., (2014) *Gene Therapy,* 21:759-766. Optionally, the Cas mRNA can be codon optimized for efficient translation into the Cas protein, or functional fragment or derivative thereof, in a particular cell or organism. For example, the nucleic acid sequence encoding the Cas protein, or a functional fragment or derivative thereof, can be modified to substitute codons having a higher frequency of usage in a bacterial cell, a yeast cell, a human cell, a non-human cell, a mammalian cell, a rodent cell, a mouse cell, a rat cell, or any other host (e.g., packaging) and/or target cell of interest, as compared to the naturally occurring polynucleotide sequence.

In certain embodiments, the nucleic acid molecule encoding the Cas fusion RNA further comprises a regulatory element, including for example, a promoter (e.g., including an enhancer), or a transcriptional repressor-binding element. Exemplary expression control sequences are known in the art and described in, for example, Goeddel, (1990) Gene Expression Technology: Methods in Enzymology, Vol. 185, Academic Press, San Diego, Calif., incorporated by reference in its entirety for all purposes.

(iii) Cas Fusion Protein

In one aspect, described herein is a recombinant Cas fusion protein that is capable of being delivered directly to a target cell via the recombinant retroviral particle, the Cas fusion protein comprising (i) a sequence of a Cas protein, or a sequence of a functional fragment or derivative thereof, and (ii) at least one sequence of an enrichment protein, or a sequence of a functional fragment or derivative thereof, that is capable of effectively incorporating (i.e., enhancing inclusion of) the Cas protein, or functional fragment or derivative thereof, into a retroviral particle. In certain embodiments, the Cas protein, or functional fragment or derivative thereof, is operably linked to the enrichment protein, or fragment or derivative thereof. In certain embodiments, the Cas fusion protein comprises one or more sequences of an enrichment protein, or functional fragment or derivative thereof. In certain embodiments, when there is more than one sequence of enrichment protein, or functional fragment or derivative thereof, each enrichment protein, or functional fragment or derivative thereof, is the same or different.

In certain embodiments, the at least one sequence of the enrichment protein, or a sequence of a fragment or derivative thereof, is operably linked to the N-terminus of the sequence of Cas protein, or a sequence of a functional fragment or derivative thereof. In certain embodiments, the at least one sequence of the enrichment protein, or a sequence of a fragment or derivative thereof, is operably linked to the C-terminus of the sequence of Cas protein, or a sequence of a functional fragment or derivative thereof. In certain embodiments, when there is more than one sequence of enrichment protein, or a fragment or derivative thereof, at least one sequence of enrichment protein, or a fragment or derivative thereof, is operably linked to the N-terminus of the sequence of Cas protein, or a sequence of a functional fragment or derivative thereof and at least one sequence of enrichment protein, or a fragment or derivative thereof, is operably linked to the C-terminus of the sequence of Cas protein, or a sequence of a functional fragment or derivative thereof.

In certain embodiments, the Cas protein, or functional fragment or derivative thereof, and the at least one enrichment protein are separated by a linker. In certain embodiments, when there is more than one enrichment protein, or functional fragment or derivative thereof, each enrichment protein, or functional fragment or derivative thereof, can be separated by a linker. In certain embodiments, the Cas fusion protein is associated with a capsid protein of the retroviral particle. In certain embodiments, the Cas fusion protein is associated with a nucleocapside domain of the retroviral particle. In other embodiments, the Cas fusion protein can be packaged into the retroviral particle.

The Cas fusion protein can be provided as a fusion protein comprising a Cas protein, or functional fragment or derivative thereof, and a Virol Protein R (Vpr), or a functional fragment or derivative thereof, which is capable of enhancing inclusion of the Cas protein, or functional fragment or derivative thereof, into a retroviral particle. Vpr is a 96 amino acid 14-kDa protein within the HIV genome that plays a significant role in regulating nuclear import of the HIV-1 pre-integration complex. See Bukrinsky and Adzhubei (1999) *Rev. Med. Virol.* 9:39-49, incorporated by reference in its entirety for all purposes. Vpr is also required for retrovirus replication in non-dividing cells such as macrophages.

The Cas fusion protein can be provided as a fusion protein comprising a Cas protein, or functional fragment or derivative thereof, and a Virol Protein X (Vpx), or a functional fragment or derivative thereof that is capable of enhancing inclusion of the Cas protein, or functional fragment or derivative thereof, into a retroviral particle. Vpx shares a close sequence similarity with Vpr. See Wu et al., (1994) *J. Virol.* 68:6161-6169, incorporated by reference in its entirety for all purposes.

Vpr and Vpx are packaged into retroviral particles in quantities comparable with retroviral Gag proteins. See Bukrinsky and Adzhubei, supra. The packaging is likely to occur via interaction with $p6^{Gag}$ region of the $Pr55^{Gag}$ precursor protein. See Lu et al., (1993) *J. Virol.* 67:6542-6550; Paxton et al., (1993) *J. Virol.* 67:7229-7237; Wu et al., (1994) *J. Virol.* 68:6161-6169, each of which incorporated by reference in their entirety for all purposes.

In certain embodiments, the Cas fusion protein molecule comprises (i) a sequence of Cas protein, or a sequence of a functional fragment or derivative thereof, and (ii) at least one sequence of Vpr, or a sequence of a functional fragment or derivative thereof, that is capable of enhancing inclusion of the Cas fusion protein, or functional fragment or derivative thereof, into a retroviral particle. In certain embodiments, the Cas protein, or functional fragment or derivative thereof, is operably linked to at least one Vpr, or fragment or derivative thereof. In certain embodiments, the at least one sequence of Vpr, or a sequence of a functional fragment or derivative thereof, is operably linked to the N-terminus of the sequence of the Cas protein, or a sequence of a functional fragment or derivative thereof. In certain embodiments, the at least one sequence of Vpr, or a sequence of functional fragment or derivative thereof, is operably linked to the C-terminus of the sequence of the Cas protein, or a sequence of a functional fragment or derivative thereof. In certain embodiments, when there is more than one sequence of Vpr, or a fragment or derivative thereof, at least one sequence of Vpr, or a fragment or derivative thereof, is operably linked to the N-terminus of the sequence of Cas protein, or a sequence of a functional fragment or derivative thereof and at least one sequence of Vpr, or a fragment or derivative thereof, is operably linked to the C-terminus of the sequence of Cas protein, or a sequence of a functional fragment or derivative thereof. In certain embodiments, the Cas fusion protein comprises a linker between the Cas protein, or functional fragment or derivative thereof, and the Vpr, or functional fragment or derivative thereof. In certain embodiments, when there is more than one Vpr, or functional fragment or derivative thereof, each Vpr, or functional fragment or derivative thereof, can be separated by a linker. The Cas protein, or functional fragment or derivative thereof, and Vpr, or functional fragment or derivative thereof, are linked such that there is no decrease in activity of the Cas protein, or functional fragment or derivative thereof, in the target cell. In certain embodiments, the Vpr, or fragment or derivative thereof, is able to interact or bind with an NC domain. In certain embodiments, the Vpr, or fragment or derivative thereof, is able to interact or bind with a Gag molecule.

In certain embodiments, the Vpr is encoded by the nucleic acid sequence of SEQ ID NO: 5. In certain embodiment, the amino acid sequence of Vpr is SEQ ID NO: 6.

In certain embodiments, the Cas fusion protein molecule comprises (i) a sequence of Cas protein, or a sequence of a functional fragment or derivative thereof, and (ii) at least one sequence of Vpx, or a sequence of a functional fragment or derivative thereof that is capable of enhancing inclusion of the Cas fusion protein, or functional fragment or derivative thereof, into a retroviral particle. In certain embodiments, the Cas protein, or functional fragment or derivative thereof, is operably linked to at least one Vpx, or fragment or derivative thereof. In certain embodiments, the at least one sequence of Vpx, or a sequence of a functional fragment or derivative thereof, is operably linked to the N-terminus of the sequence of the Cas protein, or a sequence of a functional fragment or derivative thereof. In certain embodiments, the at least one sequence of Vpx, or a sequence of a functional fragment or derivative thereof, is operably linked to the C-terminus of the sequence of the Cas protein, or a sequence of a functional fragment or derivative thereof. In certain embodiments, when there is more than one sequence of Vpx, or a fragment or derivative thereof, at least one sequence of Vpx, or a fragment or derivative thereof, is operably linked to the N-terminus of the sequence of Cas protein, or a sequence of a functional fragment or derivative thereof and at least one sequence of Vpx, or a fragment or derivative thereof, is operably linked to the C-terminus of the sequence of Cas protein, or a sequence of a functional fragment or derivative thereof. In certain embodiments, the Cas fusion protein comprises a linker between the Cas protein, or functional fragment or derivative thereof, and the Vpx, or functional fragment or derivative thereof. In certain embodiments, when there is more than one Vpx, or functional fragment or derivative thereof, each Vpx, or functional fragment or derivative thereof, can be separated by a linker. The Cas protein, or functional fragment or derivative thereof, and Vpx, or functional fragment or derivative thereof, are linked such that there is no decrease in activity of the Cas protein, or functional fragment or derivative thereof, in the target cell. In certain embodiments, the Vpx, or fragment or derivative thereof, is able to interact or bind with an NC domain. In certain embodiments, the Vpx, or fragment or derivative thereof, is able to interact or bind with a Gag molecule.

In certain embodiments, the Vpx is encoded by the nucleic acid sequence of SEQ ID NO: 7. In certain embodiment, the amino acid sequence of Vpx is SEQ ID NO: 8.

The Cas fusion protein can be provided as a fusion protein comprising a Cas protein, or functional fragment or derivative thereof, and a Cyclophilin A (CypA), or a functional fragment or derivative thereof that is capable of enhancing inclusion of the Cas protein, or functional fragment or derivative thereof, into a retroviral particle. CypA is an 18 kDa, 165-amino acid long cytosolic protein that regulates many biological processes, including intracellular signaling, transcription, inflammation, and apoptosis. CypA can also interact with several HIV proteins, and has been shown to interact with lentiviral Gag proteins and become highly enriched in lentiviral particles. See e.g., Luban et al., (1993) *Cell* 73:1067-78, incorporated by reference in its entirety for all purposes.

In certain embodiments, the Cas fusion protein molecule comprises (i) a sequence of Cas protein, or a sequence of a functional fragment or derivative thereof, and (ii) at least one sequence of CypA or a sequence of a functional fragment or derivative thereof that is capable of enhancing inclusion of the Cas fusion protein, or functional fragment or derivative thereof, into a retroviral particle. In certain embodiments, the Cas protein, or functional fragment or derivative thereof, is operably linked to at least one CypA, or fragment or derivative thereof. In certain embodiments, the at least one sequence of CypA, or a sequence of a functional fragment or derivative thereof, is operably linked to the N-terminus of the sequence of the Cas protein, or a sequence of a functional fragment or derivative thereof. In certain embodiments, the at least one sequence of CypA, or a sequence of a functional fragment or derivative thereof, is operably linked to the C-terminus of the sequence of the Cas protein, or a sequence of a functional fragment or derivative thereof. In certain embodiments, when there is more than one sequence of CypA, or a fragment or derivative thereof, at least one sequence of CypA, or a fragment or derivative thereof, is operably linked to the N-terminus of the sequence of Cas protein, or a sequence of a functional fragment or derivative thereof and at least one sequence of CypA, or a fragment or derivative thereof, is operably linked to the C-terminus of the sequence of Cas protein, or a sequence of a functional fragment or derivative thereof. In certain embodiments, the Cas fusion protein comprises a linker between the Cas protein, or functional fragment or derivative thereof, and the CypA, or functional fragment or derivative thereof. In certain embodiments, when there is more than one CypA, or functional fragment or derivative thereof, each CypA, or functional fragment or derivative thereof, can be separated by a linker. The Cas protein, or functional fragment or derivative thereof, and CypA, or functional fragment or derivative thereof, are linked such that there is no decrease in activity of the Cas protein, or functional fragment or derivative thereof, in the target cell. In certain embodiments, the CypA, or fragment or derivative thereof, is able to interact or bind with an NC domain. In certain embodiments, the CypA, or fragment or derivative thereof, is able to interact or bind with a Gag molecule.

In certain embodiments, the CypA is encoded by the nucleic acid sequence of SEQ ID NO: 9. In certain embodiment, the amino acid sequence of CypA is SEQ ID NO: 10.

In certain embodiments, the Cas protein is Cas9, or functional fragment or derivative thereof. In certain embodiments, the Cas9 is selected from the group consisting of wild type Cas9, a Cas9 nickase, a dead Cas9 (dCas9), a split Cas9, an inducible Cas9, and a Cas9 fusion protein. In certain embodiments, the Cas9 is a *Streptococcus pyogenes* or *Staphylococcus aureus* Cas9. In certain embodiments, the sequence of the Cas9 mRNA is codon optimized for expression in a eukaryotic cell. In certain embodiments, the Cas9 protein is encoded by the nucleic acid sequence of SEQ ID NO: 2. In certain embodiments, the Cas9 protein is encoded by the nucleic acid sequence of SEQ ID NO: 11.

In certain embodiments, the Cas fusion protein molecule comprises (i) a sequence of Cas9 protein, or a sequence of a functional fragment or derivative thereof, and (ii) at least one sequence of Vpr, or a sequence of a functional fragment or derivative thereof, that is capable of enhancing inclusion of the Cas9 fusion protein, or functional fragment or derivative thereof, into a retroviral particle. In certain embodiments, the Cas9 protein, or functional fragment or derivative thereof, is operably linked to at least one Vpr, or fragment or derivative thereof. In certain embodiments, the at least one sequence of Vpr, or a sequence of a functional fragment or derivative thereof, is operably linked to the N-terminus of the sequence of the Cas9 protein, or a sequence of a functional fragment or derivative thereof. In certain embodiments, the at least one sequence of Vpr, or a sequence of a functional fragment or derivative thereof, is operably linked to the C-terminus of the sequence of the Cas9 protein, or a sequence of a functional fragment or derivative thereof. In certain embodiments, when there is more than one sequence of Vpr, or a fragment or derivative thereof, at least one sequence of Vpr, or a fragment or derivative thereof, is operably linked to the N-terminus of the sequence of Cas9 protein, or a sequence of a functional fragment or derivative thereof and at least one sequence of Vpr, or a fragment or derivative thereof, is operably linked to the C-terminus of the sequence of Cas9 protein, or a sequence of a functional fragment or derivative thereof. In certain embodiments, the Cas9 fusion protein comprises a linker between the Cas9 protein, or functional fragment or derivative thereof, and the Vpr, or functional fragment or derivative thereof. In certain embodiments, when there is more than one Vpr, or functional fragment or derivative thereof, each Vpr, or functional fragment or derivative thereof, can be separated by a linker. The Cas9 protein, or functional fragment or derivative thereof, and Vpr, or functional fragment or derivative thereof, are linked such that there is no decrease in activity of the Cas9 protein, or functional fragment or derivative thereof, in the target cell. In certain embodiments, the Vpr, or fragment or derivative thereof, is able to interact or bind with an NC domain. In certain embodiments, the Vpr, or fragment or derivative thereof, is able to interact or bind with a Gag molecule.

In certain embodiments, the Cas fusion protein comprises (i) a sequence of Cas9 protein, or a sequence of a functional fragment or derivative thereof, and (ii) at least one sequence of Vpx, or a sequence of a functional fragment or derivative thereof that is capable of enhancing inclusion of the Cas9 fusion protein, or functional fragment or derivative thereof, into a retroviral particle. In certain embodiments, the Cas9 protein, or functional fragment or derivative thereof, is operably linked to at least one Vpx, or fragment or derivative thereof. In certain embodiments, the at least one sequence of Vpx, or a sequence of a functional fragment or derivative thereof, is operably linked to the N-terminus of the sequence of the Cas9 protein, or a sequence of a functional fragment or derivative thereof. In certain embodiments, the at least one sequence of Vpx, or a sequence of a functional fragment or derivative thereof, is operably linked to the C-terminus of the sequence of the Cas9 protein, or a sequence of a functional fragment or derivative thereof. In certain embodiments, when there is more than one sequence of Vpx, or a fragment or derivative thereof, at least one sequence of Vpx, or a fragment or derivative thereof, is operably linked to the N-terminus of the sequence of Cas9 protein, or a sequence of a functional fragment or derivative thereof and at least one sequence of Vpx, or a fragment or derivative thereof, is operably linked to the C-terminus of the sequence of Cas9 protein, or a sequence of a functional fragment or derivative thereof. In certain embodiments, the Cas9 fusion protein comprises a linker between the Cas9 protein, or functional fragment or derivative thereof, and the Vpx, or functional fragment or derivative thereof. In certain embodiments, when there is more than one Vpx, or functional fragment or derivative thereof, each Vpx, or functional fragment or derivative thereof, can be separated by a linker. The Cas9 protein, or functional fragment or derivative thereof, and Vpx, or functional fragment or derivative thereof, are linked such that there is no decrease in activity of the Cas9 protein in the target cell. In certain embodiments, the Vpx, or fragment or derivative thereof, is able to interact or bind with an NC domain. In certain embodiments, the Vpx, or fragment or derivative thereof, is able to interact or bind with a Gag molecule.

In certain embodiments, the Cas fusion protein molecule comprises (i) a sequence of Cas9 protein, or a sequence of a functional fragment or derivative thereof, and (ii) at least one sequence of CypA, or a sequence of a functional fragment or derivative thereof, that is capable of enhancing inclusion of the Cas9 fusion protein into a retroviral particle. In certain embodiments, the Cas9 protein, or functional fragment or derivative thereof, is operably linked to at least one CypA, or fragment or derivative thereof. In certain embodiments, the at least one sequence of CypA, or a sequence of a functional fragment or derivative thereof, is operably linked to the N-terminus of the sequence of the Cas9 protein, or a sequence of a functional fragment or derivative thereof. In certain embodiments, the at least one sequence of CypA, or a sequence of a functional fragment or derivative thereof, is operably linked to the C-terminus of the sequence of the Cas9 protein, or a sequence of a functional fragment or derivative thereof. In certain embodiments, when there is more than one sequence of CypA, or a fragment or derivative thereof, at least one sequence of CypA, or a fragment or derivative thereof, is operably linked to the N-terminus of the sequence of Cas9 protein, or a sequence of a functional fragment or derivative thereof and at least one sequence of CypA, or a fragment or derivative thereof, is operably linked to the C-terminus of the sequence of Cas9 protein, or a sequence of a functional fragment or derivative thereof. In certain embodiments, the Cas9 fusion protein comprises a linker between the Cas9 protein, or functional fragment or derivative thereof, and the CypA, or functional fragment or derivative thereof. In certain embodiments, when there is more than one CypA, or functional fragment or derivative thereof, each CypA, or functional fragment or derivative thereof, can be separated by a linker. The Cas9 protein, or functional fragment or derivative thereof, and CypA, or functional fragment or derivative thereof, are linked such that there is no decrease in activity of the Cas9 protein, or functional fragment or derivative thereof, in the target cell. In certain embodiments, the CypA, or fragment or derivative thereof, is able to interact or bind with an NC domain. In certain embodiments, the CypA, or fragment or derivative thereof, is able to interact or bind with a Gag molecule.

In certain embodiments, the nucleic acid sequence encoding Cas9 fusion protein can be SEQ ID NOs: 12, 14, 16, 18, 20, or 22. In certain embodiments, the amino acid sequence encoding Cas9 fusion protein can be SEQ ID NOs: 13, 15, 17, 19, 21, or 23.

In certain embodiments, the sequence of Cas protein, or a sequence of a functional fragment or derivative thereof, and the sequence of the enrichment protein (e.g., CypA, Vpr and/or Vpx), or a sequence of a fragment or derivative thereof, are separated by a linker.

Suitable peptide linkers used in the Cas fusion proteins can be of any of a number of suitable lengths, such as, for example, from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids. Linkers can be cleavable or non-cleavable. Non-limiting examples of linkers include, e.g., glycine polymers (G)n, glycine-serine polymers (including, for example, (GS)n, (GSGGS) (SEQ ID NO: 91) and (GGGS) (SEQ ID NO: 92) (TABLE 1), where n is an integer of at least one), glycine-alanine polymers, alanine-serine polymers, and other flexible linkers known in the art. See, e.g., Chichili et al, (2013) *Protein Science,* 22:153-167. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains. See Scheraga, (1992) *Rev. Computational Chem.* 1:1173-142. Exemplary linkers can comprise amino acid sequences including, but not limited to, GGSG (SEQ ID NO: 93), GGSGG (SEQ ID NO: 94), GSGSG (SEQ ID NO: 95), GSGGG (SEQ ID NO: 96), GGGSG (SEQ ID NO: 97), GSSSG (SEQ ID NO: 98), GCGASGGGGSGGGGS (SEQ ID NO: 99), GCGASGGGGSGGGGS (SEQ ID NO: 99), GGGASGGGGSGGGGS (SEQ ID NO: 100), GGGASGGGGS (SEQ ID NO: 101), $G_3S$ (SEQ ID NO: 92), $(G_3S)_2$ (SEQ ID NO: 102), $(G_3S)_3$ (SEQ ID NO: 103), $G_4S$ (SEQ ID NO: 104), $(G_4S)_2$ (SEQ ID NO: 105), $(G_4S)_3$ (SEQ ID NO: 89), $(G_4S)_4$ (SEQ ID NO: 106), (TABLE 1), SGGSGGS (SEQ ID NO: 107); EFGNM (SEQ ID NO: 108); EFGGNM (SEQ ID NO: 109); EFGGNGGNM (SEQ ID NO: 110); or GGSNMAG (SEQ ID NO: 111) and the like. In certain embodiments, the linker sequence is $(G_4S)_3$ (SEQ ID NO: 89).

TABLE 1

| Linker amino acids sequence | Linker codon-optimized nucleotide sequence (human) | Linker codon-optimized nucleotide sequence (mouse) |
|---|---|---|
| GGGS (SEQ ID NO: 92) | GGGGGTGGTTCC (SEQ ID NO: 112) | GGTGGCGGTAGT (SEQ ID NO: 128) |
| GGSG (SEQ ID NO: 93) | GGTGGGTCTGGG (SEQ ID NO: 113) | GGGGGATCTGGT (SEQ ID NO: 129) |
| GSGGS (SEQ ID NO: 91) | GGGTCCGGGGCTCC (SEQ ID NO: 114) | GGCAGTGGCGGTAGC (SEQ ID NO: 130) |
| GGSGG (SEQ ID NO: 94) | GGTGGGAGCGGTGGT (SEQ ID NO: 115) | GGAGGGAGTGGAGGG (SEQ ID NO: 131) |
| GSGSG (SEQ ID NO: 95) | GGCAGCGGAAGCGGA (SEQ ID NO: 116) | GGGTCTGGCTCAGGC (SEQ ID NO: 132) |
| GSGGG (SEQ ID NO: 96) | GGGAGTGGGGAGGT (SEQ ID NO: 117) | GGTTCTGGCGGAGGT (SEQ ID NO: 133) |
| GGGSG (SEQ ID NO: 97) | GGTGGGGAAGTGGA (SEQ ID NO: 118) | GGTGGTGGGAGTGGA (SEQ ID NO: 134) |

TABLE 1-continued

| Linker amino acids sequence | Linker codon-optimized nucleotide sequence (human) | Linker codon-optimized nucleotide sequence (mouse) |
|---|---|---|
| GSSSG (SEQ ID NO: 98) | GGCAGCTCATCTGGT (SEQ ID NO: 119) | GGCTCAAGCAGTGGA (SEQ ID NO: 135) |
| GCGASGGGGSGGGGS (SEQ ID NO: 99) | GGATGTGGTGCATCTG GAGGGGGAGGCTCTGG GGGGGGTGGATCT (SEQ ID NO: 120) | GGCTGTGGGGCTAGTG GGGGAGGTGGTAGTGG TGGTGGCGGTTCC (SEQ ID NO: 136) |
| GCGASGGGGSGGGGS (SEQ ID NO: 99) | GGGTGTGGTGCTAGTG GGGGTGGCGGATCAGG TGGAGGCGGGAGC (SEQ ID NO: 121) | GGATGTGGGCCTCAG GTGGGGGTGGCAGCGG TGGTGGAGGGTCA (SEQ ID NO: 137) |
| GGGGSGGGGS (SEQ ID NO: 105) | GGGGGCGGAGGATCTGGG GGAGGGGGATCA (SEQ ID NO: 122) | GGTGGCGGGGGCTCTG GTGGAGGAGGATCT (SEQ ID NO: 138) |
| GGGASGGGGSGGGGS (SEQ ID NO: 100) | GGGGGGGGCGCTTCAGGCG GAGGTGGAAGTGGTGGAG GAGGT (SEQ ID NO: 123) | GGAGGCGGCGCTTCTG GGGGCGGGGGTAGTGG GGTGGAGGT (SEQ ID NO: 139) |
| GGGGSGGGGSGGGGS (SEQ ID NO: 89) | GGAGGGGGAGGTTCTGGCG GCGGGGGATCAGGAGGCG GTGGGAGC (SEQ ID NO: 124) | GGTGGAGGTGGAAGTG GAGGAGGGGGATCAGG CGGAGGCGGGAGC (SEQ ID NO: 140) |
| GGGASGGGGS (SEQ ID NO: 101) | GGTGGGGGGGCGTCAGGTG GAGGCGGAAGT (SEQ ID NO: 125) | GGAGGGGGAGCCTCTG GCGGTGGAGGATCA (SEQ ID NO: 141) |
| GGGGSGGGGSGGGGS (SEQ ID NO: 89) | GGCGGCGAGGTTCTGGTG GGGTGGCAGTGGAGGAG GAGGCAGC (SEQ ID NO: 126) | GGGGGAGGAGGCAGTG GAGGTGGGGGAAGTGG TGGAGGGGGGTCT (SEQ ID NO: 142) |
| GGGGSGGGGSGGGGSG GGGS (SEQ ID NO: 106) | GGAGGTGGAGGTAGTGGC GTGGTGGGTCAGGGGAGG CGGGTCCGGTGGCGGTGGG AGT (SEQ ID NO: 127) | GGGGGGTGGAGGATCA GGAGGCGGTGGTTCTG GGGGAGGTGGATCCGG CGGGGGTGGTAGT (SEQ ID NO: 143) |

In certain embodiments, the linker is a cleavable linker. Preferably, such cleavable linker is susceptible to cleavage under intracellular conditions in the target cell but not in the packaging cell. Suitable cleavable linkers include, for example, a peptide linker cleavable by an intracellular protease, such as lysosomal protease or an endosomal protease. In exemplar embodiments, the linker can be a dipeptide linker, such as a valine-citrulline (val-cit) or a phenylalanine-lysine (phe-lys) linker. Other suitable linkers include linkers hydrolyzable at a pH of less than 5.5, such as a hydrazone linker. Additional suitable cleavable linkers include disulfide linkers.

Cas proteins, or functional fragment or derivative thereof, also be operably linked to other heterologous polypeptides as fusion proteins. For example, a Cas protein, or functional fragment or derivative thereof, can be fused to a cleavage domain, an epigenetic modification domain, a transcriptional activation domain, or a transcriptional repressor domain. See WO 2014/089290, herein incorporated by reference in its entirety for all purposes. Examples of transcriptional activation domains include a herpes simplex virus VP16 activation domain, VP64 (which is a tetrameric derivative of VP16), a NFκB p65 activation domain, p53 activation domains 1 and 2, a CREB (cAMP response element binding protein) activation domain, an E2A activation domain, and an NFAT (nuclear factor of activated T-cells) activation domain. Other examples include activation domains from Oct1, Oct-2A, SP1, AP-2, CTF1, P300, CBP, PCAF, SRC1, PvALF, ERF-2, OsGAI, HALF-1, C1, AP1, ARF-5, ARF-6, ARF-7, ARF-8, CPRF1, CPRF4, MYC-RP/GP, TRAB1PC4, and HSF1. See, e.g., US 2016/0237456, EP3045537, and WO 2011/145121, each of which is incorporated by reference in its entirety for all purposes. In some cases, a transcriptional activation system can be used comprising a dCas9-VP64 fusion protein paired with MS2-p65-HSF1. Guide RNAs in such systems can be designed with aptamer sequences appended to sgRNA tetraloop and stem-loop 2 designed to bind dimerized MS2 bacteriophage coat proteins. See, e.g., Konermann et al. (2015) *Nature* 517(7536):583-588, herein incorporated by reference in its entirety for all purposes. Examples of transcriptional repressor domains include inducible cAMP early repressor (ICER) domains, Kruppel-associated box A (KRAB-A) repressor domains, YY1 glycine rich repressor domains, Sp1-like repressors, E(spl) repressors, IκB repressor, and MeCP2. Other examples include transcriptional repressor domains from A/B, KOX, TGF-beta-inducible early gene (TIEG), v-erbA, SID, SID4X, MBD2, MBD3, DNMT1, DNMG3A, DNMT3B, Rb, ROM2, See, e.g., EP3045537 and WO 2011/145121, each of which is incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein, or functional fragment or derivative thereof.

As one example, a Cas protein, or functional fragment or derivative thereof, can be fused to one or more heterologous polypeptides that provide for subcellular localization. Such heterologous polypeptides can include, for example, one or more nuclear localization signals (NLS) such as the SV40 NLS and/or an alpha-importin NLS for targeting to the nucleus, a mitochondrial localization signal for targeting to the mitochondria, an ER retention signal, and the like. See, e.g., Lange et al. (2007) *J. Biol. Chem.* 282:5101-5105, herein incorporated by reference in its entirety for all purposes. Such subcellular localization signals can be located at the N-terminus, the C-terminus, or anywhere within the Cas protein, or functional fragment or derivative thereof. An NLS can comprise a stretch of basic amino acids, and can be a monopartite sequence or a bipartite sequence. Optionally, the Cas protein, or functional fragment or derivative thereof, comprises two or more NLSs, including an NLS (e.g., an alpha-importin NLS) at the N-terminus and/or an NLS (e.g., an SV40 NLS) at the C-terminus.

Cas proteins, or functional fragment or derivative thereof, can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreenl), yellow fluorescent proteins (e.g., YFP, eYFP, Citrine, Venus, YPet, PhiYFP, ZsYellow1), blue fluorescent proteins (e.g. eBFP, eBFP2, Azurite, mKalama1, GFPuv, Sapphire, T-sapphire), cyan fluorescent proteins (e.g. eCFP, Cerulean, CyPet, AmCyanl, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, hemagglutinin (HA), nus, Softag 1, Softag 3, Strep, SBP, Glu-Glu, HSV, KT3, S, 51, T7, V5, VSV-G, histidine (His), biotin carboxyl carrier protein (BCCP), and calmodulin.

The Cas fusion protein can be produced using routine molecular biology techniques, such as those described above or in He et al., supra. Alternatively, Cas fusion protein can be prepared by various other methods.

In certain embodiments, the nucleic acid encoding the Cas fusion protein comprises a regulatory element, including for example, a promoter, an enhancer, or a transcriptional repressor-binding element. Exemplary expression control sequences are known in the art and described in, for example, Goeddel, (1990) Gene Expression Technology: Methods in Enzymology, Vol. 185, Academic Press, San Diego, Calif., incorporated by reference in its entirety for all purposes.

B. Transcription Activator-Like Effector Nucleases, Zinc Figure Nucleases, Meganucleases, and Restriction Endonucleases In certain embodiments, the gene-editing molecule can be zinc finger nucleases (ZFns), transcription activator-like effector nucleases (TALENs), meganucleases, and/or restriction endonucleases. Fusion RNA and fusion protein molecules using these gene-editing molecules, or functional fragment or derivative thereof, for use in the compositions and methods of the invention can be made in the same fashion and structure as that disclosed above for Cas molecules, or functional fragment or derivative thereof Transcription activator-like effector nucleases (TALEN) are restriction enzymes that can be engineered to cut target sequences of DNA. They are made by fusing a TAL effector DNA-binding domain to a DNA cleavage domain (a nuclease which cuts DNA strands). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas.1013133107; Scholze & Boch (2010) *Virulence* 1:428-432; Christian et al. *Genetics* (2010) 186:757-761; Li et al. (2010) *Nuc. Acids Res.* doi: 10.1093/nar/gkq704; and Miller et al. (2011) *Nature Biotechnology* 29:143-148; all of which are herein incorporated by reference in their entirety and for all purposes.

Examples of suitable TAL nucleases, and methods for preparing suitable TAL nucleases, are disclosed, e.g., in US Patent Application No. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1 (each hereby incorporated by reference in their entirety and for all purposes). In various embodiments, TAL effector nucleases are engineered that cut in or near a target nucleic acid sequence in, e.g., a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors.

In one embodiment, each monomer of the TALEN comprises 12-25 TAL repeats, wherein each TAL repeat binds a 1 bp subsite. In certain embodiments, the gene-editing molecule is a chimeric protein comprising a TAL repeat-based DNA binding domain operably linked to an independent nuclease. In certain embodiments, the independent nuclease is a FokI endonuclease. In one embodiment, the gene-editing molecule comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by about 6 bp to about 40 bp cleavage site, and wherein the FokI nucleases dimerize and make a double strand break at a target sequence.

In certain embodiments, the gene-editing molecule comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by a 5 bp or 6 bp cleavage site, and wherein the FokI nucleases dimerize and make a double strand break.

The gene-editing molecule employed in the various methods and compositions disclosed herein can further comprise a zinc-finger nuclease (ZFN). Zinc finger nucleases (ZFNs) are a class of engineered DNA-binding proteins that assist targeted editing of the genome by creating double strand breaks (DSBs) in DNA at targeted locations. ZFNs comprise two functional domains: i) a DNA-binding domain comprising a chain of two-finger modules (each recognizing a unique hexamer (6 bp) sequence of DNA—two-finger modules are stitched together to form a Zinc Finger Protein, each with specificity of >24 bp) and ii) a DNA-cleaving domain comprising a nuclease domain of Fok I. When the DNA-binding and -cleaving domains are fused together, a highly-specific pair of "genomic scissors" are created.

In certain embodiments, each monomer of the ZFN comprises 3 or more zinc finger-based DNA binding domains, wherein each zinc finger-based DNA binding domain binds to a 3 bp subsite. In other embodiments, the ZFN is a chimeric protein comprising a zinc finger-based DNA binding domain operably linked to an independent nuclease. In certain embodiments, the independent endonuclease is a FokI endonuclease. In certain embodiments, the gene-editing molecule comprises a first ZFN and a second ZFN, wherein each of the first ZFN and the second ZFN is operably linked to a FokI nuclease, wherein the first and the second ZFN recognize two contiguous target DNA sequences in each strand of the target DNA sequence separated by about 6 bp to about 40 bp cleavage site or about a 5 bp to about 6 bp cleavage site, and wherein the FokI nucleases dimerize and make a double strand break. See, e.g., US20060246567; US20080182332; US20020081614; US20030021776; WO/2002/057308A2; US20130123484; 0520100291048; and, WO/2011/017293A2, each of which is herein incorporated by reference in their entirety for all purposes.

In certain embodiments of the compositions and methods provided herein, the gene-editing molecule comprises (a) a chimeric protein comprising a zinc finger-based DNA binding domain fused to a FokI endonuclease; or (b) a chimeric protein comprising a Transcription Activator-Like Effector Nuclease (TALEN) fused to a FokI endonuclease.

In still another embodiment, the gene-editing molecule is a meganuclease. Meganucleases have been classified into four families based on conserved sequence motifs, the families are the LAGLIDADG (SEQ ID NO: 24), GIY-YIG, H—N—H, and His-Cys box families. These motifs participate in the coordination of metal ions and hydrolysis of phosphodiester bonds. HEases are notable for their long recognition sites, and for tolerating some sequence polymorphisms in their DNA substrates. Meganuclease domains, structure and function are known, see e.g., Guhan and Muniyappa (2003) Crit Rev Biochem Mol Biol 38:199-248; Lucas et al., (2001) Nucleic Acids Res 29:960-9; Jurica and Stoddard, (1999) Cell Mol Life Sci 55:1304-26; Stoddard, (2006) Q Rev Biophys 38:49-95; and Moure et al., (2002) Nat Struct Biol 9:764. In some examples a naturally occurring variant, and/or engineered derivative meganuclease is used. Methods for modifying the kinetics, cofactor interactions, expression, optimal conditions, and/or recognition site specificity, and screening for activity are known, see e.g., Epinat et al., (2003) Nucleic Acids Res 31:2952-62; Chevalier et al., (2002) Mol Cell 10:895-905; Gimble et al., (2003) Mol Biol 334:993-1008; Seligman et al., (2002) Nucleic Acids Res 30:3870-9; Sussman et al., (2004) J Mol Biol 342:31-41; Rosen et al., (2006) Nucleic Acids Res 34:4791-800; Chames et al., (2005) Nucleic Acids Res 33:e178; Smith et al., (2006) Nucleic Acids Res 34:e149; Gruen et al., (2002) Nucleic Acids Res 30:e29; Chen and Zhao, (2005) Nucleic Acids Res 33:e154; WO2005105989; WO2003078619; WO2006097854; WO2006097853; WO2006097784; and WO2004031346.

Any meganuclease can be used herein, including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TeeI, F-TevI, F-TevII, I-AuraI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TeeI, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

In one embodiment, the meganuclease recognizes double-stranded DNA sequences of 12 to 40 base pairs. In one embodiment, the meganuclease recognizes one perfectly matched target sequence in the genome. In one embodiment, the meganuclease is a homing nuclease. In one embodiment, the homing nuclease is a LAGLIDADG (SEQ ID NO: 24) family of homing nuclease. In one embodiment, the LAGLIDADG (SEQ ID NO: 24) family of homing nuclease is selected from I-SceI, I-CreI, and I-DmoI.

Gene-editing molecules can further comprise restriction endonucleases, which include Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at rebase.neb.com; Roberts et al., (2003) Nucleic Acids Res 31:418-20), Roberts et al., (2003) Nucleic Acids Res 31:1805-12, and Belfort et al., (2002) in Mobile DNA II, pp. 761-783, Eds. Craigie et al., (ASM Press, Washington, D.C.).

ZFNs and TALENs introduce DSBs in a target genomic sequence and activate non-homologous end-joining (NHEJ)-mediated DNA repair, which generates a mutant allele comprising an insertion or a deletion of a nucleic acid sequence at the genomic locus of interest and thereby causes disruption of the genomic locus of interest in a cell. DSBs also stimulate homology-directed repair (HDR) by homologous recombination if a repair template is provided. HDR can result in a perfect repair that restores the original sequence at the broken site, or it can be used to direct a designed modification, such as a deletion, insertion, or replacement of the sequence at the site of the double strand break.

C. Guide RNAs

In one aspect, the retroviral particle comprises a guide RNA (gRNA). In certain embodiments, the nucleic acid sequence of gRNA is incorporated into the genomic plasmid of the retroviral particle.

A "guide RNA" or "gRNA" is an RNA molecule that binds to a Cas protein (e.g., Cas9 protein), or functional fragment or derivative thereof, and targets the Cas protein to a specific location within a target DNA. Guide RNAs can comprise two segments: a "DNA-targeting segment" and a "protein-binding segment". "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA". See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides that forms one half of the dsRNA duplex of the protein-binding segment of the gRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA.

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that hybridizes to a guide RNA recognition sequence. If used for modification within a cell, the exact sequence of a given crRNA or tracrRNA molecule can be designed to be specific to the species in which the RNA molecules will be used. See, e.g., Mali et al. (2013) Science 339:823-826; Jinek et al. (2012) Science 337:816-821; Hwang et al. (2013) Nat. Biotechnol. 31:227-229; Jiang et al. (2013) Nat. Biotechnol. 31:233-239; and Cong et al. (2013) Science 339:819-823, each of which is herein incorporated by reference in its entirety for all purposes.

The DNA-targeting segment (crRNA) of a given gRNA comprises a nucleotide sequence that is complementary to a sequence (i.e., the guide RNA recognition sequence) in a target DNA. The DNA-targeting segment of a gRNA interacts with a target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have a length of at least about 12 nucleotides, at least about 15 nucleotides, at least about 17 nucleotides, at least about 18 nucleotides, at least about 19 nucleotides, at least about 20 nucleotides, at least about 25 nucleotides, at least about 30 nucleotides, at least about 35 nucleotides, or at least about 40 nucleotides. Such DNA-targeting segments can have a length from about 12 nucleotides to about 100 nucleotides, from about 12 nucleotides to about 80 nucleotides, from about 12 nucleotides to about 50 nucleotides, from about 12 nucleotides to about 40 nucleotides, from about 12 nucleotides to about 30 nucleotides, from about 12 nucleotides to about 25 nucleotides, or from about 12 nucleotides to about 20 nucleotides. For example, the DNA targeting segment can be from about 15 nucleotides to about 25 nucleotides (e.g., from about 17 nucleotides to about 20 nucleotides, or about 17 nucleotides, about 18 nucleotides, about 19 nucleotides, or about 20 nucleotides). See, e.g., US 2016/0024523, herein incorporated by reference in its entirety for all purposes. For Cas9 from *S. pyogenes*, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting sequence and the guide RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting sequence and the guide RNA recognition sequence within the target DNA can be at least 60% over about 20 contiguous nucleotides. As an example, the percent complementarity between the DNA-targeting sequence and the guide RNA recognition sequence within the target DNA is 100% over the 14 contiguous nucleotides at the 5' end of the guide RNA recognition sequence within the complementary strand of the target DNA and as low as 0% over the remainder. In such a case, the DNA-targeting sequence can be considered to be 14 nucleotides in length. As another example, the percent complementarity between the DNA-targeting sequence and the guide RNA recognition sequence within the target DNA is 100% over the seven contiguous nucleotides at the 5' end of the guide RNA recognition sequence within the complementary strand of the target DNA and as low as 0% over the remainder. In such a case, the DNA-targeting sequence can be considered to be 7 nucleotides in length. In some guide RNAs, at least 17 nucleotides within the DNA-target sequence are complementary to the target DNA. For example, the DNA-targeting sequence can be 20 nucleotides in length and can comprise 1, 2, or 3 mismatches with the target DNA (the guide RNA recognition sequence). Preferably, the mismatches are not adjacent to a protospacer adjacent motif (PAM) sequence (e.g., the mismatches are in the 5' end of the DNA-targeting sequence, or the mismatches are at least 2, 3, 4, 5, 6, 7, 8, 9, 10, 11, 12, 13, 14, 15, 16, 17, 18, or 19 base pairs away from the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, or functional fragment or derivative thereof, and the gRNA directs the bound Cas protein, or functional fragment or derivative thereof, to a specific nucleic acid sequence within target DNA via the DNA-targeting segment.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleic acids within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

In some cases, a transcriptional activation system can be used comprising a dCas9-VP64 fusion protein paired with MS2-p65-HSF1. Guide RNAs in such systems can be designed with aptamer sequences appended to sgRNA tetraloop and stem-loop 2 designed to bind dimerized MS2 bacteriophage coat proteins. See, e.g., Konermann et al. (2015) *Nature* 517(7536):583-588, herein incorporated by reference in its entirety for all purposes.

Guide RNAs can be provided in any form. For example, the gRNA can be provided in the form of RNA, either as two molecules (separate crRNA and tracrRNA) or as one molecule (sgRNA). The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. In certain embodiments, an RNA Pol III promoter can be operatively linked to a gRNA sequence (if included in the lentivirus vector) to control expression of such sequence. RNA Pol III promoters are frequently used to express small RNAs, such as small interfering RNA (siRNA)/short hairpin RNA (shRNA) and guide RNA sequences used in CRISPR-Cas9 systems. Examples of RNA Pol III promoters that can be used in the invention include, but are not limited to, the human U6 promoter, a rat U6 polymerase III promoter, or a mouse U6 polymerase III promoter, and the H1 promoter, which are described in, for example Goomer and Kunkel, Nucl. Acids Res., 20 (18): 4903-4912 (1992), and Myslinski et al., Nucleic Acids Res., 29(12): 2502-9 (2001).

D. Guide RNA Recognition Sequences

The term "guide RNA recognition sequence" includes nucleic acid sequences present in a target DNA to which a DNA-targeting segment of a gRNA will bind, provided sufficient conditions for binding exist. For example, gRNA recognition sequences include sequences to which a gRNA is designed to have complementarity, where hybridization between a guide RNA recognition sequence and a DNA targeting sequence promotes the formation of a CRISPR complex. Full complementarity is not necessarily required, provided that there is sufficient complementarity to cause hybridization and promote formation of a CRISPR complex. Guide RNA recognition sequences also include cleavage sites for Cas proteins, described in more detail below. A gRNA recognition sequence can comprise any polynucleotide, which can be located, for example, in the nucleus or cytoplasm of a cell or within an organelle of a cell, such as a mitochondrion or chloroplast.

The gRNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "noncomplementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a guide RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "guide RNA recognition sequence." The cleavage site can be on only one strand or on both strands of a nucleic acid. Cleavage sites can be at the same position on both strands of the nucleic acid (producing blunt ends) or can be at different sites on each strand (producing staggered ends (i.e., overhangs)). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA recognition sequence of the nickase on the first strand is separated from the guide RNA recognition sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific binding and cleavage of target DNA by Cas proteins can occur at locations determined by both (i) base-pairing complementarity between the gRNA and the target DNA and (ii) a short motif, called the protospacer adjacent motif (PAM), in the target DNA. The PAM can flank the guide RNA recognition sequence. Optionally, the guide RNA recognition sequence can be flanked on the 3' end by the PAM. Alternatively, the guide RNA recognition sequence can be flanked on the 5' end by the PAM. For example, the cleavage site of Cas proteins can be about 1 to about 10 or about 2 to about 5 base pairs (e.g., 3 base pairs) upstream or downstream of the PAM sequence. In some cases (e.g., when Cas9 from S. pyogenes or a closely related Cas9 is used), the PAM sequence of the non-complementary strand can be 5'-$N_1$GG-3', where $N_1$ is any DNA nucleotide and is immediately 3' of the guide RNA recognition sequence of the non-complementary strand of the target DNA. As such, the PAM sequence of the complementary strand would be 5'-$CCN_2$-3', where N2 is any DNA nucleotide and is immediately 5' of the guide RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from S. aureus, the PAM can be NNGRRT or NNGRR, where N can A, G, C, or T, and R can be G or A. In the case of Cas9 from C. jejuni, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

Examples of gRNA recognition sequences include a DNA sequence complementary to the DNA-targeting segment of a gRNA, or such a DNA sequence in addition to a PAM sequence. For example, the target motif can be a 20-nucleotide DNA sequence immediately preceding an NGG motif recognized by a Cas9 protein, such as $GN_{19}NGG$ (SEQ ID NO: 25) or $N_{20}NGG$ (SEQ ID NO: 26). See, e.g., WO 2014/165825, herein incorporated by reference in its entirety for all purposes. The guanine at the 5' end can facilitate transcription by RNA polymerase in cells. Other examples of guide RNA recognition sequences can include two guanine nucleotides at the 5' end (e.g., $GGN_{20}NGG$; SEQ ID NO: 27) to facilitate efficient transcription by T7 polymerase in vitro. See, e.g., WO 2014/065596, herein incorporated by reference in its entirety for all purposes. Other guide RNA recognition sequences can have between 4-22 nucleotides in length of SEQ ID NOs: 28-30, including the 5' G or GG and the 3' GG or NGG. Yet other guide RNA recognition sequences can have between 14 and 20 nucleotides in length of SEQ ID NOS: 31-58.

The gRNA recognition sequence can be any nucleic acid sequence endogenous or exogenous to a cell. The gRNA recognition sequence can be a sequence coding a gene product (e.g., a protein) or a non-coding sequence (e.g., a regulatory sequence) or can include both.

E. Repair Template

In one aspect, the retroviral particle comprises a sequence corresponding to a repair template.

As used herein, the terms "repair template", "RT", "recombination template", "donor nucleic acid molecule" or "donor polynucleotide", which can be used interchangeably, refer to a segment of DNA that one desires to integrate at the target locus. In certain embodiments, the repair template comprises one or more polynucleotides of interest. In other embodiments, the repair template can comprise one or more expression cassettes. A given expression cassette can comprise a polynucleotide of interest, a polynucleotide encoding a selection marker and/or a reporter gene along with the various regulatory components that influence expression.

In certain embodiments, the repair template can comprise a segment of genomic DNA, a cDNA, a regulatory region, or any portion or combination thereof. In certain embodiments, the repair template can comprise a nucleic acid from a eukaryote, a mammal, a human, a non-human mammal, a rodent, a rat, a non-rat rodent, a mouse, a hamster, a rabbit, a pig, a bovine, a deer, a sheep, a goat, a chicken, a cat, a dog, a ferret, a primate (e.g., marmoset, rhesus monkey), a domesticated mammal, or an agricultural mammal or any other organism of interest.

In certain embodiments, the repair template comprises a knock-in allele of at least one exon of an endogenous gene. In certain embodiments, the repair template comprises a knock-in allele of the entire endogenous gene (i.e., "gene-swap knock-in").

In further embodiments, the repair template comprises a conditional allele. In certain embodiments, the conditional allele is a multifunctional allele, as described in US 2011/0104799, which is incorporated by reference in its entirety. In certain embodiments, the conditional allele comprises: (a) an actuating sequence in sense orientation with respect to transcription of a target gene, and a drug selection cassette in sense or antisense orientation; (b) in antisense orientation a nucleotide sequence of interest (NSI) and a conditional by inversion module (COIN, which utilizes an exon-splitting intron and an invertible genetrap-like module; see, for example, US 2011/0104799, which is incorporated by reference in its entirety); and (c) recombinable units that recombine upon exposure to a first recombinase to form a conditional allele that (i) lacks the actuating sequence and the DSC, and (ii) contains the NSI in sense orientation and the COIN in antisense orientation.

In certain embodiments, the repair template is under 10 kb in size.

In certain embodiments, the repair template comprises a deletion of, for example, a eukaryotic cell, a mammalian cell, a human cell, or a non-human mammalian cell genomic DNA sequence.

In certain embodiments, the repair template comprises an insertion or a replacement of a eukaryotic, a mammalian, a human, or a non-human mammalian nucleic acid sequence with a homologous or orthologous human nucleic acid sequence. In certain embodiments, the repair template comprises an insertion or replacement of a DNA sequence with a homologous or orthologous human nucleic acid sequence at an endogenous locus that comprises the corresponding DNA sequence.

In certain embodiments, the genetic modification is an addition of a nucleic acid sequence.

In certain embodiments, repair template comprises a genetic modification in a coding sequence. In certain embodiments, the genetic modification comprises a deletion mutation of a coding sequence. In certain embodiments, the genetic modification comprises a fusion of two endogenous coding sequences.

In certain embodiments, the repair template comprises an insertion or a replacement of a eukaryotic, a non-rat eukaryotic, a mammalian, a human, or a non-human mammalian, nucleic acid sequence with a homologous or orthologous human nucleic acid sequence. In certain embodiments, the repair template comprises an insertion or replacement of a rat DNA sequence with a homologous or orthologous human nucleic acid sequence at an endogenous rat locus that comprises the corresponding rat DNA sequence.

In certain embodiments, the genetic modification comprises a deletion of a non-protein-coding sequence, but does not comprise a deletion of a protein-coding sequence. In certain embodiments, the deletion of the non-protein-coding sequence comprises a deletion of a regulatory element. In certain embodiments, the genetic modification comprises a deletion of a promoter. In certain embodiments, the genetic modification comprises an addition of a promoter or a regulatory element. In certain embodiments, the genetic modification comprises a replacement of a promoter or a regulatory element.

In certain embodiments, the nucleic acid sequence of the repair template can comprise a polynucleotide that when integrated into the genome will produce a genetic modification of a region of the mammalian, human, or a non-human mammalian target locus (e.g., ApoE, IL-2, Rag1, or Rag2), wherein the genetic modification at the target locus results in a decrease in activity, increase in activity, or a modulation of activity of the target gene. In certain embodiments, a knockout ("null allele") is generated.

In further embodiments, the repair template results in the replacement of a portion of the mammalian, human cell, or non-human mammalian target locus (e.g., ApoE locus, the interleukin-2 receptor gamma locus and/or Rag2 locus, and/or Rag1 locus and/or Rag2/Rag1 locus with the corresponding homologous or orthologous portion of an ApoE locus, an interleukin-2 receptor gamma locus, a Rag2 locus, a Rag1 locus and/or a Rag2/Rag1 locus from another organism).

Still in other embodiments, the repair template comprises a polynucleotide sharing across its full length at least 80%, 85%, 90%, 91%, 92%, 93%, 94%, 95%, 96%, 97%, 98%, 99% to a portion of the locus it is replacing (e.g., an ApoE locus, an IL-2 receptor gamma locus, a Rag2 locus, a Rag1 locus and/or a Rag2/Rag).

The given repair template and the corresponding region of the mammalian, human cell, or non-human mammalian locus being replaced can be a coding region, an intron, an exon, an untranslated region, a regulatory region, a promoter, or an enhancer or any combination thereof Moreover, the given repair template and/or the region of the mammalian, human cell, or non-human mammalian locus being deleted can be of any desired length, including for example, between 10-100 nucleotides in length, 100-500 nucleotides in length, 500-1 kb nucleotides in length, 1 Kb to 1.5 kb nucleotides in length, 1.5 kb to 2 kb nucleotides in length, 2 kb to 2.5 kb nucleotides in length, 2.5 kb to 3 kb nucleotides in length, 3 kb to 5 kb nucleotides in length, 5 kb to 8 kb nucleotides in length, 8 kb to 10 kb nucleotides in length or more. In other instances, the size of the insertion or replacement is from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, from about 400 kb to about 800 kb, from about 800 kb to 1 Mb, from about 1 Mb to about 1.5 Mb, from about 1.5 Mb to about 2 Mb, from about 2 Mb, to about 2.5 Mb, from about 2.5 Mb to about 2.8 Mb, from about 2.8 Mb to about 3 Mb. In other embodiments, the given repair template and/or the region of the mammalian, human cell, or non-human mammalian locus being deleted is at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb or greater.

DNA of the repair template can be stably integrated into the genome of the cell

In certain embodiments, the promoter is a tissue-specific promoter. In certain embodiments, the promoter is a hepatocyte-specific promoter. In certain embodiments, the promoter is a neuron-specific promoter. In certain embodiments, the promoter is a glia-specific promoter. In certain embodiments, the promoter is a muscle cell-specific promoter. In certain embodiments, the promoter is a heart cell-specific promoter. In certain embodiments, the promoter is a kidney cell-specific promoter. In certain embodiments, the promoter is a bone cell-specific promoter. In certain embodiments, the promoter is an endothelial cell-specific promoter. In certain embodiments, the promoter is an immune cell-specific promoter. In certain embodiments, the immune cell promoter is a B cell promoter. In certain embodiments, the immune cell promoter is a T cell promoter.

In certain embodiments, the promoter is a developmentally-regulated promoter. In certain embodiments, the developmentally-regulated promoter is active only during an embryonic stage of development. In certain embodiments, the developmentally-regulated promoter is active only in an adult cell.

In specific embodiments, the promoter may be selected based on the cell type. Thus the various promoters find use in a eukaryotic cell, a non-rat eukaryotic cell, a mammalian cell, a non-human mammalian cell, a pluripotent cell, a non-pluripotent cell, a non-human pluripotent cell, a human pluripotent cell, a human ES cell, a human adult stem cell, a developmentally-restricted human progenitor cell, a human iPS cell, a human cell, a rodent cell, a non-rat rodent cell, a rat cell, a mouse cell, a hamster cell, a fibroblast or a CHO cell.

In some embodiments, the repair template comprises a nucleic acid flanked with site-specific recombination target sequences. It is recognized the while the entire nucleic acid can be flanked by such site-specific recombination target sequences, any region or individual polynucleotide of interest within the insert nucleic acid can also be flanked by such sites. The site-specific recombinase can be introduced into the cell by any means, including by introducing the recombinase polypeptide into the cell or by introducing a polynucleotide encoding the site-specific recombinase into the target cell. The polynucleotide encoding the site-specific recombinase can be located within the repair template or within a separate polynucleotide. The site-specific recombinase can be operably linked to a promoter active in the cell including, for example, an inducible promoter, a promoter that is endogenous to the cell, a promoter that is heterologous to the cell, a cell-specific promoter, a tissue-specific promoter, or a developmental stage-specific promoter. Site-specific recombination target sequences, which can flank the nucleic acid or any polynucleotide of interest in the nucleic acid can include, but are not limited to, loxP, lox511, lox2272, lox66, lox71, loxM2, lox5171, FRT, FRT11, FRT71, attp, att, FRT, rox, and a combination thereof.

In certain embodiments, the site-specific recombination sites flank a polynucleotide encoding a selection marker and/or a reporter gene contained within the repair template. In such instances following integration of the repair template the targeted locus the sequences between the site-specific recombination sites can be removed.

In certain embodiments, the repair template comprises a polynucleotide encoding a selection marker. The selection marker can be contained in a selection cassette. Such selection markers include, but are not limited, to neomycin phosphotransferase (neor), hygromycin B phosphotransferase (hygr), puromycin-N-acetyltransferase (puror), blasticidin S deaminase (bsrr), xanthine/guanine phosphoribosyl transferase (gpt), or herpes simplex virus thymidine kinase (HSV-k), or a combination thereof. In certain embodiments, the polynucleotide encoding the selection marker is operably linked to a promoter active in the cell, rat cell, pluripotent rat cell, the ES rat cell, a eukaryotic cell, a non-rat eukaryotic cell, a pluripotent cell, a non-pluripotent cell, a non-human pluripotent cell, a human pluripotent cell, a human ES cell, a human adult stem cell, a developmentally-restricted human progenitor cell, a human iPS cell, a mammalian cell, a non-human mammalian cell, a human cell, a rodent cell, a non-rat rodent cell, a mouse cell, a hamster cell, a fibroblast, or a CHO cell. When serially tiling polynucleotides of interest into a targeted locus, the selection marker can comprise a recognition site for a gene-editing molecule, as outlined above. In certain embodiments, the polynucleotide encoding the selection marker is flanked with a site-specific recombination target sequences.

The repair template can further comprise a reporter gene operably linked to a promoter, wherein the reporter gene encodes a reporter protein selected from the group consisting of or comprising LacZ, mPlum, mCherry, tdTomato, mStrawberry, J-Red, DsRed, mOrange, mKO, mCitrine, Venus, YPet, enhanced yellow fluorescent protein (eYFP), Emerald, enhanced green fluorescent protein (EGFP), CyPet, cyan fluorescent protein (CFP), Cerulean, T-Sapphire, luciferase, alkaline phosphatase, and/or a combination thereof. Such reporter genes can be operably linked to a promoter active in the cell. Such promoters can be an inducible promoter, a promoter that is endogenous to the reporter gene or the cell, a promoter that is heterologous to the reporter gene or to the cell, a cell-specific promoter, a tissue-specific promoter, or a developmental stage-specific promoter.

In certain embodiments, the repair template can comprise a mammalian nucleic acid comprising a genomic locus that encodes a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof. In certain embodiments, the mammalian nucleic acid comprises a genomic locus that encodes a protein expressed in a bone marrow or a bone marrow-derived cell. In certain embodiments, the nucleic acid comprises a genomic locus that encodes a protein expressed in a spleen cell. In certain embodiments, the nucleic acid comprises a genomic locus that encodes a protein expressed in a hepatocyte.

In certain embodiments, the mammalian nucleic acid comprises a genomic locus that encodes a protein expressed in the immune system, the lymphatic system, the endocrine system, the nervous system, the skeletal system, the digestive system, the circulatory system, the muscular system, the respiratory system, the cardiovascular system, the urinary system, the reproductive system, or a combination thereof. In certain embodiments, the mammalian nucleic acid comprises a genomic locus that encodes a protein expressed in a bone marrow or a bone marrow-derived cell. In certain embodiments, the nucleic acid comprises a genomic locus that encodes a protein expressed in a spleen cell. In certain embodiments, the nucleic acid comprises a genomic locus that encodes a protein expressed in a hepatocyte.

In certain embodiments, the genomic locus comprises a mouse genomic DNA sequence, a rat genomic DNA sequence, eukaryotic genomic DNA sequence, a non-rat eukaryotic genomic DNA sequence, a mammalian genomic DNA sequence, a human genomic DNA sequence, or non-human DNA sequence mammalian, or a combination thereof. In certain embodiments, the genomic locus comprises, in any order, rat and human genomic DNA sequences. In certain embodiments, the genomic locus comprises, in any order, mouse and human genomic DNA sequences. In certain embodiments, the genomic locus comprises, in any order, mouse and rat genomic DNA sequences. In certain embodiments, the genomic locus comprises, in any order, rat, mouse, and human genomic DNA sequences.

In certain embodiments, the genetic modification comprises at least one human disease allele of a human gene. In certain embodiments, the human disease is a neurological disease. In certain embodiments, the human disease is a cardiovascular disease. In certain embodiments, the human disease is a kidney disease. In certain embodiments, the human disease is a muscle disease. In certain embodiments, the human disease is a blood disease. In certain embodiments, the human disease is a bleeding disorder. In certain embodiments, the human disease is a cancer. In certain embodiments, the human disease is an immune system disease.

In certain embodiments, the human disease allele is a dominant allele. In certain embodiments, the human disease allele is a recessive allele. In certain embodiments, the human disease allele comprises a single nucleotide polymorphism (SNP) allele.

In certain embodiments, the genetic modification produces a mutant form of a protein with an altered binding characteristic, altered localization, altered expression, and/or altered expression pattern.

In certain embodiments, the repair template comprises a selection cassette. In certain embodiments, the selection cassette comprises a nucleic acid sequence encoding a selective marker, wherein the nucleic acid sequence is operably linked to a promoter active in rat ES cells. In certain embodiments, the selective marker is selected from or comprises a hygromycin resistance gene or a neomycin resistance gene.

In certain embodiments, the nucleic acid comprises a genomic locus that encodes a protein expressed in a B cell. In certain embodiments, the nucleic acid comprises a genomic locus that encodes a protein expressed in an immature B cell. In certain embodiments, the nucleic acid comprises a genomic locus that encodes a protein expressed in a mature B cell.

In certain embodiments, the nucleic acid comprises a genomic locus that encodes a protein expressed in a T cell. In certain embodiments, the nucleic acid comprises a genomic locus that encodes a protein expressed in an immature T cell. In certain embodiments, the nucleic acid comprises a genomic locus that encodes a protein expressed in a mature T cell.

In certain embodiments, the repair template comprises a regulatory element. In certain embodiments, the regulatory element is a promoter. In certain embodiments, the regulatory element is an enhancer. In certain embodiments, the regulatory element is a transcriptional repressor-binding element.

In certain embodiments, the genetic modification comprises a deletion of a non-protein-coding sequence, but does not comprise a deletion of a protein-coding sequence. In certain embodiments, the deletion of the non-protein-coding sequence comprises a deletion of a regulatory element. In certain embodiments, the genetic modification comprises a deletion of a regulatory element. In certain embodiments, the genetic modification comprises an addition of a promoter or a regulatory element. In certain embodiments, the genetic modification comprises a replacement of a promoter or a regulatory element.

F. Retroviral Particles

The viral particles described herein are derived from viruses of the family Retroviridae. The viral particles described herein can be derived from retroviruses such as, but not limited to, rous sarcoma virus, human and bovine T-cell leukaemia virus (HTLV and BLV), lentiviruses (e.g., human and simian immunodeficiency viruses (HIV and SIV), Mason-Pfizer monkey virus), foamy viruses (e.g., Human Foamy Virus (HFV)), and herpes viruses (herpes simplex virus (HSV), varicella-zoster virus, VZVEBV, HCMV, HHV). Compared to other gene transfer systems, retroviral vectors offer a wide range of advantages, including their ability to transduce a variety of cell types, to stably integrate transferred genetic material into the genome of the target cell, and to express the transduced gene at significant levels. Vectors derived from the gamma-retroviruses, for example, the murine leukemia virus (MLV), have been used in clinical gene therapy trials (Ross et al., Hum. Gen Ther. 7:1781-1790, 1996).

In one specific embodiment, the retroviral particles described herein are lentiviral particles. In one specific embodiment, the retroviral particle does not contain gp120 surface envelope protein and/or gp41 transmembrane envelope protein. In another specific embodiment, the retroviral particle contains a mutant gp120 surface envelope protein and/or a mutant gp41 transmembrane envelope protein and is not capable of binding to a cell in the absence of a targeting moiety.

In some embodiments, the retroviral particle described herein comprises components from a virus selected from the group consisting of Human Immunodeficiency Virus (e.g., HIV-1 or HIV-2), Bovine Immunodeficiency Virus (BIV), Feline Immunodeficiency Virus (FIV), Simian Immunodeficiency Virus (SIV), Equine Infectious Anemia Virus (EIAV), Murine Stem Cell Virus (MSCV), Murine Leukemia Virus (MLV), Avian leukosis virus (ALV), Feline leukemia virus (FLV), Bovine leukemia virus (BLV), Human T-lymphotropic virus (HTLV), feline sarcoma virus, avian reticuloendotheliosis virus, caprine arthritis encephalitis virus (CAEV), and Visna-Maedi virus (VMV). Retroviral vectors encoding MLV are widely available to those skilled in the art, such as PINCO (Grignani et al., 1998) or the pBabe vector series (Morgenstern and Land, 1990).

In some embodiments, the retroviral particles described herein are replication deficient and only contain an incomplete genome of the virus from which they are derived. For example, in some embodiments, the retroviral particles do not comprise the genetic information of the gag, env, and/or pol genes (which may be involved in the assembly of the retroviral particle), which is a known minimal requirement for successful replication of a retrovirus. In these cases, the minimal set of retroviral proteins needed to assemble the vector particle are provided in trans by means of a packaging cell line. In one specific embodiment, for lentiviral particles derived from HIV-1, env, tat, vif, vpu and nef genes are lacking and are not provided in trans.

G. Target Cells

In certain embodiments, the invention provides a target cell comprising the system described herein. In certain embodiments, the invention provides a target cell transduced with the retroviral particles comprising a gene-editing molecule fusion RNA, and optionally a gene-editing molecule fusion protein and/or a gRNA, and/or a repair template (RT) as described herein or a composition comprising the aforementioned retroviral particles. In certain embodiments, target cells are those that have well characterized expression systems, have reasonably fast growth rates, and can be infected, transformed, transfected, or transduced easily and efficiently with a retroviral vector. The target cell can be any suitable eukaryotic cell known in the art including, for example, yeast cells, insect cells, and mammalian cells. In certain embodiments, the target cell is a mammalian cell.

Target cells can be "autologous" or "allogeneic". In certain embodiments, autologous target cells are removed from a subject, stored (and optionally modified), and returned back to the same subject. In certain embodiments, allogeneic target cells are removed from a donor, stored (and optionally modified), and transplanted into a genetically similar, but not identical, subject (i.e., recipient). Preferably, the target cells are autologous to the subject.

In certain embodiments, the target cell is a somatic cell. The term "somatic cell" refers to any cell of a living organism other than the reproductive cells (e.g., other than a gamete, genu line cell, gametocyte, or undifferentiated stem cell). Somatic cells can be harvested from the subject or donor and used as a target cell in the context of the invention. Examples of somatic cells include, but are not limited to, keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), intimal epithelial cells constituting interfaces (e.g., type I alveolar cells), intimal epithelial cells of the obturator canal (e.g., vascular endothelial cells), cells having cilia with transporting capability (e.g., airway epithelial cells), cells for extracellular matrix secretion (e.g., fibroblasts), constrictive cells (e.g., smooth muscle cells), cells of the blood and the immune system (e.g., T lymphocytes), sense-related cells (e.g., bacillary cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), and progenitor cells thereof (tissue progenitor cells). In certain embodiments, undifferentiated progenitor cells (including somatic stem cells) and differentiated mature cells can be used as sources of somatic cells. Examples of undifferentiated progenitor cells include, but are not limited to, tissue stem cells (somatic stem cells) such as nerve stem cells, hematopoietic stem cells (discussed above), mesenchymal stem cells, and dental pulp stem cells.

III. Methods of Producing Retroviral Particles

In a related aspect, described herein is a method of producing a single retroviral particle that is capable of delivering a gene-editing fusion molecule and optionally a guide RNA (gRNA) and/or a repair template (RT). In certain embodiments, the gene-editing fusion molecule can be a Cas fusion molecule.

A. Methods of Generating and Purifying Retroviral Particles

Disclosed herein is a method of producing a single retroviral particle that is capable of delivering a gene-editing fusion molecule comprising culturing a packaging cell (described below) in conditions sufficient for the production of a plurality of retroviral particles, wherein the packaging cell comprises one or more plasmids comprising (i) one or more retroviral elements involved in the assembly of the retroviral particle and (ii) a nucleic acid sequence encoding a gene-editing fusion molecule. In certain embodiments, the packaging cell further comprises a plasmid encoding one or more gRNA and/or comprising a sequence corresponding to one or more repair templates (RT).

In certain embodiments, the method comprises culturing a packaging cell in conditions sufficient for the production of a plurality of retroviral particles, wherein the packaging cell comprises one or more plasmids comprising (i) one or more retroviral elements involved in the assembly of the retroviral particle and (ii) a nucleic acid sequence encoding a Cas fusion RNA and/or a Cas fusion protein. In certain embodiments, the packaging cell further comprises a plasmid encoding one or more gRNA and/or comprising a sequence corresponding to one or more repair templates (RT).

In some embodiments of any of the above methods, the method further comprises collecting the retroviral particles. In one specific embodiment, the collecting step comprises one or more of the following steps: clearing cell debris, treating the supernatant containing the retroviral particles with DNase I and $MgCl_2$, concentrating the retroviral particles, and purifying the retroviral particles.

In the methods described herein, plasmids/vectors used for retroviral particle production can be introduced into the packaging cells using methods well known in the art such as, e.g., electroporation (using for example Multiporator (Eppendorf), Genepulser (BioRad), MaxCyte Transfection Systems (Maxcyte)), PEI (Polysciences Inc. Warrington, Eppelheim), Ca2+-mediated transfection or via liposomes (for example: "Lipofectamine" (Invitrogen)), non-liposomal compounds (for example: "Fugene" (Roche) or nucleofection (Lonza)) into cells.

In certain embodiments, the packaging cells are present in an in vitro culture and can be cultured in a manner that allows for mass production of the retroviral particles so as to provide suitable titers useful for production of the retroviral particle preparations for various applications (e.g., for clinical application in gene therapy). In certain embodiments, where large-scale production of viral particles is desirable, the packaging cell is preferably easy to culture, stable in long term culture (e.g., healthy cells can be maintained at relatively high cell densities for several days to several weeks or months; the cells do not undergo any significant genetic changes during culturing), and allows easy isolation of the viral particles from the cell culture (e.g., by collection and concentration of cell culture supernatant to provide a crude retroviral particle preparation of an acceptable viral titer).

In certain embodiments, retroviral particles can be generated by trans-complementation in packaging cells that are co-transfected with a plasmid containing the retroviral genome and the packaging constructs that encode only the proteins essential for lentiviral assembly and function. A self-inactivating (SIN) lentiviral vector can be generated by eliminating the intrinsic promoter/enhancer activity of the HIV-1 LTR, which reduces the likelihood of aberrant expression of cellular coding sequences located adjacent to the vector integration site. See e.g., Naldini et al, (1996) *Science* 272:263-267; and Matrai et al., (2010) *Molecular Therapy* 18:477-490. In certain embodiments, the method of producing a lentiviral particle comprising co-transfecting packaging cells (e.g., 293T human embryonic kidney cells) with a lentiviral vector plasmid and three packaging constructs encoding the viral Gag-Pol, Rev-Tat, and envelope (Env) proteins. In certain embodiments, the lentiviral vector can integrate its genome into a target cell genome. In certain embodiments, the lentiviral vector is not integrated its genome into a target cell genome. In such cases, the lentiviral vector particle does not integrate its genome into a target cell genome (also referred to as a "non-integrating" vector). Non-integrating lentiviral vectors typically are generated by mutating the lentiviral integrase gene or by modifying the attachment sequences of the LTRs. See e.g., Sarkis et al., (2008) *Curr. Gene. Ther.* 6:430-437. In certain embodiments, lentiviral vectors can be produced by co-transfecting 293T human embryonic kidney cells with several different plasmid constructs, which separately contain the lentiviral cis-acting sequences and trans-acting factors that are required for retroviral particle production, infection, and integration. Lentiviral production protocols are further described in, for example, Tiscornia et al., (2006) *Nature Protocols* 1:241-245; Stevenson, M., (2002) *Curr. Top Microbiol. Immunol.* 261:1-30; Cronin et al., (2005) *Curr. Gene Ther.* 5:387-398; Sandrin et al., (2003) *Curr. Top. Microbiol. Immunol.* 281:137-178; Zufferey, R., (2002) *Curr. Top. Microbiol. Immunol.* 261:107-121; Sinn et al, (2005) *Gene Ther.* 12:1089-1098; and Saenz, D. T. and Poeschla, E. M., (2004) *J. Gene Med.* 6:S95-S104. Other methods for producing lentiviral vectors are known in the art and described in, for example, U.S. Patent Application Publications 2008/0254008 and 2010/0003746; and Yang et al, (2012) *Hum Gene Ther. Methods* 23:73-83.

For additional packaging techniques see, for example, Polo, et al, Proc Natl Acad Sci USA, (1999) 96:4598-4603. Methods of packaging include using packaging cells that permanently express the retroviral components, or by transiently transfecting cells with plasmids.

B. Packaging Cells and Vectors

Also disclosed herein is a packaging cell for producing the retroviral particles described herein comprising one or more plasmids comprising (i) one or more retroviral elements involved in assembly of the retroviral particles and (ii) a nucleic acid sequence encoding a gene-editing fusion molecule. In certain embodiments, the packaging cell further comprises one or more plasmids encoding one or more gRNA and/or comprising a sequence corresponding to one or more repair templates (RT).

In certain embodiments, the invention provides a packaging cell for producing the retroviral particles described herein comprising one or more plasmids comprising (i) one or more retroviral elements involved in assembly of the retroviral particles and (ii) a nucleic acid sequence encoding a Cas fusion RNA and/or a Cas fusion protein. In certain embodiments, the packaging cell further comprises one or more plasmids encoding one or more gRNA and/or comprising one or more sequences corresponding to one or more repair templates (RT).

Packaging cells useful for production of the retroviral particles described herein include, e.g., animal cells permissive for the virus, or cells modified so as to be permissive for the virus; or the packaging cell construct, for example, with the use of a transformation agent such as calcium phosphate. Non-limiting examples of packaging cell lines useful for producing retroviral particles described herein include, e.g., human embryonic kidney 293 (HEK-293) cells (e.g., American Type Culture Collection [ATCC] No. CRL-1573), HEK-293 cells that contain the SV40 Large T-antigen (HEK-293T or 293T), HEK293T/17 cells, human sarcoma cell line HT-1080 (CCL-121), lymphoblast-like cell line Raj i (CCL-86), glioblastoma-astrocytoma epithelial-like cell line U87-MG (HTB-14), T-lymphoma cell line HuT78 (TIB-161), NIH/3T3 cells, Chinese Hamster Ovary cells (CHO) (e.g., ATCC Nos. CRL9618, CCL61, CRL9096), HeLa cells (e.g., ATCC No. CCL-2), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RATI cells, mouse L cells (ATCC No. CCLI.3), HLHepG2 cells, CAP cells, CAP-T cells, and the like.

L929 cells, the FLY viral packaging cell system outlined in Cosset et al (1995) J Virol 69,7430-7436, NS0 (murine myeloma) cells, human amniocytic cells (e.g., CAP, CAP-T), yeast cells (including, but not limited to, *S. cerevisiae, Pichia pastoris*), plant cells (including, but not limited to, Tobacco NT1, BY-2), insect cells (including but not limited to SF9, S2, SF21, Tni (e.g. High 5)) or bacterial cells (including, but not limited to, *E. coli*).

When generating retroviral (e.g., lentiviral) particles of the invention, 2-4 basic components, usually (but not necessarily) provided on separate plasmids, are used: (i) sequences encoding molecules involved in assembly of the lentiviral particle (e.g., a psi-negative gag/pol gene) provided on a packaging plasmid, (ii) sequences encoding a retroviral env protein or a binding molecule to replace the env protein (or as a fusion molecule with a retroviral env protein) provided on an envelope expression plasmid, optionally (iii) sequence(s) encoding one or more gRNA and/or sequence(s) corresponding to one or more repair templates (RT), e.g., provided on a transfer vector together, optionally with one or more retroviral elements needed for facilitating transfer of the transfer vector (e.g., psi packaging signal and LTR), and, optionally, (iv) a sequence encoding a fusogen provided on a fusogen encoding plasmid. The term "fusogen" or "fusogenic molecule" is used herein to refer to any molecule that can trigger membrane fusion when present on the surface of a virus particle. A fusogen can be, for example, a protein (e.g., a viral glycoprotein) or a fragment, mutant or derivative thereof.

Nucleic acids encoding a gene-editing molecule fusion protein (e.g., a Cas fusion RNA) can be transiently expressed in a target cell. A nucleic acid encoding a gene-editing molecule fusion protein can be operably linked to a promoter in an expression construct. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES)

cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters.

In certain embodiments of any of the described methods, the packaging cell comprises an expression plasmid for expressing the gene-editing fusion molecule. In some embodiments of any of the described methods, the packaging cell comprises an expression plasmid for expressing the Cas fusion RNA and/or Cas fusion protein. Suitable expression plasmids are known to those of skill in the art. In certain embodiments, the expression plasmid is pRG984.

In some embodiments of any of the described methods, the packaging cell further comprises one or more transfer vectors or an RNA molecule(s) encoded by the transfer vector, wherein the transfer vector or RNA molecule comprises at least one retroviral element and a sequence encoding one or more gRNA(s) and/or one or more sequences corresponding to one or more repair templates (RT) and, wherein the retroviral particles comprise the transfer vector(s) or RNA molecule(s). In another specific embodiment, the at least one retroviral element is a lentiviral element. In one specific embodiment, the at least one retroviral element is a Psi (ψ) packaging signal. In one specific embodiment, in addition to a Psi (ψ) packaging signal, the retroviral element further comprises a 5' Long Terminal Repeat (LTR) and/or a 3' LTR, or a derivative or mutant thereof. In one specific embodiment, the at least one retroviral element is selected from the group consisting of a 5' Long Terminal Repeat (LTR), a Psi (ψ) packaging signal, a Rev Response Element (RRE), a promoter that drives expression of a gRNA (e.g., H1 or U6), a Central Polypurine Tract (cPPT), a Woodchuck hepatitis virus post-transcriptional regulatory element (WPRE), a Unique 3' (U3), a Repeat (R) region, a Unique 5' (U5), a 3' LTR, a 3' LTR with the U3 element deleted (e.g., to make the lentivirus non-replicative), a Trans-activating response element (TAR), and any combination thereof.

In some embodiments the transfer vector preferably comprises at least one RNA Polymerase II or III promoter. The RNA Polymerase II or III promoter is operably linked to the nucleic acid sequence of interest and can also be linked to a termination sequence. RNA polymerase II and III promoters are well known to one of skill in the art. A suitable range of RNA polymerase III promoters can be found, for example, in Paule and White. Nucleic Acids Research., Vol 28, pp 1283-1298 (2000); Ohkawa and Taira Human Gene Therapy, Vol. 11, pp 577-585 (2000); Meissner et al. Nucleic Acids Research, Vol. 29, pp 1672-1682 (2001). Non-limiting examples of useful promoters include, e.g., cytomegalovirus (CMV)-promoter, the spleen focus forming virus (SFFV)-promoter, the elongation factor 1 alpha (EF1a)-promoter (the 1.2 kb EF1a-promoter or the 0.2 kb EF1a-promoter), the chimeric EF 1 a/IF4-promoter, and the phospho-glycerate kinase (PGK)-promoter. An internal enhancer may also be present in the retroviral construct to increase expression of the gene of interest. For example, the CMV enhancer (Karasuyama et al. 1989. J. Exp. Med. 169:13) may be used. In some embodiments, the CMV enhancer can be used in combination with the chicken β-actin promoter. One of skill in the art will be able to select the appropriate enhancer based on the desired expression pattern. In addition, transfer vector may contain one or more genetic elements designed to enhance expression of the gene of interest. For example, a woodchuck hepatitis virus responsive element (WRE) may be placed into the construct (Zufferey et al. 1999. J. Virol. 74:3668-3681; Deglon et al. 2000. Hum. Gene Ther. 11:179-190).

In some embodiments of any of the described methods, the packaging cell further comprises one or more packaging vectors. In certain embodiments, a packaging plasmid comprises (a) GAG, (b) POL, (c) TAT and/or REV retroviral (e.g., lentiviral) elements, each of which may be considered involved with the assembly of the retroviral particle. In certain embodiments, the packaging plasmid is psPAX2.

In some embodiments of any of the above methods, the one or more plasmids comprise an envelope plasmid. In certain embodiments, an envelope plasmid comprises (a) but not limit to VSV-G, Ebola virus envelope, MLV envelope, LCMV envelope, Rabies virus envelope and/or (b) PolyA. In certain embodiments, the envelope plasmid can be pMD2.G.

In certain embodiments, the envelope of the retroviral particle can be pseudotyped. Pseudotyping is to alter the tropism of the retroviral particle or for generating an increased or decreased stability of a retrovirus particle. As such, foreign viral envelope proteins (heterologous envelope proteins) are introduced into retroviral particle and are typically glycoproteins derived from portions of the membrane of the virus infected host cells or glycoproteins encoded by the virus genome. The structural envelope proteins (e.g., Env, VP1, VP2, or VP3) can determine the range of target cells that can ultimately be infected and transformed by recombinant retroviruses. In the case of lentiviruses, such as HIV-1, HIV-2, SIV, FIV and EIV, the Env proteins include gp41 and gp120. When producing recombinant retroviruses (e.g., recombinant lentiviruses), a wild type retroviral (e.g., lentiviral)) env, vp1, vp2, or vp3 gene can be used, or can be substituted with any other viral env, vp1, vp2, or vp3 gene from another lentivirus or AAV or other virus (such as vesicular stomatitis virus GP (VSV-G)). Methods of pseudotyping recombinant viruses with envelope proteins from other viruses in this manner are well known in the art (see, e.g., WO 99/61639, WO 98/05759, Mebatsion et al., Cell 90:841-847 (1997); Cronin et al., Curr. Gene Ther. 5:387-398 (2005)).

In some embodiments of any of the above methods, the plasmids present in the packaging cell do not comprise a retroviral ENV gene or comprise a mutant non-functional ENV gene. In another embodiment, the one or more plasmids comprise a mutant lentiviral ENV gene, which does not produce gp120 surface envelope protein or gp41 transmembrane envelope or which encodes a mutant gp120 surface envelope protein and/or a mutant gp41 transmembrane envelope protein and wherein the resulting retroviral particle is not capable of binding to a target cell in the absence of an exogenous protein that specifically binds to the target cell.

In some embodiments of any of the above methods, retroviral particle further comprises a fusogen. Many different protein and non-protein fusogens can be used. In some embodiments, the fusogen is a protein. In one specific embodiment, the fusogen is a viral protein. Non-limiting examples of useful viral fusogens include, e.g., vesiculovirus fusogens (e.g., vesicular stomatitis virus G glycoprotein (VSVG)), alphavirus fusogens (e.g., a Sindbis virus glycoprotein), orthomyxovirus fusogens (e.g., influenza HA protein), paramyxovirus fusogens (e.g., a Nipah virus F protein or a measles virus F protein) as well as fusogens from Dengue virus (DV), Lassa fever virus, tick-borne encephalitis virus, Dengue virus, Hepatitis B virus, Rabies virus, Semliki Forest virus, Ross River virus, Aura virus, Borna disease virus, Hantaan virus, SARS-CoV virus, and various fragments, mutants and derivatives thereof. Other exemplary fusogenic molecules and related methods are described, for example, in U.S. Pat. Appl. Pub. 2005/0238626 and 2007/0020238.

In one specific embodiment, the fusogen is heterologous to the virus from which the particle is derived. In one specific embodiment, the fusogen is a mutated protein which does not bind its natural ligand.

There are two recognized classes of viral fusogens and both can be used as targeting molecules (D. S. Dimitrov, Nature Rev. Microbio. 2, 109 (2004)). The class I fusogens trigger membrane fusion using helical coiled-coil structures, whereas the class II fusogens trigger fusion with 13 barrels. In some embodiments, class I fusogens are used. In other embodiments, class II fusogens are used. In still other embodiments, both class I and class II fusogens are used. See, e.g., Skehel and Wiley, Annu. Rev. Biochem. 69, 531-569 (2000); Smit, J. et al. J. Virol. 73, 8476-8484 (1999), Morizono et al. J. Virol. 75, 8016-8020 (2005), Mukhopadhyay et al. (2005) Rev. Microbiol. 3, 13-22.

In some specific embodiments, a form of hemagglutinin (HA) from influenza A/fowl plague virus/Rostock/34 (FPV), a class I fusogen, is used (Hatziioannou et al., J. Virol. 72, 5313 (1998)). In some specific embodiments, a form of FPV HA is used (Lin et al., Hum. Gene. Ther. 12, 323 (2001)). HA-mediated fusion is generally considered to be independent of receptor binding (Lavillette et al., Cosset, Curr. Opin. Biotech. 12, 461 (2001)).

In other embodiments, the Sindbis virus glycoprotein (a class II fusogen) from the alphavirus family is used (Wang et al., J. Virol. 66, 4992 (1992); Mukhopadhyay et al., Nature Rev. Microbio. 3, 13 (2005), Morizono et al., Nature Med. 11, 346 (2005)).

In some embodiments, mutant fusogens are used which maintain their fusogenic ability but have a decreased or eliminated binding ability or specificity. Functional properties of mutant fusogens can be tested, e.g., in cell culture or by determining their ability to stimulate an immune response without causing undesired side effects in vivo.

To select most effective and non-toxic combinations of pseudotyping protein and fusogens (either wild type or mutant), retroviral particles bearing these molecules can be tested for their selectivity and/or their ability to facilitate penetration of the target cell membrane. Retroviral particles that display wild type fusogens can be used as controls for examining titer effects in mutants. For example, cells can be transduced by the retroviral particles using a standard infection assay. After a specified time, for example 48 hours post-transduction, cells can be collected, and the percentage of transduced cells can be determined by, for example, monitoring reporter gene expression (e.g., using FACS analysis). The selectivity can be scored by calculating the percentage of cells infected by the retroviral particles. Similarly, the effect of mutations on viral titer can be quantified by dividing the percentage of cells infected by retroviral particles comprising a mutant targeting molecule by the percentage of cells infected by retrovirus comprising the corresponding wild type targeting molecule. The titers of retroviral particles can be determined, e.g., by limited dilution of the stock solution and transduction of cells expressing the proteins of interest. A preferred mutant will give the best combination of selectivity and infectious titer.

To investigate whether fusogen-mediated cell penetration is dependent upon pH, and select fusogens with the desired pH dependence, $NH_4Cl$ or other compound that alters pH can be added at the infection step ($NH_4Cl$ will neutralize the acidic compartments of endosomes). In the case of $NH_4Cl$, the disappearance of cells expressing the reporter will indicate that penetration of viruses is low pH-dependent. In addition, to confirm that the activity is pH-dependent, lysosomotropic agents, such as ammonium chloride, chloroquine, concanamycin, bafilomycin Al, monensin, nigericin, etc., may be added into the incubation buffer. These agents can elevate the pH within the endosomal compartments (Drose and Altendorf, J. Exp. Biol. 200, 1-8, 1997). The inhibitory effect of these agents will reveal the role of pH for viral fusion and entry. The different entry kinetics between retroviruses displaying different fusogenic molecules may be compared and the most suitable selected for a particular application.

PCR-based retroviral particle entry assays may be utilized to measure kinetics of viral DNA synthesis as an indication of the kinetics of retroviral particle entry. For example, retroviral particles comprising a particular pseudotyping molecule and fusogen can be incubated with target cells, unbound retroviruses can be then removed, and aliquots of the cells can be analyzed by extracting DNA and performing semi-quantitative PCR (e.g., using LTR-specific primers for retroviral particles). The appearance of LTR-specific DNA products will indicate the success of retroviral particle entry and uncoating.

In some embodiments, the pseudotyping molecule and a fusogen are two separate molecules. In other embodiments, they form a single fusion protein.

In preferred embodiments, the fusogen is a viral glycoprotein that mediates fusion or otherwise facilitates delivery of the nucleic acid of interest to the target cell. The fusogen preferably exhibits fast enough kinetics that the retroviral particle contents can empty into the cytosol before the degradation of the retroviral particle. In addition, the fusogen can be modified to reduce or eliminate any binding activity and thus reduce or eliminate any non-specific binding. That is, by reducing the binding ability of the fusogen, binding of the retroviral particles to the target cell is determined predominantly or entirely by the pseudotyping molecule, allowing for high target specificity and reducing undesired side-effects.

The measles virus (MeV), a prototype morbillivirus of the genus Paramyxoviήdae, utilizes two envelope glycoproteins (the fusion protein (F) and the hemagglutinin protein (H)) to gain entry into the target cell. Protein F is a type I transmembrane protein, while protein H is a type II transmembrane domain, i.e., its amino-terminus is exposed directly to the cytoplasmic region. Both proteins thus comprise a transmembrane and a cytoplasmic region. One known function of the F protein is mediating the fusion of viral membranes with the cellular membranes of the target cell. Functions attributed to the H protein include recognizing the receptor on the target membrane and supporting F protein in its membrane fusion function. The direct and highly efficient membrane fusion at the cellular surface membrane is a particular property of measles virus and the morbilliviruses, thus distinguishing themselves from many other enveloped viruses that become endocytosed and will only fuse upon pH drop upon endocytosis. Both proteins are organized on the viral surface in a regular array of tightly packed spikes, H tetramers, and F trimers (Russell et al., Virology 199:160-168, 1994).

In certain embodiments, the fusogenic molecule is a Sindbis virus envelope protein (SIN). The SINdbis virus transfers its RNA into the cell by low pH mediated membrane fusion. SIN contains five structural proteins, E1, E2, E3, 6K and capsid. E2 contains the receptor binding sequence that allows the wild type SIN to bind, while E1 is known to contain the properties necessary for membrane fusion (Konoochik et al., Virology Journal 2011, 8:304). E1, E2, and E3 are encoded by a polyprotein, the amino acid sequence of which is provided, e.g., by Accession No. VHWVB, VHWVB2, and P03316: the nucleic acid sequence is provided, e.g., by Accession No. SVU90536 and V01403 (see also Rice & Strauss, Proc. Nat'l Acad. Sci USA 78:2062-2066 (1981); and Strauss et al., Virology 133:92-110 (1984)).

In certain embodiments, the Sindbis virus envelope protein is mutated (SINmu). In certain embodiments, the mutation reduces the natural tropism of the Sindbis virus. In certain embodiments, a SINmu comprising SIN proteins E1, E2, and E3, wherein at least one of E1, E2, or E3 is mutated as compared to a wild type sequence. For example, one or more of the E1, E2, or E3 proteins can be mutated at one or more amino acid positions. In addition, combinations of mutations in E1, E2, and E3 are encompassed by fusogen as described herein, e.g., mutations in E1 and E2, or in E2 and E3, or E3 and E1, or E1, E2, and E3. In certain embodiments, at least E2 is mutated.

In certain embodiments, the SINmu comprises the following envelope protein mutations in comparison to wild type Sindbis virus envelope proteins: (i) deletion of E3 amino acids 61-64; (ii) E2 KE159-160AA; and (iii) E2 SLKQ68-71AAAA (SEQ ID NOS 144 and 145). In a further embodiment, the SINmu additionally comprises the envelope protein mutation E1 AK226-227SG. Examples of SINmu may be found in, for example, in U.S. Pat. No. 9,163,248; WO2011011584; Cronin et. al., Curr Gene Ther. 2005 August; 5(4): 387-398.

Other Togaviridae family envelopes, e.g., from the Alphavirus genus, e.g., Semliki Forest Virus, Ross River Virus, and equine encephalitis virus, can also be used to pseudotype the vectors described herein. The envelope protein sequences for such Alphaviruses are known in the art.

In certain embodiments, the fusogen is a vesicular stomatitis virus (VSV) envelope protein. In certain embodiments, the fusogen is the G protein of VSV (VSV-G; Burns et al., Proc. Natl. Acad. Sci. U.S.A. 1993, vol. 90, no. 17, p. 1833-'7) or a fragment, mutant, derivative or homolog thereof. VSV-G interacts with a phospholipid component of the cell (e.g., T cell) membrane to mediate viral entry by membrane fusion (Mastromarino et al., J Gen Virol. 1998, vol. 68, no. 9, p. 2359-69; Marsh et al., Adv Virus Res. 1989, vol. 107, no. 36, p. 107-51. Examples of VSV-G may be found in, for example, WO2008058752.

The constructs described herein may also contain additional genetic elements. The types of elements that may be included in the constructs are not limited in any way and will be chosen by the skilled practitioner to achieve a particular result. For example, a signal that facilitates nuclear entry of the RNA corresponding to the transfer vector in the target cell may be included. An example of such a signal is the HIV-1 flap signal.

For additional packaging cells and systems and vectors for packaging the nucleic acid genome into the retroviral particle (including pseudotyped retroviral particles) see, for example, Polo, et al, Proc Natl Acad Sci USA, (1999) 96:4598-4603.

IV. Methods of Treatment and Use

The retroviral particles described herein can be used for various therapeutic applications (in vivo and ex vivo) and as research tools. In one aspect, described herein is a method for treating a disease in a subject in need thereof, the method comprising administering to the subject a therapeutically effective amount of the retroviral particle of the invention or the pharmaceutical composition thereof.

In certain embodiments, target cells may be transduced with the lentiviral particle in vivo, ex vivo or in vitro.

In certain embodiments, the method is for targeted editing of a gene in a target cell comprising introducing into the target cell the retroviral particle of the invention by infection. In certain embodiments, the method is for targeted deletion or addition of a gene in a target cell comprising introducing into the target cell the retroviral particle of the invention. In certain embodiments, the method is for modulating an activity of a gene in a target cell comprising introducing into the target cell the retroviral particle of the invention. In certain embodiments, the method inhibits, suppresses, down regulates, knocks down, knocks out, or silences the expression of a gene product. In certain embodiments, the gene product is a protein. In certain embodiments, the gene product is an RNA. In certain embodiments, the retroviral particle is administered to a subject, wherein the target cell is in the subject. In certain embodiments, the target cell is harvested from the subject prior to introducing the retroviral particle into the target cell, wherein the retroviral particle is introduced to the target cell ex vivo.

In certain embodiments, the method is for treating a disease in a subject in need thereof, the method comprising administering to the subject a therapeutically effective amount of the retroviral particle of the invention or the pharmaceutical composition of the invention. In certain embodiments, the retroviral particle or the pharmaceutical composition is administered, by way of example and not limitation, intravenously, subcutaneously, intramuscularly, transdermally, intranasally, orally, or mucosally.

In certain embodiments, the method is for treating a disease in a subject in need thereof, the method comprising: a) harvesting a target cell from the subject; b) introducing into the target cell from step a) a therapeutically effective amount of the retroviral particle of the invention or the pharmaceutical composition of the invention; and c) returning the target cell from step b) to the subject.

In certain embodiments, the target cell is a HSC. In certain embodiments, the HSCs are transduced in vitro with the retroviral particle or composition comprising the retroviral particle followed by infusion of the transduced stem cells into the subject. For example, the subject's (e.g., human's) stem cell can be removed from the subject using methods well known in the art and transduced as described above. The transduced HSCs are then reintroduced into the same (autologous) or different subject (allogeneic).

Once harvested and transduced with the retroviral particle or composition in vitro, HSCs can be cultured under suitable conditions known in the art (e.g., Csaszar et al., *Cell Stem Cell,* 10(2): 218-29 (2012); Madlambayan et al., *Biol Blood Marrow Transplant.,* 72(10): 1020-1030 (2006); Woods et al., *Stem Cells,* 29(1): 1 158-1 164 (2011); U.S. Patent Application Publications 2002/0061293 and 2012/0071397; and International Patent Application Publication WO 2014/043131; or using commercially available systems (e.g., Life Technologies Corp. and Stem Cell Technologies, Inc.).

In certain embodiments, the target cell can be a somatic cell. In certain embodiments, the somatic cell can be transduced in vitro with the retroviral particle or composition comprising the retroviral particle and cultured under conditions to generate induced pluripotent stem cells (also known as iPS cells or iPSCs). An iPS cell is a type of pluripotent stem cell that can be generated directly from somatic (e.g., adult) cells by introducing appropriate reprogramming factors into somatic cells. A "reprogramming factor" refers to any substance(s) capable of inducing an iPS cell from a somatic cell, and can be a proteinaceous molecule, a nucleic acid sequence encoding same, or a low-molecular compound. Reprogramming factors typically used to generate iPS cells include, but are not limited to, the four genes Oct3/4, Sox2, Klf4, and c-Myc. See e.g., U.S. Pat. No. 8,951,801; International Patent Application Publication WO 2007/069666; and Takahashi, K. and Yamanaka, S., Cell, 126: 663-676 (2006)).

In certain embodiments, the target cell can be a mammalian induced pluripotent stem (iPS) cell that can be derived from various types of somatic cells. The iPS cell preferably is transduced in vitro with the inventive system or composition comprising the inventive system and can be differentiated into hematopoietic stem cells, red blood cells, or other suitable cell type.

In certain embodiments, the somatic cell is a hepatocyte. For example, the present invention also relates to the delivery to the liver, for gene therapy of liver conditions or the creation of liver models. Liver or liver tissue includes parenchymal cells commonly referred to as hepatocytes. Liver or Liver tissue can also be liver cells that are non-parenchymal cells (e.g., sinusoidal hepatic endothelial cells, upffer cells and hepatic stellate cells). Cells of the liver express one or more liver gene product(s). In certain embodiments, the invention is directed to the liver, whether that is the organ per se or a tissue within it or simply one or more liver cells, e.g., hepatocytes. Primary hepatocytes are preferred.

Hepatic targets include, but are not limited to amyloid neuropathy (TTR, PALB); Amyloidosis (APOA1, APP, AAA, CVAP, AD1, GSN, FGA, LYZ, TTR, PALB); Cirrhosis (RT18, T8, CIRH1A, NAIC, TEX292, KJAA1988); cystic fibrosis (CFTR, ABCC7, CF, MRP7); glycogen storage diseases (SLC2A2, GLUT2, G6PC, G6PT, G6PT1, GAA, LAMP2, LAMPB, AGL, GDE, GBE1, GYS2, PYGL, PFKM); hepatic adenoma, 142330 (TCF1, HNF1A, MODY3), hepatic failure, early onset, and neurologic disorder (SCOD1, SCO1), Hepatic lipase deficiency (LIPC), hepatoblastoma, cancer and carcinomas (CTNNB1, PDGFRL, PDGRL, PRLTS, AXIN1, AXFN, CTNNB1, TP53, P53, LFS1, IGF2R, MPRI, MET, CASP8, MCH5; Medullary cystic kidney disease (UMOD, HNFJ, FJHN, MCKD2, ADMCKD2); phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63); blood clotting factors (factor V, factor VII, factor VIII, factor IX, factor X, factor XI, factor XII, factor XIII, prothrombin, fibrinogen, von Willebrand factor or recombinant soluble tissue factor (rsTF) or activated forms of any of the preceding); PCSK9; Hmgcr; SERPINA1; ApoB; and/or LDL.

In certain embodiments, the somatic cell is a lymphocyte. In certain embodiments, the lymphocyte is a T cell. In certain embodiments, the lymphocyte is a B cell. Non-limiting examples of lymphocyte targets include TCRs, BCRs, regulatory elements, artificial TCR like molecules, CARs, etc.

Somatic cells harvested from a subject such as human or mouse can be pre-cultured using any suitable medium known in the art, depending on the cell type. Examples of such media include, but are not limited to, a minimal essential medium (MEM) comprising about 5 to 20% fetal calf serum, Dulbecco's modified Eagle medium (DMEM), RPMI1640 medium, 199 medium, F12 medium, and the like. Methods for culturing somatic cells to produce iPS cells are described in, for example, U.S. Pat. No. 8,951,801, International Patent Application Publication WO 2007/069666; and Takahashi, K. and Yamanaka, S., supra.

In certain aspects, the invention provides a method of altering a DNA sequence in a target cell, the method comprising contacting a target cell comprising a DNA sequence comprising a target locus with the retroviral particle described herein. In certain embodiments, at least one gRNA sequence binds to the DNA sequence in the target cell genome, and the Cas9 protein, or functional fragment or derivative thereof, induces a double strand break in the DNA sequence, thereby altering a DNA sequence in a target cell. In certain embodiments, at least one ZFns and/or TALENs, or functional fragments or derivatives thereof, induces a double strand break in the DNA sequence, thereby altering a DNA sequence in a target cell. In certain embodiments, the method further comprises a repair template. Descriptions of the retroviral particle, the guide RNA sequence, repair template, the target cell, target locus, and gene-editing molecules, or functional fragment or derivative thereof, (e.g., Cas protein, or functional fragment or derivative thereof) are set forth above.

In certain embodiments, the gene-editing molecule cleaves a target locus, to produce double strand DNA breaks. The double strand breaks can be repaired by the target cell by either non-homologous end joining (NHEJ) or homologous recombination. For example, in NHEJ, the double-strand breaks can be repaired by direct ligation of the broken ends to one another. As such, no new nucleic acid material is inserted into the target locus—although, some nucleic acid material may be lost, resulting in a deletion. Homologous recombination entails a repair in which a repair template comprising a second DNA sequence with homology to the cleaved target locus sequence is used as a template for repair of the cleaved target locus sequence, resulting in the transfer of genetic information from the repair template to the target locus. As a result, new nucleic acid material is inserted/copied into the DNA break site. These methods lead to, for example but not limited to, gene correction, gene replacement, gene tagging, transgene insertion, nucleotide deletion, gene disruption, gene mutation, and/or gene knockdown.

In certain embodiments, the invention further comprises a repair template comprising a second DNA sequence, which can be different from the first DNA sequence of the target locus. For example, the first DNA sequence of the target cell can be replaced with the second DNA sequence by homologous recombination following gene-editing-induced cleavage of the first DNA sequence of the target locus. When the retroviral particles are used to correct one or more mutations or defects in a gene, the target locus contains a first DNA sequence that encodes a defective protein and the repair template contains a second DNA sequence that encodes a wild type or corrective version of the defective protein. For example, the first DNA sequence can be a gene associated with a disease, which refers to any gene or polynucleotide whose gene products are expressed at an abnormal level or in an abnormal form in the cells obtained from a subject affected by the disease. In certain embodiments, the disease-associated gene may be expressed at an abnormally high level, where the altered expression correlates with the occurrence and/or progression of the disease. In certain embodiments, the disease-associated gene may be expressed at an abnormally low level, where the altered expression correlates with the occurrence and/or progression of the disease. In certain embodiments, a disease-associated gene can be a mutation or genetic variation of the gene, which is directly or indirectly responsible for the etiology of a disease.

In certain embodiments, the method can be used to delete nucleic acids from a target locus in a target cell by cleaving the target sequence and allowing the target cell to repair the cleaved sequence in the absence of a repair template. Deletion of a nucleic acid sequence in this manner can be used to, as an example but not a limitation, create gene knockouts or knock-downs, knock-ins and generate mutations for disease models in research.

In certain embodiments, the method can be used to knock-in a nucleic acid that encodes by way of example but not limitation, a protein, an siRNA, an miRNA, etc or a tag (e.g., FLAG, HA, His, GPF), a regulatory sequence to a gene (e.g., a promoter, polyadenylation signal, internal ribosome entry sequence (IRES), 2A peptide, start codon, stop codon, splice signal, localization signal, etc.), or to modify a nucleic acid sequence (e.g., introduce a mutation).

V. Pharmaceutical Compositions, Dosage Forms and Administration

Also disclosed herein are pharmaceutical compositions comprising the retroviral particles described herein and a pharmaceutically acceptable carrier and/or excipient. In addition, disclosed herein are pharmaceutical dosage forms comprising the retroviral particle described herein.

Pharmaceutical compositions based on the vector particles disclosed herein can be formulated in any conventional manner using one or more physiologically acceptable carriers and/or excipients. The vector particles may be formulated for administration by, for example, injection, inhalation or insulation (either through the mouth or the nose) or by oral, buccal, parenteral or rectal administration, or by administration directly to a tumor.

The pharmaceutical compositions can be formulated for a variety of modes of administration, including systemic, topical or localized administration. Techniques and formulations can be found in, for example, Remmington's Pharmaceutical Sciences, Meade Publishing Co., Easton, Pa. For systemic administration, injection is preferred, including intramuscular, intravenous, intraperitoneal, and subcutaneous. For the purposes of injection, the pharmaceutical compositions can be formulated in liquid solutions, preferably in physiologically compatible buffers, such as Hank's solution or Ringer's solution. In addition, the pharmaceutical compositions may be formulated in solid form and redissolved or suspended immediately prior to use. Lyophilized forms of the pharmaceutical composition are also suitable.

For oral administration, the pharmaceutical compositions may take the form of, for example, tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycolate); or wetting agents (e.g. sodium lauryl sulfate). The tablets can also be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. ationd oil, oily esters, ethyl alcohol or fractionated vegetable oils); and preservatives (e.g. methyl or propyl-p-hydroxybenzoates or sorbic acid). The preparations can also contain buffer salts, flavoring, coloring and sweetening agents as appropriate.

The pharmaceutical compositions can be formulated for parenteral administration by injection, e.g. by bolus injection or continuous infusion. Formulations for injection can be presented in a unit dosage form, e.g. In ampoules or in multi-dose containers, with an optionally added preservative. The pharmaceutical compositions can further be formulated as suspensions, solutions or emulsions in oily or aqueous vehicles, and may contain other agents including suspending, stabilizing and/or dispersing agents.

Additionally, the pharmaceutical compositions can also be formulated as a depot preparation. These long acting formulations can be administered by implantation (e.g. subcutaneously or intramuscularly) or by intramuscular injection. Thus, for example, the compounds may be formulated with suitable polymeric or hydrophobic materials (e.g. as an emulsion in an acceptable oil) or ion exchange resins, or as sparingly soluble derivatives, for example, as a sparingly soluble salt. Other suitable delivery systems include microspheres, which offer the possibility of local noninvasive delivery of drugs over an extended period of time. This technology can include microspheres having a precapillary size, which can be injected via a coronary catheter into any selected part of an organ without causing inflammation or ischemia. The administered therapeutic is men slowly released from the microspheres and absorbed by the surrounding cells present in the selected tissue.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts, and fusidic acid derivatives. In addition, detergents may be used to facilitate permeation. Transmucosal administration can occur using nasal sprays or suppositories. For topical administration, the vector particles described herein can be formulated into ointments, salves, gels, or creams as generally known in the art. A wash solution can also be used locally to treat an injury or inflammation in order to accelerate healing.

Pharmaceutical forms suitable for injectable use can include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid. It must be stable under the conditions of manufacture and certain storage parameters (e.g. refrigeration and freezing) and must be preserved against the contaminating action of microorganisms, such as bacteria and fungi.

If formulations disclosed herein are used as a therapeutic to boost an immune response in a subject, a therapeutic agent can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents known in the art. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions can be prepared by incorporating the active compounds or constructs in the required amount in the appropriate solvent with various of the other ingredients enumerated above, as required, followed by filtered sterilization.

Upon formulation, solutions can be administered in a manner compatible with the dosage formulation and in such amount as is therapeutically effective. The formulations are easily administered in a variety of dosage forms, such as the type of injectable solutions described above, but slow release capsules or microparticles and microspheres and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intratumorally, intramuscular, subcutaneous and intraperitoneal administration. In this context, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion.

The person responsible for administration will, in any event, determine the appropriate dose for the individual subject. For example, a subject may be administered retroviral particles described herein on a daily or weekly basis for a time period or on a monthly, bi-yearly or yearly basis depending on need or exposure to a pathogenic organism or to a condition in the subject (e.g. cancer).

In addition to the compounds formulated for parenteral administration, such as intravenous, intratumorally, intradermal or intramuscular injection, other pharmaceutically acceptable forms include, e.g., tablets or other solids for oral administration; liposomal formulations; time release capsules; biodegradable and any other form currently used.

One may also use intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 7.5. In addition, antimicrobial preservatives, similar to those used in ophthalmic preparations, and appropriate drug stabilizers, if required, may be included in the formulation. Various commercial nasal preparations are known and can include, for example, antibiotics and antihistamines and are used for asthma prophylaxis.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will include an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

Further embodiments disclosed herein can concern kits for use with methods and compositions. Kits can also include a suitable container, for example, vials, tubes, mini- or microfuge tubes, test tube, flask, bottle, syringe or other container. Where an additional component or agent is provided, the kit can contain one or more additional containers into which this agent or component may be placed. Kits herein will also typically include a means for containing the retroviral particles and any other reagent containers in close confinement for commercial sale. Such containers may include injection or blow-molded plastic containers into which the desired vials are retained. Optionally, one or more additional active agents such as, e.g., anti-inflammatory agents, anti-viral agents, anti-fungal or anti-bacterial agents or anti-tumor agents may be needed for compositions described.

Dose ranges and frequency of administration can vary depending on the nature of the retroviral particles and the medical condition as well as parameters of a specific patient and the route of administration used. In some embodiments, retroviral particle compositions can be administered to a subject at a dose ranging from about $1 \times 10^5$ plaque forming units (pfu) to about $1 \times 10^{15}$ pfu, depending on mode of administration, the route of administration, the nature of the disease and condition of the subject. In some cases, the retroviral particle compositions can be administered at a dose ranging from about $1 \times 10^6$ pfu to about $1 \times 10^8$ pfu, or from about $1 \times 10^8$ pfu to about $1 \times 10^{12}$ pfu. A more accurate dose can also depend on the subject in which it is being administered. For example, a lower dose may be required if the subject is juvenile, and a higher dose may be required if the subject is an adult human subject. In certain embodiments, a more accurate dose can depend on the weight of the subject.

Compositions disclosed herein may be administered by any means known in the art.

For example, compositions may include administration to a subject intravenously, intratumorally, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intrathecally, subcutaneously, subconjunctival, intravesicularlly, mucosally, intrapericardially, intraumbilically, intraocularly, orally, locally, by inhalation, by injection, by infusion, by continuous infusion, by localized perfusion, via a catheter, via a lavage, in a cream, or in a lipid composition.

Any method known to one skilled in the art maybe used for large scale production of retroviral particles, packaging cells and vector constructs described herein. For example, master and working seed stocks may be prepared under GMP conditions in qualified primary CEFs or by other methods. Packaging cells may be plated on large surface area flasks, grown to near confluence and retroviral particles purified. Cells may be harvested, and retroviral particles released into the culture media isolated and purified, or intracellular retroviral particles released by mechanical disruption (cell debris can be removed by large-pore depth filtration and packaging cell DNA digested with endonuclease). retrovirus particles may be subsequently purified and concentrated by tangential-flow filtration, followed by diafiltration. The resulting concentrated bulk maybe formulated by dilution with a buffer containing stabilizers, filled into vials, and lyophilized. Compositions and formulations may be stored for later use. For use, lyophilized retroviral particles may be reconstituted by addition of diluent.

Certain additional agents used in the combination therapies can be formulated and administered by any means known in the art.

Compositions as disclosed herein can also include adjuvants such as aluminum salts and other mineral adjuvants, tensoactive agents, bacterial derivatives, vehicles and cytokines. Adjuvants can also have antagonizing immunomodulating properties. For example, adjuvants can stimulate Th1 or Th2 immunity. Compositions and methods as disclosed herein can also include adjuvant therapy.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Analysis of the Ability of CypA and Vpr Fusions to Effectively Enrich Cas9 Protein into Lentiviral Particles This example investigated the ability of CyclophilinA (CypA) and Vpr fusions to effectively enrich Cas9 protein into lentiviral particles. FIG. 1A depicts retroviral particle structure with Cas9 protein fusions and lentiviral genome carrying a gRNA that targets the GFP nucleotide sequence (SEQ ID NO: 59) driven by hU6 promoter (pLVX hU6 GFP gRNA IRES puro, SEQ ID NO: 60). CypA is a host protein interacting with lentivirus Gag proteins and highly enrich in lentiviral particles (Human immunodeficiency virus type 1 Gag protein binds to cyclophilins A and B Cell. 1993 Jun. 18; 73(6):1067-78). Vpr is a lentiviral accessory protein. Two Cas9 constructs, pRG984 CypA-Cas9 (SEQ ID NO: 61) and pRG984 Cas9-Vpr (SEQ ID NO: 62) were made to express CypA-Cas9 and Cas9-Vpr fusion proteins. The ability of CypA and Vpr to enrich functional Cas9 proteins into lentiviral particles was assayed by measuring the level of eGFP knockout in a cell, wherein eGFP was introduced by lentivirus and named 293 T pLVX EF1a eGFP IRES puro c12 cell (SEQ ID NO: 63). Once the functional Cas9/GFP gRNA targets the GFP nucleotide sequence, the cells modified to express GFP will not fluoresce when detected by FACS. Constructs pLVX EF1a eGFP IRES puro (SEQ ID NO: 63). The eGFP DNA was inserted into pLVX EF1a IRES puro (Clontech) vector using Spe1 and Not 1 restriction sites.

pLVX hU6 GFP gRNA EF1a IRES puro (SEQ ID NO: 60). Gblock containing the hU6 promoter and GFP guide RNA (gRNA) sequence (GGGCGAGGAGCTGTTCACCG; SEQ ID NO: 59) was ordered and cloned into pLVX EF1a IRES puro plasmid at the Cla1 restriction site using sequence and ligation independent cloning.

pRG984 Cas9 (SEQ ID NO: 64). 5 g blocks (from Integrated DNA technologies) of Cas9 gene with overhangs were ordered from IDT and cloned into pRG984 plasmid using Gibson assembly methods.

pRG984 CypA-Cas9 (SEQ ID NO: 61). Gblock containing CypA nucleotide sequences was ordered from IDT and inserted into pRG984 Cas9 plasmid using Xho1 restriction site and sequence and ligation-independent cloning (Methods Mol Biol., 2012; 852:51-9).

pRG984 Cas9-Vpr (SEQ ID NO: 62). Gblock containing Vpr nucleotide sequences were ordered from IDT and inserted into pRG984 Cas9 plasmid using Not1 restriction site and sequence and ligation-independent cloning.

| Plasmids used in making lentiviral particles in FIG. 2 | | | | |
|---|---|---|---|---|
| Panel | Envelope | Helper | Genome | Cas9 |
| B | pMD2.G | psPAX2 | pLVX EF1a IRES puro SEQ ID NO: 68 (Clontech Cat# 631988) | pRG984 Cas9 SEQ ID NO: 64 |
| C | pMD2.G | psPAX2 | pLVX hU6 gGFP EF1a IRES puro SEQ ID NO: 60 | pRG984 Cas9 SEQ ID NO: 64 |
| D | pMD2.G | psPAX2 | pLVX hU6 gGFP EF1a IRES puro SEQ ID NO: 60 | pRG984 CypA-Cas9 SEQ ID NO: 61 |
| E | pMD2.G | psPAX2 | pLVX hU6 gGFP EF1a IRES puro SEQ ID NO: 60 | pRG984 Cas9-Vpr SEQ ID NO: 62 |

Lentiviral Particle Production

Lentiviral production was performed using three- or four-plasmid transfection method. Cells are plated one day prior to PEFpro (Polyplus transfection, New York, NY)-mediated transfection with appropriate vectors, one envelope plasmid, pMD2.G, one plasmid containing lentiviral gag/pol psPAX2 and one genome plasmid. When preparing a lentivirus carrying Cas9 mRNA, one more plasmid expressing Cas9 was added. For each 10 cm plate, 4 μg of envelope and gag/pol plasmids, 8 μg of genome plasmid and 8 μg of Cas9 plasmid (if required) were mixed with PEIpro at 1:1 ratio (1 μg DNA: 1 μPEIpro). 48 hours after transfection, the culture medium was collected, filtered through 0.45 µm filter, and treated with DNase I at 37° C. for 1 hour. Then the medium was ultra-centrifuged at 25000 rpm for 90 min. Pellet was suspended with PBS buffer. Virol titer was measured by quantitative PCR (qPCR) using Lenti-X™ qRT-PCR Titration Kit (Takara) according to the manufacturer's protocol.
Construction of 293T pLVX EF1a eGFP IRES Puro c12 Cell Line Lentivirus with LVX EF1a eGFP IRES (SEQ ID NO: 60) puro genome was produced and titrated. 1E7 vg of virus was added to 1E7 cells in 15 cm cells. 24 hours after infection, cells were put in 1 µg/ml selection for 7 days. Single colonies were picked and analyzed by FACS. Clone 12 with low GFP intensity was used in the following experiment.

Figure 2A:
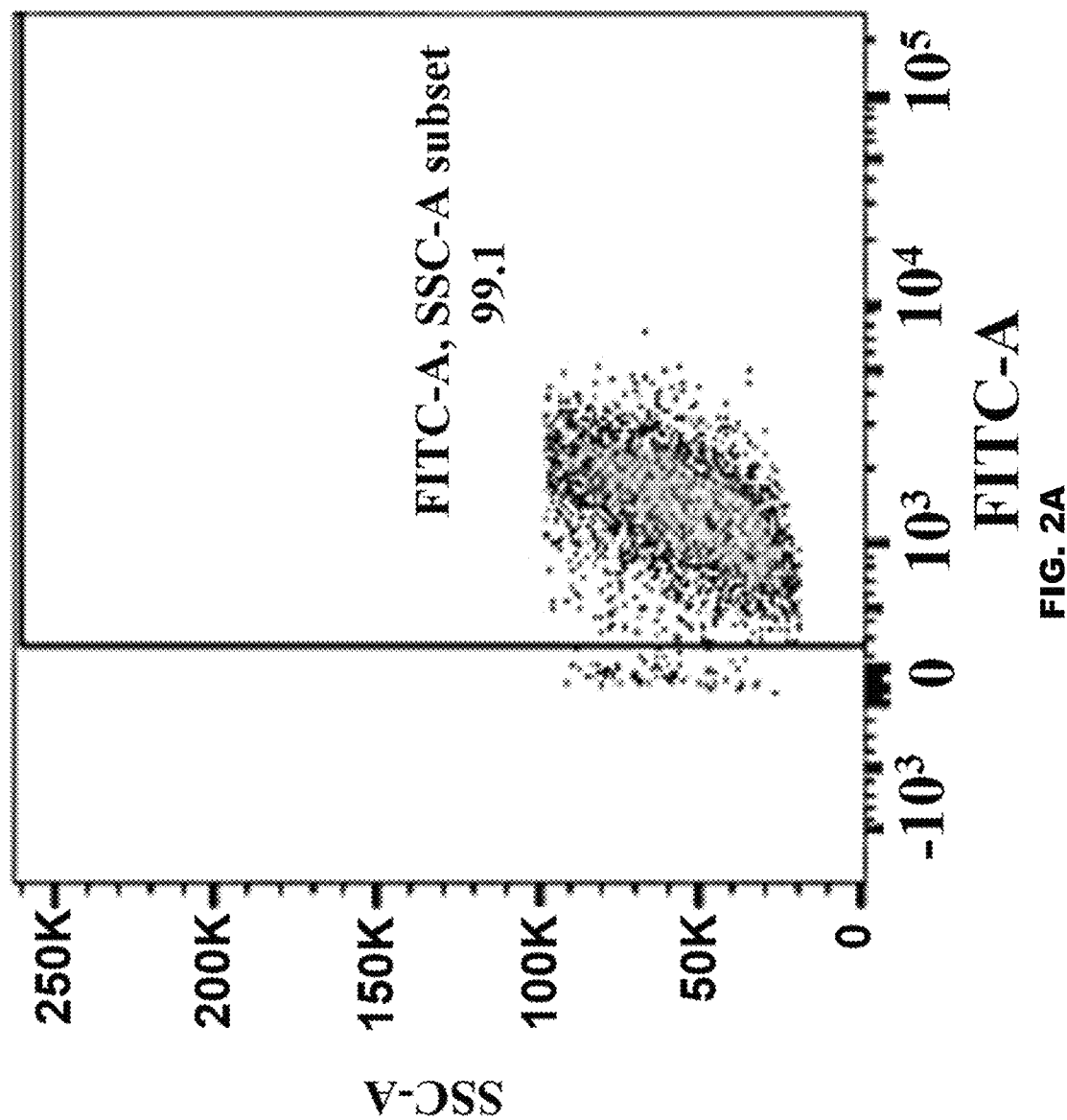
(FIG. 2A) mock infection.
Figure 2B:
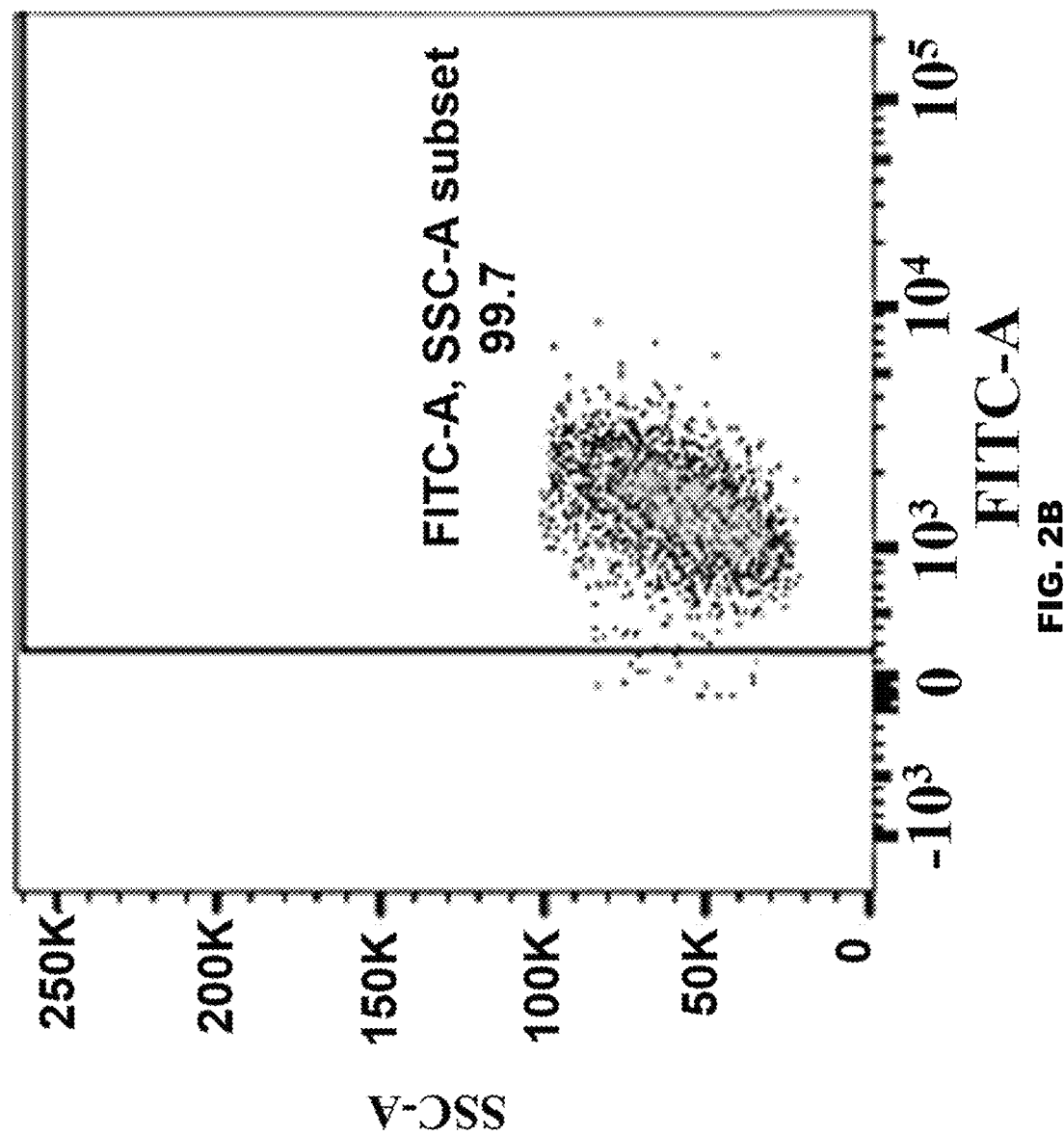
(FIG. 2B) Cas9/non-gRNA: a lentiviral particle carrying randomly packaged Cas9 mRNA or proteins, but no gRNA on lentiviral genome.
Figure 2D:
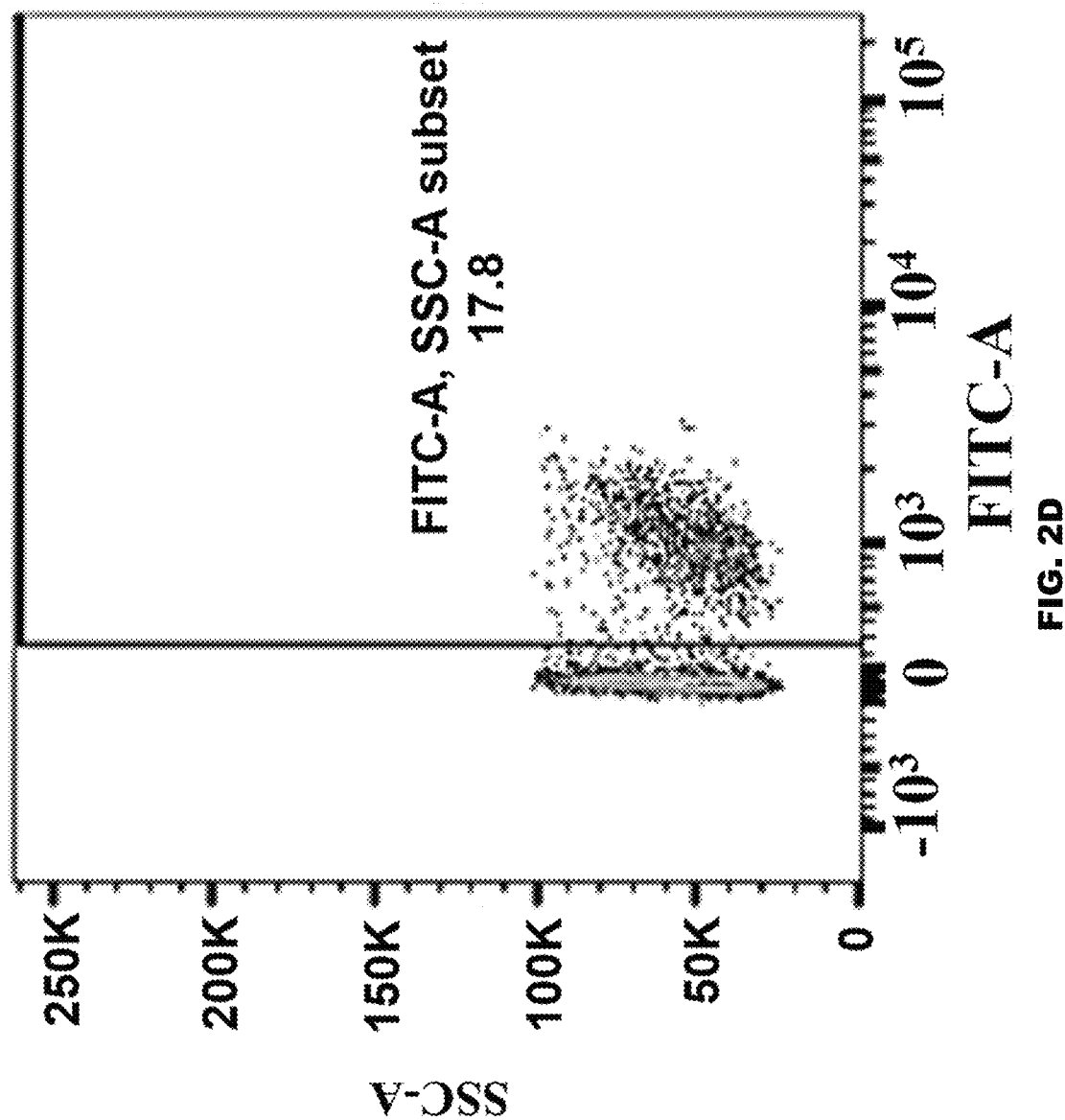
(FIG. 2D) CypA-Cas9/GFP gRNA: a lentiviral particle carrying CypA-Cas9 fusion protein and gRNA.
Figure 2E:
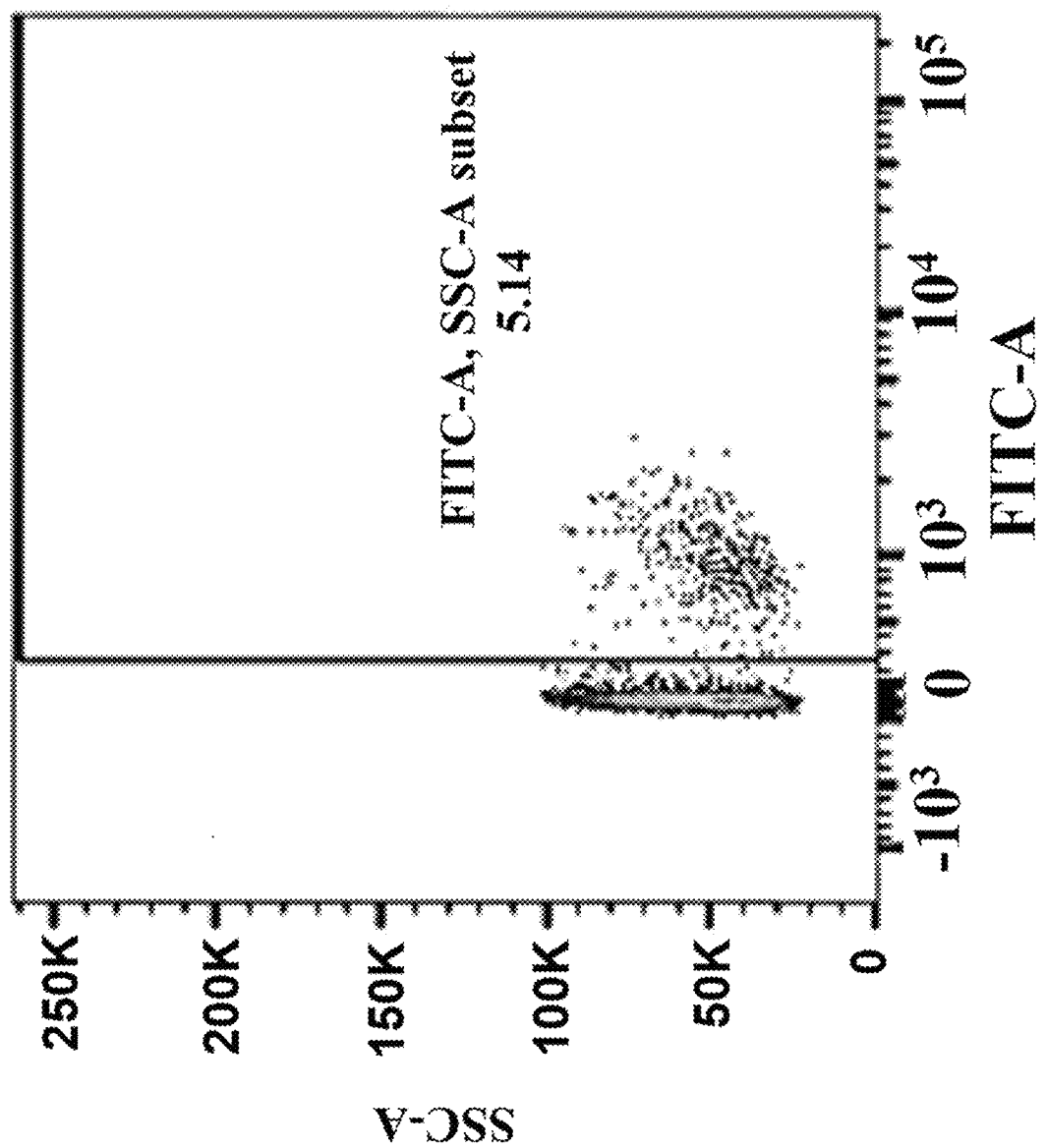
(FIG. 2E) Cas9-Vpr/GFP gRNA: a lentiviral particle carrying Cas9-Vpr fusion protein and gRNA.
Figure 2F:
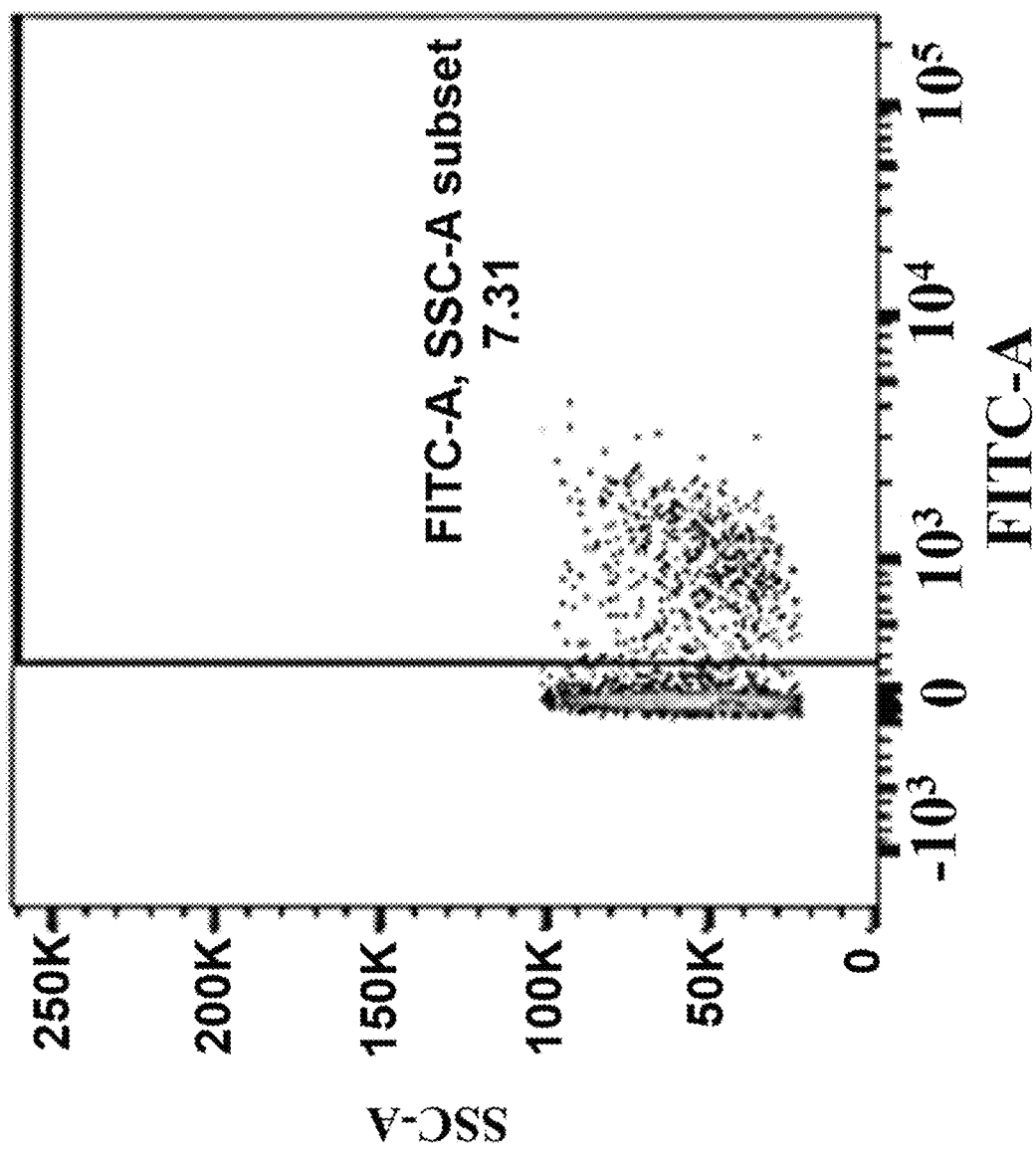
(FIG. 2F) a lentiviral particle carrying 7SL RNA-Cas9 mRNA fusion RNA and gRNA.
Figure 2G:
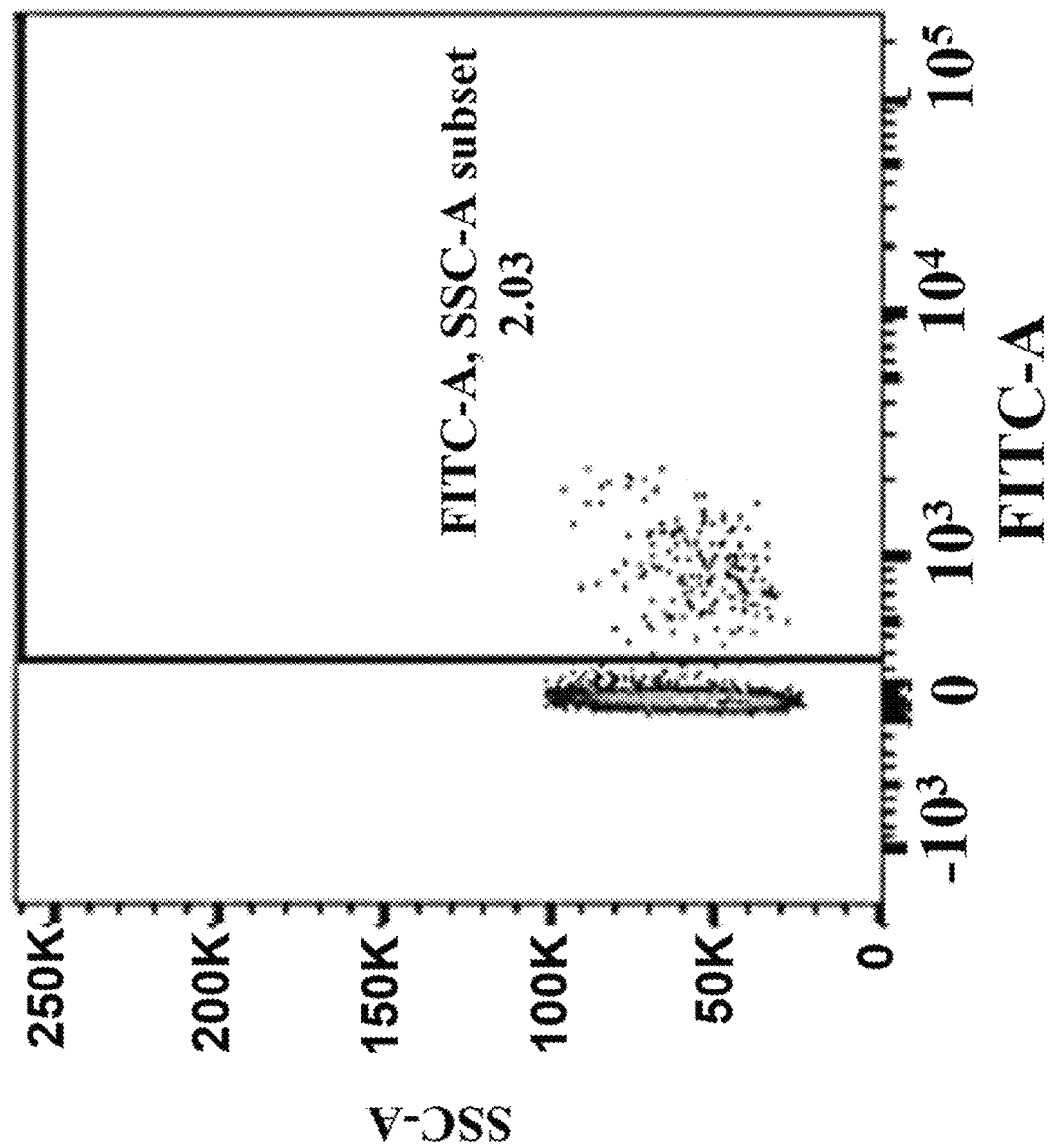
(FIG. 2G) a lentiviral particle carrying Cas9 mRNA-7SL RNA fusion RNA and gRNA. All gRNAs are on the lentiviral genome driven by hU6 promoter. Lentiviral particles are produced by transfecting corresponding plasmids in Tables 2 and 3 into 293T cells and harvested by ultracentrifugation. 1E9 vg of viruses were added to 50,000 of 293T pLVX EF1a eGFP IRES puro c12 cells. FACS was performed 7 days after infection.

1E10 vg of lentiviral particles were added to 50,000 293T pLVX EF1a eGFP IRES puro c12 cells. Six days after infection, the GFP signal was analyzed by FACS. Without GFP gRNA, Cas9/non-gRNA lentiviral particles did not knock out GFP (FIG. 2B). In cells infected with Cas9/GFP gRNA lentiviral particles, about 16.4% of cells were GFP negative which indicates that Cas9 protein could be randomly packaged into lentiviral particles. Cells infected with CypA-Cas9/GFP gRNA lentiviral particles were 82.2% GFP negative (FIG. 2D), which indicates that fusion to CypA sequence enriches Cas9 protein in lentiviral particles. Cells infected with Cas9-Vpr/GFP gRNA lentiviral particles were 94.9% GFP negative (FIG. 2E), which indicates that fusion to Vpr sequence enriches Cas9 protein in lentiviral particles.

Example 2: Recruitment of Cas9 Proteins and mRNAs in Lentiviral Particles

This example investigated the use of 7SL RNA-Cas9 mRNA fusion RNA molecules (FIGS. 1A and B) to enrich Cas9 mRNA in lentiviral particles. This study took advantage of the fact that 7SL RNA, highly enriched in retroviral particles via interacting with Gag protein (J Virol. 2010 September; 84(18): 9070-9077), is the most abundant non-viral RNA found in lentiviruses (see, e.g., Eckwahl et al., mBio, 2016, 7(1):e02025-15). In particular, lentiviral particles were produced in a cell culture in the presence of the Cas9 mRNA (SEQ ID NO: 2), 7SL RNA-Cas9 mRNA fusion RNA (SEQ ID NO: 3) or Cas9 mRNA-7SL RNA fusion RNA (SEQ ID NO: 4). The ability of 7SL RNA to enrich Cas9 mRNA into lentiviral particles was assayed by measuring the level of eGFP knockout in a cell, wherein eGFP was introduced by lentivirus and named 293 T pLVX EF1a GFP IRES puro c12 cell (SEQ ID NO: 63). Once the functional Cas9/GFP gRNA targets the GFP nucleotide sequence, the cells modified to express GFP will not fluoresce when detected by FACS.
Constructs pRG984 7SL RNA-Cas9 (SEQ ID NO: 66). Gblocks containing 7SL RNA sequence were ordered and inserted into pRG984 Cas9 plasmid using Spe1 restriction site and sequence and ligation-independent cloning (SLIC) to make pRG984 7SL RNA-Cas9, in which the 7SL sequence is located before the start codon of Cas9.

pRG984 Cas9-7SL RNA (SEQ ID NO: 67). Gblocks containing 7SL RNA sequence were ordered and inserted into pRG984 Cas9 plasmid using Not1 restriction site and sequence and ligation-independent cloning (SLIC) to make pRG984 Cas9-7SL RNA, in which the 7SL sequence is located at after the stop codon of Cas9.

TABLE 3

Plasmids used in making lentiviral particles in FIG. 2

| Panels | Envelope | Helper | Genome | Cas9 |
|---|---|---|---|---|
| B | pMD2.G | psPAX2 | pLVX EF1a IRES puro SEQ ID NO: 68 | pRG984 Cas9 SEQ ID NO: 64 |
| C | pMD2.G | psPAX2 | pLVX hU6 gGFPEF1a IRES puro SEQ ID NO: 60 | pRG984 Cas9 SEQ ID NO: 64 |
| F | pMD2.G | psPAX2 | pLVX hU6 gGFPEF1a IRES puro SEQ ID NO: 60 | pRG984 7SL-Cas9 SEQ ID NO: 66 |
| G | pMD2.G | psPAX2 | pLVX hU6 gGFPEF1a IRES puro SEQ ID NO: 60 | pRG984 Cas9-7SL SEQ ID NO: 67 |

Figure 3:
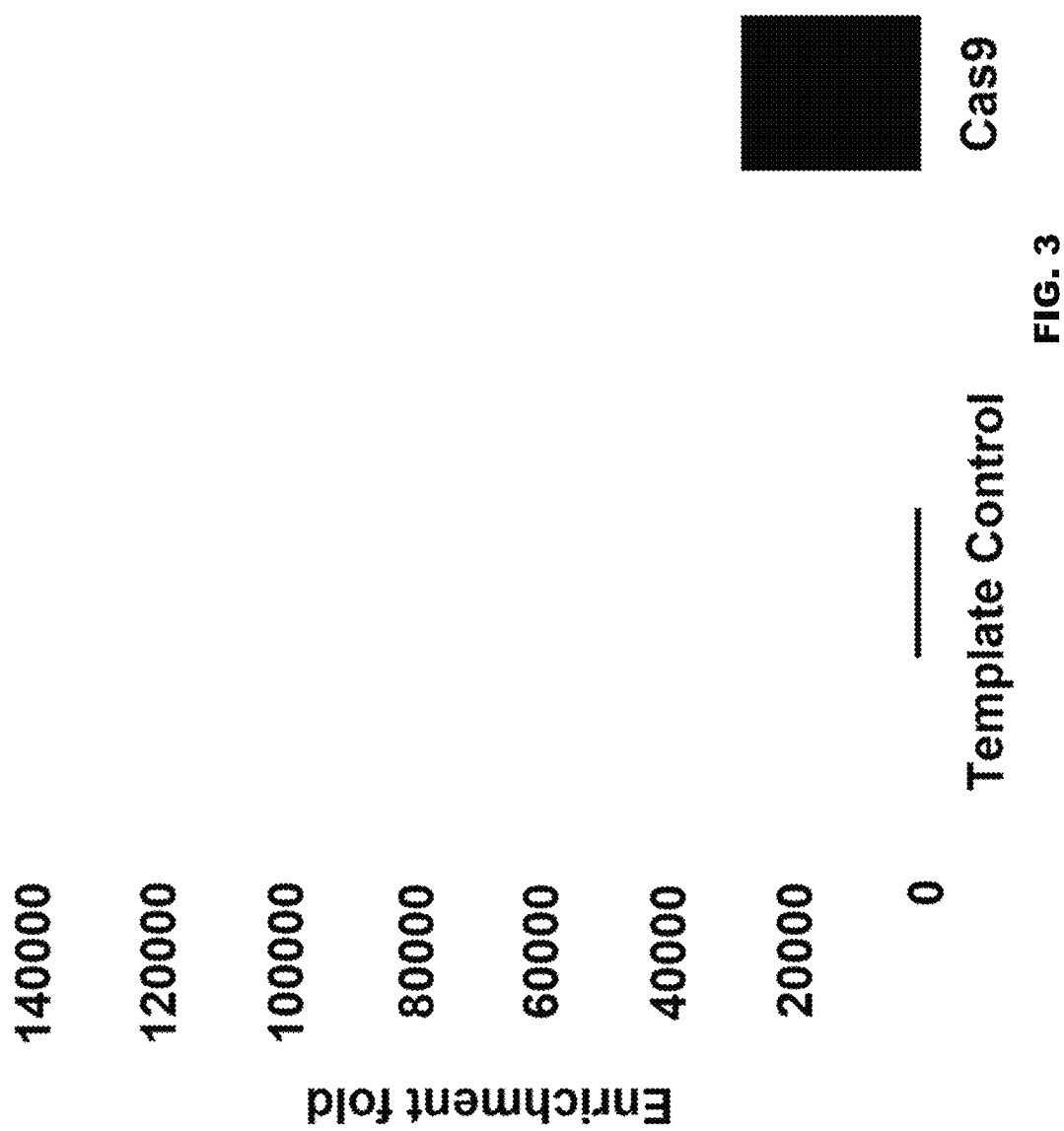
FIG. 3 shows Sybr green quantitative PCR (qPCR) data (Thermofisher scientific Cat #11762100) demonstrating the enrichment of Cas9 mRNA in the lentiviral particles upon fusion to 7SL RNA. Depicted are the qPCR results obtained using RNA extracted from: (i) a standard lentiviral RNA from the Lenti-X qPCR titration kit (Clontech #631235), lentiviral particles randomly packaged; (ii) Cas9 mRNA; and/or (iii) 7SL RNA-Cas9 mRNA fusion RNA molecule. Two primers detecting lentiviral genome and Cas9 mRNA were used (sequences: Cas9F GACAGGCACAGCAT-CAAGAA (SEQ ID NO: 69) Cas9R TTCTGGCGGTTCTCTTCAGT (SEQ ID NO: 70)). The Cas9 mRNA level was normalized to lentiviral genome level.

The amount of Cas9 mRNA recruited in the lentiviral particles was assayed using qPCR and primers specific for Cas9 [Cas9F GACAGGCACAGCATCAAGAA (SEQ ID NO: 69) Cas9R TTCTGGCGGTTCTCTTCAGT (SEQ ID NO: 70)]. Assembly of lentiviral particles in the presence of the Cas9 mRNA-7SL RNA fusion RNA surprisingly resulted in a 4-fold increase in the amount of Cas9 mRNA in lentiviral particles as compared to the amount of Cas9 mRNA in lentiviral particles assembled in the presence of Cas9 mRNA without 7SL RNA fusion (FIG. 3).

1E10 vg of lentiviral particles were added to 50,000 293T pLVX EF1a eGFP IRES puro c12 cells. Six days after infection, the GFP signal was analyzed by FACS. Without GFP gRNA, Cas9/non-gRNA lentiviral particles did not knock out GFP (FIG. 2B). In cells infected with Cas9/GFP gRNA lentiviral particles, about 17% of cells were GFP negative, which indicates that Cas9 proteins or mRNA could be randomly packaged into lentiviral particles. Cells infected with 7SL Cas9/GFP gRNA or Cas9 7SL/GFP gRNA lentiviral particles were 93% or 97% GFP negative (FIGS. 2F and G), which indicates that fusion to 7SL RNA sequence enriches Cas9 mRNA in lentiviral particles.

Figure 4:
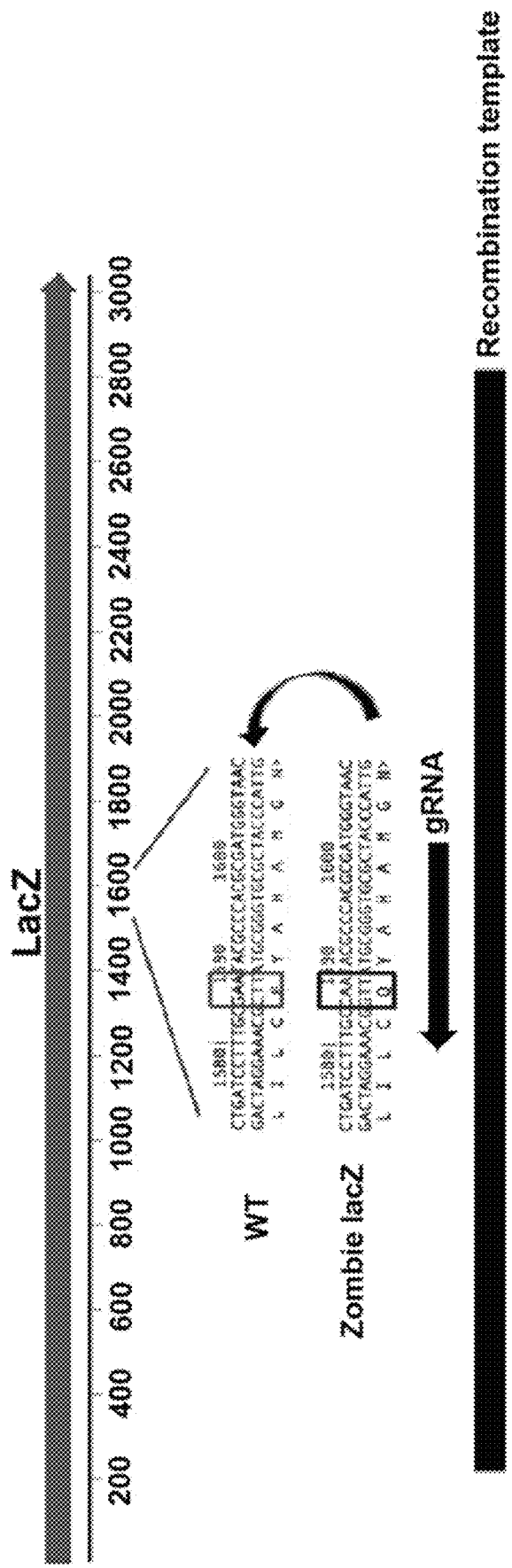
FIG. 4 is a schematic representation of a nucleic acid molecule comprising the wild type (WT) LacZ and Zombie LacZ (Q585E mutation), which has abolished enzymatic activity. A functional Cas9/gRNA system can convert the Zombie LacZ to WT LacZ.
Figure 5A:
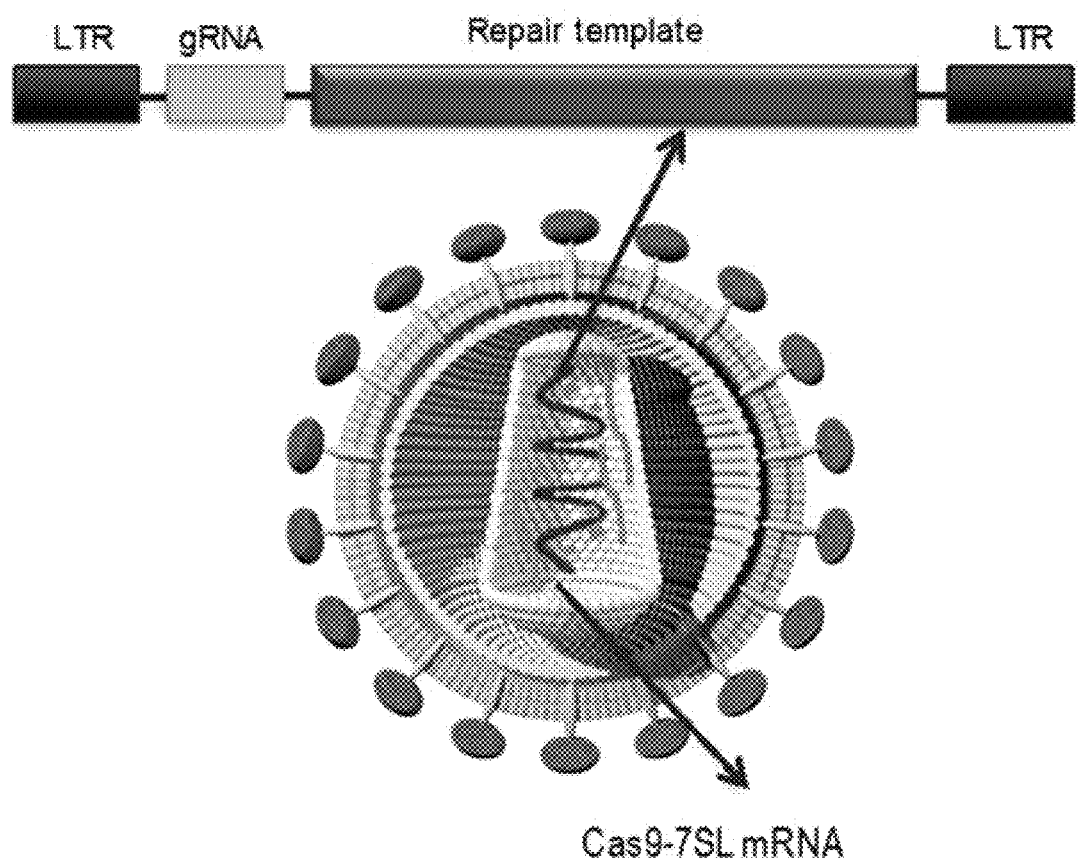
FIG. 5A is a schematic representation of LV gRNA/RT/Cas9 7SL, a lentivirus carrying Zombie LacZ gRNA and repair template on its genome and Cas9-7SL fusion RNA.
Figure 5B:
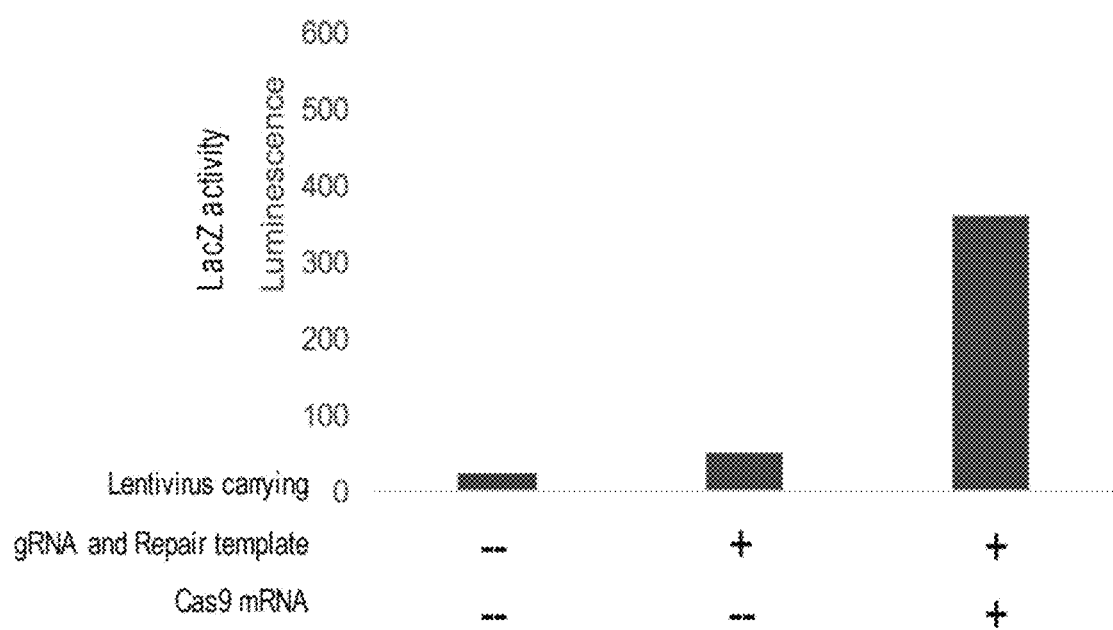
FIG. 5B is a graph showing the results of luminescence assay analysis evaluating β-galactosidase expression (i.e., the ability to convert the Zombie LacZ to WT LacZ) upon infection of pShuttle CMV Zombie lacZ transfected 293T cells with (i) a mock lentiviral vector system; (ii) gRNA/RT: a lentiviral particle carrying Zombie lacZ gRNA and repair template (RT); and (iii) gRNA/RT/Cas9 7SL: a lentiviral particle carrying gRNA and RT in its genome and Cas9 mRNA-7SL RNA fusion RNA. Lentiviral particles are produced by transfecting corresponding plasmids in Table 4 into 293T cells and harvested by ultracentrifugation.

Example 3: Testing of Functionality of the Cas9 mRNA 7SL RNA Fusions Incorporated in Lentiviral Particles by Assaying Rescue of Zombie LacZ Zombie LacZ is a defective lacZ which contains a mutation of Q530E (FIG. 4). 293T cells were transfected with pShuttle CMV zombie lacZ (SEQ ID NO: 71). 24 hours after transfection, lentiviral particles which contain zombie lacZ gRNA (SEQ ID NO: 72 and repair template (SEQ ID NO: 73) in their genome and Cas9 mRNA-7SL RNA fusion RNA (SEQ ID NO: 4) were added to the cells (FIG. 5A). 96 hours after infection, cells were lysed and lacZ activity was analyzed by the Beta-Glo® Assay System (Promega). Infection with lentiviral particles carrying lacZ gRNA and repair template resulted in slightly higher lacZ activity than the background which indicates background recombination between repair template and zombie lacZ. Infection with lentiviral particles carrying zombie lacZ gRNA and repair template (RT) in their genome and Cas9 mRNA-7SL RNA fusion RNA significantly increased the lacZ activity.
Constructs pShuttle CMV Zombie lacZ (SEQ ID NO: 71). LacZ gene was cloned into pShuttle CMV vector using XhoI and HindIII restriction site to make pShuttle CMV lacZ. Mutation Q530 (GAA) was introduced into pShuttle CMV lacZ to make pShuttle CMV zombie lacZ by SLIC methods. Two fragments with overhangs were amplified by PCR using primers listed below and put back into pShuttle CMV lacZ vector digested by XhoI and HindIII site.

lacZF
(SEQ ID NO: 74)
CGACGCGGCCGCTCGAG (XhoI)

QtoER
(SEQ ID NO: 75)
TGGGCGTATTGGCAAAGGAT

QtoEF
(SEQ ID NO: 76)
ATCCTTTGCCAATACGCCCA lacZR
(SEQ ID NO: 77)
CGGATATCTTATCTAGAAGCTT pLVX hU6 gZlacZ repair template (RT) (SEQ ID NO: 78). Gblock containing hU6 promoter and zombie lacZ gRNA was ordered form IDT and cloned into pLVX EF1a IRES Puro vector at ClaI site. 2.8 kb of lacZ repair template with PAM site mutated was synthesized and replaced the EF1a promoter in pLVX EF1a IRES puro.

TABLE 4

Plasmids used in making lentiviral particles

| Construct | Envelope | Helper | Genome | Cas9 |
|---|---|---|---|---|
| (ii) | pMD2.G | psPAX2 | pLVX hU6 zombie lacZ gRNA repair template SEQ ID NO: 78 | N/A |
| (iii) | pMD2.G | psPAX2 | pLVX hU6 zombie lacZ gRNA repair template SEQ ID NO: 78 | pRG984 Cas9-7SL SEQ ID NO: 67 |
| (iv) - gRNA/RT/Cas9 7S particle | pMD2.G | psPAX2 | pLVX hU6 zombie lacZ gRNA repair template SEQ ID NO: 78 | pRG984 Cas9-7SL SEQ ID NO: 67 |
| (iv) - Cas9 particle | pMD2.G | psPAX2 | pLVX CAGG Cas9 SEQ ID NO: 79 | |

Example 4: Dual Enrichment Methods to Enrich Cas9 Proteins and mRNA

As described in example 3, providing Cas9 in trans could increase homologous recombination activity. To introduce more Cas9 into a target cell, dual enrichment methods could be used. CypA-Cas9-7SL RNA fusion or Cas9-Vpr-7SL RNA fusion is made to enrich both Cas9 proteins and mRNA in lentiviral particles to introduce more Cas9 into a target cell. Such a method can provide extended Cas9 activity in the host cell by providing two phases of Cas9 protein—direct from the Cas9 fusion protein and a second phase of Cas9 protein via translation from the Cas9 fusion mRNA.

Example 5: Engineering T Cells for Immunotherapy of Cancer

This example outlines the use of the lentiviral particles of the invention for cancer immunotherapy by engineering T cells to express chimeric antigen receptors (CARs) while eliminating the T cells' native T cell receptor (TCR) and/or programmed cell death-1 (PD1) receptor. To promote the specific targeting of cancer cells, T cells can be transduced with CARs which redirect the T cells against antigens expressed at the surface of target cancer cells. The native TCR can be eliminated from the engineered T cells to prevent recondition of host tissue as foreign by the TCR and to avoid graft versus host disease. The PD1 expressed in the transduced T cell can be eliminated to prevent suppression of the T cell's anti-tumor activity. T cells are harvested from a blood sample from an individual patient or from a blood bank and activated using anti-CD3/CD28 activator beads. The cells are then transduced with lentiviral particles containing a multi-chain CAR derived from FcεRI directed towards cancer antigen CD20 driven by EF1α promoter in their genome and CypA-Cas9 fusion protein and CypA-Cas9-7SL RNA fusion RNA and a gRNA targeting TCRα, a gRNA targeting PD1, or both. 96 hours after infection, the TCR inactivated and CAR positive T cells are sorted using FACS and expanded in vitro prior to administration to the patient (or in vivo following administration to the patient) through stimulation of CD3 complex and are administered to the patient for the treatment of cancer.

T cells could also be transduced with lentiviral particles containing gRNA targeting TCRα and/or PD1 and a homologous recombination template with a multi-chain CAR derived from FcεRI directed towards cancer antigen CD20 flanked by homologous arms targeting TCRα in their genome and CypA-Cas9 fusion protein and CypA-Cas9-7SL RNA fusion RNA. CAR is integrated into TCRα locus and expressed by endogenous TCR promoter. The expression of TCRα is disrupted simultaneously. 96 hours after infection, the TCR inactivated and CAR positive T cells are sorted using FACS and expanded in vitro prior to administration to the patient (or in vivo following administration to the patient) through stimulation of CD3 complex and are administered to the patient for the treatment of cancer.

Example 6: Treatment of Sickle Cell Disease

This example outlines the use of the lentiviral particles of the invention for repairing sickle cell anemia-causing mutations within the β-globin (HBB) gene. The presence of atypical HBB gene cluster haplotypes within the red blood cells results in sickle cell anemia. Subject derived haematopoietic stem cells are harvested and incubated with lentiviral particles which contain HBB gRNA and repair template in their genome and CypA-Cas9 fusion protein and CypA-Cas9-7SL RNA fusion RNA. 96 hours after infection, cells are tested for the presence of anemia-causing mutations (or their reparation) by sequencing. Upon achieving 90% or more mutation reparation, the cells are transplanted back into the subject. Subject's bone marrow is tested for the presence of the repaired cells after 16 weeks.

The claimed subject matter is not to be limited in scope by the specific embodiments described herein. Indeed, various modifications of the claimed subject matter in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A recombinant RNA molecule comprising (i) a sequence of a gene-editing molecule mRNA, or a sequence of a functional fragment thereof, and (ii) a sequence of a non-coding enrichment RNA, wherein said non-coding enrichment RNA comprises 7SL RNA, or a functional fragment thereof, and is capable of enhancing inclusion of said gene-editing molecule mRNA, or functional fragment thereof, into a retroviral particle.

2. The RNA molecule of claim 1, wherein the gene-editing molecule is a Cas protein.

3. The RNA molecule of claim 2, wherein the Cas protein is a Cas9 protein.

4. The RNA molecule of claim 1, wherein the 7SL RNA fragment comprises the Alu domain, the S domain, the 5c helix, or a combination thereof.

5. The RNA molecule of claim 1, wherein the retroviral particle is a lentiviral particle.

6. An isolated nucleic acid molecule encoding the RNA molecule of claim 1.

7. A vector comprising the nucleic acid molecule of claim 6, wherein said nucleic acid molecule is operably linked to a promoter.

8. An isolated host cell comprising the RNA molecule of claim 1.

9. An isolated host cell comprising the nucleic acid molecule of claim 6.

10. An isolated host cell comprising the vector of claim 7.

11. A recombinant retroviral particle comprising the RNA molecule of claim 1.

12. The retroviral particle of claim 11, wherein the retroviral particle is a lentiviral particle.

13. The retroviral particle of claim 11, further comprising a nucleic acid molecule encoding one or more guide RNAs (gRNA) and/or a nucleic acid molecule comprising one or more nucleic acid sequences corresponding to one or more repair templates (RT).

14. The retroviral particle of claim 11, further comprising a gene-editing molecule fusion protein comprising (i) a sequence of a gene-editing protein, or a sequence of a functional fragment thereof, and (ii) a sequence of an enrichment protein, or a sequence of a functional fragment thereof, wherein said enrichment protein, or functional fragment thereof, is capable of enhancing inclusion of said gene-editing protein, or functional fragment thereof, into the retroviral particle.

15. The retroviral particle of claim 14, wherein the gene-editing molecule is a Cas protein.

16. The retroviral particle of claim 15, wherein the Cas protein is a Cas9 protein.

17. The retroviral particle of claim 14, wherein the enrichment protein is cyclophilin A (CypA) protein and/or a viral protein R (Vpr).

18. A method of producing a recombinant retroviral particle comprising the RNA molecule of claim 1, said method comprising culturing a packaging cell in conditions sufficient for the production of a plurality of retroviral particles, wherein the packaging cell comprises one or more plasmids comprising (i) one or more retroviral elements involved in the assembly of the retroviral particle, and (ii) a nucleic acid sequence encoding the RNA molecule of claim 1.

19. The method of claim 18, wherein the packaging cell further comprises a plasmid encoding one or more guide RNAs (gRNA) and/or comprising one or more sequences corresponding to one or more repair templates (RT).

20. The method of claim 18, wherein the packaging cell comprises (a) GAG, (b) POL, and (c) TAT and/or REV retroviral elements.

21. The method of claim 18, comprising one or more of the following steps:
   a) clearing cell debris,
   b) treating a supernatant containing the retroviral particles with DNase I and $MgCl_2$,
   c) concentrating the retroviral particles, and
   d) purifying the retroviral particles.

22. A pharmaceutical composition comprising the retroviral particle of claim 11 and a pharmaceutically acceptable carrier or excipient.

23. A pharmaceutical dosage form comprising the retroviral particle of claim 11.

24. A method for modifying a genome of a target cell or modulating an activity of a gene in a target cell comprising introducing into said cell the retroviral particle of claim 11.

25. The method of claim 24, wherein the target cell is in a subject and the retroviral particle is administered to the subject.

26. The method of claim 24, further comprising harvesting the target cell from a subject prior to introducing the retroviral particle into the target cell, introducing the retroviral particle into the target cell ex vivo and returning the target cell to the subject.

27. A method for treating a disease in a subject in need thereof, said method comprising administering to the subject a therapeutically effective amount of the retroviral particle of claim 11, wherein the retroviral particle targets a cell in the subject.

28. A method for treating a disease in a subject in need thereof, said method comprising:
   a) harvesting a target cell from the subject;
   b) introducing into the target cell from step (a) ex vivo a therapeutically effective amount of the retroviral particle of claim 11; and
   c) returning the target cell from step (b) to the subject.

* * * * *